(12) United States Patent
Pauls et al.

(10) Patent No.: US 8,765,748 B2
(45) Date of Patent: Jul. 1, 2014

(54) INDAZOLYL, BENZIMIDAZOLYL, BENZOTRIAZOLYL SUBSTITUTED INDOLINONE DERIVATIVES AS KINASE INHIBITORS USEFUL IN THE TREATMENT OF CANCER

(75) Inventors: Heinz W. Pauls, Oakville (CA); Bryan T. Forrest, Toronto (CA); Radoslaw Laufer, Oakville (CA); Miklos Feher, Toronto (CA); Peter Brent Sampson, Oakville (CA); Guohua Pan, Oakville (CA); Sze-Wan Li, Toronto (CA); Yong Liu, Toronto (CA)

(73) Assignee: University Health Network, Toronto (CA)

( * ) Notice: Subject to any disclaimer, the term of this patent is extended or adjusted under 35 U.S.C. 154(b) by 810 days.

(21) Appl. No.: 12/808,961

(22) PCT Filed: Dec. 19, 2008

(86) PCT No.: PCT/CA2008/002227
§ 371 (c)(1),
(2), (4) Date: Nov. 29, 2010

(87) PCT Pub. No.: WO2009/079767
PCT Pub. Date: Jul. 2, 2009

(65) Prior Publication Data
US 2011/0065702 A1    Mar. 17, 2011

Related U.S. Application Data

(60) Provisional application No. 61/008,865, filed on Dec. 21, 2007, provisional application No. 61/131,717, filed on Jun. 11, 2008.

(51) Int. Cl.
| | | |
|---|---|---|
| A61P 35/00 | (2006.01) |
| A61P 35/02 | (2006.01) |
| C07D 401/14 | (2006.01) |
| C07D 403/06 | (2006.01) |
| C07D 403/12 | (2006.01) |
| C07D 403/10 | (2006.01) |
| C07D 403/14 | (2006.01) |
| C07D 409/14 | (2006.01) |
| C07D 413/14 | (2006.01) |
| C07D 417/14 | (2006.01) |
| C07D 471/04 | (2006.01) |
| A61K 31/416 | (2006.01) |
| A61K 31/4192 | (2006.01) |
| A61K 31/4184 | (2006.01) |
| A61K 31/4439 | (2006.01) |
| A61K 31/496 | (2006.01) |
| A61K 31/437 | (2006.01) |
| A61K 31/5377 | (2006.01) |

(52) U.S. Cl.
USPC ............ 514/234.5; 514/253.09; 514/254.06; 514/300; 514/338; 514/394; 514/406; 514/407; 514/414; 544/131; 544/333; 544/364; 544/371; 546/113; 546/268.4; 546/275.7; 548/261; 548/305.1; 548/361.1; 548/362.1; 548/362.5

(58) Field of Classification Search
None
See application file for complete search history.

(56) References Cited

U.S. PATENT DOCUMENTS

| | | | |
|---|---|---|---|
| 4,642,309 A * | 2/1987 | Michel et al. | ................ 514/269 |
| 5,182,397 A | 1/1993 | Condon et al. | |
| 6,506,763 B2 * | 1/2003 | Tang et al. | ................... 514/274 |
| 7,205,328 B2 | 4/2007 | He et al. | |
| 2007/0135509 A1 | 6/2007 | Blackburn et al. | |
| 2011/0263598 A1 | 10/2011 | Sampson et al. | |

FOREIGN PATENT DOCUMENTS

| | | |
|---|---|---|
| CA | 2 383 623 A1 | 2/2000 |
| CA | 2383623 A1 | 2/2000 |
| CA | 2 498 781 A1 | 4/2004 |
| CA | 2498781 A1 | 4/2004 |
| CA | 2690567 A1 | 12/2008 |
| CA | 2709536 A1 | 7/2009 |
| WO | 9632380 A1 | 10/1996 |
| WO | 9640116 A1 | 12/1996 |

(Continued)

OTHER PUBLICATIONS

Blackburn et al., caplus an 2002:594639.*

(Continued)

*Primary Examiner* — Sun Jae Yoo
(74) *Attorney, Agent, or Firm* — McCarter & English, LLP; Steven G. Davis; Wei Song

(57) ABSTRACT

The present invention is directed to a compound is represented by Structural Formula (A): or a pharmaceutically acceptable salt thereof. The present invention is also directed to a pharmaceutical composition comprising a compound represented by Structural Formula (A) described above or a pharmaceutically acceptable salt thereof, and a pharmaceutically acceptable carrier or diluent. Also disclosed is a method of treating a subject having cancer, wherein the method comprises administering a therapeutically effective amount of a compound represented by Structural Formula (A) described above or a pharmaceutically acceptable salt thereof.

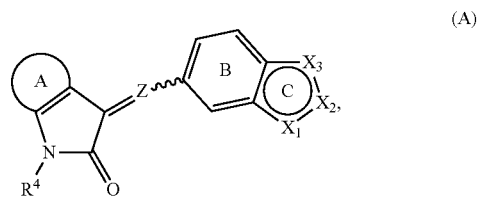

(A)

17 Claims, 1 Drawing Sheet

(56) References Cited

FOREIGN PATENT DOCUMENTS

| WO | 9910325 A1 | 3/1999 |
|---|---|---|
| WO | 0056709 A1 | 9/2000 |
| WO | 2005058309 A1 | 6/2005 |
| WO | WO 2005/058309 A1 | 6/2005 |
| WO | WO9807695 * | 6/2005 |
| WO | 2007008664 A1 | 1/2007 |
| WO | 2009079767 A1 | 7/2009 |
| WO | 2009124692 A1 | 10/2009 |
| WO | 2009132774 A1 | 11/2009 |
| WO | 2010115279 A1 | 10/2010 |
| WO | 2011123946 A1 | 10/2011 |

OTHER PUBLICATIONS

Tang et al., WO9807695, pp. 1-150, 2005.*
Tang et al. 2, WO9807695, pp. 151-293, 2005.*
International Search Report mailed Apr. 6, 2009 received in PCT/CA2008/002227.
Lin et al., "Synthesis and biological evaluation of 3-ethlidene-1,3-dihydro-indol-2-ones as novel checkpoint 1 inhibitors", Bioorganic & Medicinal Chemistry Letter, vol. 16, pp. 421-426 (2006).
Moshinsky et al., "SU9516:bilchemicalanalysis of cdk inhibition and crystal structure in complex with cdk2", BIochemical and Biophysical Research Communications, vol. 310, pp. 1026-1031 (2003).
Guan et al., "Design and synthesis of aminopropyl tetrahydroindole-based indolin-2-ones as selective and potent inhibitors of Src and Yes tyrosin Kinase", Bioorganic & Medicinal Chemistry Letters, vol. 14, pp. 187-190 (2004).
International Search Report mailed Apr. 6, 2009 for WO 2009/079767 A9.
International Search Report mailed Aug. 2, 2011 for WO 2011/123946 A1.
International Search Report mailed Jul. 8, 2010 for WO 2010/115279 A1.
Lin et al., "Synthesis and biological evaluation of 3-ethlidene-1,3-dihydro-indol-2-ones as novel checkpoint 1 inhibitors", Bioorganic & Medicinal Chemistry Letter, vol. 16, pp. 421-426 (2006).
Zhu et al., "Discovery and SAR of oxindole-pyridine-based protein kinase B/Akt inhibitors for treating cancers", Bioorganic & Medicinal Chemistry Letter, vol. 16, pp. 3424-3429 (2006).
Hauf et al., "The small molecule Hesperadin reveals a role for Aurora B in correcting kinetochore-microtubule attachment and in maintaining the spindle assembly checkpoint", The Journal of Cell Biology, vol. 161, No. 2, pp. 281-294 (2003).
Sessa et al., "Mechanism of Aurora B Activation by INCENP and Inhibition by Hesperadin", Molecular Cell, vol. 18, 379-391, (2005).
Mohammadi et al., "Structures of the Tyrosine Kinase Domain of Fibroblast Growth Factor Receptor in Complex with Inhibitors", Science, vol. 276, pp. 955-960 (1997).
Moshinsky et al., "SU9516:bilchemicalanalysis of cdk inhibition and crystal structure in complex with cdk2", BIochemical and Biophysical Research Communications, vol. 310, pp. 1026-1031 (2003).
Howard et al., "Synthesis and aldose reductase inhibitory activity of substituted 2(1H)-benzimidazolone and oxindole-1-acetic acids", Eur. J. Med. Chem. vol. 27, pp. 779-789 (1992).
Rellos et al., "Structure and Regulation of the Human Nek2 Centrosomal Kinase", The Journal of Biological Chemistry, vol. 282, No. 9, pp. 6833-6842 (2007).
Guan et al., "Design and synthesis of aminopropyl tetrahydroindole-based indolin-2-ones as selective and potent inhibitors nhibitors of Src and Yes tyrosin Kinase", Bioorganic & Medicinal Chemistry Letters, vol. 14, pp. 187-190 (2004).
Adams et al., "Mapping the Kinase Domain of the Janus Kinase 3", Bioorganic & Medicinal Chemistry Letters, vol. 13, pp. 3105-3110(2003).
Johnson et al., "Pharmacological and Functional Comparison of the Polo-like Kinase Family: Insight into Inhibitor and Substrate Specificity", Biochemistry, 46(33), 9551-9563 (2007).
Moldvai et al., "Synthesis of Spiro[cyclopropone-1,3'[3H]indol]-2'(1'H)-ones with Antihypoxic Effects", Arch. Pharm. Pharm. Med. Chem., 329(12), 541-549, (1996).
Jiang et al., "Design, synthesis, and biological evaluations of novel oxindoles as HIV-1 non-nucleosoide reverse transcriptase inhibitors. Part 2", Bioorganic & Medicinal Chemistry Letters., vol. 16, pp. 2109-2112 (2006).

* cited by examiner

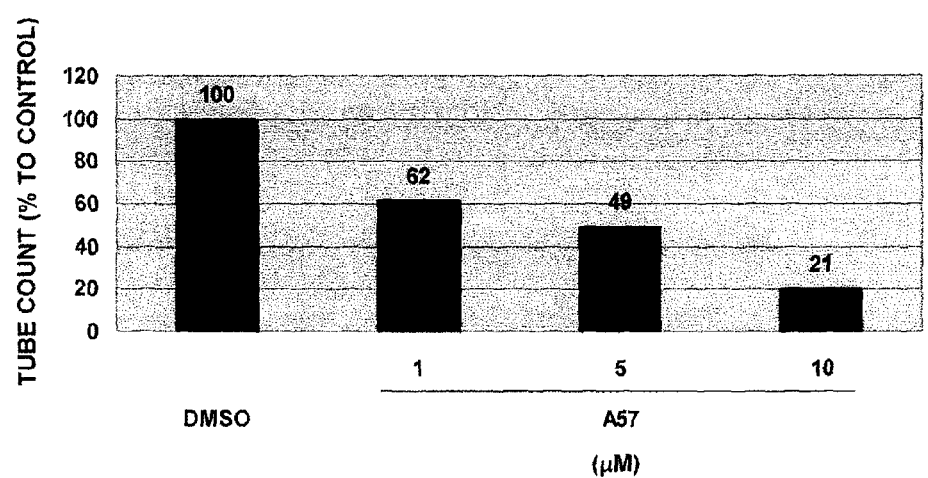

INDAZOLYL, BENZIMIDAZOLYL, BENZOTRIAZOLYL SUBSTITUTED INDOLINONE DERIVATIVES AS KINASE INHIBITORS USEFUL IN THE TREATMENT OF CANCER

RELATED APPLICATIONS

This application is the US National Stage of PCT Application No. PCT/CA2008/02227, filed Dec. 19, 2008, which published in English and designates the Unites States and claims priority to U.S. Provisional Application Nos., 61/008,865 filed Dec. 21, 2007 and 61/131,717, filed Jun. 11, 2008. The entire teachings of these applications are incorporated herein by reference.

BACKGROUND OF THE INVENTION

Protein kinases have been the subject of extensive study in the search for new therapeutic agents in various diseases, for example, cancer. Protein kinases are known to mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell.

The polo-like kinase (PLK) family of serine/threonine kinases comprises at least four known members: PLK1, PLK2 (also known as Snk), PLK3 (also known as Fnk or Prk) and PLK4 (also known as Sak). PLK4 is the least understood and most divergent member of the PLK family. The N-terminal catalytic domain of PLK4 has a different substrate specificity from that of PLK1-3. PLK4 also has a divergent C-terminus comprising only a single polo-box sequence, not the tandem PB sequences in PLK1-3, that appears to act as a homodimerization domain rather than a localization domain (Lowery et al., (2005) Oncogene 24: 248-259).

PLK4 is known to be involved in the control of mitotic entry and exit, and a regulator of centrosome duplication (Habedanck et al. Nature Cell Biology 7: 1140-1146, 2005). PLK4 transcripts increase from S through M phase, and the protein is ubiquitylated and destroyed by the anaphase promoting complex (APC) (Hudson et al. Curr. Biol. 11: 441-446, 2001; Fode et al. Mol. Cell. Biol. 16: 4665-4672, 1996). PLK4 is required for late mitotic progression (Fode et al. PNAS. 91: 6388-6392, 1994; Hudson et al. Curr. Biol. 11: 441-446, 2001), cell survival and postgastrulation embryonic development (Hudson et al. Curr. Biol. 11: 441-446, 2001). PLK4 knockout mice are embryonic lethal (E7.5), with a marked increase in mitotic and apoptotic cells (Hudson et al. Curr. Biol. 11: 441-446, 2001). PLK4 is transcriptionally repressed by p53 (Li et al. Neoplasia 7: 312-323, 2005). This repression is likely mediated through the recruitment of histone deacetylase (HDAC) repressors and repression appears to contribute to p53-induced apoptosis (Li et al. Neoplasia 7: 312-323, 2005).

PLK4 has been reported to be overexpressed in colorectal tumors with expression reported as low in adjacent normal intestinal mucosa (Macmillian et al. Ann. Surg. Oncol. 8: 729-740, 2001). In addition, PLK4 mRNA has been reported to be overexpressed in some tumor cell lines (Hitoshi, et al., U.S. Patent Application No. US 2003/0027756). In addition, Applicants described overexpression of PLK4 in basal-like tumors in a co-pending U.S. Provisional Application No. 61/003,825, filed on Nov. 20, 2007 (the entire teachings of which are incorporated herein by reference).

Therefore, agents which inhibit a protein kinase, in particular PLK4, have the potential to treat cancer. There is a need for additional agents which can act as protein kinase inhibitors, in particular PLK4 inhibitors.

SUMMARY OF THE INVENTION

Applicants have now discovered that certain indolinone compounds are potent kinase inhibitors, such as polo-like kinases (PLK) (see Example B). Applicants have also now discovered that these indolinone compounds have potent anticancer activity (see Example C). Based on these discoveries, indolinone compounds, pharmaceutical compositions thereof, and methods of treating cancer with the indolinone compounds are disclosed herein.

In one embodiment, the present invention is directed to a compound represented by Structural Formula (A):

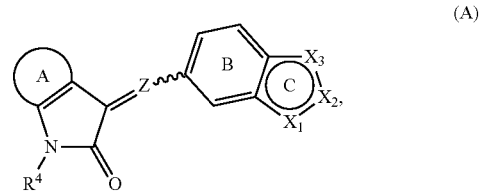

(A)

or a pharmaceutically acceptable salt thereof.

Ring A is an optionally substituted 5- or 6-membered aromatic ring.

Ring B is an optionally substituted phenyl ring.

Ring C is a 5-membered heteroaromatic ring wherein one of X1-X3 is N, one of X1-X3 is $NR^5$, and one of X1-X3 is N or $CR^6$.

Z is =N— or =$CR^3$—.

$R^3$ is —H, halogen, C1-C6 alkyl or C1-C6 haloalkyl.

each of $R^4$ and $R^5$ independently is —H, C1-C6 alkyl, phenyl, —C(O)(C1-C6 alkyl), —C(O)(phenyl), —C(O)O (C1-C6 alkyl), —C(O)O(phenyl), —S(O)$_2$(C1-C6 alkyl) or —S(O)$_2$(phenyl), wherein each said alkyl in the groups represented by $R^4$ and $R^5$ independently is optionally substituted with one or more substituents selected from the group consisting of halogen, hydroxy, nitro, cyano, amino, phenyl, 5-6 membered heteroaryl, C1-C6 alkoxy and C1-C6 haloalkoxy, and wherein each said phenyl in the groups represented by $R^4$ and $R^5$ independently is optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy.

$R^6$ is hydrogen, halogen, nitro, cyano, R', —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOR', —SO$_2$R', —SO$_3$R', —SO$_2$N(R)$_2$, —NRS(O)R', —NRSO$_2$R', —NRC(O)N(R)$_2$, —NRC(O)ON(R)$_2$, or —NRSO$_2$N(R)$_2$.

each R independently is hydrogen, $C_{1-10}$ aliphatic, phenyl or 5-6 membered heteroaryl, wherein said aliphatic is optionally substituted with one or more substituents selected from the group consisting of halogen, hydroxy, nitro, cyano, amino, phenyl, 5-6 membered heteroaryl, C1-C6 alkoxy, C1-C6 haloalkoxy, and wherein each of the phenyl and heteroaryl groups represented by R, and the phenyl and heteroaryl groups in the substituents for the aliphatic group represented by R independently is optionally substituted with one or more substituents selected from the group consisting of halogen, hydroxy, nitro, cyano, amino, C1-C6 alkyl, C1-C6 haloalkyl, C1-C6 alkoxy, C1-C6 haloalkoxy, or N(R)$_2$ forms a non-aromatic heterocyclic group optionally substituted with one or more substituents selected from the group consisting of =O, =S, halogen, nitro, cyano, hydroxy, C$_{1-6}$ alkyl, C$_{1-6}$ haloalkyl, C$_{1-6}$ hydroxyalkyl, amino, C$_{1-6}$ alkylamino, C$_{1-6}$ dialkylamino, C$_{1-6}$ aminoalkyl, (C$_{1-6}$ alkylamino)C$_{1-6}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, C$_{1-6}$ alkoxy, C$_{1-6}$ haloalkoxy, C$_{1-6}$ alkylcarbonyloxy, C$_{1-6}$ alkoxycarbonyl, C$_{1-6}$ alkylcarbonyl, phenyl and 5-6 membered heteroaryl.

each R' independently is C$_{1-10}$ aliphatic, phenyl or 5-14 membered heteroaryl, wherein said aliphatic is optionally substituted with one or more substituents selected from the group consisting of halogen, hydroxy, nitro, cyano, amino, phenyl, 5-6 membered heteroaryl, C1-C6 alkoxy, C1-C6 haloalkoxy, C$_{1-6}$ alkylamino, C$_{1-6}$ dialkylamino, —C(O)(C1-C6 alkyl), —C(O)(C1-C6 haloalkyl), —C(O)(phenyl), —C(O)(non-aromatic heterocyclic group), —C(O)O(optionally substituted C1-C6 alkyl), —C(O)O(C1-C6 haloalkyl), —C(O)O(phenyl), —OC(O)(C1-C6 alkyl), —OC(O)(optionally substituted C1-C6 haloalkyl), —OC(O)(phenyl), —S(O)$_2$(C1-C6 alkyl), —S(O)$_2$(C1-C6 haloalkyl) and —S(O)$_2$(phenyl), and wherein each of the phenyl and heteroaryl groups represented by R', and the phenyl and heteroaryl groups in the substituents for the aliphatic group represented by R' independently is optionally substituted with one or more substituents selected from the group consisting of halogen, hydroxy, nitro, cyano, amino, C1-C6 alkyl, C1-C6 haloalkyl, C$_{1-6}$ aminoalkyl, (C$_{1-6}$ alkylamino)C$_{1-6}$ alkyl, (C$_{1-6}$ dialkylamino)C$_{1-6}$ alkyl, (phenyl)C$_{1-6}$ alkyl C1-C6 alkoxy, C1-C6 haloalkoxy, non-aromatic heterocyclic group, C$_{1-6}$ alkylamino, C$_{1-6}$ dialkylamino, —C(O)(C1-C6 alkyl), —C(O)(C1-C6 haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)(C1-C6 alkyl), —OC(O)(C1-C6 haloalkyl), —OC(O)(phenyl), —S(O)$_2$(C1-C6 alkyl), —S(O)$_2$(C1-C6 haloalkyl), —S(O)$_2$(phenyl), —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperazinyl is optionally N'-substituted with C$_{1-6}$ alkyl or C$_{1-6}$ acyl.

In another embodiment, the present invention is directed to a pharmaceutical composition comprising a compound represented by Structural Formula (A) described above or a pharmaceutically acceptable salt thereof, and a pharmaceutically acceptable carrier or diluent.

The present invention also includes a method of treating a subject having cancer comprising administering a therapeutically effective amount of a compound of the invention disclosed herein or a pharmaceutically acceptable salt thereof.

The present invention also includes a method of inhibiting Aurora B and/or PLK-4 in a subject in need of inhibition of Aurora B and/or PLK-4, comprising administering a therapeutically effective amount of a compound of the invention disclosed herein or a pharmaceutically acceptable salt thereof.

Also, use of a compound of the invention disclosed herein or a pharmaceutically acceptable salt thereof in therapy is included in the present invention. In one embodiment, the therapy is for treating a subject with cancer. In another embodiment, the therapy is for inhibiting Aurora B and/or PLK-4 in a subject in need of inhibition of Aurora B and/or PLK-4.

Also included in the present invention is the use of a compound of the invention disclosed herein or a pharmaceutically acceptable salt thereof for the manufacture of a medicament for treating a subject with cancer.

Also included in the present invention is the use of a compound of the invention disclosed herein or a pharmaceutically acceptable salt thereof for the manufacture of a medicament for inhibiting Aurora B and/or PLK-4 in a subject in need of inhibition of Aurora B and/or PLK-4.

BRIEF DESCRIPTION OF THE DRAWINGS

The figure is a bar graph showing the inhibition of HUVEC-C Cell Tube Formation by compound Example A57.

DETAILED DESCRIPTION OF THE INVENTION

In one aspect, the present invention is directed to an indolinone compound represented by Structural Formula (A). A first set of values and specific values for the variables in Structural Formula (A) are provided in the following paragraphs:

Ring A is an optionally substituted 5- or 6-membered aromatic ring. In one embodiment, ring A is optionally substituted benzene ring. In another embodiment, ring A is optionally substituted pyridine ring. In another embodiment, ring A is optionally substituted pyrrole ring. In another embodiment, ring A is optionally substituted thiophene ring. In another embodiment, ring A is optionally substituted thiozole ring.

In one embodiment, ring A is optionally substituted with one or more substituents $Q^a$, and phenyl ring B is optionally substituted with one or more substituents $Q^b$. Typically, each of $Q^a$ and $Q^b$ independently is selected from the group consisting of halogen, —X—R$^1$, —NO$_2$, —CN, —NCS, Ak$^1$, Ar$^1$, (C$_{1-10}$ alkylene)-Ar$^1$, (C$_{2-10}$alkenylene)-Ar$^1$, —O—[CH$_2$]$_p$—O—, —S—[CH$_2$]$_p$—S— and —[CH$_2$]$_q$—. In one embodiment, one of $Q^a$ and $Q^b$ is halogen, —NO$_2$, —CN, Ak$^1$, Ar$^1$, (C$_{1-10}$ alkylene)-Ar$^1$, (C$_{2-10}$alkenylene)-Ar$^1$ or —X—R$^1$; and the other of $Q^a$ and $Q^b$ is halogen, hydroxy, nitro, cyano, amino, methyl, methoxy, halomethyl or halomethoxy. In another embodiment, one of $Q^a$ and $Q^b$ is halogen, hydroxy, cyano, nitro, C1-C6 alkyl, C1-C6 haloalkyl, —C(O)(C1-C6 alkyl), —C(O)NH$_2$, —C(O)NH(C1-C6 alkyl), —C(O)N(C1-C6 alkyl)$_2$, —SO$_2$NH$_2$, —SO$_2$NH(C1-C6 alkyl), —SO$_2$N(C1-C6 alkyl)$_2$, —OH, —O(C1-C6 alkyl), —O(C1-C6 haloalkyl), —SH, —S(C1-C6 alkyl), —S(C1-C6 haloalkyl), —NH$_2$, —NH(C1-C6 alkyl), —N(C1-C6 alkyl)$_2$, —NHC(O)(C1-C6 alkyl), —NHC(O)O(C1-C6 alkyl), —NHC(O)NH$_2$, —NHC(O)NH(C1-C6 alkyl), —NHC(O)N(C1-C6 alkyl)$_2$, —NHC(O)ONH$_2$, —NHC(O)ONH(C1-C6 alkyl), —NHC(O)ON(C1-C6 alkyl)$_2$, —NHSO$_2$NH$_2$, —NHSO$_2$NH(C1-C6 alkyl), —NHSO$_2$N(C1-C6 alkyl)$_2$ or —NHSO$_2$(C1-C6 alkyl); and the other $Q^a$ and $Q^b$ is halogen, hydroxy, nitro, cyano, amino, methyl, methoxy, halomethyl or halomethoxy. In yet another embodiment, one of $Q^a$ and $Q^b$ is halogen, hydroxy, cyano, nitro, Ph, —CH$_2$Ph, —C(O)Ph, —C(O)NH(Ph), —C(O)N(C1-C6 alkyl)(Ph), —SO$_2$NH(Ph), —SO$_2$N(C1-C6 alkyl)(Ph), —O(Ph), —S(Ph), —NH(Ph), —N(C1-C6 alkyl)(Ph), —NHC(O)(Ph), —NHC(O)O(Ph), —NHC(O)NH(Ph), —NHC(O)N(C1-C6 alkyl)(Ph), —NHC(O)ONH(Ph), —NHC(O)ON(C1-C6 alkyl)(Ph), —NHSO$_2$NH(Ph), —NHSO$_2$N(C1-C6 alkyl)(Ph) or —NHSO$_2$(Ph), wherein each Ph is a phenyl group independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy; and the other $Q^a$ and $Q^b$ is halogen, hydroxy, nitro, cyano, amino, methyl, methoxy, halomethyl or halomethoxy. In yet another example, both of $Q^a$ and $Q^b$ are independently halogen, hydroxy, nitro, cyano, amino, methyl, methoxy, halomethyl or halomethoxy. In another embodiment, $Q^a$ is halogen, cyano, —$NR^1R^2$, —$NR^2C(O)R^1$, —$C(O)OR^1$, —$OC(O)R^1$, —$N(R^2)C(O)NR^1R^2$, —$OR^1$, $C_{1-6}$ alkyl, wherein the $C_{1-6}$ alkyl is optionally substituted with one or more substituents selected from the group consisting of halogen, —OH, —SH, —O($C_{1-6}$ alkyl), —S($C_{1-6}$ alkyl) and $C_{1-6}$ haloalkoxy; and $Q^b$ is halogen, $C_{1-3}$ alkyl, $C_{1-3}$ haloalkyl, $C_{1-3}$ alkoxy, or $C_{1-3}$ haloalkoxy. In another embodiment, $Q^a$ is —OH, $C_{1-6}$ alkoxy or $C_{1-6}$ haloalkoxy; and $Q^b$ is halogen, $C_{1-3}$ alkyl, $C_{1-3}$ haloalkyl, $C_{1-3}$ alkoxy, or $C_{1-3}$ haloalkoxy.

X is —C(O)O—, —C(O)—, —C(S)—, —OC(O)—, —C(O)N($R^2$)—, —C(S)N($R^2$)—, —OC(O)N($R^2$)—, —S(O)—, —S(O)$_2$—, —SO$_3$—, —SO$_2$N$R^2$—, —O—, —S—, —N$R^2$—, —N$R^2$C(O)—, —N$R^2$S(O)—, —N$R^2$C(O)O—, —N$R^2$C(O)ON$R^2$—, —N($R^2$)C(O)N$R^2$—, —N$R^2$SO$_2$N$R^2$— or —N$R^2$SO$_2$—. Alternatively, X is —C(O)—, —C(S)—, —C(O)N($R^2$)—, —OC(O)N($R^2$)—, —SO$_2$N$R^2$—, —O—, —S—, —N$R^2$—, —N$R^2$C(O)—, —N$R^2$C(O)O—, —N$R^2$C(O)ON$R^2$—, —N($R^2$)C(O)N$R^2$—, —N$R^2$SO$_2$N$R^2$— or —N$R^2$SO$_2$—.

Each $R^1$ independently is: i) hydrogen; ii) an optionally substituted $C_{6-14}$ aryl group or an optionally substituted 5-14 membered heteroaryl group; or iii) an optionally substituted $C_{1-10}$ aliphatic group, provided that $R^1$ is other than hydrogen when X is —S(O)—, —S(O)$_2$—, —SO$_3$—, —N$R^2$S(O)— or —N$R^2$SO$_2$—. In one embodiment, each $R^1$ independently is i) hydrogen; ii) an optionally substituted phenyl group or an optionally substituted 5-6 membered heteroaryl group; or iii) an optionally substituted $C_{1-10}$ alkyl, provided that $R^1$ is other than hydrogen when X is —S(O)—, —S(O)$_2$—, —SO$_3$—, —N$R^2$S(O)— or —N$R^2$SO$_2$—. Typically, each of the aryl and heteroaryl groups represented by $R^1$ is independently and optionally substituted with one or more substituents selected from the group consisting of halogen, —NO$_2$, —CN, —NCS, A$k^{10}$, ($C_{1-10}$ alkylene)-A$r^{10}$, ($C_{2-10}$ alkenylene)-A$r^{10}$, —C(O)O$R^{10}$, —C(O)$R^{10}$, —C(S)$R^{10}$, —OC(O)$R^{10}$, —C(O)N($R^{11}$)$_2$, —C(S)N($R^{11}$)$_2$, —OC(O)N($R^{11}$)$_2$, —S(O)$R^{12}$, —S(O)$_2R^{12}$, —SO$_3R^{12}$, —SO$_2$N($R^{11}$)$_2$, —O$R^{10}$, —S$R^{10}$, —N($R^{11}$)$_2$, —N$R^{11}$C(O)$R^{10}$, —N$R^{11}$S(O)$R^{12}$, —N$R^{11}$C(O)O$R^{12}$, —N($R^{11}$)C(O)N($R^{11}$)$_2$, —N$R^{11}$SO$_2$N($R^{11}$)$_2$ and —N$R^{11}$SO$_2R^{12}$. In one embodiment, each of the aryl and heteroaryl groups represented by $R^1$ is independently and optionally substituted with one or more substitutents selected from the group consisting of halogen, nitro, cyano, A$k^{10}$, ($C_{1-10}$ alkylene)-A$r^{10}$, ($C_{2-10}$ alkenylene)-A$r^{10}$, —O$R^{10}$, —S$R^{10}$, —OC(O)N($R^{11}$)$_2$, —N($R^{11}$)$_2$, —C(O)N$R^{11}$, —N$R^{11}$C(O)$R^{10}$, —N($R^{11}$)C(O)N($R^{11}$)$_2$, —N$R^{11}$SO$_2$N($R^{11}$)$_2$, —N$R^{11}$SO$_2R^{12}$, —SO$_2$N($R^{11}$)$_2$, —OC(O)$R^{10}$, —C(O)O$R^{10}$ and —C(O)$R^{10}$. Typically, the aliphatic group, including alkyl group, represented by $R^1$ is optionally substituted with one or more substituents selected from the group consisting of halogen, —NO$_2$, —CN, —NCS, A$r^{10}$, —C(O)O$R^{10}$, —C(O)$R^{10}$, —C(S)$R^{10}$, —OC(O)$R^{10}$, —C(O)N($R^{11}$)$_2$, —C(S)N($R^{11}$)$_2$, —OC(O)N($R^{11}$)$_2$, —S(O)$R^{12}$, —S(O)$_2R^{12}$, SO$_3R^{12}$, —SO$_2$N($R^{11}$)$_2$, —O$R^{10}$, —S$R^{10}$, —N($R^{11}$)$_2$, —N$R^{11}$C(O)$R^{10}$, —N$R^{11}$S(O)$R^{12}$, —N$R^{11}$C(O)O$R^{12}$, —N($R^{11}$)C(O)N($R^{11}$)$_2$, —N$R^{11}$SO$_2$N($R^{11}$)$_2$ and —N$R^{11}$SO$_2R^{12}$. In one embodiment, the aliphatic group, including alkyl group, represented by $R^1$ is optionally substituted with one or more substituents selected from the group consisting of halogen, nitro, cyano, A$r^{10}$, —O$R^{10}$, —S$R^{10}$, —N($R^{11}$)$_2$, —OC(O)$R^{10}$, —C(O)O$R^{10}$ and —C(O)$R^{10}$. In another embodiment, $R^1$ is —H— or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$ haloalkoxy.

Each $R^2$ independently is $R^1$, —CO$_2R^1$, —SO$_2R^1$ or —C(O)$R^1$, or, taken together with $NR^1$, forms an optionally substituted non-aromatic heterocyclic group represented by $NR^1R^2$. In one embodiment, each $R^2$ is —H or C1-C6 alkyl. Typically, the non-aromatic heterocyclic group represented by $NR^1R^2$ is optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl. In one embodiment, the non-aromatic heterocyclic group represented by $NR^1R^2$ is optionally substituted with one or more substituents selected from the group consisting of halogen, hydroxy, nitro, cyano, =O, C1-C3 alky, C1-C3 haloalkyl, C1-C3 alkoxy, C1-C3 haloalkoxy and amino. In another embodiment, $R^2$ is —H— or $C_{1-6}$ alkyl, wherein the $C_{1-6}$ alkyl is optionally substituted with one or more substituents independently selected from the group consisting of halogen, —OH, —SH, —O($C_{1-3}$alkyl), —S($C_{1-3}$ alkyl) and $C_{1-6}$ haloalkoxy.

Z is =N— or =C$R^3$—. In one embodiment, when Z is =N—,

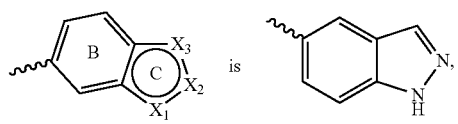

is $R^4$ is H or C1-C6 alkyl, then ring A is not phenyl or phenyl substituted with halogen or trifluoromethyl. In another embodiment, when Z is =N—, then

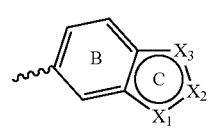

is not

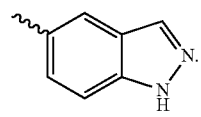

$R^3$ is —H, halogen, C1-C6 alkyl or C1-C6 haloalkyl. In one embodiment, $R^3$ is —H or C1-C6 alkyl. In another embodiment, $R^3$ is —H, halogen, C1-C6 alkyl or C1-C6 haloalkyl, wherein when $R^3$ is halogen, then

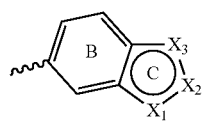

is not

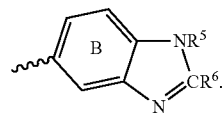

Each of $R^4$ and $R^5$ independently is —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl). Typically, each alkyl in the groups represented by $R^4$ and $R^5$ is independently and optionally substituted with one or more substituents selected from the group consisting of halogen, hydroxy, nitro, cyano, amino, phenyl, 5-6 membered heteroaryl, C1-C6 alkoxy and C1-C6 haloalkoxy. Typically, each phenyl in the groups represented by $R^4$ and $R^5$ independently is optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy. In one embodiment, $R^4$ and $R^5$ are both —H.

$R^6$ is hydrogen, halogen, nitro, cyano, R', —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOR', —SO$_2$R', —SO$_3$R', —SO$_2$N(R)$_2$, —NRS(O)R', —NRSO$_2$R', —NRC(O)N(R)$_2$, —NRC(O)ON(R)$_2$ or —NRSO$_2$N(R)$_2$. In one embodiment, $R^6$ is hydrogen, halogen, nitro, cyano, R', —OR, —SR or —N(R)$_2$. In another embodiment, $R^6$ is hydrogen, halogen, nitro, cyano, hydroxy, C1-C6 alkyl, C1-C6 haloalkyl, C1-C6 alkoxy, C1-C6 haloalkoxy, —S(C1-C6 alkyl), —S(C1-C6 haloalkyl), amino, C1-C6 alkylamino, C1-C6 dialkylamino, phenoxy or phenyl, wherein each of said alkyl and said alkoxy in the groups represented by $R^6$ is independently and optionally substituted with one or more substituents selected from the group consisting of halogen, hydroxy, nitro, cyano, amino, phenyl, C1-C3 alkoxy and C1-C3 haloalkoxy, and wherein each said phenyl in the groups represented by $R^6$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy. In another embodiment, $R^6$ is hydrogen, halogen, C1-C6 alkyl or C1-C6 haloalkyl. In another embodiment, $R^6$ is optionally substituted phenyl, optionally substituted 5-12 membered heteroaryl, —CH$_2$-(optionally substituted phenyl), —CH$_2$-(optionally substituted 5-12 membered heteroaryl), —CH$_2$—CH$_2$-(optionally substituted phenyl), —CH$_2$—CH$_2$-(optionally substituted 5-12 membered heteroaryl), —CH=CH-(optionally substituted phenyl), —CH=CH—(optionally substituted 5-12 membered heteroaryl), —CH=CH—C(O)O(optionally substituted C$_{1-6}$ alkyl), or —CH=CH—OC(O)(optionally substituted C$_{1-6}$ alkyl). In another embodiment, $R^6$ is an optionally substituted phenyl or an optionally substituted 5-6 membered heteroaryl. In another embodiment, the phenyl and 5-6 membered heteroaryl represented by $R^6$ are independently and optionally substituted with one or more substitutents selected from the group consisting of: halogen, hydroxy, nitro, cyano, amino, C1-C6 alkyl, C1-C6 haloalkyl, C1-C6 alkoxy and C1-C6 haloalkoxy. In yet another embodiment, $R^6$ is an optionally substituted phenyl group, an optionally substituted pyridyl group, an optionally substituted pyrrolyl group, an optionally substituted pyrazolyl, an optionally substituted thiazolyl, an optionally substituted pyrimidyl, or an optionally substituted thienyl. In yet another embodiment, $R^6$ is an —CH=CH-(optionally substituted phenyl) —CH=CH-(optionally substituted 5-12 membered heteroaryl), —C≡C-(optionally substituted phenyl) or —C≡C-(optionally substituted 5-12 membered heteroaryl), wherein the heteroaryl is an optionally substituted pyridyl group, an optionally substituted pyrrolyl group, an optionally substituted pyrazolyl, an optionally substituted thiazolyl, an optionally substituted pyrimidyl, or an optionally substituted thienyl.

Each $R^{10}$ independently is: i) hydrogen; ii) an optionally substituted $C_{6-14}$ aryl group or an optionally substituted 5-14 membered heteroaryl group; or iii) an optionally substituted $C_{1-10}$ alkyl group. In one embodiment, each $R^{10}$ independently is i) hydrogen; ii) an optionally substituted phenyl group or an optionally substituted 5-6 membered heteroaryl group; or iii) an optionally substituted $C_{1-6}$ alkyl group. Typically, each of the aryl, including phenyl, and heteroaryl groups represented by $R^{10}$ is independently and optionally substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl. In one embodiment, each of the aryl, including phenyl, and heteroaryl groups represented by $R^{10}$ is independently and optionally substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, amino, $C_{1-6}$ alkylamino, $C_{1-6}$ dialkylamino, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl. In another embodiment, each of the aryl, including phenyl, and heteroaryl groups represented by $R^{10}$ is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloaloxy. Typically, the alkyl group represented by $R^{10}$ is optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy. In one embodiment, the alkyl group represented by $R^{10}$ is optionally substituted with one or more substituents selected from the group consisting halogen, nitro, cyano, hydroxy, $C_{1-6}$ haloalkyl, $C_{1-6}$ alkoxy, $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl, $C_{1-6}$ alkylcarbonyl and phenyl. In another embodiment, the alkyl group represented by $R^{10}$ is optionally substituted with one or more substituents selected from the group consisting of halogen, hydroxy, amino, cyano, nitro, C1-C3 alkoxy, C1-C3 haloaloxy and phenyl.

Each $R^{11}$ independently is $R^{10}$, —$CO_2R^{10}$, —$SO_2R^{10}$ or —$C(O)R^{10}$, or —$N(R^{11})_2$ taken together is an optionally substituted non-aromatic heterocyclic group. Typically, the non-aromatic heterocyclic group represented by $N(R^{11})_2$ is optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl alkylcarbonyl, phenyl and 5-6 membered heteroaryl. In one example, the non-aromatic heterocyclic group represented by $N(R^{11})_2$ is optionally substituted with one or more substituents selected from the group consisting of halogen, hydroxy, nitro, cyano, =O, C1-C3 alky, C1-C3 haloalkyl, C1-C3 alkoxy, C1-C3 haloalkoxy and amino.

Each $R^{12}$ independently is: i) an optionally substituted $C_{6-14}$ aryl group or an optionally substituted 5-14 membered heteroaryl group; or ii) an optionally substituted $C_{1-10}$ alkyl group. Alternatively, each $R^{12}$ independently is i) an optionally substituted phenyl group or an optionally substituted 5-6 membered heteroaryl group; or ii) an optionally substituted $C_{1-6}$ alkyl group. Typically, each of the aryl, including phenyl, and heteroaryl groups represented by $R^{12}$ is independently and optionally substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, alkylcarbonyloxy, $C_{1-10}$ alkoxycarbonyl and $C_{1-10}$ alkylcarbonyl. In one example, each of the aryl, including phenyl, and heteroaryl groups represented by $R^{12}$ is independently and optionally substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, amino, $C_{1-6}$ alkylamino, $C_{1-6}$ dialkylamino, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl. In another example, each of the aryl, including phenyl, and heteroaryl groups represented by $R^{12}$ is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloaloxy. Typically, the alkyl group represented by $R^{12}$ is optionally substituted with one or more substituents selected from the group consisting of halogen, nitro, cyano, hydroxy, $C_{1-10}$ haloalkyl, $C_{1-10}$ alkoxy, haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy. In one example, the alkyl group represented by $R^{12}$ is optionally substituted with one or more substituents selected from the group consisting halogen, nitro, cyano, hydroxy, $C_{1-6}$ haloalkyl, $C_{1-6}$ alkoxy, $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl, $C_{1-6}$ alkylcarbonyl and phenyl. In another example, the alkyl group represented by $R^{12}$ is optionally substituted with one or more substituents selected from the group consisting of halogen, hydroxy, amino, cyano, nitro, C1-C3 alkoxy, C1-C3 haloaloxy and phenyl.

Each $R^{21}$ independently is hydrogen, optionally substituted $C_{1-6}$ alkyl, optionally substituted phenyl or optionally substituted 5-6 membered heteroaryl, or $N(R^{21})_2$ forms an optionally substituted non-aromatic heterocyclic group. Alternatively, each $R^{21}$ independently is hydrogen, optionally substituted $C_{1-6}$ alkyl or optionally substituted phenyl. Typically, each of the phenyl and heteroaryl groups represented by $R^{21}$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy. Typically, the alkyl group represented by $R^{21}$ is optionally substituted with one or more substituents selected from the group consisting of halogen, hydroxy, nitro, cyano, amino, C1-C3 alkoxy, C1-C3 haloalkoxy and phenyl. Typically, the non-aromatic heterocyclic represented by $N(R^{21})_2$ is optionally substituted with one or more substituents selected from the group consisting of halogen, hydroxy, nitro, cyano, =O, C1-C3 alky, C1-C3 haloalkyl, C1-C3 alkoxy, C1-C3 haloalkoxy and amino.

Each $R^{22}$ independently is optionally substituted $C_{1-6}$ alkyl, optionally substituted phenyl or optionally substituted 5-6 membered heteroaryl. Alternatively, each $R^{22}$ independently is optionally substituted $C_{1-6}$ alkyl or optionally substituted phenyl. Typically, each of the phenyl and heteroaryl groups represented by $R^{22}$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy. Typically, the alkyl group represented by $R^{22}$ is optionally substituted with one or more substituents selected from the group consisting of halogen, hydroxy, nitro, cyano, amino, C1-C3 alkoxy, C1-C3 haloalkoxy and phenyl.

Each R independently is hydrogen, optionally substituted $C_{1-10}$ aliphatic, optionally substituted phenyl or optionally substituted 5-6 membered heteroaryl. Alternatively, $N(R)_2$ forms an optionally substituted non-aromatic heterocyclic group. Typically, the aliphatic group represented by R is optionally substituted with one or more substituents selected from the group consisting of halogen, hydroxy, nitro, cyano, amino, phenyl, 5-6 membered heteroaryl, C1-C6 alkoxy and C1-C6 haloalkoxy, wherein each of the phenyl and the 5-6 membered heteroaryl groups are independently and optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy. Typically, each of the phenyl and the heteroaryl groups represented by R is independently and optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy. Typically, the non-aromatic heterocyclic group represented by $N(R)_2$ is optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl. In one example, the non-aromatic heterocyclic group represented by $N(R)_2$ is optionally substituted with one or more substituents selected from the group consisting of halogen, hydroxy, nitro, cyano, =O, C1-C3 alky, C1-C3 haloalkyl, C1-C3 alkoxy, C1-C3 haloalkoxy and amino.

Each R' independently is optionally substituted $C_{1-10}$ aliphatic, optionally substituted phenyl or optionally substituted 5-14 membered heteroaryl. Alternatively, each R' independently is —$CH_2$-(optionally-substituted phenyl), —$CH_2$-(optionally-substituted 5-6 membered heteroaryl), —$CH_2$—$CH_2$-(optionally-substituted phenyl), —$CH_2$—$CH_2$-(optionally-substituted 5-6 membered heteroaryl), CH=CH-(optionally-substituted phenyl) or —CH=$CH_2$-(optionally-substituted 5-6 membered heteroaryl). Alternatively, each R' independently is —$CH_2$-(optionally-substituted phenyl), —$CH_2$-(optionally-substituted pyridyl), —$CH_2$—$CH_2$-(optionally-substituted phenyl), —$CH_2$—$CH_2$-(optionally-substituted pyridyl), CH=CH-(optionally-substituted phenyl) or —CH=$CH_2$-(optionally-substituted pyridyl). Typically, the aliphatic group represented by R' is optionally substituted with one or more substituents selected from the group consisting of halogen, hydroxy, nitro, cyano, amino, phenyl, 5-6 membered heteroaryl, C1-C6 alkoxy and C1-C6 haloalkoxy, $C_{1-6}$ alkylamino, $C_{1-6}$ dialkylamino, —C(O)(C1-C6 alkyl), —C(O)(C1-C6 haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)(C1-C6 alkyl), —OC(O)(C1-C6 haloalkyl), —OC(O)(phenyl), —$S(O)_2$(C1-C6 alkyl), —$S(O)_2$(C1-C6 haloalkyl) and —$S(O)_2$(phenyl), wherein each of the phenyl and the 5-6 membered heteroaryl groups are independently and optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy. Typically, each of the phenyl and the heteroaryl groups represented by R' is independently and optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy, non-aromatic heterocyclic group, $C_{1-6}$ alkylamino, $C_{1-6}$ dialkylamino, —C(O)(C1-C6 alkyl), —C(O)(C1-C6 haloalkyl), —C(O)(phenyl), —C(O)(non-aromatic heterocyclic group), —C(O)O(C1-C6 alkyl), —C(O)O(C1-C6 haloalkyl), —C(O)O(phenyl), —OC(O)(C1-C6 alkyl), —OC(O)(C1-C6 haloalkyl), —OC(O)(phenyl), —$S(O)_2$(C1-C6 alkyl), —$S(O)_2$(C1-C6 haloalkyl), and —$S(O)_2$(phenyl).

Each $Ak^1$ independently is an optionally substituted $C_{1-10}$ aliphatic group. Alternatively, each $Ak^1$ independently is an optionally substituted $C_{1-6}$ alkyl group. Alternatively, each $Ak^1$ independently is an optionally substituted $C_{1-6}$ alkyl group. Typically, each of the aliphatic and alkyl groups represented by $Ak^1$ is independently and optionally substituted with one or more substituents selected from the group consisting of halogen, nitro, cyano, —$N(R^{21})_2$, —$C(O)N(R^{21})_2$, —$C(O)N(R^{21})_2$, $NR^{21}C(O)R^{21}$, —$SO_2R^{22}$, —$SO_2N(R^{21})_2$, —$NR^{21}SO_2R^{22}$, —$NR^{21}X(O)OR^{21}$, —$OC(O)N(R^{21})_2$, —$NR^{21}C(O)N(R^{21})_2$, —$NRC(O)ON(R)_2$, —$NR^{21}SO_2N(R^{21})_2$, —$OR^{21}$, —$SR^{21}$, $C_{1-10}$ haloalkoxy, —$C(O)R^{21}$, —$C(O)OR^{21}$ and —$OC(O)R^{21}$. In one example, each of the aliphatic and alkyl groups represented by $Ak^1$ is independently and optionally substituted with one or more substituents selected from the group consisting of halogen, hydroxy, amino, cyano, nitro, C1-C3 alkoxy, C1-C3 haloaloxy and phenyl.

Each $Ak^{10}$ independently is an optionally substituted $C_{1-10}$ alkyl group. Alternatively, each $Ak^1$ independently is an optionally substituted $C_{1-6}$ alkyl group. Typically, the alkyl group represented by $Ak^{10}$ is optionally substituted with one or more substituents selected from the group consisting of halogen, nitro, cyano, —OH, —SH, —O($C_{1-6}$ alkyl), —S($C_{1-6}$ alkyl), $C_{1-6}$ haloalkyl, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl. In one example, the alkyl group represented by $Ak^{10}$ is optionally substituted with one or more substituents selected from the group consisting of halogen, hydroxy, amino, cyano, nitro, C1-C3 alkoxy, C1-C3 haloaloxy and phenyl.

Each $Ar^1$ independently is an optionally substituted $C_{6-14}$ aryl group or an optionally substituted 5-14 membered heteroaryl group. Alternatively, each $Ar^1$ independently is an optionally substituted phenyl group or an optionally substituted 5-6 membered heteroaryl group. Typically, suitable substituents for each of the aryl and heteroaryl groups represented by $Ar^1$ independently include halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, —$NR^{21}_2$, —$C(O)NR^{21}_2$, —$C(O)NR^{21}_2$, —$NR^{21}C(O)R^{21}$, —$S(O)_2R^{22}$, —$SO_2NR^{21}_2$, —$NR^{21}SO_2R^{22}$, —$NR^{21}C(O)NR^{22}_2$, —$NR^{21}SO_2NR^{21}_2$, —$OR^{21}$, —$SR^{21}$, $C_{1-6}$ haloalkoxy, —$C(O)R^{21}$, —$C(O)OR^{21}$, —$OC(O)R^{21}$ and benzyl. Additional suitable substituents include a phenyl group and a 5-6 membered heteroaryl group, each of which is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy. In one example, each of the phenyl and heteroaryl groups represented by $Ar^1$ is independently and optionally substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, —$NR^{21}_2$, —$C(O)NR^{21}_2$, —$C(O)NR^{21}_2$, —$NR^{21}C(O)R^{21}$, —$S(O)_2R^{22}$, —$SO_2NR^{21}_2$, —$NR^{21}SO_2R^{22}$, —$NR^{21}C(O)NR^{22}_2$, —$NR^{21}SO_2NR^{21}_2$, —$OR^{21}$, —$SR^{21}$, $C_{1-6}$ haloalkoxy, —$C(O)R^{21}$, —$C(O)OR^{21}$, —$OC(O)R^{21}$, phenyl, benzyl and 5-6 membered heteroaryl. In another example, each of the phenyl and heteroaryl groups represented by $Ar^1$ is independently and optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl. In yet another example, each of the phenyl and heteroaryl groups represented by $Ar^1$ is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloaloxy.

Each $Ar^{10}$ independently is an optionally substituted $C_{6-14}$ aryl group or an optionally substituted 5-14 membered heteroaryl group. Alternatively, each $Ar^{10}$ independently is an optionally substituted phenyl group or an optionally substituted 5-6 membered heteroaryl group. Typically, suitable substituents for each of the aryl and heteroaryl groups represented by $Ar^{10}$ include halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl, ($C_{1-10}$ alkylamino)$C_{1-10}$ alkyl, ($C_{1-10}$ dialkylamino)$C_{1-10}$ alkyl, (phenyl) $C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl. In one example, each of the phenyl and heteroaryl groups represented by $Ar^{10}$ is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloalkoxy.

Each p independently is 1, 2 or 3.

Each q independently is 2, 3, 4 or 5.

Examples of the heteroaryl groups, including 5-14 membered heteroaryl groups or 5-6 membered heteroaryl groups, referred to in the definitions of the variables for Structural Formula (A) are as described later. Typical examples of the 5-6 membered heteroaryl groups referred to in the definitions of variables for Structural Formula (A) include a furanyl group, an imidazolyl group, an isoxazolyl group, an oxadiazolyl group, an oxazolyl, a pyrazolyl group, a pyrrolyl group, a pyridyl group, a pyrimidinyl group, a pyridazinyl group, a thiazolyl group, a triazolyl group, a tetrazolyl group, a thienyl group, a pyrimidinyl group, a pyridinyl group or a pyridazinyl group. Typical 5-14 membered heteroaryl groups referred to in the definitions of variables for Structural Formula (A) include an indolyl group, a quinolinyl group, a furanyl group, an imidazolyl group, an isoxazolyl group, an oxadiazolyl group, an oxazolyl, a pyrazolyl group, a pyrrolyl group, a pyridyl group, a pyrimidinyl group, a pyridazinyl group, a thiazolyl group, a triazolyl group, a tetrazolyl group, a thienyl group, a pyrimidinyl group, a pyridinyl group or a pyridazinyl group.

In one embodiment, the compound of the present invention is represented by Structural Formula (B), (C), (D), (E), (F), (G), (H), (I'), (J) or (K):

(B)

(C)

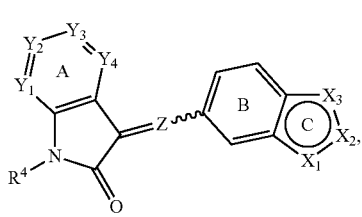

(D)

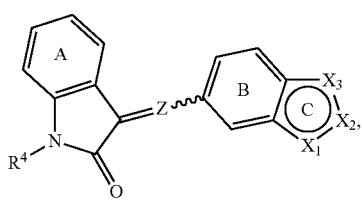

(E)

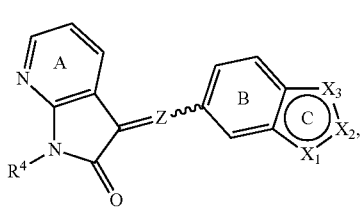

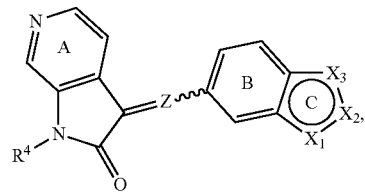

(F)

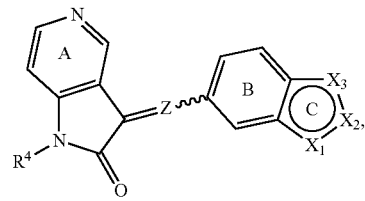

(G)

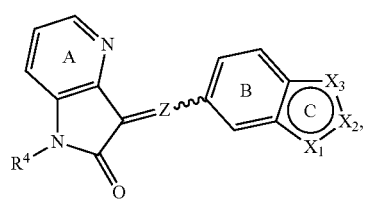

(H)

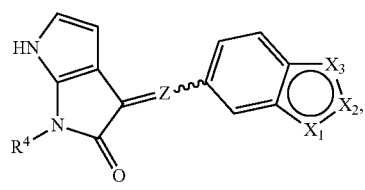

(I')

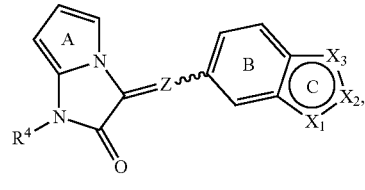

(J)

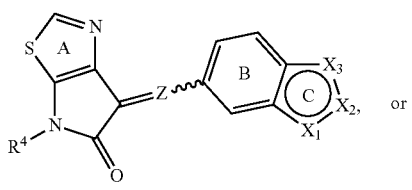 or (K)

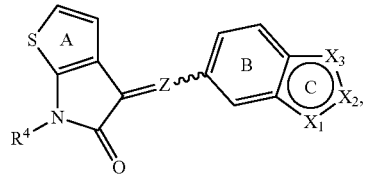

or a pharmaceutically acceptable salt thereof.

Each of $Y_1$, $Y_2$, $Y_3$ and $Y_4$ in Structural Formula (B) is independently —N or —CH.

Ring A and ring B of Structural Formulas (B)-(K) are optionally substituted. Values and specific values for the remainder of the variables are as described above for Structural Formula (A).

In a first embodiment, the compound of the present invention is represented by Structural Formula (I):

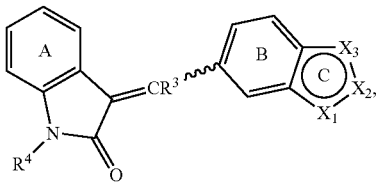

or a pharmaceutically acceptable salt thereof. Value and specific values are as described above for Structural Formula (A). In a more specific embodiment, $R^3$ is —H, halogen, C1-C6 alkyl or C1-C6 haloalkyl, provided when $R^3$ is halogen, then then

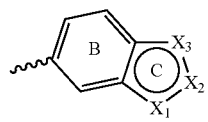

is not

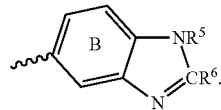

In another more specific embodiment, $R^3$ is H, C1-C6 alkyl or C1-C6 haloalky.

In a second embodiment, the compound of the present invention is represented by Structural Formula (I), wherein a first set of values for the variables of Structural Formula (I) is provided in the following paragraphs:

$R^3$ is —H, C1-C6 alkyl or C1-C6 haloalkyl.

each R' independently is $C_{1-10}$ aliphatic, phenyl or 5-6 membered heteroaryl, wherein said aliphatic is optionally substituted with one or more substituents selected from the group consisting of halogen, hydroxy, nitro, cyano, amino, phenyl, 5-6 membered heteroaryl, C1-C6 alkoxy, C1-C6 haloalkoxy, and wherein each of the phenyl and heteroaryl groups represented by R', and the phenyl and heteroaryl groups in the substituents for the aliphatic group represented by R' independently is optionally substituted with one or more substituents selected from the group consisting of halogen, hydroxy, nitro, cyano, amino, C1-C6 alkyl, C1-C6 haloalkyl, C1-C6 alkoxy, C1-C6 haloalkoxy.

Values and specific values for the remainder of the variables are as described above for Structural Formula (A).

A second set of values for the variables in Structural Formula (I) is provided in the following paragraphs:

X is —C(O)—, —C(S)—, —C(O)N($R^2$—, —OC(O)N ($R^2$)—, —SO$_2$N$R^2$—, —O—, —S—, —N$R^2$—, —N$R^2$C (O)—, —N$R^2$C(O)O—, —N$R^2$C(O)ON$R^2$—, —N($R^2$)C(O) N$R^2$—, —N$R^2$SO$_2$N$R^2$— or —N$R^2$SO$_2$—.

Each $R^1$ independently is i) hydrogen; ii) an optionally substituted phenyl group or an optionally substituted 5-6 membered heteroaryl group; or iii) an optionally substituted $C_{1-10}$ alkyl group. Suitable substitutents for each of the alkyl, phenyl and heteroaryl groups represented by $R^1$ independently are as described above for the first set of values.

Each $Ak^1$ independently is an optionally substituted $C_{1-10}$ alkyl group. Suitable substitutents for the alkyl group represented by Ale are as described above for the first set of values.

Each $Ar^1$ independently is a phenyl group or a 5-6 membered heteroaryl group, each optionally and independently substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, —NR$^{21}$$_2$, —C(O)NR$^{21}$$_2$, —C(O)NR$^{21}$$_2$, —NR$^{21}$C(O)R$^{21}$, —S(O)$_2$R$^{22}$, —SO$_2$NR$^{21}$$_2$, —NR$^{21}$SO$_2$R$^{22}$, —NR$^{21}$C(O) NR$^{22}$$_2$, —NR$^{21}$SO$_2$NR$^{21}$$_2$, —OR$^{21}$, —SR$^{21}$, $C_{1-6}$ haloalkoxy, —C(O)R$^{21}$, —C(O)OR$^{21}$, —OC(O)R$^{21}$, phenyl, benzyl and 5-6 membered heteroaryl.

Values and specific values for the remainder of the variables of Structural Formula (I) are each independently as described above in first set of values of the second embodiment.

A third set of values for the variables in Structural Formula (I) is provided in the following paragraphs Each $Ak^{10}$ independently is an optionally substituted $C_{1-6}$ alkyl group. Suitable substitutents for the alkyl group represented by $Ak^{10}$ are as described above for the first set of values.

Each $Ar^{10}$ independently is a phenyl group or a 5-6 membered heteroaryl group, each optionally and independently substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, $C_{1-6}$ aminoalkyl, ($C_{1-6}$ alkylamino)$C_{1-6}$ alkyl, ($C_{1-6}$ dialkylamino)$C_{1-6}$ alkyl, benzyl, phenyl, $C_{1-6}$ alkoxy, $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl.

Each $R^{10}$ independently is: i) hydrogen; ii) an optionally substituted phenyl group or an optionally substituted 5-6 membered heteroaryl group; or iii) an optionally substituted $C_{1-6}$ alkyl group. Each of the phenyl and heteroaryl groups represented by $R^{10}$ is optionally and independently substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino) $C_{1-6}$ alkyl, ($C_{1-6}$ dialkylamino)$C_{1-6}$ alkyl, amino, $C_{1-6}$ alkylamino, $C_{1-6}$ dialkylamino, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl. The alkyl group represented by $R^{10}$ is optionally substituted with one or more substituents selected from the group consisting halogen, nitro, cyano, hydroxy, $C_{1-6}$ haloalkyl, $C_{1-6}$ alkoxy, $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl, $C_{1-6}$ alkylcarbonyl and phenyl.

Each $R^{11}$ independently is $R^{10}$, —CO$_2$R$^{10}$, —SO$_2$R$^{10}$ or —C(O)R$^{10}$, or —N(R$^{11}$)$_2$ taken together is a 5-6 membered non-aromatic heterocyclic group optionally substituted with halogen, hydroxy, nitro, cyano, =O, C1-C3 alky, C1-C3 haloalkyl, C1-C3 alkoxy, C1-C3 haloalkoxy and amino.

Each $R^{12}$ independently is: i) an optionally substituted phenyl group or an optionally substituted 5-6 membered heteroaryl group; or ii) an optionally substituted $C_{1-6}$ alkyl group. Each of the phenyl and heteroaryl groups represented by $R^{12}$ is optionally and independently substituted with one or more substituents selected from the group consisting of halogen, nitro, cyano, hydroxy, $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, amino, $C_{1-6}$ alkylamino, $C_{1-6}$ dialkylamino, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl. The alkyl group represented by $R^{12}$ is optionally substituted with one or more substituents selected from the group consisting halogen, nitro, cyano, hydroxy, $C_{1-6}$ haloalkyl, $C_{1-6}$ alkoxy, $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl, $C_{1-6}$ alkylcarbonyl and phenyl.

Each $R^{21}$ independently is hydrogen, $C_{1-6}$ alkyl or optionally substituted phenyl. Suitable substitutents for the phenyl group represented by $R^{21}$ are as described above for the first set of values.

Each $R^{22}$ independently is $C_{1-6}$ alkyl or optionally substituted phenyl. Suitable substitutents for the phenyl group represented by $R^{22}$ are as described above for the first set of values.

Values and specific values for X, $R^1$, $Ak^1$ and $Ar^1$ are each independently as described above in the second set of values of the second embodiment.

Values and specific values for the remainder of the variables of Structural Formula (I) are each independently as described above in the first set of values of the second embodiment.

A fourth set of values for the variables in Structural Formula (I) is provided in the following paragraphs:

Each $R^1$ independently is i) hydrogen; ii) an optionally substituted phenyl group or an optionally substituted 5-6 membered heteroaryl group; or iii) an optionally substituted $C_{1-10}$ alkyl group. Each of the phenyl and heteroaryl groups represented by $R^1$ is optionally and independently substituted with one or more substituents selected from the group consisting of halogen, nitro, cyano, $Ak^{10}$, ($C_{1-10}$ alkylene)-$Ar^{10}$, ($C_{2-10}$ alkenylene)-$Ar^{10}$, —$OR^{10}$, —$SR^{10}$, $OC(O)N(R^{11})_2$, —$N(R^{11})_2$, —$C(O)NR^{11}$, —$NR^{11}C(O)N(R^{10}$, —$N(R^{11})C(O)N(R^{11})_2$, —$NR^{11}SO_2N(R^{11})_2$, —$NR^{11}SO_2R^{12}$, —$SO_2N(R^{11})_2$, —$OC(O)R^{10}$, —$C(O)OR^{10}$ and —$C(O)R^{10}$. The alkyl group represented by $R^1$ is optionally substituted with one or more substituents selected from the group consisting of halogen, nitro, cyano, $Ar^{10}$, —$OR^{10}$, —$SR^{10}$, —$N(R^{11})_2$, —$OC(O)R^{10}$, —$C(O)OR^{10}$ and —$C(O)R^{10}$.

Each $Ak^1$ independently is a $C_{1-10}$ alkyl group optionally substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl.

Each $Ar^1$ independently is a phenyl group or a 5-6 membered heteroaryl group, each optionally and independently substituted with one or more substituents selected from the group consisting of halogen, nitro, cyano, —OH, —SH, alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl.

Values and specific values for X, $R^{10}$, $R^{11}$, $R^{12}$, $R^{21}$, $R^{22}$, $Ak^{10}$ and $Ar^{10}$ are each independently as described above in the third set of values of the second embodiment.

Values and specific values for the remainder of the variables of Structural Formula (I) are each independently as described above in the first set of values of the second embodiment.

A fifth set of values for the variables in Structural Formula (I) is provided in the following paragraphs:

Each $R^{10}$ independently is i) hydrogen, ii) a phenyl group or a 5-6 membered heteroaryl group, each of which is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloaloxy, or iii) a $C_{1-10}$ alkyl group optionally substituted with one or more substituents selected from the group consisting of halogen, hydroxy, amino, cyano, nitro, C1-C3 alkoxy, C1-C3 haloaloxy and phenyl.

Each $R^{12}$ independently i) a phenyl group or a 5-6 membered heteroaryl group, each of which is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloaloxy, or ii) a $C_{1-10}$ alkyl group optionally substituted with one or more substituents selected from the group consisting of halogen, hydroxy, amino, cyano, nitro, C1-C3 alkoxy, C1-C3 haloaloxy and phenyl.

Each $Ar^{10}$ independently is a phenyl group or a 5-6 membered heteroaryl group, each of which is independently and optionally substituted with one or more substituents selected from the group consisting of halogen, hydroxy, amino, cyano, nitro, C1-C3 alkyl, C1-C3 haloalkyl, C1-C3 alkoxy and C1-C3 haloaloxy.

Values and specific values for X, $R^1$, $R^{11}$, $R^{21}$, $R^{22}$, $Ak^1$, $Ak^{10}$ and $Ar^1$ are each independently as described above in the fourth set of values of the second embodiment.

Values and specific values for the remainder of the variables of Structural Formula (I) are each independently as described above in the first set of values of the second embodiment.

In a third embodiment, the compound of the invention is represented by Structural Formula (II) or a pharmaceutically acceptable salt thereof:

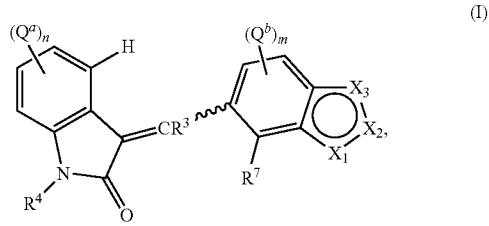

(I)

wherein values and specific values for the variables of Structural Formula (II) are provided in the following paragraphs:

Each of n and m is independently 0, 1 or 2.

Each $R^2$ is —H or C1-C6 alkyl.

Each of $R^4$ and $R^5$ is independently —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each said phenyl in the groups represented by $R^4$ and $R^5$ independently is optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy, and wherein each said alkyl in the groups represented by $R^4$ and $R^5$ independently is optionally substituted with one or more substituents selected from the group consisting of halogen, hydroxy, nitro, cyano, amino, C1-C6 alkoxy, C1-C6 haloalkoxy and phenyl.

$R^7$ is —H, F, Cl or methyl.

Values and specific values for the remainder of the variables of Structural Formula (II) are each independently as described above in the second embodiment for the variables of Structural Formula (I).

Alternatively, each of n and m is independently 0, 1 or 2; and values and specific values for the remaining variables of Structural Formula (II) are each independently as described in the first set, the second set, the third set, the fourth set or the fifth set of values for the variables of Structural Formula (I) in the second specific embodiment.

In a fourth embodiment, the compound of the invention is represented by Structural Formula (III), (IV), (V), (VI) or (VII), or a pharmaceutically acceptable salt thereof:

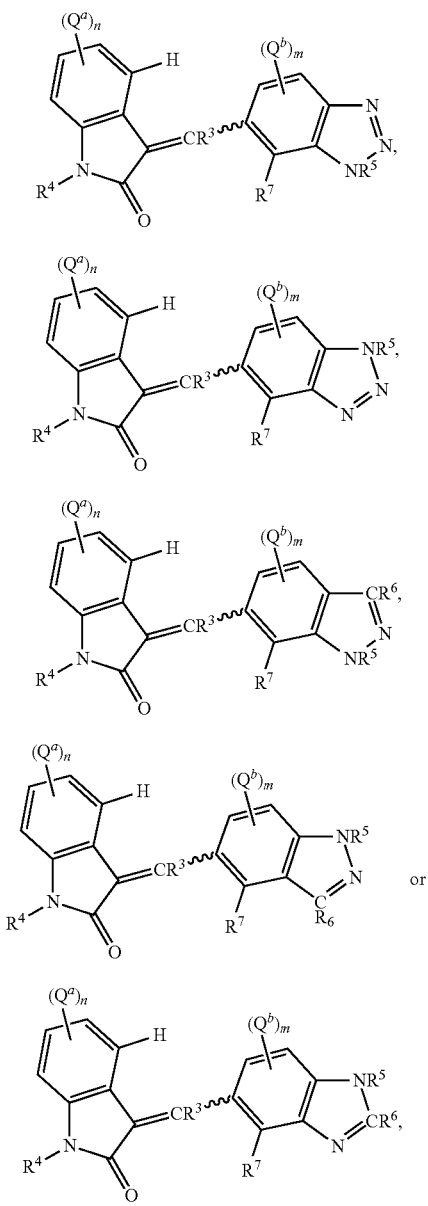

wherein a first set of values and specific values for the variables of Structural Formulas (III)-(VII) is provided in the following paragraphs:

One of $Q^a$ and $Q^b$ is halogen, —$NO_2$, —CN, $Ak^1$, $Ar^1$, ($C_{1-10}$ alkylene)-$Ar^1$, ($C_{2-10}$ alkenylene)-$Ar^1$ or —X—$R^1$; and the other of $Q^a$ and $Q^b$ is halogen, hydroxy, nitro, cyano, amino, methyl, methoxy, halomethyl or halomethoxy.

Each of n and m independently is 0, 1 or 2.

Each $R^2$ is —H or C1-C6 alkyl.

$R^3$ is —H, halogen, C1-C6 alkyl or C1-C6 haloalkyl.

Each of $R^4$ and $R^5$ independently is —H, C1-C6 alkyl, phenyl, —C(O)(C1-C6 alkyl), —C(O)(phenyl), —C(O)O (C1-C6 alkyl), —C(O)O(phenyl), —S(O)$_2$(C1-C6 alkyl) or —S(O)$_2$(phenyl), wherein each said phenyl in the groups represented by $R^4$ and $R^5$ independently is optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy, and wherein each said alkyl in the groups represented by $R^4$ and $R^5$ independently is optionally substituted with one or more substituents selected from the group consisting of halogen, hydroxy, nitro, cyano, amino, C1-C6 alkoxy, C1-C6 haloalkoxy and phenyl.

$R^6$ is hydrogen, halogen, nitro, cyano, R', —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOR', —SO$_2$R', —SO$_3$R', —SO$_2$N(R)$_2$, —NRS(O)R', —NRSO$_2$R', —NRC(O)N(R)$_2$, —NRC(O)ON(R)$_2$ or —NRSO$_2$N(R)$_2$. Alternatively, each $R^6$ is hydrogen, halogen, nitro, cyano, R', —OR, —SR or —N(R)$_2$; and each R independently is hydrogen, optionally substituted $C_{1-6}$ alkyl, optionally substituted $C_{2-6}$ alkenyl, optionally substituted phenyl or optionally substituted 5-6 membered heteroaryl, or N(R)$_2$ taken together is a non-aromatic heterocyclic group optionally substituted with one or more substituents selected from the group consisting of halogen, hydroxy, nitro, cyano, =O, C1-C3 alky, C1-C3 haloalkyl, C1-C3 alkoxy, C1-C3 haloalkoxy and amino; and each R' independently is optionally substituted $C_{1-6}$ alkyl, optionally substituted $C_{2-6}$ alkenyl, optionally substituted phenyl or optionally substituted 5-6 membered heteroaryl.

Each $R^7$ independently is —H, F, Cl or methyl.

Values and specific values for the remainder of the variables of Structural Formulas (III)-(VII) are each independently as described above in the first set of values for the variables of Structural Formula (I).

A second set of values and specific values for the variables of Structural Formulas (III)-(VII) is provided in the following paragraphs:

Each of $R^4$ and $R^5$ independently is —H, C1-C6 alkyl, phenyl, —C(O)(C1-C6 alkyl), —C(O)(phenyl), —C(O)O (C1-C6 alkyl), —C(O)O(phenyl), —S(O)$_2$(C1-C6 alkyl) or —S(O)$_2$(phenyl).

Values and specific values for n, m, $Q^a$ and $Q^b$, $R^2$, $R^6$ and $R^7$ are each independently as described above in the first set of values for Structural Formulas (III)-(VII).

Values and specific values for the remainder of the variables of Structural Formulas (III)-(VII) are each independently as described above in the first set of values for the variables of Structural Formula (I).

A third set of values and specific values for the variables of Structural Formulas (III)-(VII) is provided in the following paragraphs:

Both of $Q^a$ and $Q^b$ are independently halogen, hydroxy, nitro, cyano, amino, methyl, methoxy, halomethyl or halomethoxy.

Values and specific values for n, m, $R^2$, $R^2$, $R^4$, $R^5$, $R^6$ and $R^7$ are each independently as described above in the second set of values for Structural Formulas (III)-(VII).

Values and specific values for the remainder of the variables of Structural Formulas (III)-(VII) are each independently as described above in the first set of values for the variables of Structural Formula (I).

A fourth set of values and specific values for the variables of Structural Formulas (III)-(VII) is provided in the following paragraphs:

One of $Q^a$ and $Q^b$ is halogen, hydroxy, cyano, nitro, C1-C6 alkyl, C1-C6 haloalkyl, —C(O)(C1-C6 alkyl), —C(O)NH$_2$, —C(O)NH(C1-C6 alkyl), —C(O)N(C1-C6 alkyl)$_2$, —SO$_2$NH$_2$, —SO$_2$NH(C1-C6 alkyl), —SO$_2$N(C1-C6 alkyl)$_2$, —OH, —O(C1-C6 alkyl), —O(C1-C6 haloalkyl), —SH, —S(C1-C6 alkyl), —S(C1-C6 haloalkyl), —NH$_2$, —NH(C1-C6 alkyl), —N(C1-C6 alkyl)$_2$, —NHC(O)(C1-C6 alkyl), —NHC(O)O(C1-C6 alkyl), —NHC(O)NH$_2$, —NHC(O)NH(C1-C6 alkyl), —NHC(O)N(C1-C6 alkyl)$_2$, —NHC(O)ONH$_2$, —NHC(O)ONH(C1-C6 alkyl), —NHC(O)ON(C1-C6 alkyl)$_2$, —NHSO$_2$NH$_2$, —NHSO$_2$NH(C1-C6 alkyl), —NHSO$_2$N(C1-C6 alkyl)$_2$ or —NHSO$_2$(C1-C6 alkyl); and the other of V and V is halogen, hydroxy, nitro, cyano, amino, methyl, methoxy, halomethyl or halomethoxy.

Alternatively, one of $Q^a$ and $Q^b$ is halogen, hydroxy, cyano, nitro, Ph, —CH$_2$Ph, —C(O)Ph, —C(O)NH(Ph), —C(O)N(C1-C6 alkyl)(Ph), —SO$_2$NH(Ph), —SO$_2$N(C1-C6 alkyl)(Ph), —O(Ph), —S(Ph), —NH(Ph), —N(C1-C6 alkyl)(Ph), —NHC(O)(Ph), —NHC(O)O(Ph), —NHC(O)NH(Ph), —NHC(O)N(C1-C6 alkyl)(Ph), —NHC(O)ONH(Ph), —NHC(O)ON(C1-C6 alkyl)(Ph), —NHSO$_2$NH(Ph), —NHSO$_2$N(C1-C6 alkyl)(Ph) or —NHSO$_2$(Ph), wherein each Ph independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy; and the other of V and $Q^b$ is halogen, hydroxy, nitro, cyano, amino, methyl, methoxy, halomethyl or halomethoxy.

Values and specific values for the remainder of the variables of Structural Formulas (III)-(VII) are each independently as described above in the first set of values for the variables of Structural Formula (I) in second embodiment.

In a fifth set, each of n and m independently is 0, 1 or 2; and values and specific values for the remaining variables of each Structural Formula (III)-(VII) are independently as described in the first set, the second set, the third set, the fourth set or the fifth set of values for the variables of Structural Formula (I) in the second embodiment.

In a sixth set, values and specific values for the remaining variables of each Structural Formula (III)-(VII) are independently as described in the first set of values for the variables of Structural Formula (II) in the third embodiment.

In a fifth embodiment, the compound of the invention is represented by a structural formula selected from Structural Formulas (VIII)-(XXXV) or a pharmaceutically acceptable salt thereof:

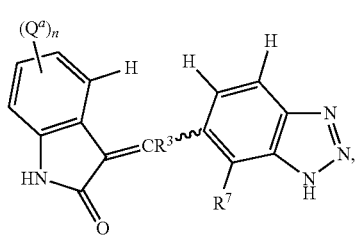
(VIII)

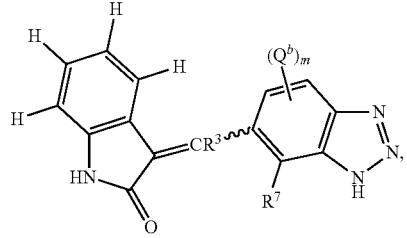
(IX)

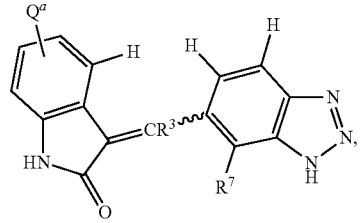
(X)

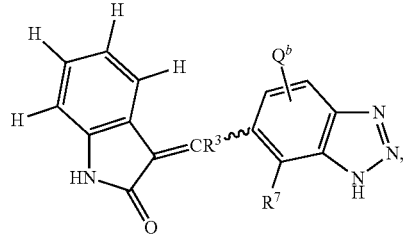
(XI)

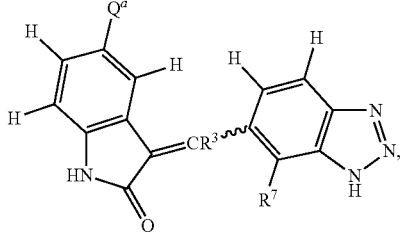
(XII)

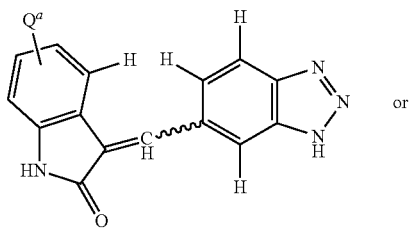
(XIII)
or

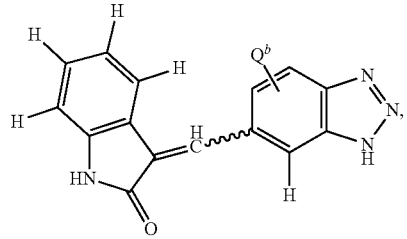
(XIV)

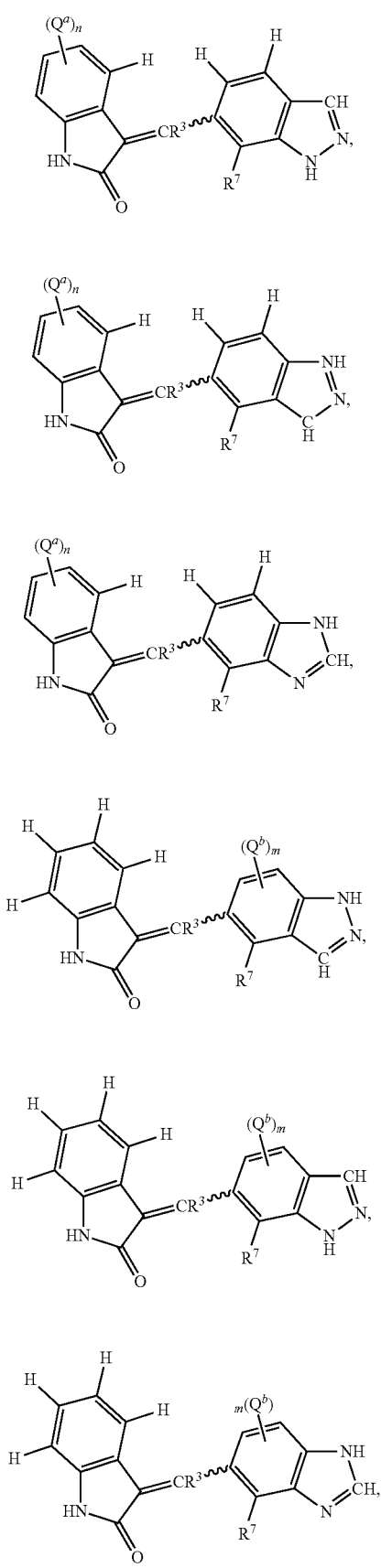
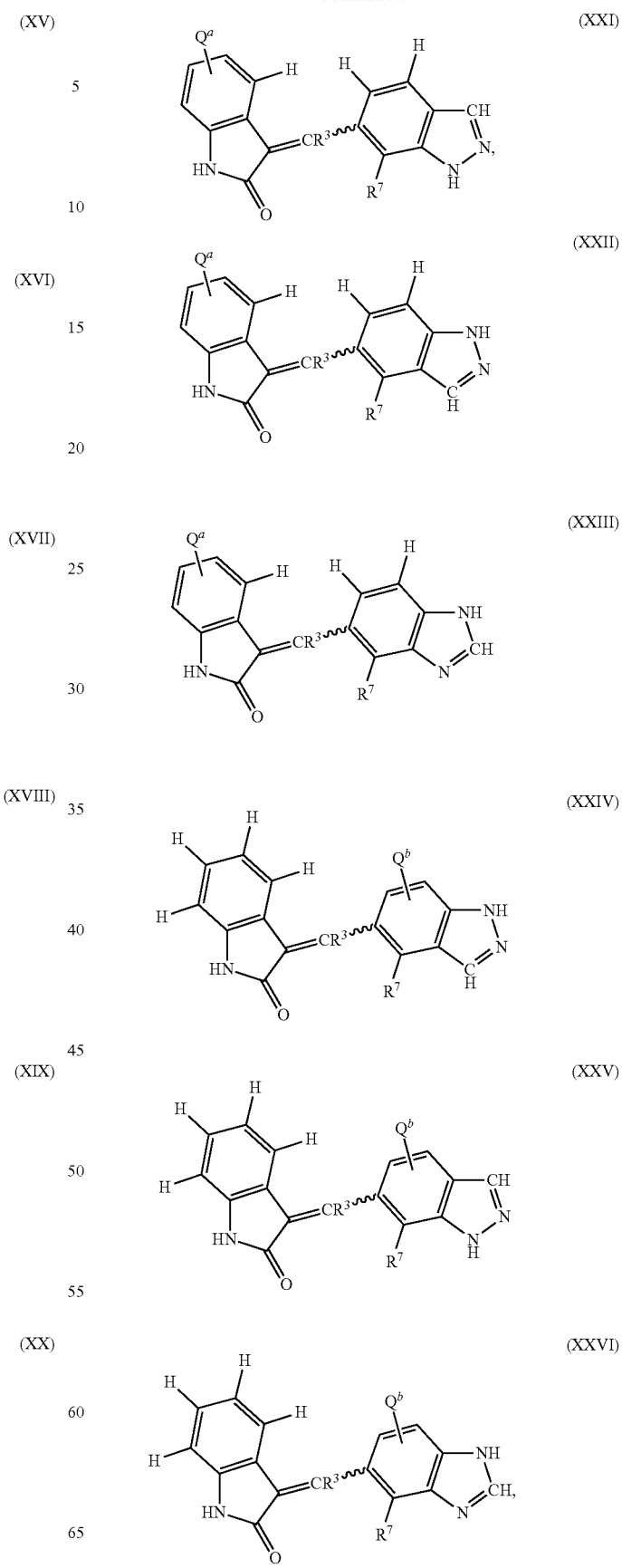

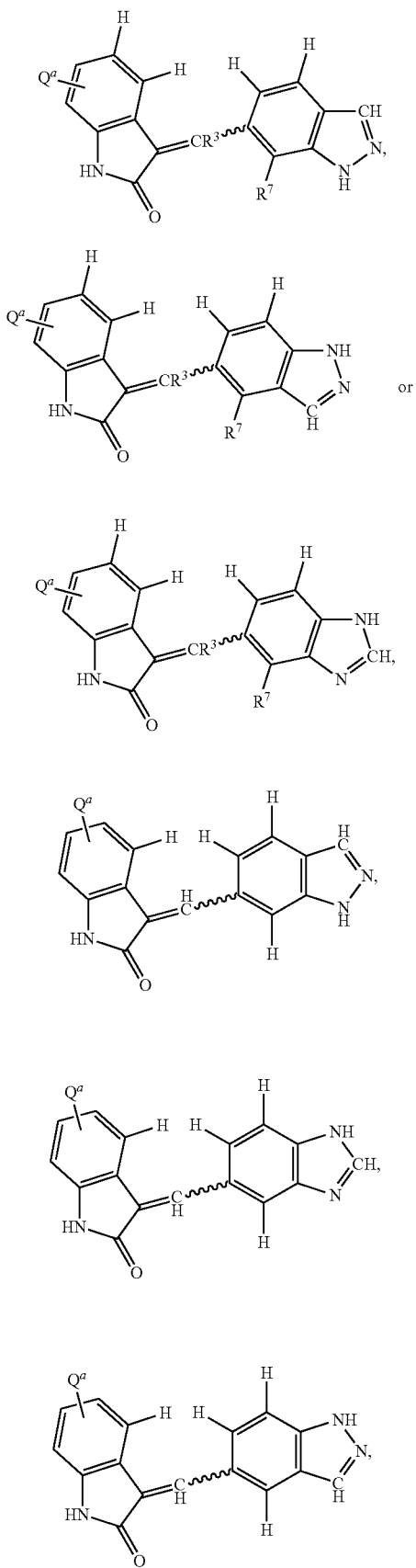

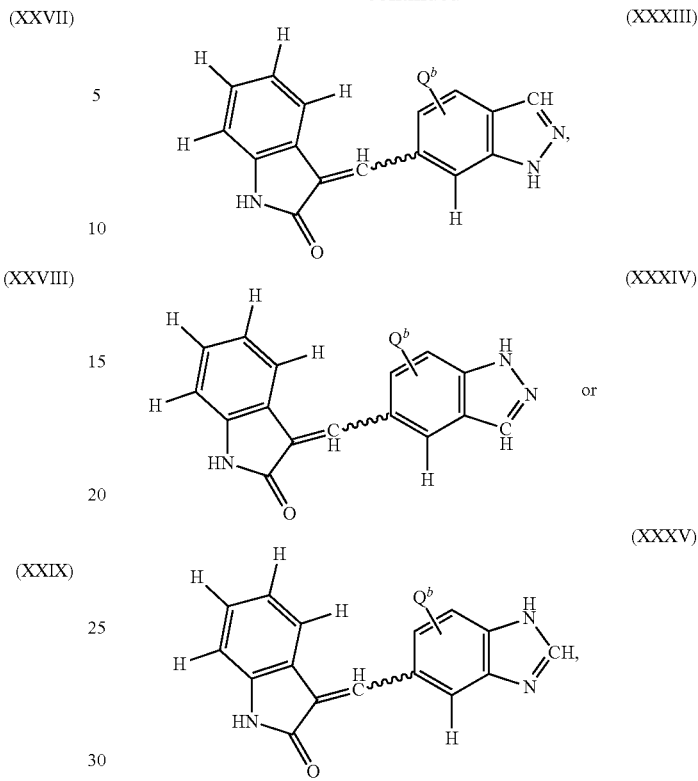

wherein a first set of values and preferred values for the variables of Structural Formulas (VIII)-(XXXV) is provided in the following paragraphs:

Each $Q^1$ in Structural Formulas (VIII), (X), (XII), (XIII), (XV), (XVI), (XVII), (XXI), (XXII), (XXIII), (XXVII), (XXVIII), (XXIX), (XXX), (XXXI) and (XXXII) independently is halogen, —$NO_2$, —CN, $Ak^1$, $Ar^1$, ($C_{1-10}$ alkylene)-$Ar^1$, ($C_{2-10}$ alkenylene)-$Ar^1$ or —X—$R^1$. Each $Q^b$ in Structural Formulas (IX), (XI), (XIV), (XVIII), (XIX), (XX), (XXIV), (XXV), (XXVI), (XXXIII), (XXXIV) and (XXXV) independently is halogen, —$NO_2$, —CN, $Ak^1$, $Ar^1$, ($C_{1-10}$ alkylene)-$Ar^1$, ($C_{2-10}$ alkenylene)-$Ar^1$ or —X—$R^1$.

Each of n and m in Structural Formulas (VIII), (IX), (XV), (XVI), (XVII), (XVIII), (XIX) and (XX) independently is 0, 1 or 2.

Each $R^2$ is —H or C1-C6 alkyl.

$R^3$ is —H, halogen, C1-C6 alkyl or C1-C6 haloalkyl.

Each $R^7$ in Structural Formulas (VIII)-(XII) and (XV)-(XXIX) independently is —H, F, Cl or methyl.

Values and specific values for the remainder of the variables of Structural Formulas (VIII)-(XXXV) are each independently as described above in the first set of values for the variables of Structural Formula (I).

A second set of values and specific values for the variables of Structural Formulas (VIII)-(XXXV) is provided in the following paragraphs:

Each V in Structural Formulas (VIII), (X), (XII), (XIII), (XV), (XVI), (XVII), (XXI), (XXII), (XXIII), (XXVII), (XXVIII), (XXIX), (XXX), (XXXI) and (XXXII) independently is halogen, hydroxy, cyano, nitro, C1-C6 alkyl, C1-C6 haloalkyl, —C(O)(C1-C6 alkyl), —C(O)$NH_2$, —C(O)NH (C1-C6 alkyl), —C(O)N(C1-C6 alkyl)$_2$, —$SO_2NH_2$, —$SO_2$NH(C1-C6 alkyl), —$SO_2$N(C1-C6 alkyl)$_2$, —OH, —O(C1-C6 alkyl), —O(C1-C6 haloalkyl), —SH, —S(C1-C6 alkyl), —S(C1-C6 haloalkyl), —$NH_2$, —NH(C1-C6 alkyl), —N(C1-C6 alkyl)$_2$, —NHC(O)(C1-C6 alkyl), —NHC(O)O(C1-C6 alkyl), —NHC(O)NH$_2$, —NHC(O)NH(C1-C6 alkyl), —NHC(O)N(C1-C6 alkyl)$_2$, —NHC(O)ONH$_2$, —NHC(O)ONH(C1-C6 alkyl), —NHC(O)ON(C1-C6 alkyl)$_2$, —NHSO$_2$NH$_2$, —NHSO$_2$NH(C1-C6 alkyl), —NHSO$_2$N(C1-C6 alkyl)$_2$ or —NHSO$_2$(C1-C6 alkyl). Alternatively, each $Q^a$ in Structural Formulas (VIII), (X), (XII), (XIII), (XV), (XVI), (XVII), (XXI), (XXII), (XXIII), (XXVII), (XXVIII), (XXIX), (XXX), (XXXI) and (XXXII) independently is halogen, hydroxy, cyano, nitro, Ph, —CH$_2$Ph, —C(O)Ph, —C(O)NH(Ph), —C(O)N(C1-C6 alkyl)(Ph), —SO$_2$NH(Ph), —SO$_2$N(C1-C6 alkyl)(Ph), —O(Ph), —S(Ph), —NH(Ph), —N(C1-C6 alkyl)(Ph), —NHC(O)(Ph), —NHC(O)O(Ph), —NHC(O)NH(Ph), —NHC(O)N(C1-C6 alkyl)(Ph), —NHC(O)ONH(Ph), —NHC(O)ON(C1-C6 alkyl)(Ph), —NHSO$_2$NH(Ph), —NHSO$_2$N(C1-C6 alkyl)(Ph) or —NHSO$_2$(Ph), wherein each Ph is a phenyl group independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy.

Each $Q^b$ in Structural Formulas (IX), (XI), (XIV), (XVIII), (XIX), (XX), (XXIV), (XXV), (XXVI), (XXXIII), (XXXIV) and (XXXV) independently is halogen, hydroxy, cyano, nitro, C1-C6 alkyl, C1-C6 haloalkyl, —C(O)(C1-C6 alkyl), —C(O)NH$_2$, —C(O)NH(C1-C6 alkyl), —C(O)N(C1-C6 alkyl)$_2$, —SO$_2$NH$_2$, —SO$_2$NH(C1-C6 alkyl), —SO$_2$N(C1-C6 alkyl)$_2$, —OH, —O(C1-C6 alkyl), —O(C1-C6 haloalkyl), —SH, —S(C1-C6 alkyl), —S(C1-C6 haloalkyl), —NH$_2$, —NH(C1-C6 alkyl), —N(C1-C6 alkyl)$_2$, —NHC(O)O(C1-C6 alkyl), —NHC(O)O(C1-C6 alkyl), —NHC(O)NH$_2$, —NHC(O)NH(C1-C6 alkyl), —NHC(O)N(C1-C6 alkyl)$_2$, —NHC(O)ONH$_2$, —NHC(O)ONH(C1-C6 alkyl), —NHC(O)ON(C1-C6 alkyl)$_2$, —NHSO$_2$NH$_2$, —NHSO$_2$NH(C1-C6 alkyl), —NHSO$_2$N(C1-C6 alkyl)$_2$ or —NHSO$_2$(C1-C6 alkyl). Alternatively, each $Q^b$ in Structural Formulas (IX), (XI), (XIV), (XVIII), (XIX), (XX), (XXIV), (XXV), (XXVI), (XXXIII), (XXXIV) and (XXXV) independently is halogen, hydroxy, cyano, nitro, Ph, —CH$_2$Ph, —C(O)Ph, —C(O)NH(Ph), —C(O)N(C1-C6 alkyl)(Ph), —SO$_2$NH(Ph), —SO$_2$N(C1-C6 alkyl)(Ph), —O(Ph), —S(Ph), —NH(Ph), —N(C1-C6 alkyl)(Ph), —NHC(O)(Ph), —NHC(O)O(Ph), —NHC(O)NH(Ph), —NHC(O)N(C1-C6 alkyl)(Ph), —NHC(O)ONH(Ph), —NHC(O)ON(C1-C6 alkyl)(Ph), —NHSO$_2$NH(Ph), —NHSO$_2$N(C1-C6 alkyl)(Ph) or —NHSO$_2$(Ph), wherein each Ph is a phenyl group independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy.

Values and specific values for $R^3$, $R^7$, n and m are each independently as described above in the first set of values for the variables of Structural Formulas (VIII)-(XXXV).

In a third set, each of n and m independently is 0, 1 or 2; and values and preferred values of the remaining variables of Structural Formulas (VIII)-(XXXV) are each independently as described above for the first set, second set, third set, fourth set or the fifth set of values for the variables of Structural Formula (I) of the second embodiment.

In a fourth set, values and specific values for the remaining variables of each Structural Formulas (VIII)-(XXXV) are each independently as described in the first set of values for the variables of Structural Formula (II).

In a sixth embodiment, the compound of the present invention is represented by Structural Formula (Ia), (Ib), (Ic), (Id), (Ie), (If), (Ig), (Ih), (Ii), (Ij), (Ik), (Il), (C1)-(C4), (D1)-(D8), (E1)-(E8), (F1)-(F8), (G1)-(G8), (H1)-(H8), (I'1)-(I'8), (J1)-(J8), (K1)-(K8):

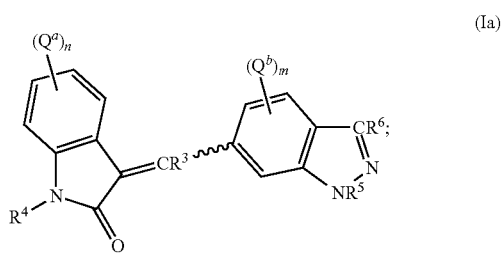

(Ia)

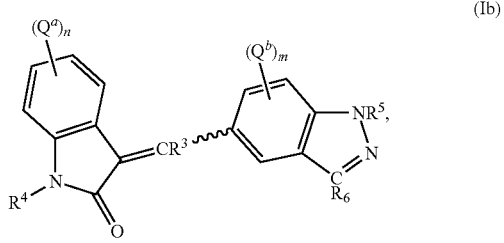

(Ib)

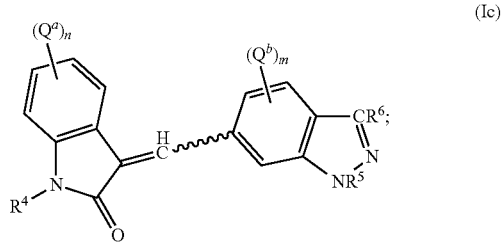

(Ic)

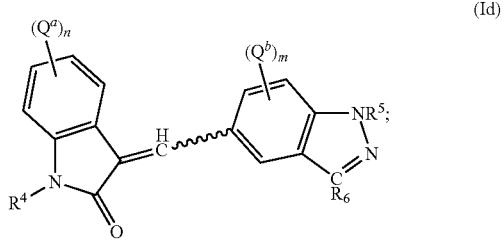

(Id)

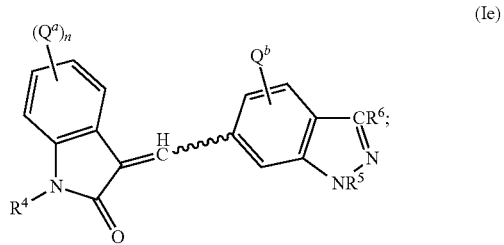

(Ie)

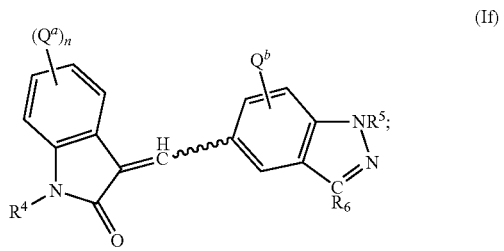

(If)

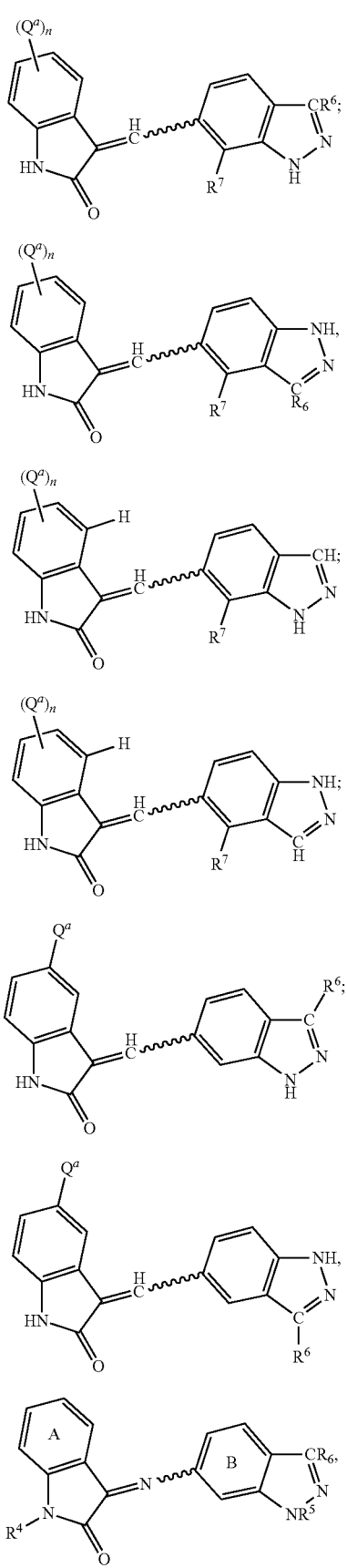
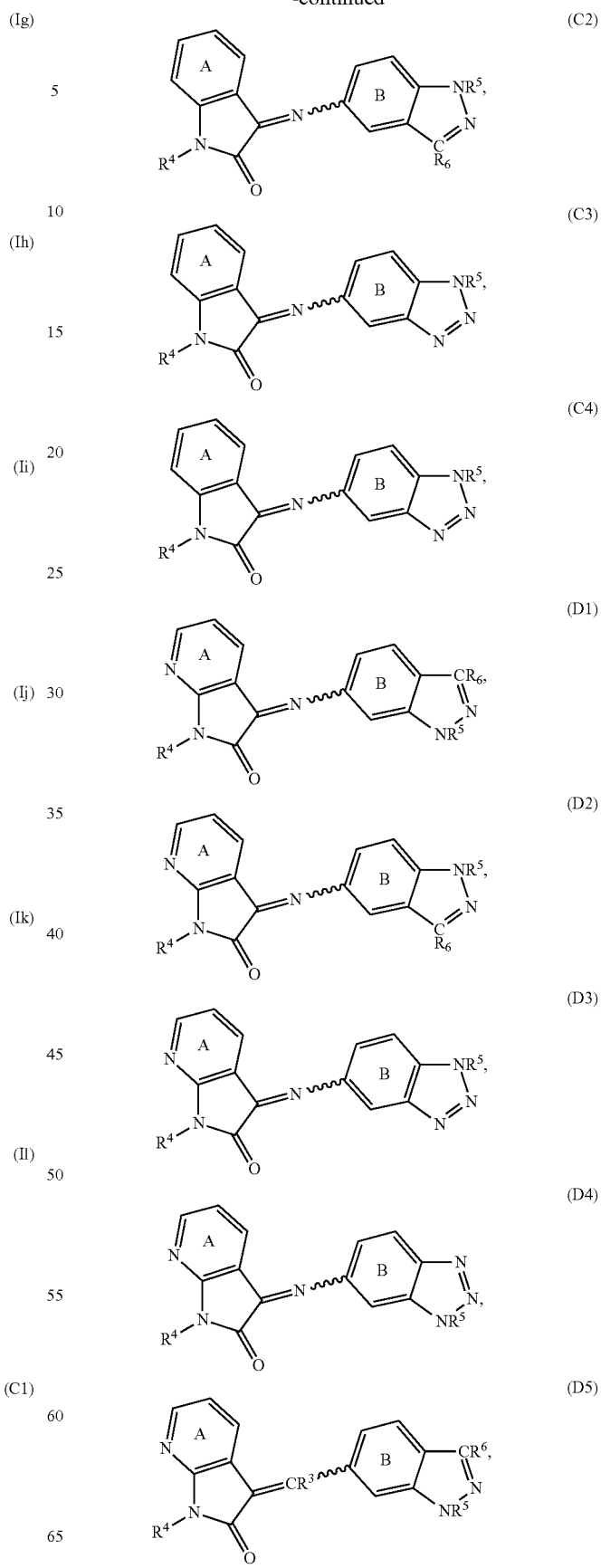

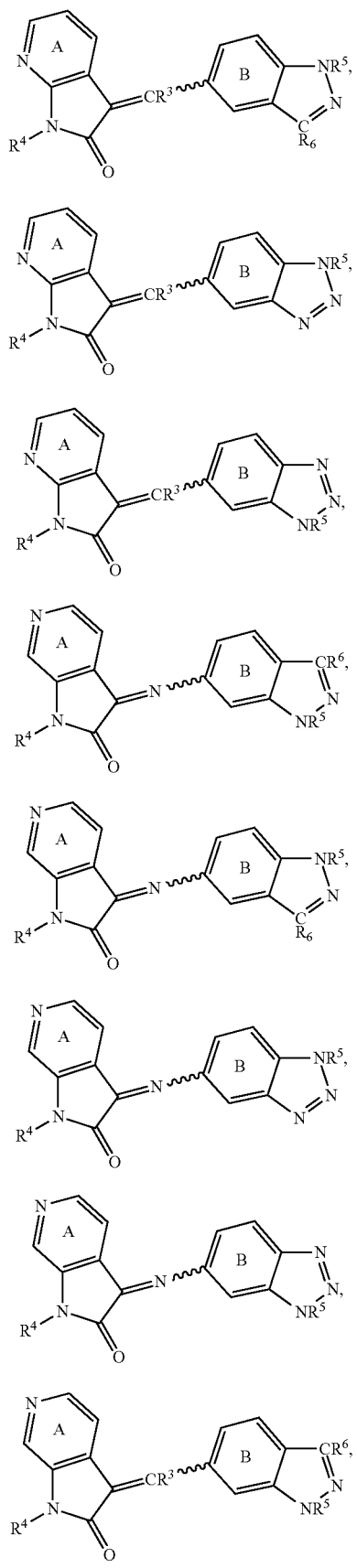
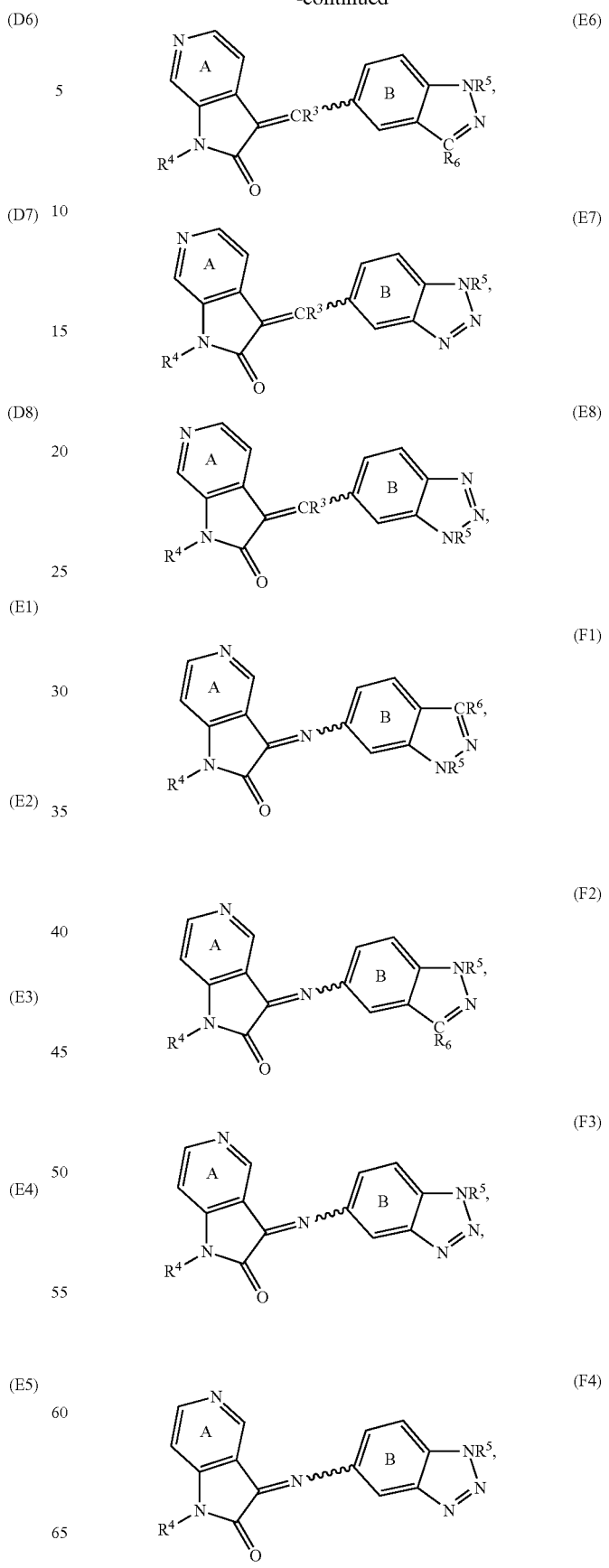

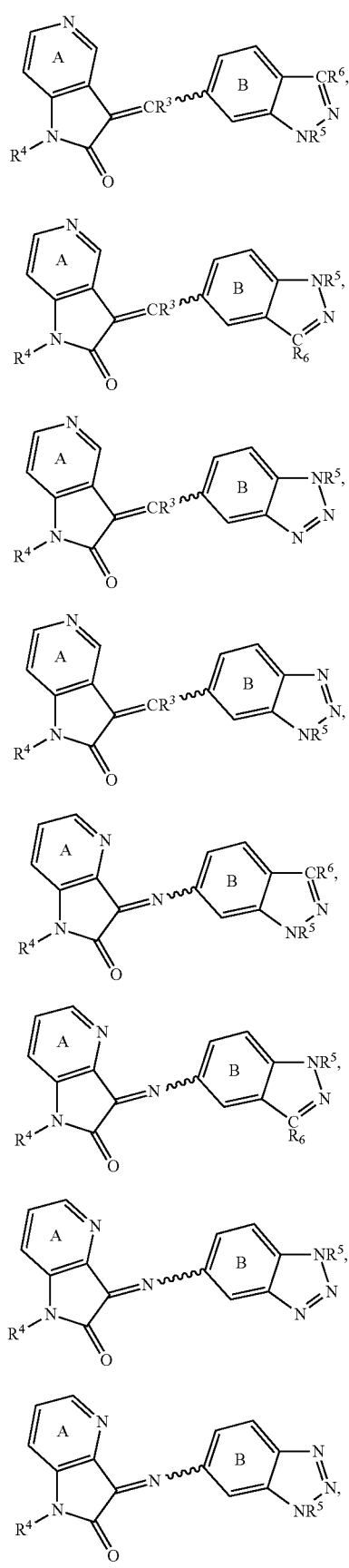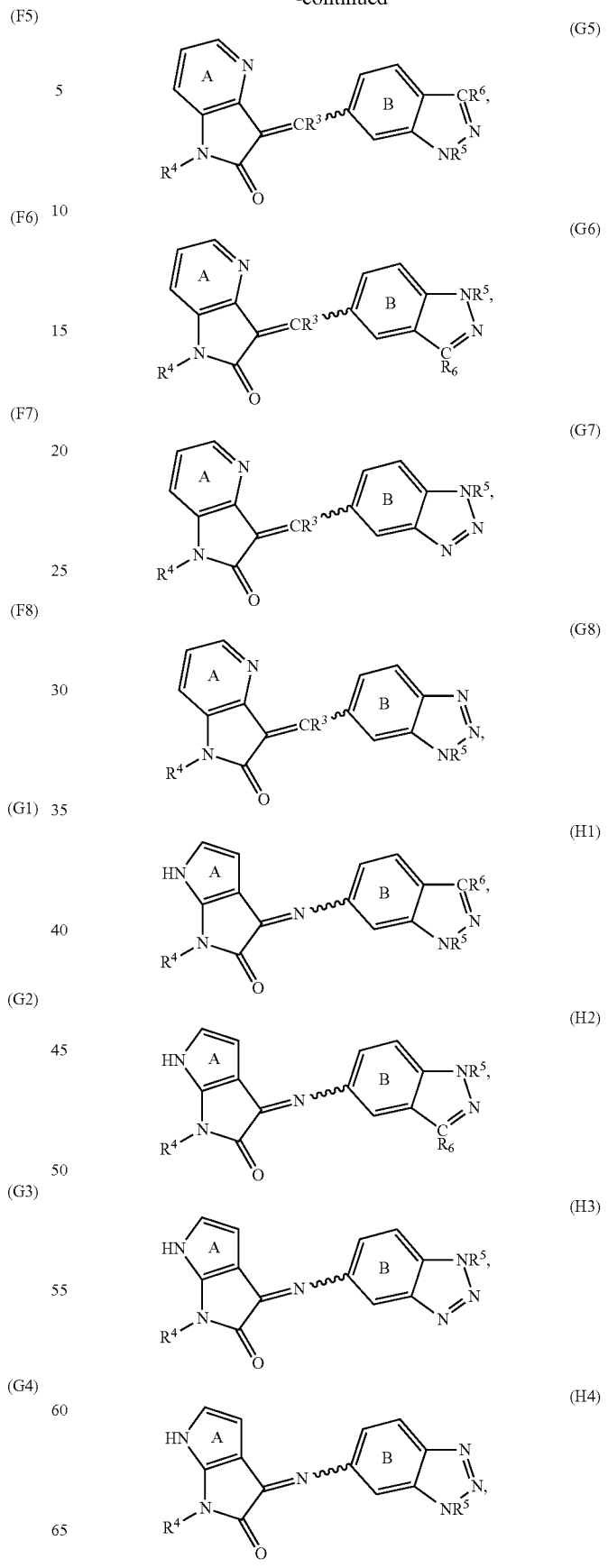

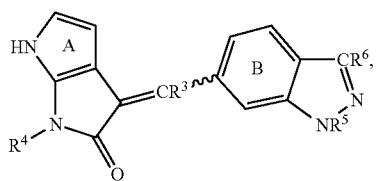 (H5)
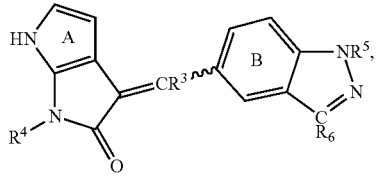 (H6)
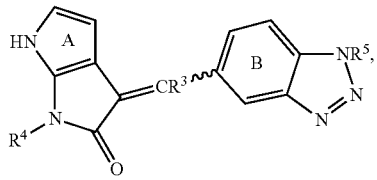 (H7)
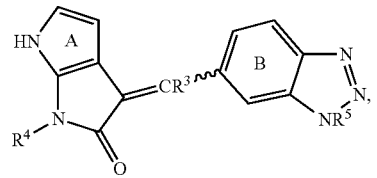 (H8)
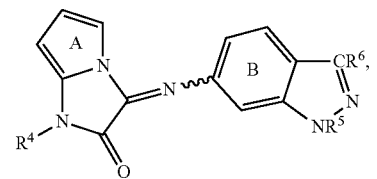 (I'1)
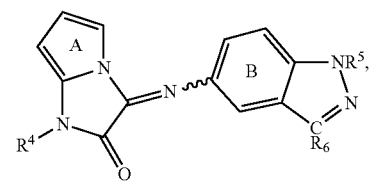 (I'2)
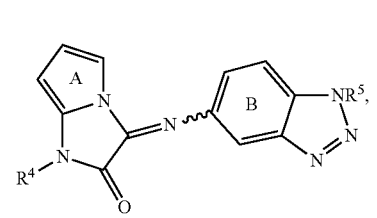 (I'3)
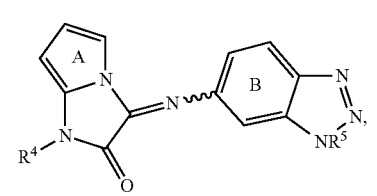 (I'4)
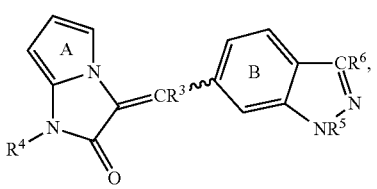 (I'5)
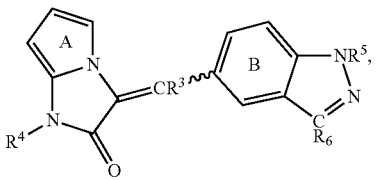 (I'6)
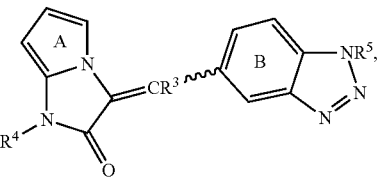 (I'7)
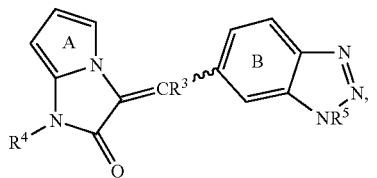 (I'8)
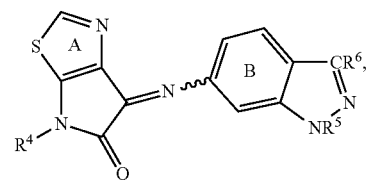 (J1)
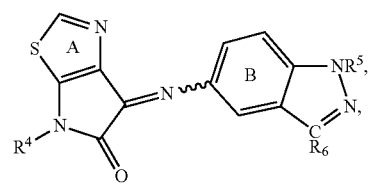 (J2)
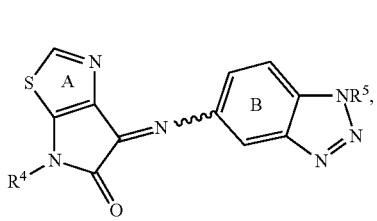 (J3)
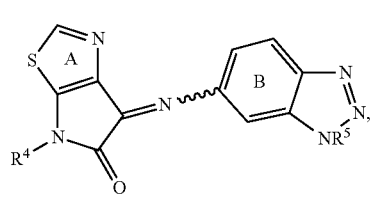 (J4)

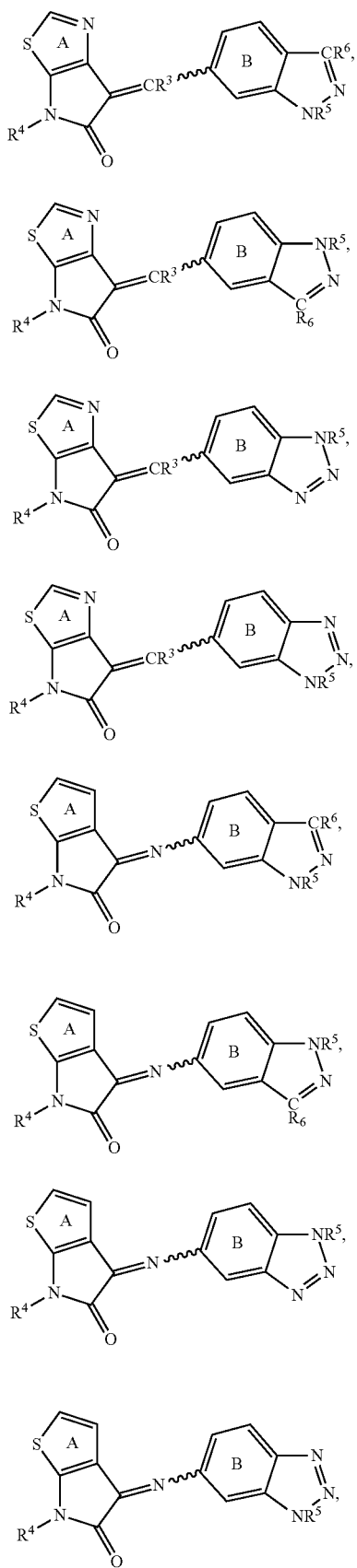

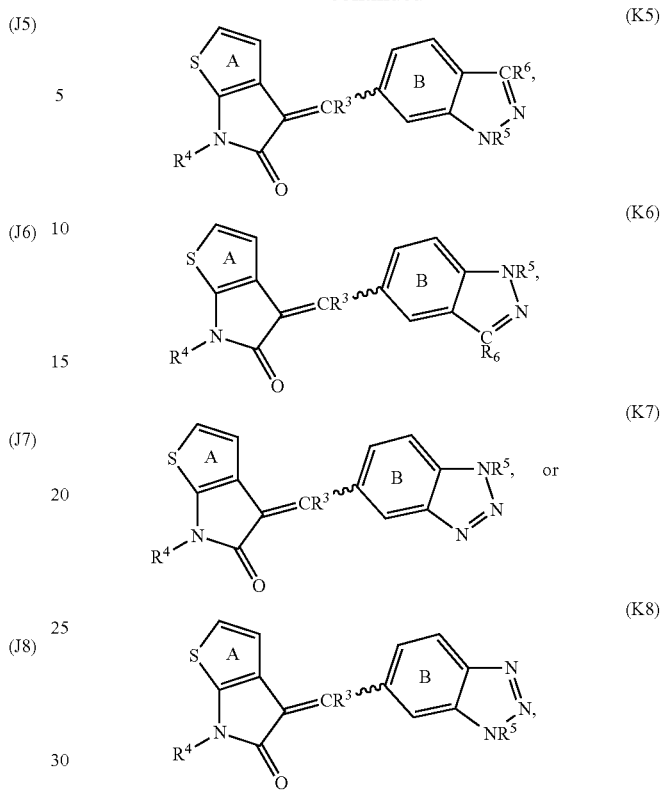

or a pharmaceutically acceptable salt thereof, wherein:

R⁶ for Structural Formulas (Ia), (Ib), (Ic), (Id), (Ie), (If), (Ig), (Ih), (Ik), (C1), (C2), (D1), (D2), (D5), (D6), (E1), (E2), (E5), (E6), (F1), (F2), (F5), (F6), (G1), (G2), (G5), (G6), (H1), (II2), (H5), (H6), (I'1), (I'2), (I'5), (I'6), (J1), (J2), (J5), (J6), (K1), (K2), (K5) and (K6) is optionally substituted phenyl, optionally substituted 5-12 membered heteroaryl, —CH₂-(optionally substituted phenyl), —CH₂-(optionally substituted 5-12 membered heteroaryl), —CH₂—CH₂-(optionally substituted phenyl), —CH₂—CH₂-(optionally substituted 5-12 membered heteroaryl), —CH═CH-(optionally substituted phenyl), —CH═CH-(optionally substituted 5-12 membered heteroaryl), —CH═CH—C(O)O(optionally substituted $C_{1-6}$ alkyl), or —CH═CH—OC(O)(optionally substituted $C_{1-6}$ alkyl). R⁶ can also be —C≡C-(optionally substituted phenyl), —C≡C-(optionally substituted 5-12 membered heteroaryl), C(O)O(optionally substituted $C_{1-6}$ alkyl), or —C≡C—OC(O)(optionally substituted $C_{1-6}$ alkyl);

R⁷ of Structural Formulas (Ig), (Ih), (Ii) and (Ij) is —H, —F, —Cl or methyl and n in Structural Formulas (Ii), (Ij), (Ik) and (Il) is 0 or 1.

Values and specific values for the remainder of the variables of Structural Formulas (Ia), (Ib), (Ic), (Id), (Ie), (If), (Ig), (Ih), (Ii), (Ij), (Ik), and (Il) are as describe above for Structural Formula (I) in the first embodiment. Values and specific values for the remainder of the variables of Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are as described above for Structural Formula (A).

In one embodiment, for Structural Formula (C1), when R⁶ is —H, R⁵ is H and R⁴ is H or C1-C6 alkyl, then ring A is not phenyl or phenyl substituted with halogen or trifluoromethyl. In another embodiment, for Structural Formula (C1), R⁵ and $R^6$ are not both —H. In one embodiment for Structural Formulas (Ia) and (Ib), $R^3$ is —H, C1-C6 alkyl or C1-C6 haloalkyl.

In a seventh embodiment, $R^4$ and $R^5$ of Structural Formulas (Ia), (Ib), (Ic), (Id), (Ie), (If), (C1)-(C4), (D1)-(D8), (E1)-(E8), (F1)-(F8), (G1)-(G8), (H1)-(H8), (I'1)-(I'8), (J1)-(J8), and (K1)-(K8) are each independently —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each phenyl in the group represented by $R^4$ and $R^5$ is optionally substituted with one or more substituents independently selected from the group consisting of halogen, $C_{1-6}$ alkyl, —O($C_{1-5}$ alkyl), $C_{1-6}$ haloalkyl, $C_{1-6}$ haloalkoxy, cyano and nitro. Values and specific values for the remainder of the variables are as described above in the sixth embodiment.

In an eighth embodiment, $R^4$ and $R^5$ of Structural Formulas (Ia), (Ib), (Ic), (Id), (Ie) (If), (C1)-(C4), (D1)-(D8), (E1)-(E8), (F1)-(F8), (G1)-(G8), (H1)-(H8), (I'1)-(I'8), (J1)-(J8) and (K1)-(K8) are as described above in the seventh embodiment and $R^6$ for Structural Formulas (Ia), (Ib), (Ic), (Id), (Ie), (If), (Ig), (Ih), (Ii), (Ij), (Ik), (Il), (C1), (C2), (D1), (D2), (D5), (D6), (E1), (E2), (E5), (E6), (F1), (F2), (F5), (F6), (G1), (G2), (G5), (G6), (H1), (H2), (H5), (H6), (I'1), (I'2), (I'5), (I'6), (J1), (J2), (J5), (J6), (K1), (K2), (K5) and (K6) is optionally substituted phenyl, optionally substituted 5-12 membered heteroaryl, —CH$_2$-(optionally substituted phenyl), —CH$_2$-(optionally substituted 5-12 membered heteroaryl), —CH$_2$—CH$_2$-(optionally substituted phenyl), —CH$_2$—CH$_2$-(optionally substituted 5-12 membered heteroaryl), —CH═CH-(optionally substituted phenyl), —CH═CH-(optionally substituted 5-12 membered heteroaryl), —CH═CH—C(O)O(optionally substituted $C_{1-6}$ alkyl), or —CH═CH—OC(O)(optionally substituted $C_{1-6}$ alkyl). Alternatively, $R^6$ can also be —C≡C-(optionally substituted phenyl), —C≡C-(optionally substituted 5-12 membered heteroaryl), —C≡C—C(O)O(optionally substituted $C_{1-6}$ alkyl), or —C≡C—OC(O)(optionally substituted $C_{1-6}$ alkyl). The 5-12 membered heteroaryl in the group represented by $R^6$ is selected from the group consisting of pyridyl, thiazolyl, pyrazinyl, thiophenyl, indolyl, quinolinyl, pyrrolyl, pyrazolyl, and pyrimidyl, each of which is optionally substituted. Values and specific values for the remainder of the variables are as described above in the sixth embodiment.

In a ninth embodiment, values for the variables in Structural Formulas (Ia), (Ib), (Ic), (Id), (Ie), (If), (Ig), (Ih), (Ii), (Ij), (Ik), (Il), (C1)-(C4), (D1)-(D8), (E1)-(E8), (F1)-(F8), (G1)-(G8), (H1)-(H8), (I'1)-(I'8), (J1)-(J8) and (K1)-(K8) are provided in the following paragraphs:

Ring A in Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are optionally substituted with one or more $Q^a$ and ring B in Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are optionally substituted with one or more $Q^b$.

$Q^a$ and $Q^b$ are each independently halogen, cyano, —NR$^1$R$^2$, —NR$^2$C(O)R$^1$, —C(O)OR$^1$, —OC(O)R$^1$, —C(O)NR$^1$R$^2$, —NR$^2$C(O)OR$^1$, —N(R$^2$)C(O)NR$^1$R$^2$, —OR$^1$, —SO$_2$NR$^1$R$^2$, —NR$^2$SO$_2$R$^1$, $C_{1-6}$ alkyl, phenyl or 5-12 membered heteroaryl, wherein the $C_{1-6}$ alkyl represented by $Q_a$ and $Q_b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl represented by $Q_a$ and $Q_b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl;

$R^1$ and $R^2$ are each independently —H— or $C_{1-6}$ alkyl, wherein the $C_{1-6}$ alkyl is optionally substituted with one or more substituents independently selected from the group consisting of halogen, —OH, —SH, —O($C_{1-3}$alkyl), —S($C_{1-3}$ alkyl) and $C_{1-6}$ haloalkoxy;

the phenyl or the 5-12 membered heteroaryl in the group represented by $R^6$ for Structural Formulas (Ia), (Ib), (Ic), (Id), (Ie), (If), (Ig), (Ih), (Ii), (Ij), (Ik), (Il), (C1), (C2), (D1), (D2), (D5), (D6), (E1), (E2), (E5), (E6), (F1), (F2), (F5), (F6), (G1), (G2), (G5), (G6), (H1), (H2), (H5), (H6), (I'1), (I'2), (I'5), (I'6), (J1), (J2), (J5), (J6), (K1), (K2), (K5) and (K6) is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl. In another embodiment, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperaziinyl is optionally N'-substituted with $C_{1-6}$ alkyl or $C_{1-6}$ acyl are additional permissible substituents for the phenyl or the 5-12 membered heteroaryl in the group represented by $R^6$; and the $C_{1-6}$ alkyl in the group represented by $R^6$ for Structural Formulas (Ia), (Ib), (Ic), (Id), (Ie), (If), (Ig), (Ih), (Ii), (Ij), (Ik), (Il), (C1), (C2), (D1), (D2), (D5), (D6), (E1), (E2), (E5), (E6), (F1), (F2), (F5), (F6), (G1), (G2), (G5), (G6), (H1), (H2), (H5), (H6), (I'1), (I'2), (I'5), (I'6), (J1), (J2), (J5), (J6), (K1), (K2), (K5) and (K6) is optionally substituted one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl.

Values and specific values for the remainder of the variables are as described above in the sixth, seventh or eighth embodiments.

In a tenth embodiment, values for the variables in Structural Formulas (Ia), (Ib), (Ic), (Id), (Ie), (If), (Ig), (Ih), (Ii), (Ij), (Ik), (Il), (C1)-(C4), (D1)-(D8), (E1)-(E8), (F1)-(F8), (G1)-(G8), (H1)-(H8), (I'1)-(I'8), (J1)-(J8), and (K1)-(K8) are provided in the following paragraphs:

Ring A in Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are optionally substituted with one or more $Q^a$ and ring B in Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are optionally substituted with one or more $Q^b$.

$Q^a$ is halogen, cyano, —NR$^1$R$^2$, —NR$^2$C(O)R$^1$, —C(O)OR$^1$, —OC(O)R$^1$, —N(R$^2$)C(O)NR$^1$R$^2$, —OR$^1$, $C_{1-6}$ alkyl, wherein the $C_{1-6}$ alkyl is optionally substituted with one or more substituents selected from the group consisting of halogen, —OH, —SH, —O($C_{1-6}$ alkyl), —S($C_{1-6}$ alkyl) and $C_{1-6}$ haloalkoxy;

$Q^b$ is halogen, $C_{1-3}$ alkyl, $C_{1-3}$ haloalkyl, $C_{1-3}$ alkoxy, or $C_{1-3}$ haloalkoxy; and the phenyl, the 5-12 membered heteroaryl and the $C_{1-6}$ alkyl in the group represented by $R^6$ is optionally substituted with one or more substituents selected from the group consisting of halogen, nitro, cyano, —O($C_{1-6}$ alkyl), $C_{1-6}$ alkyl, $C_{1-6}$ haloalkyl and $C_{1-6}$ haloalkoxy.

Values and specific values for the remainder of the variables are as described above in the sixth, seventh, eighth or ninth embodiments.

In a eleventh embodiment, values for the variables in Structural Formulas (Ia), (Ib), (Ic), (Id), (Ie), (If), (Ig), (Ih), (Ii), (Ij), (Ik), (Il), (C1)-(C4), (D1)-(D8), (E1)-(E8), (F1)-(F8), (G1)-(G8), (H1)-(H8), (I'1)-(I'8), (J1)-(J8) and (K1)-(K8) are provided in the following paragraphs:

Ring A in Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are optionally substituted with one or more $Q^a$ and ring B in Structural Formulas (C1)-(C4), (D1)-(D8), (E1)-(E8), (F1)-(F8), (G1)-(G8), (H1)-(H8), (I'1)-(I'8), (J1)-(J8) and (K1)-(K8) are optionally substituted with one or more $Q^b$.

$Q^a$ is —OH, $C_{1-6}$ alkoxy or $C_{1-6}$ haloalkoxy;

$Q^b$ is halogen, $C_{1-3}$ alkyl, $C_{1-3}$ haloalkyl, $C_{1-3}$ alkoxy, or $C_{1-3}$ haloalkoxy and the phenyl, the 5-12 membered heteroaryl and the $C_{1-6}$ alkyl in the group represented by $R^6$ are each optionally substituted with one or more substituents independently selected from the group consisting of halogen, methyl, methoxy and trifluoromethyl.

In a twelfth embodiment, the compound of the present invention is represented by a structural formula selected from (I1) and (I2):

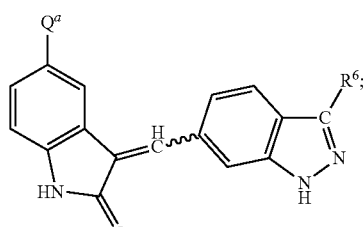

(I1)

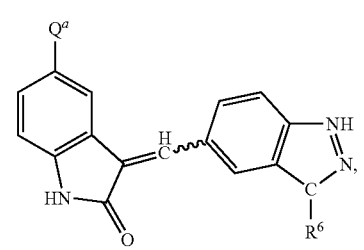

(I2)

or a pharmaceutically acceptable salt thereof, wherein:

$Q^a$ is —H, halogen, —$NH_2$, ($C_{1-6}$ alkyl)amine or $C_{1-6}$ alkoxy;

$R^6$ is phenyl, 5-6 membered heteroaryl, —CH═CH-(phenyl), —CH═CH-(5-6 membered heteroaryl), —C≡C-(phenyl), —C≡C-(5-6 membered heteroaryl) wherein each phenyl and heteroaryl in the group represented by $R^6$ is optionally substituted with halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ alkylamino)$C_{1-6}$ alkyl, (phenyl)$C_{1-6}$ alkyl, amino, $C_{1-6}$ alkylamino, $C_{1-6}$ dialkylamino, —$(CH_2)_{0-3}$—N-piperidinyl, —$(CH_2)_{0-3}$—N-morpholinyl, —$(CH_2)_{0-3}$—N-pyrrolidinyl and —$(CH_2)_{0-3}$—N-piperazinyl, wherein the N-piperazinyl is optionally N'-substituted with $C_{1-6}$ alkyl or $C_{1-6}$ acyl. Alternatively for Structural Formulas (I1) and (I2), each heteroaryl in the group represented by $R^6$ is pyridinyl, pyrimidinyl or pyrazinyl and each is optionally substituted halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —$(CH_2)_{0-3}$—N-piperidinyl, —$(CH_2)_{0-3}$-N-morpholinyl, —$(CH_2)_{0-3}$—N-pyrrolidinyl and —$(CH_2)_{0-3}$—N-piperazinyl, wherein the N-piperazinyl is optionally N'-substituted with $C_{1-6}$ alkyl or $C_{1-6}$ acyl.

Values and specific values for the remainder of the variables are as described above in the sixth, seventh, eighth, ninth or tenth embodiments.

As used herein, the phenyl, the 5-12 membered heteroaryl and the $C_{1-6}$ alkyl in the group represented by $R^6$ refers to the phenyl, the 5-12 membered heteroaryl and the $C_{1-6}$ alkyl represented by $R^6$ as well as the phenyl, the 5-12 membered heteroaryl and the $C_{1-6}$ alkyl in the groups represented by $R^6$, for example, —$CH_2$-(optionally substituted phenyl), —$CH_2$-(optionally substituted 5-12 membered heteroaryl), —$CH_2$—$CH_2$-(optionally substituted phenyl), —$CH_2$—$CH_2$-(optionally substituted 5-12 membered heteroaryl), —CH═CH-(optionally substituted phenyl), —CH═CH-(optionally substituted 5-12 membered heteroaryl), —CH═CH—C(O)O(optionally substituted $C_{1-6}$ alkyl), and —CH═CH—OC(O)(optionally substituted $C_{1-6}$ alkyl) represented by $R^6$. Similarly, the language "a specific moiety in the group represented by a variable" refers to the moiety represented by the variable or the moiety in a group represented by the variable.

Specific examples of the compounds of the invention include compounds exemplified in the examples below, stereoisomers thereof, and pharmaceutically acceptable salts thereof.

In Structural Formulas described herein, when a hydrogen atom(s) is depicted at a particular position(s) of the aromatic ring(s) of the structural formula(s), no substitution is permitted at that (those) particular position(s).

Tautomeric forms exist when a compound is a mixture of two or more structurally distinct compounds that are in rapid equilibrium. Certain compounds of the invention exist as tautomeric forms. For example, the following compound represented by Structural Formula (A), wherein two of X1-X3 are N, one of X1-X3 is NH or compound represented by Structural Formula (I), wherein two of X 1-X3 are N, one of X1-X3 is NH, include at least the following tautomers forms:

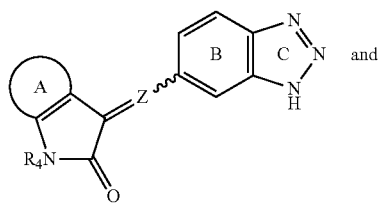

-continued

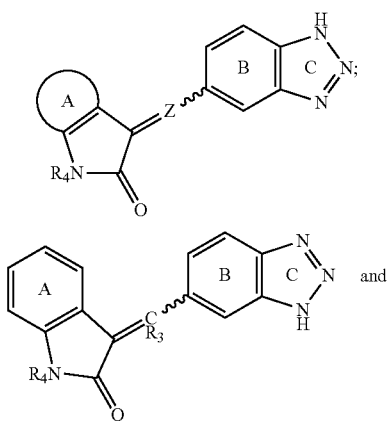

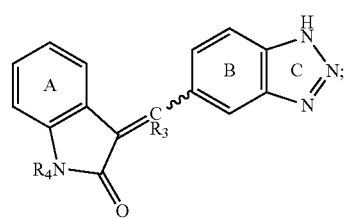
and

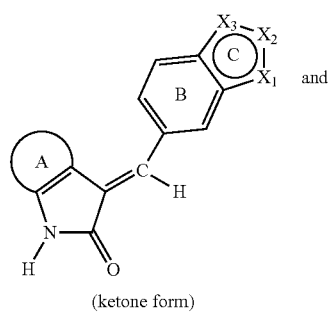

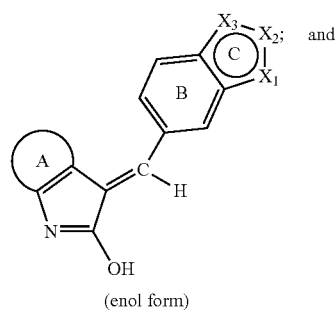
(ketone form)

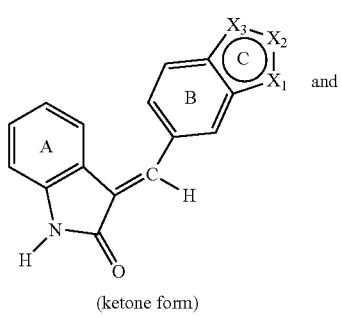
and

-continued

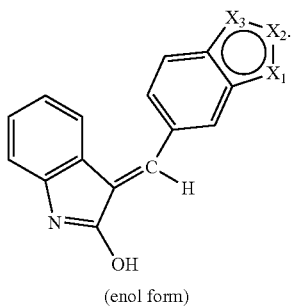
(enol form)

It is to be understood that when one tautormeric form of a compound is depicted by name or structure, all tautomeric forms of the compound are included.

The compounds of the invention may contain one or more chiral center and/or double bond and, therefore, exist as stereoisomers, such as double-bond isomers (i.e., geometric isomers), enantiomers, and/or diastereomers. When compounds of the invention are depicted or named without indicating the stereochemistry, it is to be understood that both stereomerically pure forms (e.g., geometrically pure, enantiomerically pure, or diastereomerically pure) and stereoisomeric mixtures are encompassed. For example, compounds represented by Structural Formulas (A) or (I) have E and Z geometric isomers shown below:

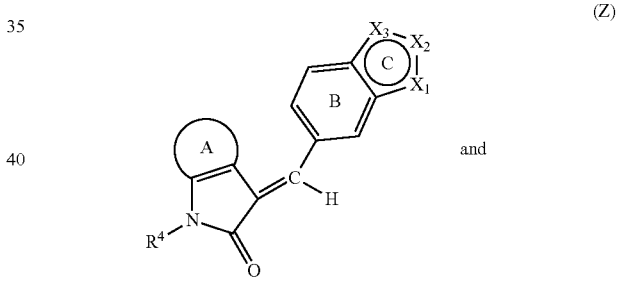
(Z)
and

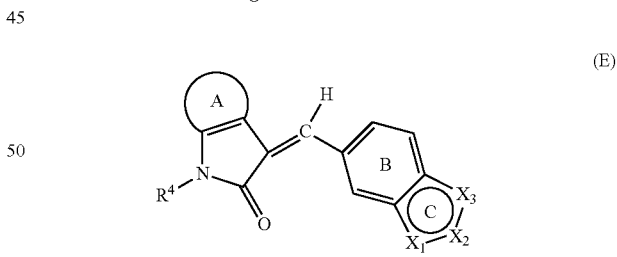
(E)

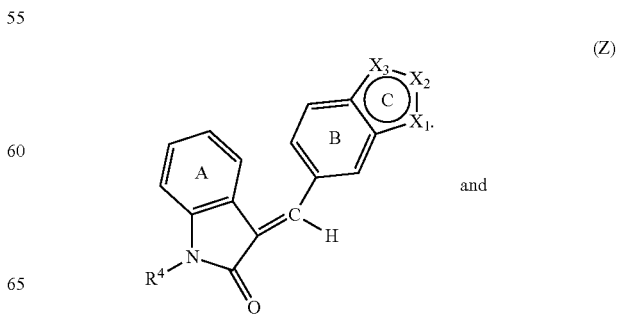
(Z)
and

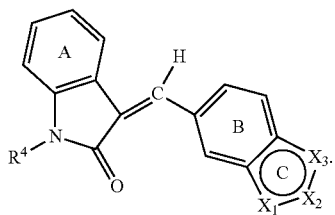

(E)

Accordingly, the compounds of the invention depicted by Structural Formula (A) or (I) include the pure E geometric isomer, the pure Z geometric isomer, and mixtures thereof.

The invention encompasses all geometrically-pure forms and geometrically-enriched (i.e. greater than 50% of either E or Z isomer) mixtures, of the compounds disclosed herein. Mixtures include 1:20, 1:10, 20:80, 30:70, 40:60 and 50:50 E:Z and Z:E ratios by mole.

As used herein, a racemic mixture means 50% of one enantiomer and 50% of is corresponding enantiomer relative to all chiral centers in the molecule. The invention encompasses all enantiomerically-pure, enantiomerically-enriched, diastereomerically pure, diastereomerically enriched, and racemic mixtures, and diastereomeric mixtures of the compounds of the invention which have chiral center(s).

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When the stereochemistry of the disclosed compounds is named or depicted by structure, the named or depicted stereoisomer is at least 60%, 70%, 80%, 90%, 99% or 99.9% by weight pure relative to the other stereoisomers. When a single stereoisomer is named or depicted by structure, the depicted or named stereoisomer is at least 60%, 70%, 80%, 90%, 99% or 99.9% pure. Percent purity by weight is the ratio of the weight of the named stereoisomer over the weight of the named stereoisomer plus the weight of its stereoisomers.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

The term "halo" as used herein means halogen and includes chloro, fluoro, bromo and iodo.

An "aliphatic group" is non-aromatic, consists solely of carbon and hydrogen and may optionally contain one or more units of unsaturation, e.g., double and/or triple bonds. An aliphatic group may be straight chained, branched or cyclic. When straight chained or branched, an aliphatic group typically contains between about one and about twenty carbon atoms, typically between about one and about ten carbon atoms, more typically between about one and about six carbon atoms. When cyclic, an aliphatic group typically contains between about three and about ten carbon atoms, more typically between about three and about seven carbon atoms. A "substituted aliphatic group" is substituted at any one or more "substitutable carbon atom". A "substitutable carbon atom" in an aliphatic group is a carbon in an aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms. Suitable substituents on a substitutable carbon atom of an aliphatic group are the same as those for an alkyl group.

The term "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, includes as used herein means saturated straight-chain, cyclic or branched aliphatic group. As used herein, a C1-C6 alkyl group is referred to "lower alkyl." Similarly, the terms "lower alkoxy", "lower haloalkyl", "lower arylalkyl", "lower alkylamine", "lower cycloalkylalkyl", "lower dialkyamine", "lower alkylamino", "lower dialkyamino" "lower alkylcarbonyl", "lower alkoxycarbonyl" include straight and branched, saturated chains containing one to six carbon atoms, and cyclic saturated chains containing three to six carbon atoms.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)—R, wherein R is alkyl; "alkoxycarbonyl" means —C(O)—OR, wherein R is alkyl; and where alkyl is as defined above.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)R, wherein R is an optionally substituted alkyl group or aryl group (e.g., optionally substituted phenyl). R is preferably an unsubstituted alkyl group or phenyl.

An "alkylene group" is represented by —[CH$_2$]$_z$—, wherein z is a positive integer, preferably from one to eight, more preferably from one to four.

An "alkenylene group" is an alkylene in which at least a pair of adjacent methylenes are replaced with —CH=CH—.

An "alkynylene group" is an alkylene in which at least a pair of adjacent methylenes are replaced with —C≡C—.

The term "aryl group" used alone or as part of a larger moiety as in "aralkyl", "aralkoxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has six-fourteen ring atoms. A "substituted aryl group" is substituted at any one or more substitutable ring atom. The term "$C_{6-14}$aryl" as used herein means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to aromatic ring groups having five to fourteen ring atoms selected from carbon and at least one (typically 1-4, more typically 1 or 2) heteroatom (e.g., oxygen, nitrogen or sulfur). They include monocyclic rings and polycyclic rings in which a monocyclic heteroaromatic ring is fused to one or more other carbocyclic aromatic or heteroaromatic rings. The term "5-14 membered heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N, NH, N($C_{1-6}$ alkyl), O and S and includes thienyl, furyl, pyrrolyl, pyrididyl, indolyl, quinolyl, isoquinolyl, tetrahydroquinolyl, benzofuryl, benzothienyl and the like.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

Other examples for the aryl and heteroaryl groups include:

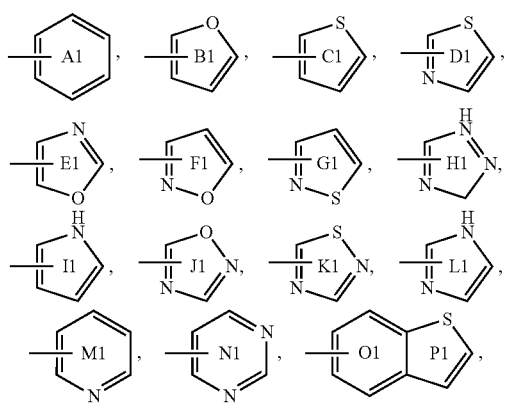

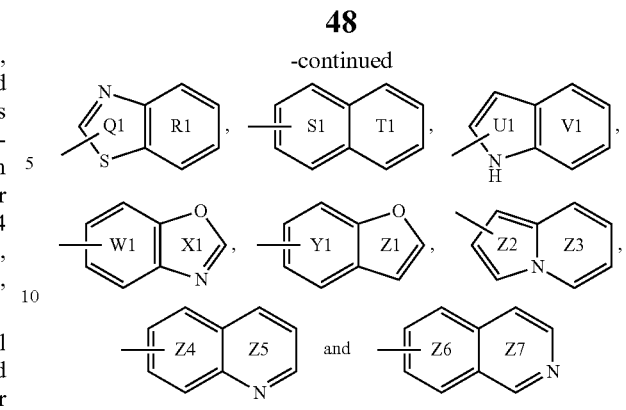

wherein each of rings A1-Z7 is optionally substituted. It is noted that, as shown above, rings O1-Z7 can be attached to their designated atom through any ring carbon of the rings which is not at a position bridging two aryl groups. For example,

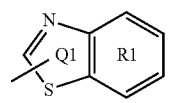

means that the group is attached to its designated atom through either ring Q1 or ring R1. Yet other examples for the aryl and heteroaryl groups include:

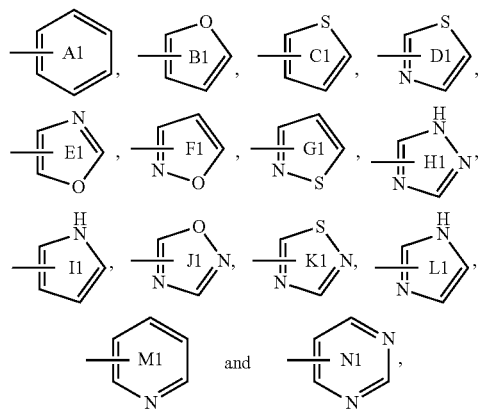

wherein each of rings A1-N1 is optionally substituted. More specific values for the aryl and heteroaryl groups include:

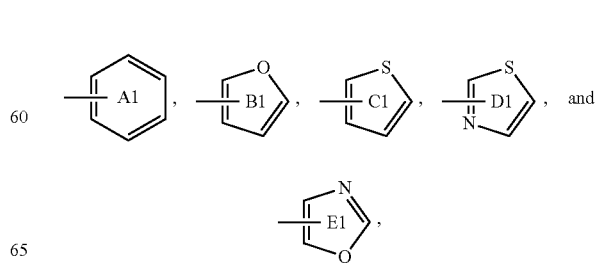

wherein each of rings A1-E1 is optionally substituted. Even more specific values for the aryl and heteroaryl groups include:

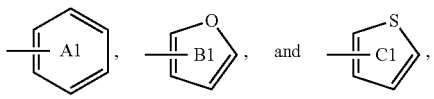

wherein each of rings A1-C1 is optionally substituted. An optionally substituted ring A1 is the most common specific value for each of the aryl group, including the $C_{6-14}$ aryl group.

As used herein, the term "non-aromatic heterocyclic group" means a monocyclic (typically having 3- to 10-members) or a polycyclic (typically having 7- to 20-members) heterocyclic ring system which is an unsaturated non-aromatic ring. A 3- to 10-membered heterocycle can contain up to 5 heteroatoms; and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like.

The aryl group, and the aromatic and non-aromatic heteroaryl groups, unless otherwise indicated, can be optionally substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl. Typical substituents include halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy$)C_{1-10}$ alkyl, $C_{1-10}$ haloalkoxy, $(C_{1-6}$ haloalkoxy$)C_{1-10}$ alkyl and $C_{1-10}$ haloalkyl. More typical substituents include $C_{1-10}$ alkyl, —OH, $C_{1-10}$ alkoxy, $C_{1-10}$ haloalkyl, halogen, $C_{1-10}$ haloalkoxy, amino, nitro and cyano.

In accordance with another aspect of the present invention, the compounds of the invention can be prepared by processes analogous to those established in the art. By way of illustration, compounds of Structural Formula (A) (wherein Z is $=CR^3$—) or (I), wherein Rings A, B and C are as defined herein may be prepared by the methods outlined in Scheme 1. Reaction of an appropriately substituted A1 or indolin-2-one A2 wherein ring A is as defined herein is reacted with a suitable aldehyde ($R^3=H$) or a ketone ($R^3$ is not H) in the presence of a secondary amine (such as piperidine) in a protic solvent (such as ethanol) at the reflux temperature of the solvent (generally about 60° C. to 120° C.). In addition this reaction can be carried out under a variety of alternative conditions including secondary amines in aprotic solvents such as DMSO or DMF; solventless with $KF/Al_2O_3$; acidic conditions (p-TsOH) in toluene or a strong base (e.g. LDA) in THF.

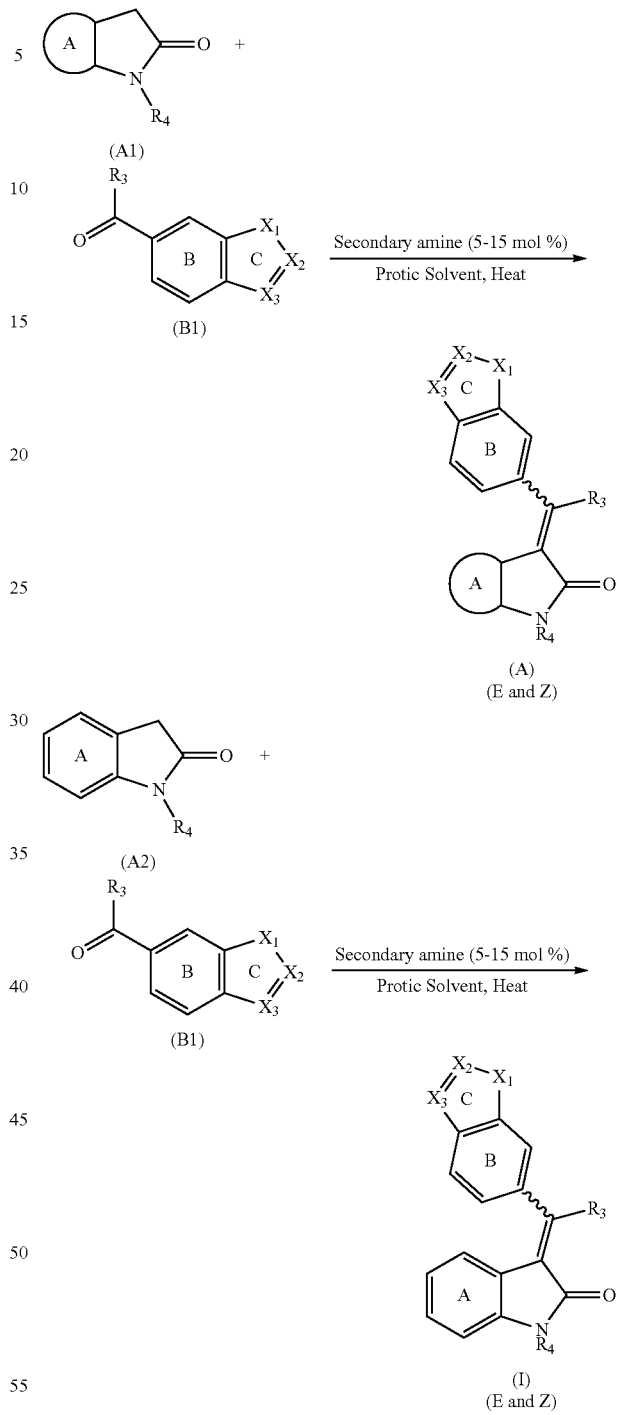

In another aspect of the invention (Scheme 2) in which $R^3$ of compound B1 is not H, the ketone B1 is first converted to an enamine B2 (wherein Y and Z are proton or small alkyl) by reaction with a secondary amine (wherein R* and R** are small alkyl or together form five or six membered ring such as pyrrolidine or piperidine). Subsequent reaction of the enamine B2 with the indolin-2-one A2 in a refluxing organic solvent (such as toluene) yields compounds of Structural Formula (I) (wherein Z is $=CR^3$—).

Scheme 2.

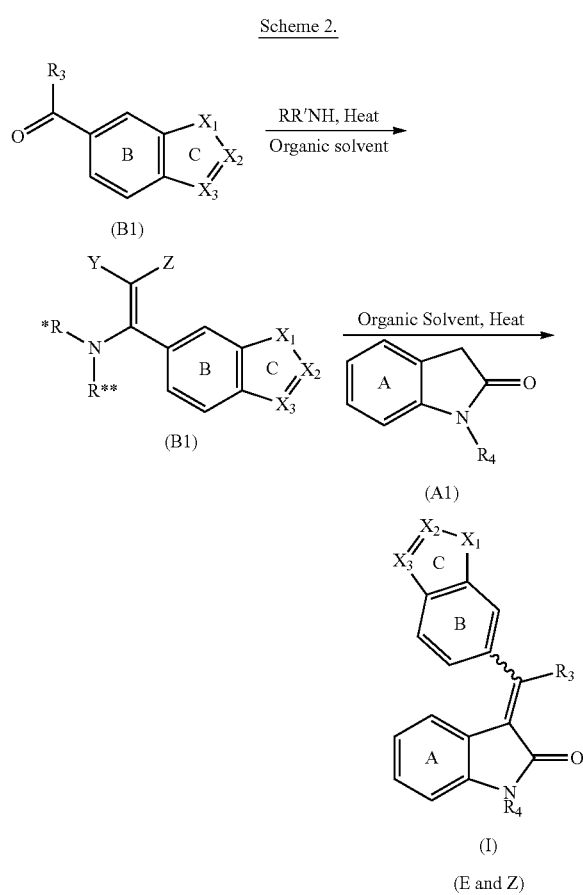

Compounds of Structural Formula (A) (wherein Z is =N—) or compounds of Structural Formula (C) (wherein Z is =N—), wherein Rings A, B and C are as defined herein may be prepared by the methods outlined in Scheme 3.

Scheme 3

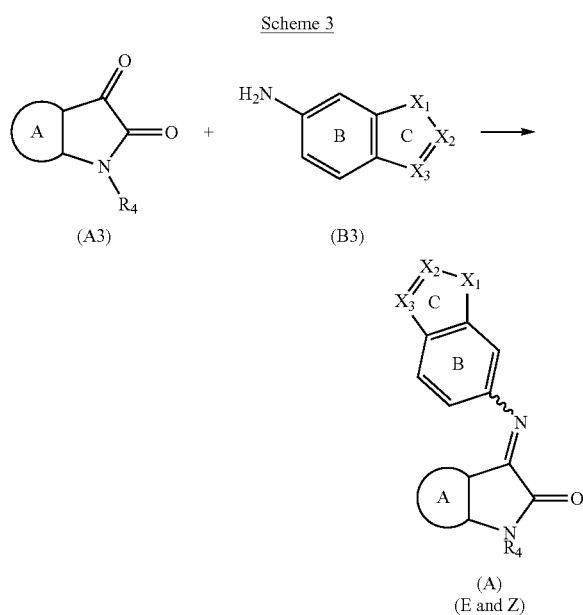

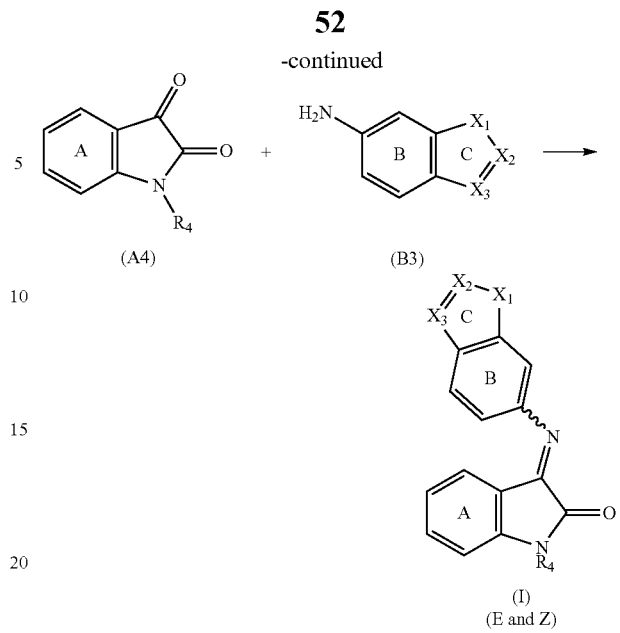

The present invention includes radiolabeled forms of the compounds of the invention, for example, compounds of the invention labeled by incorporation within the structure of $^3$H, $^{11}$C or $^{14}$C or a radioactive halogen such as $^{125}$I and $^{18}$F. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo-, suitably iodo-, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the invention containing a radioactive fluorine may be prepared, for example, by reaction of K[$^{18}$F]/K222 with a suitable precursor compound, such as a compound of Formula I comprising a suitable leaving group, for example a tosyl group, that may be displaced with the $^{18}$F anion.

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999.

Indolinone compounds of the invention can inhibit various kinases, including the PLK4, PLK1, PLK2, Aurora A, Aurora B and FLT-3 (see Examples B, C, D, E, F, and H). Thus, generally, the indolinone compounds of the invention are useful in the treatment of diseases or conditions associated with such kinases. For example, PLK4, PLK1, Aurora A and Aurora B are believed to be involved in cellular miotic progression. Thus, small molecule inhibitors of these enzymes can be potential anti-tumor agents.

In a specific embodiment, the compounds of the invention are PLK, Aurora A, Aurora B and/or FLT-3 inhibitors, and are useful for treating diseases, such as cancer, associated with such a kinase(s). In another specific embodiment, the compounds of the invention are PLK inhibitors and are useful for treating diseases associated with PLK, such as cancer. Typically, the PLK is PLK4, PLK2 and PLK 1. In one example, the PLK is PLK1 and PLK4. In another example, the PLK is PLK4. In another specific embodiment, the compounds of the invention are Aurora A and/or B inhibitors and are useful in inhibiting Aurora A and/or B activity for the treatment of various conditions such as cancers. In yet another specific embodiment, the compounds of the invention are FLT-3 inhibitors and are useful in inhibiting FLT-3 activity for the treatment of various conditions such as cancers.

Another aspect of the invention relates to a method of treating cancer comprising administering an effective amount of a compound of the invention disclosed herein. In one embodiment, the compounds of the invention inhibit the growth of a tumor. Specifically, the compounds of the invention inhibit the growth of a tumor that overexpresses at least one of PLK, Aurora A, Aurora B, and FLT-3. More specifically, the compounds of the invention inhibit the growth of a tumor that overexpresses PLK, for example, PLK1, PLK2 and/or PLK4. Even more specifically, the compounds of the invention inhibit the growth of a tumor that overexpresses PLK4. In another embodiment, the compounds of the invention inhibit the growth of the tumor by inducing apoptosis of the tumor cells or by inhibiting proliferation of the tumor cells.

Cancers that can be treated or prevented by the methods of the present invention include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one specific embodiment, the cancer is lung cancer, colon cancer, brain cancer, neuroblastoma, prostate cancer, melanoma, glioblastoma multiform or ovarian cancer. In another specific embodiment, the cancer is lung cancer, breast cancer, colon cancer, brain cancer, neuroblastoma, prostate cancer, melanoma, glioblastoma multiform or ovarian cancer. In yet another specific embodiment, the cancer is a breast cancer. In yet another specific embodiment, the cancer is a basal sub-type breast cancer or a luminal B sub-type breast cancer. In yet another specific embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

The invention further relates to a method of treating a subject with tumor cells, comprising administering to the subject, an amount of a compound disclosed herein that is effective to reduce effectively PLK activity, such as PLK 2 or PLK4 activity, in the subject. In a specific embodiment, the PLK is PLK4.

The invention further relates to a method of inhibiting Aurora B and/or PLK-4 in a subject in need of inhibition of Aurora B and/or PLK-4. As used herein, a "subject in need of inhibition of Aurora B and/or PLK-4" means the subject has a disease(s) or condition(s) associated with overexpression of Aurora B and/or PLK-4, or a disease(s) or condition(s) on which inhibition of Aurora B and/or PLK-4 have a beneficial effect(s).

The term a "therapeutically effective amount", "effective amount" or a "sufficient amount" of a compound of the present invention is a quantity sufficient to, when administered to the subject, including a mammal, for example a human, effect beneficial or desired results, including clinical results. A "therapeutically effective amount" of a compound of the invention is an amount which prevents, inhibits, suppresses or reduces the cancer (e.g., as determined by clinical symptoms or the amount of cancer cells) in a subject as compared to a control. Specifically, "treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

Generally, a therapeutically effective amount of a compound of the invention varies depending upon various factors, such as the given drug or compound, the pharmaceutical formulation, the route of administration, the type of disease or disorder, the identity of the subject or host being treated, and the like, but can nevertheless be routinely determined by one skilled in the art. As defined herein, a therapeutically effective amount of a compound of the present invention may be readily determined by one of ordinary skill by routine methods known in the art.

In an embodiment, a therapeutically effective amount of a compound of the invention ranges from about 0.1 to about 15 mg/kg body weight, suitably about 1 to about 5 mg/kg body weight, and more suitably, from about 2 to about 3 mg/kg body weight. The skilled artisan will appreciate that certain factors may influence the dosage required to effectively treat a subject suffering from cancer and these factors include, but are not limited to, the severity of the disease or disorder, previous treatments, the general health and/or age of the subject and other diseases present.

Moreover, a "treatment" regime of a subject with a therapeutically effective amount of the compound of the present invention may consist of a single administration, or alternatively comprise a series of applications. For example, the compound of the present invention may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "subject" or "patient" or synonym thereto, as used herein includes all members of the animal kingdom, especially mammals, including human. The subject or patient is suitably a human.

In one embodiment, the method of the present invention is a mono-therapy where the pharmaceutical compositions of the invention are administered alone. Accordingly, in this embodiment, the compound of the invention is the only pharmaceutically active ingredient in the pharmaceutical compositions or the only pharmaceutically active ingredient administered to the subject.

In another embodiment, the method of the invention is a co-therapy with one or more of other therapeutically active drugs or therapies known in the art for treating the desired diseases or indications. In one example, one or more other anti-proliferative or anticancer therapies are combined with the compounds of the invention. In another example, the compounds disclosed herein are co-administered with one or more of other anticancer drugs known in the art. Anticancer therapies that may be used in combination with the compound of the invention include surgery, radiotherapy (including, but not limited to, gamma-radiation, neutron beam radiotherapy, electron beam radiotherapy, proton therapy, brachytherapy, and systemic radioactive isotopes) and endocrine therapy. Anticancer agents that may be used in combination with the compounds of the invention include biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs (e.g. taxol and analogs thereof).

When the compounds of the invention are combined with other anticancer drugs, they can be administered contemporaneously. As used herein, "administered contemporaneously" means that two substances are administered to a subject such that they are both biologically active in the subject at the same time. The exact details of the administration will depend on the pharmacokinetics of the two substances in the presence of each other, and can include administering one substance within a period of time of one another, e.g., 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances. Alternatively, the two agents can be administered separately, such that only one is biologically active in the subject at the same time.

The compounds of the invention can be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds of the invention can be suitably formulated into pharmaceutical compositions for administration to a subject. The pharmaceutical compositions of the invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the invention may be incorporated with excipient and used in the form of ingestible tablets, buccal tablets, troches, capsules, elixirs, suspensions, syrups, wafers, and the like.

Typically for parenteral administration, solutions of a compound of the invention can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the invention for the extemporaneous preparation of sterile injectable solutions or dispersions.

For nasal administration, the compounds of the invention can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the invention can be formulated with a carrier such as sugar, acacia, tragacanth, or gelatin and glycerine, as tablets, lozenges or pastilles.

For rectal administration, the compounds of the invention can be formulated in the form of suppositories containing a conventional suppository base such as cocoa butter.

The compounds of the invention, can be formulated alone or for contemporaneous administration with other agents for treating cancer. Therefore, in another aspect, a pharmaceutical composition of the invention comprises a pharmaceutically acceptable carrier or diluent, a compound disclosed herein or a pharmaceutically acceptable salt thereof and another anti-cancer agent, for example, but not limited to a glucose metabolism inhibitor or taxol.

Meanings for the abbreviations used herein are provided below:

| Chemicals: | |
|---|---|
| THF | tetrahydrofuran |
| EtOAc | ethyl acetate |
| Et2O | diethyl ether |
| PDC | pyridinium dichromate |
| MeOH | methanol |
| DMSO | dimethylsulfoxide |
| DMF | N,N-dimethylformamide |
| H$_2$NMe | methyl amine |
| AcOH, HOAc | acetic acid |
| DMAP | dimethylaminopyridine |
| dba | dibenzylidineacetone |
| n-BuOH | n-butanol |
| DCM | dichloromethane |
| DI-H$_2$O | distilled or deionized water |
| $^t$BuOK | potassium tert-butoxide |
| Et$_3$N | triethylamine |
| EtOH | ethanol |
| TBTU | . . . uranium** |
| HOBt | 1-hydroxy-benzotriazole |
| DIPEA | diisopropylethylamine (Hunig's base) |
| TFA | trifluoroacetic acid |
| MeCN | acetonitrile |
| OAc | acetate (e.g. Pd(OAc)$_2$) |
| o-Tol | ortho-toluenyl** |
| o-tolyl | ortho-toluenyl** |
| o-MeC$_6$H$_4$ | ortho-toluenyl** |
| EDC | ** |
| Hex | hexane |
| TBAB | tetrabutylammonium bromide |
| SEMCl | (2-(Chloromethoxy)ethyl)trimethylsilane |
| mCPBA | meta-cloroperoxybenzoic acid |
| DME | dimethoxyethane |
| TBAF | tetrabutylammonium fluoride |
| PPh$_3$ | triphenylphosphine |
| PhMe | toluene |
| n-BuLi | n-butyllithium |
| Other: | |
| NMR | nuclear magnetic resonance |
| s, d, t, q, br. s, m | singlet, doublet, triplet, quartet, broad singlet, multiplet |
| MS ESI | mass spectroscopy, electrospray ionization |
| LC-MS | liquid chromatography coupled to mass spectroscopy |
| HPLC | high pressure liquid chromatography |
| prep-HPLC | preparative scale high pressure liquid chromatography |
| prepTLC | preparative scale thin layer chromatography |
| calcd | calculated |
| mL, L, uL | milliliters, liters, microliters |
| mmol, mol | millimoles, moles |
| mg, g | milligrams, grams |
| MHz | megaHertz |
| M | molar |
| N | normal |
| rt | room temperature |
| ° C. | degrees Celsius |
| min | minutes |
| hrs, h | hour(s) |
| d | day(s) |
| sep. | separatory |
| wt. % | percent by weight |
| atm | atmospheres of pressure |
| temp. | temperature |
| sat., sat | saturated |
| O/N | overnight |
| quant | quantitative |
| xs. | excess |
| anh, anh. | anhydrous |
| aq | aqueous |
| SPE | solid phase extraction |

The invention is illustrated by the following examples which are not intended to be limiting in any way.

EXEMPLIFICATION

A. Syntheses of Compounds of the Invention

General Experimental Methods

All starting materials, reagents, and solvents were used as received from commercial sources. In general, anhydrous reactions were performed under an inert atmosphere such as nitrogen or argon. Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000). Work-up means drying over sodium or magnesium sulfate, filtering, and concentrating in vacuo. Flash column chromatographic purification of intermediates or final products was performed using 230-400 mesh silica gel 60 from EMD chemicals. Final products were sometimes purified by preparative reverse-phase HPLC. Purification was performed on a Varian PrepStar model SD-1 HPLC system with a Varian Monochrom 10u C-18 reverse-phase column using a gradient of about 5-30% acetonitrile/0.05% TFA water to 70-100% acetonitrile/0.05% TFA water over a 20-40-min period at a flow rate of 30-50 mL/min. Fractions containing the desired material were concentrated and lyophilized to obtain the final products. Proton NMRs were recorded on a Bruker Avance III 400 MHz spectrometer, and mass spectra were obtained using a Bruker Esquire 4000 spectrometer.

Preparation of Starting Materials

Synthesis of
1H-benzo[d][1,2,3]triazole-5-carbaldehyde

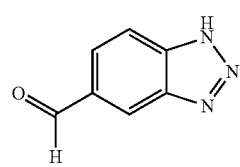 [SMILES: O=Cc1ccc2[nH]nnc2c1]

A. Synthesis of
(1H-benzo[d][1,2,3]triazol-5-yl)methanol

Under a nitrogen atmosphere a dry round-bottom flask was charged with LiAlH$_4$ (0.316 g, 7.90 mmol) and THF (15 mL).

Methyl 1H-benzo[d][1,2,3]triazole-5-carboxylate (1.0 g, 5.64 mmol) was then added portion-wise over 10 min at room temperature and reaction allowed to stir for 4 hours at which time the reaction was quenched with EtOAc (5 mL), and the mixture poured into ice-water. The mixture was acidified to pH=3 with 10% $H_2SO_4$ and extracted 4× with EtOAc. The combined organics were washed with brine, dried ($MgSO_4$) and the solvent removed. The resulting brown solid was boiled in $Et_2O$ and the solids filtered and dried to give the title compound as a light brown solid (678 mg, 81%). $^1$H NMR (400 MHz, $CD_3OD$) δ 7.85 (m, 2H), 7.47 (d, J=8.4 Hz, 1H), 4.79 (s, 2H); MS ESI 150.0 [M+H]$^+$, calcd for [$C_7H_7N_3O$+H]$^+$ 150.16.

B. 1H-benzo[d][1,2,3]triazole-5-carbaldehyde

A suspension of (1H-benzo[d][1,2,3]triazol-5-yl)methanol (0.860 g, 5.77 mmol) in acetone (25 mL) was purged with Ar, by bubbling through solution, then PDC (2.60 g, 6.92 mmol) was added portion-wise over 20 min. The reaction was stirred overnight (18 hrs). The acetone was removed in vacuo, the solids dissolved in MeOH and silica gel was added. The MeOH was then removed and the silica dry-loaded onto a silica gel column, and the product eluted with 1:1 Hexanes/EtOAc to give 444 mg, 52% of a white solid. $^1$H NMR (400 MHz, $CD_3OD$) δ 10.14 (s, 1H), 8.55 (s, 1H), 8.04 (d, J=8.8 Hz, 1H), 7.96 (d, J=8.4 Hz, 1H); MS ESI 148.0 [M+H]$^+$, calcd for [$C_7H_5N_3O$+H]$^+$ 148.14.

Synthesis of 1H-indazole-6-carbaldehyde

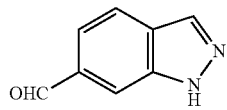 [SMILES: O=Cc1ccc2cn[nH]c2c1]

A. 6-bromo-1H-indazole

To a vigorously stirred solution of 5-bromo-2-fluorobenzaldehyde (40.6 g, 0.2 mol) in DMSO (80 mL) was added $N_2H_4$·$xH_2O$ (40 mL, 0.8 mol) dropwise over 15 min (slow addition to keep the reaction not too hot). The resulting yellow slurry was heated at 120° C. (oil temp.) for 21 h. The whole mixture was transferred to a 1 L flask and cooled for 10 min in air before quenching with ice (300 mL) and ice-cold $H_2O$ (100 mL). The resulting mixture was stirred for 30 min at rt. Precipitated formed was collected by suction filtration, rinsed thoroughly with $H_2O$ (100 mL×2), 2 M HCl (100 mL×2), $H_2O$ (100 mL×2), 0.5 M $Na_2CO_3$ (100 mL×2), $H_2O$ (100 mL×2), dried in air for 1 h and under high vacuum for 2 days to give 6-bromo-1H-indazole (30.05 g, 76%) as a light yellow solid. MS ESI 196.9 [M+H]$^+$, calcd for [$C_7H_5BrN_2$+H]$^+$ 197.0.

B. 1H-indazole-6-carbaldehyde

To a suspension of 60% NaH (10.0 g, 0.24 mol) in THF (240 mL) was added a suspension of 6-bromo-1H-indazole (39.4 g, 0.2 mol) in THF (280 mL) dropwise over 45 min. After addition, the resulting mixture was stirred for 1 h at rt to give a dark red clear solution which was cooled to −78° C. s-BuLi (1.4 M in hexane, 300 mL, 0.42 mol) was added dropwsie over 1 h. During this addition, additional THF (130 mL) was added to keep the mixture stirring. After the addition, the resulting mixture was stirred for 75 min at −78° C.; DMF (90 mL) was added dropwise (note: reaction solidified upon addition of DMF, occasional warming was needed to keep the mixture stirring). The resulting mixture was stirred at rt overnight and cooled to 0° C. Solid $NH_4Cl$ and saturated $NH_4Cl$ were added to quench the reaction and bring the pH to about 7. The product was extracted with EtOAc (800 mL+200 mL+300 mL, 1.3 L in total) and the combined extracts were washed with $H_2O$ (300 mL×3) and dried ($Na_2SO_4$). Evaporation of the solvent gave a dark red solid which was triturated by EtOAc (4 times, the last filtrate was purified by flash chromatography) to give the title compound (16.96 g in total, 58%) as yellow brown solid. $^1$H NMR (400 MHz, DMSO-d6) δ 13.62 (s, 1H, NH), 10.12 (s, 1H, CHO), 8.23 (s, 1H), 8.17 (s, 1H), 7.93 (d, J=8.4 Hz, 1H), 7.59 (d, J=8.4 Hz, 1H); MS ESI 147.0 [M+H]$^+$, calcd for [$C_8H_6N_2O$+H]$^+$ 147.0.

Synthesis of 3-iodo-1H-indazole-6-carbaldehyde

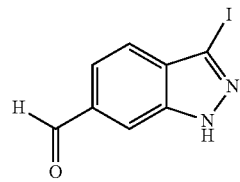 [SMILES: O=Cc1ccc2c(I)n[nH]c2c1]

To a solution of 1H-Indazole-6-carbaldehyde (2.00 g, 13.7 mmol), $K_2CO_3$ (3.79 g, 27.4 mmol) in DMF (15 mL) was added dropwise a solution of $I_2$ (5.91 g, 23.3 mmol) in DMF (15 mL) and the reaction allowed to stir for two hours. An aqueous solution consisting of $Na_2S_2O_4$ (3.30 g)/$K_2CO_3$ (0.20 g)/$H_2O$ (30 mL) was then added and the solution stirred for one hour. The product was then precipitated by pouring the solution over ice-water (300 mL) and collected by vacuum filtration to give after drying 3.02 g, 81% of a beige powder. $^1$H NMR (400 MHz, $CD_3OD$) δ 10.11 (s, 1H), 8.11 (s, 1H), 7.74 (d, J=8.34 Hz, 1H), 7.62 (d, J=8.34 Hz, 1H); MS ESI 272.9 [M+H]$^+$, calcd for [$C_8H_5IN_2O$+H]$^+$ 272.95.

Synthesis of 3-iodo-1-((2-(trimethylsilyl)ethoxy)methyl)-1H-indazole-6-carbaldehyde and 3-iodo-2-((2-(trimethylsilyl)ethoxy)methyl)-2H-indazole-6-carbaldehyde

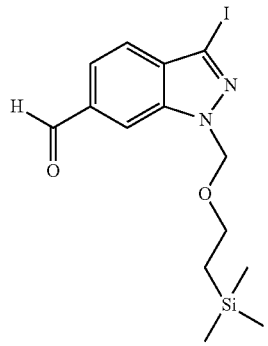

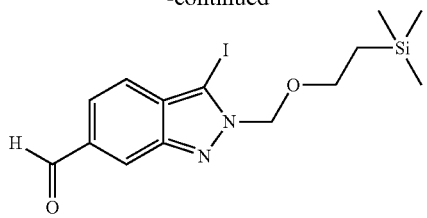

To a suspension of 3-iodo-1H-indazole-6-carbaldehyde (3.01 g, 11.1 mmol) in CH$_2$Cl$_2$ (70 mL) and 50% aq. KOH (20 mL) was added tetrabutylammonium bromide (36 mg, 0.111 mmol) and the solution cooled to 0° C. (2-(Chloromethoxy)ethyl)trimethylsilane (2.3 mL, 13.3 mmol) was then added dropwise and the reaction stirred at 0° C. for 3 hours. The solution was then transferred to a sep. funnel containing CH$_2$Cl$_2$ (200 mL) and the organic layer was washed with brine (2×100 mL), dried (MgSO$_4$) and the solvent removed in vacuo. The resulting residue was purified by column chromatography (100% CH$_2$Cl$_2$) to give 2.88 g, 65% of the N-1 isomer (higher eluting spot) and 757 mg, 17% of the N-2 isomer (lower eluting spot). N-1 isomer: $^1$H NMR (400 MHz, CDCl$_3$) δ 10.18 (s, 1H), 8.11 (s, 1H), 7.81 (d, J=8.4 Hz, 1H), 7.65 (d, J=8.4 Hz, 1H), 5.82 (s, 2H), 3.60 (m, 2H), 0.91 (m, 2H), −0.042 (s, 9H); MS ESI 425.0 [M+Na]$^+$, calcd for [C$_{14}$H$_{19}$IN$_2$O$_2$Si+Na]$^+$ 425.02.

N-2 isomer: $^1$H NMR (400 MHz, CD$_3$OD) 10.09 (s, 1H), 8.31 (s, 1H), 7.62 (m, 2H), 5.91 (s, 2H), 3.71 (m, 2H), 0.92 (m, 2H), −0.039 (s, 9H); MS ESI 425.0 [M+Na]$^+$, calcd for [C$_{14}$H$_{19}$IN$_2$O$_2$Si+Na]$^+$ 425.02

Synthesis of N-methyl-2-oxoindoline-5-sulfonamide

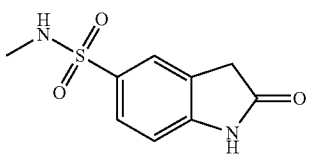

A dry round-bottom flask was charged with 1 mL of a 2.0 M solution of H$_2$NMe in THF. 2-oxoindoline-5-sulfonyl chloride (100 mg, 0.432 mmol) was then added and the reaction stirred overnight. The solvents were removed and the residue purified by column chromatography (silica gel, 93:7 CH$_2$Cl$_2$/MeOH) to give 73 mg, 74% of a brown solid. $^1$H NMR (400 MHz, CD$_3$OD) δ 7.73 (d, J=8.8 Hz, 1H), 7.72 (s, 1H), 7.03 (d, J=8.0 Hz, 1H), 3.35 (s, 2H), 2.52 (s, 3H); MS ESI 226.9 [M+H]$^+$, calcd for [C$_9$H$_{10}$N$_2$O$_3$S+H]$^+$ 227.05.

Synthesis of 6-aminoindolin-2-one

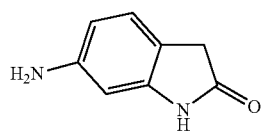 [SMILES: Nc1ccc2c(c1)NC(=O)C2]

A solution of 2-(2,4-dinitrophenyl)acetic acid (1.0 g, 4.42 mmol), AcOH (10 mL), and MeOH (5 mL) was purged with Ar for 15 minutes at which time 10 wt. % Pd/C (100 mg) was added. The mixture was then purged briefly with H$_2$ and then stirred under 1 atm of H$_2$ overnight. The mixture was filtered through a pad of celite, the solvent removed in vacuo, and the residue purified by column chromatography (silica gel, 90:10 CH$_2$Cl$_2$/MeOH) to give 462 mg, 71% of a brown solid. $^1$H NMR (400 MHz, CD$_3$OD) δ 6.95 (d, J=7.7 Hz, 1H), 6.37 (d, J=7.8 Hz, 1H), 6.34 (s, 1H), 3.38 (s, 2H); MS ESI 149.0 [M+H]$^+$, calcd for [C$_8$H$_8$N$_2$O+H]$^+$ 149.07.

Synthesis of N-(2-oxoindolin-6-yl)acetamide

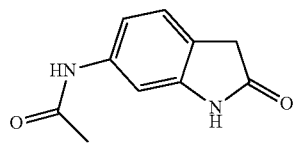

To 6-aminoindolin-2-one (30 mg, 0.202 mmol) in THF (1 mL) was added acetic anhydride (19 uL, 0.202 mmol). After 2 hrs the product was precipitated with ether, filtered and dried to give 25 mg, 66% of a white solid. $^1$H NMR (400 MHz, CD$_3$OD) δ 7.41 (s, 1H), 7.16 (d, J=7.0 Hz, 1H), 7.00 (d, J=8.0 Hz, 1H), 3.49 (s, 2H), 2.12 (s, 3H); MS ESI 191.0 [M+H]$^+$, calcd for [C$_{10}$H$_{10}$N$_2$O$_2$+H]$^+$ 191.08.

Synthesis of N-(2-oxoindolin-5-yl)acetamide

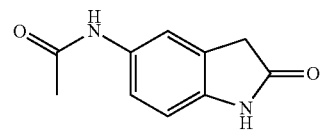

According to procedure for the synthesis of N-(2-oxoindolin-6-yl)acetamide, except substituting 5-aminoindolin-2-one (50 mg, 0.34 mmol), the title compound was prepared as a beige solid (46 mg, 71%). $^1$H NMR (400 MHz, CDCl$_3$) δ 7.49 (s, 1H), 7.31 (d, J=7.0 Hz, 1H), 6.83 (d, J=8.0 Hz, 1H), 3.52 (s, 2H), 2.10 (s, 3H).

Synthesis of N,N-dimethyl-N'-(2-oxo-2,3-dihydro-1H-indol-5-yl)sulfamide

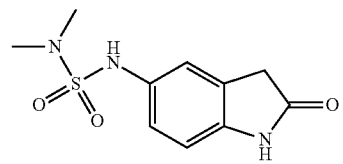 [SMILES: CN(C)S(=O)(=O)Nc1ccc2c(c1)CC(=O)N2]

To 5-aminoindolin-2-one (100 mg, 0.68 mmol) in ethyl acetate/DMF 1:1 (2 mL) was added dimethylsulfamoyl chloride (290 mg, 2.04 mmol) and DMAP (1 mg). After 72 h the product was precipitated with ether, filtered and dried to give 56 mg, 32% of a white solid. $^1$H NMR (400 MHz, CD$_3$OD) δ 7.21 (s, 1H), 7.16 (d, J=7.0 Hz, 1H), 7.00 (d, J=8.0 Hz, 1H), 3.53 (s, 2H), 2.77 (s, 6H).

Synthesis of 1-isopropyl-3-(2-oxoindolin-5-yl)urea

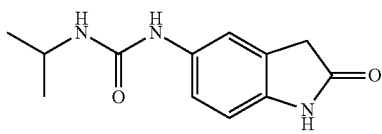 [SMILES: CC(C)NC(=O)Nc1ccc2c(c1)CC(=O)N2]

To 5-aminoindolin-2-one (50 mg, 0.34 mmol) in ethyl acetate (1 mL) was added isopropylisocyanate (0.04 mL, 0.4 mmol). The solution was stirred at rt for 16 h and the product was precipitated with ether, filtered and dried to give 46 mg, 58% of a yellow solid. $^1$H NMR (400 MHz, CD$_3$OD) δ 7.31 (s, 1H), 7.13 (d, J=8.3 Hz, 1H), 6.80 (d, J=8.3 Hz, 1H), 3.90-3.83 (m, 1H), 3.51 (s, 2H), 1.77 (d, J=7.3 Hz, 6H).

Synthesis of N-(2-oxoindolin-5-yl)methanesulfonamide

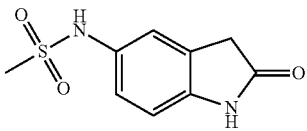

To 5-aminoindolin-2-one (50 mg, 0.34 mmol) in DMF (1 mL) was added methanesulfonyl chloride (51 mg, 0.51 mmol) and DMAP (1 mg). The solution was stirred at rt for 16 h and the product was precipitated with ether, filtered and dried to give 10 mg, 13% of a yellow solid. $^1$H NMR (400 MHz, CD$_3$OD) δ 7.22 (s, 1H), 7.13 (d, J=8.3 Hz, 1H), 6.87 (d, J=7.6 Hz, 1H), 3.55 (s, 2H), 2.91 (s, 3H).

Synthesis of 6-(Pyridin-3-yl)indolin-2-one

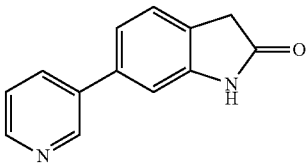 [SMILES: O=C1Cc2ccc(-c3cccnc3)cc2N1]

A mixture 6-chloroindolin-2-one (100 mg, 0.60 mmol), 3-(3,3,4,4-tetramethylborolan-1-yl)pyridine (184 mg, 0.90 mmol), Pd$_2$dba$_3$ (5.4 mg, 0.0060 mmol) and powdered K$_3$PO$_4$ (252 mg, 1.2 mmol) in n-BuOH (2 mL) was degassed by evacuation and refilling with Ar. Dicyclohexyl(2',4',6'-triisopropylbiphenyl-2-yl)phosphine (11.4 mg, 0.024 mmol) was added under the atmosphere of Ar. The reaction mixture was sealed and heated with stirring under microwave irradiation at 100° C. for 99 min. Later the reaction was cooled to rt and treated with degassed H$_2$O (0.25 mL). The mixture was reheated under microwave irradiation at 110° C. for 1 h. The crude reaction mixture was concentrated under reduced pressure and purified by flash chromatography on silica gel using MeOH (0 to 6%) in DCM as the eluent to provide the title compound as a pale yellow solid (100 mg, 80%). %). $^1$H NMR (400 MHz, CD$_3$OD) δ ppm 8.77 (d, J=1.52 Hz, 1H), 8.52 (dd, J4.80, 1.52 Hz, 1H), 8.05-8.10 (m, 1H), 7.52 (dd, J7.33, 4.80 Hz, 1H), 7.39 (d, J=7.6 Hz, 1H), 7.30 (dd, J=7.71, 1.39 Hz, 1H), 7.17 (s, 1H), 3.59 (s, 2H); MS ESI 211.0 (100) [M+H]$^+$, calcd for [C$_{13}$H$_{10}$N$_2$O+H]$^+$ 211.2.

Synthesis of 3-formyl-1H-indazole-6-carbonitrile

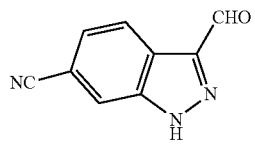 [SMILES: N#Cc1ccc2c(C=O)n[nH]c2c1]

To a solution of NaNO$_2$ (11.04 g, 160 mmol) in DI—H$_2$O (200 mL) was added 6-cyanoindole (5.68 g, 40 mmol) in one portion slowly. The resulting suspension was stirred for 5 min at rt. 6N HCl (32 mL, 192 mmol) was added dropwise via a dropping funnel over 30 min and the pH was about 1. The resulting suspension was stirred for 4.5 h at rt before 400 mL of EtOAc was added. After stirring for additional 10 min to dissolve the precipitate, the two layers were separated and the aqueous layer was extracted with EtOAc (150 mL). Combined extracts were dried over Na$_2$SO$_4$. Removal of solvents afforded 6.864 g (100%) of title compound as brown (coffee color) solid. $^1$H NMR (400 MHz, DMSO-d6) δ 14.70 (s, 1H, NH), 10.22 (s, 1H, CHO), 8.38 (s, 1H), 8.28 (d, J=8.4 Hz, 1H), 7.69 (d, J=8.4 Hz, 1H). MS ESI 172.0 [M+H]$^+$, calcd for [C$_9$H$_5$N$_3$O+H]$^+$ 172.0.

Synthesis of (E)-3-(2-(pyridin-4-yl)vinyl)-1H-indazole-6-carbaldehyde

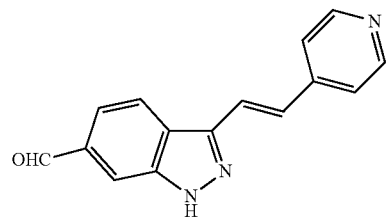 [SMILES: O=Cc1ccc2c(/C=C/c3ccncc3)n[nH]c2c1]

a) (E)-3-(2-(pyridin-4-yl)vinyl)-1H-indazole-6-carbonitrile

To a suspension of 4-chloropyridine hydrochloride (3.28 g, 20 mmol) in benzene (50 mL) was added 40% NaOH (1.35 mL). The resulting mixture was sonicated for 10 min and filtered. The residue was treated with additional benzene (15 mL), sonicated and filtered. The combined benzene layers were dried (Na$_2$SO$_4$) to give a solution of 4-chloropyridine which was used without further characterization (vida infra). A solution of diethyl phosphate (3.03 g, 22 mmol) in benzene (35 mL) was treated with freshly cut Na (510 mg, 22 mmol). The resulting mixture was refluxed for 30 min (oil temp. 90° C.), cooled to 0° C., then treated added dropwise over 10 min. with the solution of 4-chloropyridine in benzene (prepared as described above). After addition, the resulting mixture was refluxed for 3 h (oil temp. 100° C.) under argon then cooled to rt. The insoluble white precipitate was removed by filtration and rinsed with benzene (20 mL). The combined filtrate was concentrated and dried under high vacuum to give 3.5 g of diethyl pyridin-4-ylmethylphosphonate as a colorless liquid.

Diethyl pyridin-4-ylmethylphosphonate was redissolved in DMF (25 mL) and cooled to 0° C. ᵗBuOK (3.36 g, 30 mmol) was added portion wise over 2 min and the reaction mixture turned dark brown red. After stirring for 2 min at 0° C., a solution of 3-formyl-1H-indazole-6-carbonitrile (1.71 g, 10 mmol) in DMF (15 mL) was added dropwise by pipette over 5 min. The resulting mixture was stirred for 40 min at 0° C. before quenching with ice, 2N HCl (20 mL) and H$_2$O (20 mL). After stirring for 10 min at rt, the reaction mixture was carefully basified with sat. NaHCO$_3$ to pH about 8 and copious amounts of yellow precipitate formed. The solid was collected by suction filtration and rinsed with H$_2$O. After dying under high vacuum, 2.016 g (82%) of title compound was obtained as beige solid. $^1$H NMR (400 MHz, DMSO-d6) δ 13.90 (s, 1H, NH), 8.60-8.54 (m, 2H), 8.43 (d, J=8.0 Hz, 1H), 8.20 (s, 1H), 7.93 (d, J=16.0 Hz, 1H), 7.70 (d, J=4.0 Hz, 2H), 7.58 (d, J=8.0 Hz, 1H, partially overlapping with the doublet at 7.55 ppm), 7.55 (d, J=16.0 Hz, 1H, partially overlapping with the doublet at 7.58 ppm); MS ESI 250.0 [M+H]$^+$, calcd for [C$_{15}$H$_{11}$N$_3$O+H]$^+$ 250.1.

b) (E)-3-(2-(pyridin-4-yl)vinyl)-1H-indazole-6-carbaldehyde

To a solution of (E)-3-(2-(pyridin-4-yl)vinyl)-1H-indazole-6-carbonitrile (246 mg, 1 mmol) in HOAc/pyridine (3 mL/6 mL) was added a solution of sodium hypophosphite (352 mg, 4 mmol) in H$_2$O (3 mL), followed by Raney-Nickel 2400 (slurry in H$_2$O, 0.2 mL). The resulting mixture was heated at 55° C. (oil temp.) for 1 h then cooled to rt. Water (30 mL) was added and the mixture was extracted with EtOAc (30 mL×3). The combined extracts were washed with H$_2$O (20 mL×3), brine (10 mL) and dried (Na$_2$SO$_4$). Removal of solvent gave a yellow solution containing pyridine. H$_2$O (60 mL) was added with swirling and large amounts of yellow precipitate formed which was collected by suction filtration and rinsed with H$_2$O. After dying under high vacuum, the title compound (75 mg, 30%) was obtained as a beige solid. $^1$H NMR (400 MHz, DMSO-d6) δ 13.90 (s, 1H, NH), 10.14 (s, 1H, CHO), 8.57 (d, J=5.6 Hz, 2H), 8.40 (d, J=8.4 Hz, 1H), 8.20 (s, 1H), 7.89 (d, J=16.8 Hz, 1H), 7.73-7.69 (m, 3H), 7.55 (d, J=16.4 Hz, 1H). MS ESI 247.0 [M+H]$^+$, calcd for [C$_{15}$H$_{11}$N$_3$O+H]$^+$ 247.1.

Synthesis of ((E)-3-(2-(pyridin-3-yl)vinyl)-1H-indazole-6-carbaldehyde

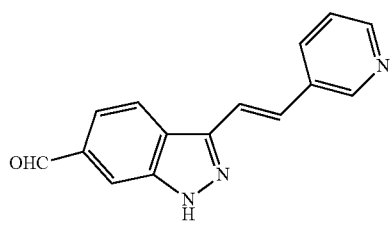 [SMILES: O=Cc1ccc2c(/C=C/c3cccnc3)n[nH]c2c1]

a) (E)-3-(2-(pyridin-3-yl)vinyl)-1H-indazole-6-carbonitrile

To a suspension of 3-chloropyridine hydrochloride (6.54 g, 40 mmol) in benzene (75 mL) was added 40% NaOH (2.7 mL). The resulting mixture was sonicated for 10 min and filtered. The residue was treated with additional benzene (25 ml), sonicated and filtered. The combined benzene layers were dried (Na$_2$SO$_4$) to give a solution of 4-chloropyridine in benzene.

To a solution of diethyl phosphate (6.06 g, 44 mmol) in benzene (50 mL) was added freshly cut Na (1.02 g, 44 mmol). The resulting mixture was refluxed (oil temp. 95° C.) for 30 min then cooled to 0° C. The solution of 4-chloropyridine in benzene obtained above was added dropwise to this solution via dropping funnel over 15 min. After addition, the resulting mixture was refluxed for 2 h (oil temp. 100° C.) and LC-MS indicated the completion of reaction. After cooling to rt, the insoluble white precipitate (NaCl) was filtered off and rinsed with benzene (50 mL). The filtrate was concentrated and dried under high vacuum to give 6.30 g of diethyl pyridin-3-ylmethylphosphonate as a light yellow liquid.

Diethyl pyridin-3-ylmethylphosphonate was redissolved in DMF (50 mL), cooled to 0° C. and treated with ᵗBuOK (6.72 g, 60 mmol) portion wise over 3 min; the reaction turned a dark reddish brown. After stirring for 3 min at 0° C., a solution of 3-formyl-1H-indazole-6-carbonitrile (3.42 g, 20 mmol) in DMF (25 mL) was added dropwise by pipette over 5 min. After addition, the resulting mixture was stirred for 1 h at 0° C. before quenching with ice (100 mL). The reaction mixture was cooled to 0° C. and slowly acidified with 2M HCl until pH 5. During this addition, a copious amount of precipitate was formed. After stirring for 2 min at this temperature, sat NaHCO$_3$ was added slowly until pH 8 and the mixture was stirred for an additional 2 min. Water was added until the total volume reached 600 mL. After stirring for 10 min, the resulting precipitate was collected by suction filtration and rinsed thoroughly with water, then dried under high vacuum to give the title compound (3.30 g, 67%) as a beige solid. $^1$H NMR (400 MHz, DMSO-d6) δ 13.80 (s, 1H, NH), 8.89 (s, 1H), 8.48 (d, J=4.4 Hz, 1H), 4.42 (d, J=8.4 Hz, 1H), 8.22-8.17 (m, 2H), 7.74 (d, J=16.8 Hz, 1H), 7.59 (d, J=18.0 Hz, 1H, partially overlapping with the doublet at 7.55 ppm), 7.55 (d, J=10.0 Hz, 1H, partially overlapping with the doublet at 7.59 ppm), 7.43 (dd, J=8.0 Hz, 5.6 Hz, 1H); MS ESI 247.0 [M+H]$^+$, calcd for [C$_{15}$H$_{10}$N$_4$+H]$^+$ 247.1.

b) (E)-3-(2-(pyridin-3-yl)vinyl)-1H-indazole-6-carbaldehyde

To a suspension of (E)-3-(2-(pyridin-4-yl)vinyl)-1H-indazole-6-carbonitrile (984 mg, 3 mmol) in pyridine (30 mL) was added HOAc (8 mL), followed by DMF (30 mL). The resulting mixture was heated and sonicated to make a clear solution. After cooling to 0° C., a solution of sodium hypophosphite (1.408 g, 16 mmol) in H$_2$O (8 mL) was added, followed by Raney-Nickel 2400 (slurry in H$_2$O, 0.8 mL). The resulting mixture was heated at 60° C. (oil temp.) for 1 h before cooling to rt. H$_2$O (50 mL) was added and the mixture was extracted with EtOAc (100 mL+50 mL×2). The combined extracts were dried (Na$_2$SO$_4$). Removal of low boiling point solvents gave a yellow solution in DMF (about 30 mL); H$_2$O (500 mL) was added with swirling and a yellow precipitate formed. After standing 10 min, the resulting precipitate was collected by suction filtration, rinsed with H$_2$O and dried under high vacuum to give the title compound (500 mg, 50%) as a yellow solid. $^1$H NMR (400 MHz, DMSO-d6) δ 13.79 (s, 1H, NH), 10.14 (s, 1H, CHO), 8.90 (s, 1H), 8.48 (d, J=4.8 Hz, 1H), 8.39 (d, J=8.0 Hz, 1H), 8.19 (d, J=9.2 Hz, 1H, partially overlapping with the singlet at 8.18 ppm), 8.18 (s, 1H, partially overlapping with the doublet at 8.19 ppm), 7.75 (d, J=16.4 Hz, 1H), 7.69 (d, J=8.4 Hz, 1H), 7.59 (d, J=16.8 Hz, 1H), 7.43 (dd, J=8.0 Hz, 5.2 Hz, 1H); MS ESI 250.0 [M+H]$^+$, calcd for [$C_{15}H_{11}N_3O$+H]$^+$ 250.1.

Synthesis of (E)-ethyl 3-(6-formyl-1H-indazol-3-yl)acrylate

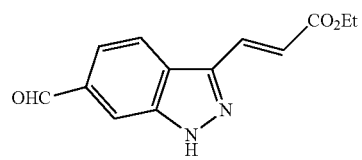 [SMILES: CCOC(=O)/C=C/c1n[nH]c2cc(C=O)ccc12]

A) (E)-ethyl 3-(6-cyano-1H-indazol-3-yl)acrylate

To a mixture of triethyl phosphonoacetate (125 mg, 0.55 mmol) and LiOH (26.4 mg, 1.1 mmol) in DMF (3 mL) at rt was added 3-formyl-1H-indazole-6-carbonitrile (85.5 mg, 0.5 mmol) in one portion. The resulting mixture was stirred at rt O/N. It was quenched with ice, followed by 2 M HCl (6 mL). After stirring for 5 min, the resulting precipitate was collected by suction filtration, washed with H$_2$O, hexane, dried to give the title compound (75 mg, 62%) as a beige solid. $^1$H NMR (400 MHz, DMSO-d6) δ 14.18 (s, 1H, NH), 8.35 (d, J=8.8 Hz, 1H), 8.25 (s, 1H), 7.92 (d, J=16.0 Hz, 1H), 7.55 (d, J=8.4 Hz, 1H), 6.82 (d, J=16.4 Hz, 1H), 4.22 (q, J=7.2 Hz, 2H), 1.28 (t, J=7.2 Hz, 3H); MS ESI 242.0 [M+H]$^+$, calcd for [$C_{13}H_{11}N_2O_3$+H]$^+$ 242.1.

B) ((E)-ethyl 3-(6-formyl-1H-indazol-3-yl)acrylate

To a solution of (E)-ethyl 3-(6-cyano-1H-indazol-3-yl)acrylate (723 mg, 3 mmol) in pyridine (10 mL) was added acetic acid (3 mL), followed by a solution of NaH$_2$PO$_2$ (1.056 g, 12 mmol) in H$_2$O (3 mL). The resulting mixture was stirred for 0.5 min at rt before Raney-Nickel 2400 (slurry in H$_2$O, 0.6 mL) was added in one portion. The resulting mixture was heated at 55° C. (oil temp.) for 1 h before cooling to rt. H$_2$O (30 mL) was added and the mixture was extracted with EtOAc (50 mL×2). Combined extracts were washed with H$_2$O (20 mL), 2 M HCl (20 mL), H$_2$O (20 mL×2), brine (15 mL) and dried (Na$_2$SO$_4$). Removal of solvent gave an orange red oil which solidified upon standing O/N under high vacuum. It was then triturated with H2O (30 mL) and suction filtered, rinsed with H$_2$O, dried to give the title compound (476 mg, 65%) as an orange red solid. $^1$H NMR (400 MHz, DMSO-d6) δ 14.16 (s, 1H, NH), 10.14 (s, 1H, CHO), 8.30 (d, J=8.8 Hz, 1H), 8.22 (s, 1H), 7.92 (d, J=16.4 Hz, 1H), 7.71 (d, J=7.6 Hz, 1H), 6.82 (d, J=8.4 Hz, 1H), 4.22 (q, J=6.8 Hz, 2H), 1.28 (t, J=6.8 Hz, 3H); MS ESI 245.0 [M+H]$^+$, calcd for [$C_{13}H_{12}N_2O_3$+H]$^+$ 245.1.

Synthesis of (E)-methyl 4-(2-(6-formyl-1H-indazol-3-yl)vinyl)benzoate

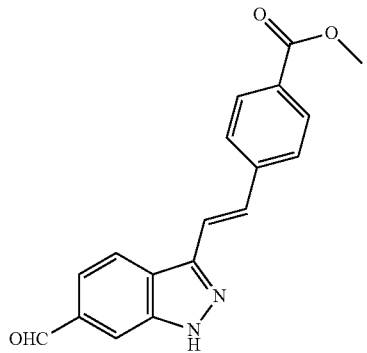 [SMILES: COC(=O)c1ccc(/C=C/c2n[nH]c3cc(C=O)ccc23)cc1]

A mixture of methyl 4-(bromomethyl)benzoate (4.58 g, 20 mmol) and trimethyl phosphite (3.54 mL, 30 mmol) was refluxed (oil temp. 125° C.) for 1 h under argon. After cooling to rt, the reaction mixture was diluted with DMF (50 mL) and cooled to 0° C. using ice bath. $^t$BuOK (3.92 g, 35 mmol) was added slowly. After addition, the resulting dark brown solution was stirred for 5 min at 0° C. before a solution of 3-formyl-1H-indazole-6-carbonitrile (2.0 g, 11.7 mmol) in DMF (15 mL) was added dropwise via a pasteur pipette over 5 min. The reaction mixture was then stirred for 90 min at 0° C.; 2N HCl (25 mL) was added slowly over 2 min, followed by H$_2$O (100 mL). The resulting suspension was stirred for 5 min at 0° C. The precipiates collected by suction filtration were rinsed well with H$_2$O and dried to give crude (E)-methyl 4-(2-(6-cyano-1H-indazol-3-yl)vinyl)benzoate (3.70 g) as an orange solid. Trituration with 50 mL of ether, followed by sonication and suction filtration gave pure (E)-methyl 4-(2-(6-cyano-1H-indazol-3-yl)vinyl)benzoate (2.56 g, 72%) as an orange solid. $^1$H NMR (400 MHz, DMSO-d6) δ 13.83 (s, 1H), 8.43 (d, J=8.8 Hz, 1H), 8.18 (s, 1H), 7.97 (d, J=8.4 Hz, 2H), 7.87 (d, J=8.4 Hz, 2H), 7.76 (d, J=16.4 Hz, 1H), 7.63 (d, J=16.8 Hz, 1H), 7.55 (d, J=8.4 Hz, 1H), 3.86 (s, 3H); MS ESI 304.1 [M+H]$^+$, calcd for [$C_{18}H_{13}N_3O_2$+H]$^+$ 304.1.

To a mixture of (E)-methyl 4-(2-(6-cyano-1H-indazol-3-yl)vinyl)benzoate (606 mg, 2 mmol) in HOAc/pyridine/DMF (4 mL/8 mL/6 mL) was added a solution of NaH$_2$PO$_2$ (704 mg, 8 mmol) in H$_2$O (4 mL), followed by Raney-Nickel 2400 (slurry in H$_2$O, 0.4 mL). The resulting mixture was heated for 1 h at 55° C. (oil temp.). After cooling to rt, it was diluted with EtOAc (80 mL) and washed with H$_2$O (30 mL). Aqueous layer was extracted with EtOAc (50 mL). Combined organic layers were washed with 2 N HCl (20 mL), H$_2$O (20 mL) and dried (Na$_2$SO$_4$). Evaporation of solvent gave crude title compound as an orange solid which was triturated with EtOAc (10 mL), followed by suction filtration to give the title compound (240 mg, 39%) as light beige solid. The filtrate was concentrated, triturated with H$_2$O, sonicated and the resulting precipitates were collected by suction filtration and rinsed with H$_2$O, dried to give additional title compound (151 mg, 25%) as orange solid. $^1$H NMR (400 MHz, DMSO-d6) δ 13.82 (s, 1H), 10.14 (s, 1H), 8.40 (d, J=8.8 Hz, 1H), 8.18 (s, 1H), 7.97 (d, J=8.0 Hz, 2H), 7.88 (d, J=7.6 Hz, 2H), 7.77 (d, J=16.8 Hz, 1H), 7.79 (d, J=8.4 Hz, 1H), 7.64 (d, J=15.6 Hz, 1H), 3.86 (s, 3H); MS ESI 307.0 [M+H]$^+$, calcd for [C$_{18}$H$_{14}$N$_2$O$_3$+H]$^+$ 307.1.

Synthesis of (E)-4-(2-(6-formyl-1H-indazol-3-yl)vinyl)benzoic acid

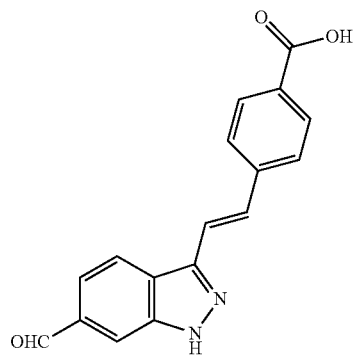 [SMILES: O=Cc1ccc2c(/C=C/c3ccc(C(=O)O)cc3)n[nH]c2c1]

To a round bottom flash containing (E)-methyl 4-(2-(6-cyano-1H-indazol-3-yl)vinyl)benzoate (606 mg, 2 mmol) was added 2 M NaOH (20 mL, 40 mmol), followed by THF (10 mL) and MeOH (10 mL). The resulting mixture was stirred O/N at rt. After removal of THF and MeOH via rotavap, the residue was cooled to 0° C. and treated with 2 M HCl (25 mL) and stirred for 2 min at that temp. The precipitates collected by suction filtration were rinsed with H$_2$O to give crude (E)-4-(2-(6-cyano-1H-indazol-3-yl)vinyl)benzoic acid as a brown red solid. It was redissolved in HOAc/pyridine/DMF (4 mL/8 mL/6 mL) and a solution of NaH$_2$PO$_2$ (704 mg, 8 mmol) in H$_2$O (4 mL) was added, followed by Raney-Nickel 2400 (slurry in H$_2$O, 0.4 mL). The resulting mixture was heated for 1 h at 55° C. (oil temp.). Usual aqueous workup, followed by trituration with H$_2$O gave the title compound (332 mg, 54%) as a beige solid. $^1$H NMR (400 MHz, DMSO-d6) δ 13.81 (s, 1H), 12.90 (s, br, 1H), 10.14 (s, 1H), 8.39 (d, J=8.0 Hz, 1H), 8.19 (s, 1H), 7.96 (d, J=8.0 Hz, 2H), 7.86 (d, J=8.0 Hz, 2H), 7.76 (d, J=16.8 Hz, 1H), 7.79 (d, J=8.4 Hz, 1H), 7.64 (d, J=16.4 Hz, 1H); MS ESI 293.0 [M+H]$^+$, calcd for [C$_{17}$H$_{12}$N$_2$O$_3$+H]$^+$ 293.1.

Synthesis of 3-(pyridin-3-ylethynyl)-1H-indazole-6-carbaldehyde

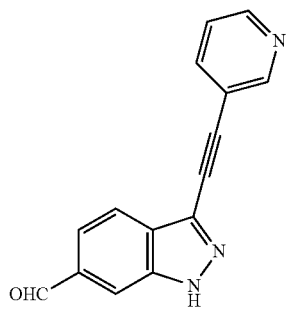 [SMILES: O=Cc1ccc2c(C#Cc3cccnc3)n[nH]c2c1]

To a solution of 3-iodo-1H-indazole-6-carbaldehyde (136 mg, 0.5 mmol), Pd(PPh$_3$)$_2$Cl$_2$ (14 mg, 0.02 mmol) and CuI (7.6 mg, 0.04 mmol) in DMF (3 mL) was added Et$_3$N (5 mL), followed by 3-ethynylpyridine (77 mg, 0.75 mmol). The resulting mixture was heated at 100° C. (oil temp.) for 45 min. After removal of Et$_3$N, the residue was loaded directly onto a silical gel column. Flash chromatography (eluent: hex to ethyl acetate), followed by trituration with water and suction filtration gave the title compound (112 mg, 91%) as a light yellow solid. $^1$H NMR (400 MHz, DMSO-d6) δ 14.16 (s, 1H), 10.16 (s, 1H), 8.90 (s, 1H), 6.64 (d, J=4.0 Hz, 1H), 8.26 (s, 1H), 8.12 (d, J=8.0 Hz, 1H), 8.07 (d, J=8.4 Hz, 1H), 7.74 (d, J=8.4 Hz, 1H), 7.52 (dd, J=8.0 Hz, J=5.2 Hz, 1H); MS ESI 248.0 [M+H]$^+$, calcd for [C$_{15}$H$_9$N$_3$O+H]$^+$ 248.1.

Preparation of Compounds of the Invention

Example A1

(E)-3-((1H-benzo[d][1,2,3]triazol-5-yl)methylene)indolin-2-one

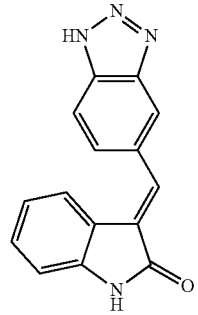 [SMILES: O=C1Nc2ccccc2/C1=C\c1ccc2[nH]nnc2c1]

A scintillation vial was charged with indolin-2-one (101 mg, 0.760 mmol), 1H-benzo[d][1,2,3]triazole-5-carbaldehyde (123 mg, 0.836 mmol), piperidine (7.5 uL, 0.076 mmol) and EtOH (4 mL). The reaction was then heated to 90° C. for 2 hrs. A yellow precipitate formed which was further precipitated by cooling to room temperature and adding more EtOH (5 mL). The yellow solid was then filtered and washed with EtOH (20 mL) giving 149 mg, 75% of the title compound. $^1$H NMR (400 MHz, d$_6$-DMSO) δ 15.94 (s, 1H), 10.65 (s, 1H), 8.27 (bs, 1H), 8.05 (bs, 1H), 7.80 (s, 1H), 7.77 (bs, 1H), 7.51 (d, J=7.6 Hz, 1H), 7.24 (t, J=7.6 Hz, 1H), 6.88 (d, J=7.6 Hz, 1H), 6.84 (d, J=7.6 Hz, 1H); MS ESI 263.0 [M+H]$^+$, calcd for [C$_{15}$H$_{10}$N$_4$O+H]$^+$ 263.09.

Example A2

(E)-3-((1H-benzo[d][1,2,3]triazol-5-yl)methylene)-5-aminoindolin-2-one

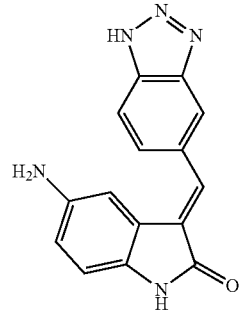 [SMILES: Nc1ccc2c(c1)/C(=C\c1ccc3[nH]nnc3c1)C(=O)N2]

A scintillation vial was charged with 5-aminoindolin-2-one (37 mg, 0.247 mmol), 1H-benzo[d][1,2,3]triazole-5-carbaldehyde (40 mg, 0.272 mmol), piperidine (2.5 uL, 0.025 mmol) and EtOH (2 mL). The reaction was then heated to 90° C. for 2 hrs. The EtOH was removed in vacuo and the residue loaded onto a silica gel column eluting with 92:8 $CH_2Cl_2$/MeOH to give 14 mg, 20% of a red solid. $^1$H NMR (400 MHz, $d_6$-DMSO) δ 15.96 (bs, 1H), 10.15 (s, 1H), 8.21 (bs, 1H), 8.02 (bs, 1H), 7.73 (bs, 1H), 7.67 (s, 1H), 6.87 (s, 1H), 6.59-6.47 (m, 2H), 4.65 (bs, 2H); MS ESI 278.0 [M+H]$^+$, calcd for $[C_{15}H_{11}N_5O+H]^+$ 278.10.

Example A3

(E)-3-((1H-benzo[d][1,2,3]triazol-5-yl)methylene)-5-bromoindolin-2-one

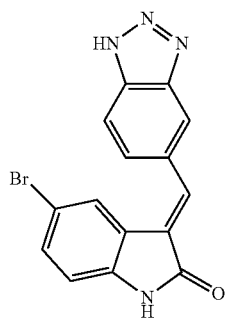 [SMILES: O=C1Nc2ccc(Br)cc2/C1=C\c1ccc2[nH]nnc2c1]

The title compound was synthesized according to the method described for Example A1, except reacting 5-bromooxindole (39 mg, 0.185 mmol) with 1H-benzo[d][1,2,3]triazole-5-carbaldehyde (30 mg, 0.204 mmol) to obtain 32 mg, 51%. $^1$H NMR (400 MHz, $d_6$-DMSO) δ 15.97 (s, 1H), 10.85 (s, 1H), 9.27 (s, 1H), 8.37 (d, J=9.2 Hz, 1H), 8.16 (s, 1H), 8.02 (s, 1H), 7.95 (d, J=8.4 Hz, 1H), 7.39 (d, J=8.2 Hz, 1H), 6.80 (d, J=8.3 Hz, 1H); MS ESI 341.0 [M+H]$^+$, calcd for $[C_{15}H_9BrN_4O+H]^+$ 341.00.

Example A4

(E)-3-((1H-benzo[d][1,2,3]triazol-5-yl)methylene)-6-chloroindolin-2-one

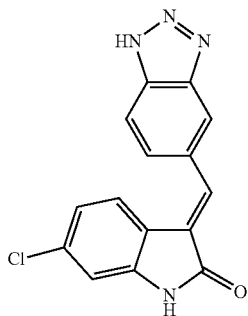 [SMILES: O=C1Nc2cc(Cl)ccc2/C1=C\c1ccc2[nH]nnc2c1]

The title compound was synthesized according to the method described for Example A1 except reacting 6-chlorooxindole (36 mg, 0.216 mmol) with 1H-benzo[d][1,2,3]triazole-5-carbaldehyde (35 mg, 0.238 mmol) to obtain 32 mg, 51%. $^1$H NMR (400 MHz, $d_6$-DMSO) δ 15.95 (s, 1H), 10.81 (s, 1H), 8.27 (bs, 1H), 8.04 (bs, 1H), 7.85 (s, 1H), 7.76 (bs, 1H), 7.49 (d, J=8.8 Hz, 1H), 6.91 (bs, 2H); MS ESI 297.0 [M+H]$^+$, calcd for $[C_{15}H_9ClN_4O+H]^+$ 297.05.

Example A5

(E)-3-((1H-indazol-6-yl)methylene)indolin-2-one

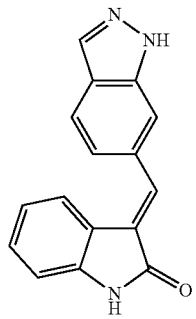 [SMILES: O=C1Nc2ccccc2/C1=C\c1ccc2cn[nH]c2c1]

The title compound was synthesized according to the method described for Example A1 except reacting oxindole (67 mg, 0.216 mmol) with 1H-indazole-6-carbaldehyde (73 mg, 0.238 mmol) to obtain 32 mg, 51%. $^1$H NMR (400 MHz, $CD_3OD$) δ 8.14 (s, 1H), 7.91 (d, J=8.5 Hz, 1H), 7.89 (s, 2H), 7.65 (d, J=7.6 Hz, 1H), 7.47 (d, J=8.4 Hz, 1H), 7.25 (t, J=7.7 Hz, 1H), 6.93 (d, J=7.8 Hz, 1H), 6.87 (t, J=7.6 Hz, 1H); MS ESI 262.0 [M+H]$^+$, calcd for $[C_{16}H_{11}N_3O+H]^+$ 262.10.

Example A6

(E)-3-((1H-indazol-5-yl)methylene)indolin-2-one

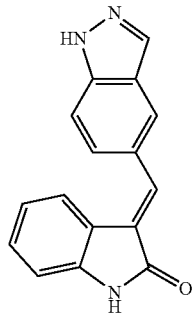 [SMILES: O=C1Nc2ccccc2/C1=C\c1ccc2[nH]ncc2c1]

A scintillation vial was charged with indolin-2-one (67 mg, 0.500 mmol), 1H-indazole-5-carbaldehyde (73 mg, 0.550 mmol), piperidine (5.0 uL, 0.076 mmol) and EtOH (2 mL). The reaction was then heated to 90° C. for 2 hrs. The EtOH was removed and the product purified by preparatory reverse-phase HPLC to give 10 mg, 7.6% of the title compound. $^1$H NMR (400 MHz, $CD_3OD$) δ 8.20-8.18 (m, 2H), 7.89 (s, 1H), 7.76 (d, J=7.9 Hz, 1H), 7.71-7.67 (m, 2H), 7.24 (t, J=7.4 Hz, 1H), 6.93 (d, J=7.7 Hz, 1H), 6.90 (t, J=7.5 Hz, 1H); MS ESI 262.0 [M+H]+, calcd for [C₁₆H₁₁N₃O+H]+ 262.10.

Example A7

3-((1H-benzo[d][1,2,3]triazol-5-yl)methylene)-N-methyl-2-oxoindoline-5-sulfonamide

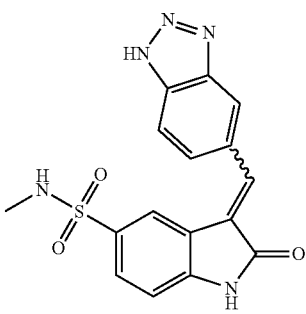 [SMILES: CNS(=O)(=O)c1ccc2c(c1)C(=Cc1ccc3[nH]nnc3c1)C(=O)N2]

The compound was synthesized according to the method described for Example A6 except reacting N-methyl-2-oxoindoline-5-sulfonamide (14 mg, 0.0618 mmol) with 1H-benzo[d][1,2,3]triazole-5-carbaldehyde (10 mg, 0.0680 mmol) to obtain 5.6 mg, 12% of the title compound as a mixture of (E) and (Z) isomers (69:21 by NMR). ¹H NMR (400 MHz, d₆-DMSO) δ 16.02, 16.00 (bs, 1H), 11.10, 11.15 (s, 1H), 8.55-8.10 (m, 2H), 7.95-7.80 (m, 3H), 7.77-7.60 (m, 1H), 7.27, 7.21 (q, J=5.2 Hz, 1H), 7.07, 7.03 (d, J=8.3 Hz, 1H), 2.44, 2.36 (s, 3H); MS ESI 356.1 [M+H]+, calcd for [C₁₆H₁₃N₅O₃S+H]+ 356.08.

Example A8

(E)-3-((1H-indazol-6-yl)methylene)-N-methyl-2-oxoindoline-5-carboxamide

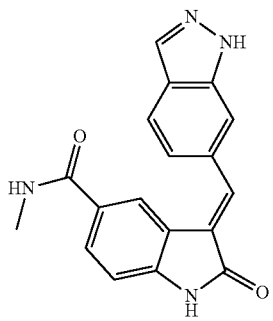 [SMILES: CNC(=O)c1ccc2c(c1)/C(=C\c1ccc3cn[nH]c3c1)C(=O)N2]

A. N-methyl-2-oxoindoline-5-carboxamide

An oven-dried round-bottom flask was charged with 2-oxoindoline-5-carboxylic acid (89 mg, 0.500 mmol), TBTU (193 mg, 0.600 mmol), HOBt hydrate (81 mg, 0.600 mmol), DIPEA (0.13 mL, 0.750 mmol) and DMF (3.0 mL) and stirred for 5 minutes. Methyl amine (0.75 mL of a 2.0 M solution in THF) was then added and reaction was stirred for 4 hours at which time NaHCO₃(sat) (2 mL) was added. Solvents were removed in vacuo and the residue was purified by column chromatography (silica gel, 92:8 CH₂Cl₂/MeOH) to give the title compound (11 mg, 12%). 1H NMR (400 MHz, CD₃OD) δ ppm 7.69-7.75 (m, 2H), 6.94 (d, J=8.1 Hz, 1H), 3.58 (s, 2H), 2.97 (s, 3H); MS ESI 191.0 [M+H]+, calcd for [C₁₀H₁₀N₂O₂+H]+ 191.08.

B. (E)-3-((1H-indazol-6-yl)methylene)-N-methyl-2-oxoindoline-5-carboxamide

The title compound was synthesized from N-methyl-2-oxoindoline-5-carboxamide (11 mg, 0.0578 mmol) and 1H-indazole-6-carbaldehyde (10 mg, 0.0636 mmol) according to the method described for Example A1 to obtain 3.0 mg, 17%. ¹H NMR (400 MHz, d₆-DMSO) δ 13.33 (s, 1H), 10.88 (s, 1H), 8.24-8.22 (m, 1H), 8.18 (s, 2H), 7.93-7.88 (m, 2H), 7.84 (s, 1H), 7.72 (d, J=7.9 Hz, 1H), 7.46 (d, J=8.0 Hz, 1H), 6.91 (d, J=8.0 Hz, 1H), 2.68 (d, J=4.0 Hz, 3H); MS ESI 319.1 [M+H]+, calcd for [C₁₈H₁₄N₄O₂+H]+ 319.12.

Example A9

(E and Z)-3-((1H-indazol-6-yl)methylene)-N-methyl-2-oxoindoline-5-sulfonamide

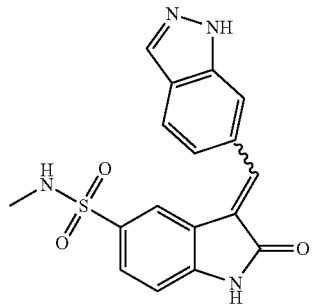 [SMILES: CNS(=O)(=O)c1ccc2c(c1)C(=Cc1ccc3cn[nH]c3c1)C(=O)N2]

According to the method described for Example A1 the title compound was prepared from N-methyl-2-oxoindoline-5-sulfonamide (41 mg, 0.181 mmol) and 1H-indazole-6-carbaldehyde (29 mg, 0.199 mmol) as a mixture of geometric isomers (24 mg, 38%). (E) and (Z) isomers: 55:45 by NMR. ¹H NMR (400 MHz, d₆-DMSO) δ 13.43, 13.38 (s, 1H), 11.13, 11.11 (s, 1H), 9.03, 8.23 (s, 1H), 8.20-7.82 (m, 5H), 7.65, 7.47 (d, J=8.4 Hz, 1H), 7.25, 7.20 (m, 1H), 7.06, 7.01 (d, J=8.4 Hz, 1H), 2.45, 2.32 (s, 3H); MS ESI 355.1 [M+H]+, calcd for [C₁₇H₁₄N₄O₃S+H]+ 355.09.

Example A10

(E and Z)-(3-((1H-indazol-6-yl)methylene)-N-methyl-2-oxoindoline-6-carboxamide

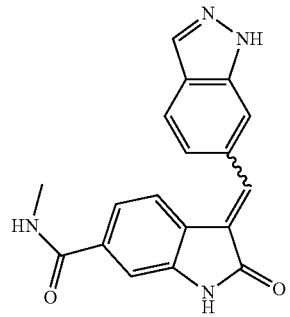 [SMILES: CNC(=O)c1ccc2c(c1)NC(=O)C2=Cc1ccc2cn[nH]c2c1]

A. N-methyl-2-oxoindoline-6-carboxamide

The compound was synthesized according to the method described for N-methyl-2-oxoindoline-5-carboxamide except substituting 2-oxoindoline-6-carboxylic acid (89 mg, 0.500 mmol), to obtain the title compound (18 mg, 19%). $^1$H NMR (400 MHz, CD$_3$OD) δ 7.52 (d, J=7.6 Hz, 1H), 7.15 (d, J=8.0 Hz, 1H), 6.40 (d, J=7.6 Hz, 1H), 3.33 (s, 2H), 2.87 (s, 31-1); MS ESI 191.0 [M+H]$^+$, calcd for [C$_{10}$H$_{10}$N$_2$O$_2$+H]$^+$ 191.08.

B. (3-((1H-indazol-6-yl)methylene)-N-methyl-2-oxoindoline-6-carboxamide

According to the method described for Example A6, the title compound (2.8 mg, 9.3%) was obtained from N-methyl-2-oxoindoline-6-carboxamide (18 mg, 0.0950 mmol) as a mixture of (E) and (Z) isomers (70:30 by NMR). $^1$H NMR (400 MHz, CD$_3$OD) δ 8.99, 8.16 (s, 1H), 8.10-7.69 (m, 4H), 7.52-7.36 (m, 1H), 7.37-7.28 (m, 2H), 2.94, 2.91 (s, 3H); MS ESI 319.1 [M+H]$^+$, calcd for [C$_{18}$H$_{14}$N$_4$O$_2$+H]$^+$ 319.12.

Example A11

(E)-3-((1H-indazol-6-yl)methylene)-2-oxo-N-phenylindoline-5-carboxamide

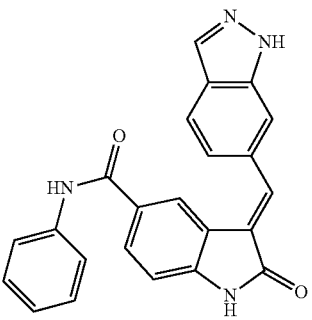 [SMILES: O=C1Nc2ccc(C(=O)Nc3ccccc3)cc2/C1=C\c1ccc2cn[nH]c2c1]

A. 2-oxo-N-phenylindoline-5-carboxamide

The title compound was synthesized according to the method described for N-methyl-2-oxoindoline-5-carboxamide from 2-oxoindoline-6-carboxylic acid (89 mg, 0.500 mmol) and aniline (0.14 mL, 1.50 mmol) to obtain 45 mg, 36%. $^1$H NMR (400 MHz, CD$_3$OD) δ 7.88 (d, J=8.4 Hz, 1H), 7.87 (s, 1H), 7.67 (d, J=7.9 Hz, 2H), 7.36 (t, J=7.9 Hz, 2H), 7.15 (t, J=7.4 Hz, 1H), 7.00 (d, J=8.0 Hz, 1H), 3.34 (s, 2H); MS ESI 253.0 [M+H]$^+$, calcd for [C$_{15}$H$_{12}$N$_2$O$_2$+H]$^+$ 253.10.

B. (E)-3-((1H-indazol-6-yl)methylene)-2-oxo-N-phenylindoline-5-carboxamide

A scintillation vial was charged with 2-oxo-N-phenylindoline-5-carboxamide (22 mg, 0.087 mmol), 1H-indazole-6-carbaldehyde (14 mg, 0.096 mmol), piperidine (1 uL, 0.008 mmol) and MeOH (2 mL). The reaction was then heated to 60° C. for 2 hrs. A yellow precipitate formed which was further precipitated by cooling to room temperature and adding more MeOH (2 mL). The yellow solid was then filtered and washed with MeOH (10 mL) to give 8.0 mg, 24% of the title compound. $^1$H NMR (400 MHz, d$_6$-DMSO) δ 13.42 (s, 1H), 11.02 (s, 1H), 10.16 (s, 1H), 9.01 (s, 1H), 8.39 (s, 1H), 8.14 (s, 2H), 8.03 (d, J=7.3 Hz, 1H), 7.89-7.82 (m, 2H), 7.79 (d, J=6.5 Hz, 2H), 7.36 (t, J=6.6 Hz, 2H), 7.11-7.09 (m, 1H), 6.96 (d, J=6.9 Hz, 1H); MS ESI 381.1 [M+H]$^+$, calcd for [C$_{23}$H$_{16}$N$_4$O$_2$+H]$^+$ 381.14.

Example A12

(E)-tert-butyl 3-((1H-indazol-6-yl)methylene)-2-oxoindolin-5-ylcarbamate

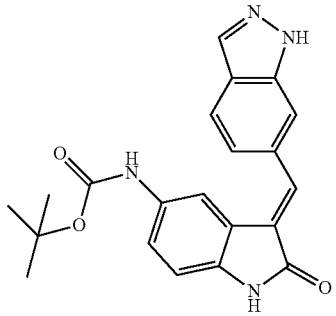 [SMILES: CC(C)(C)OC(=O)Nc1ccc2c(c1)/C(=C\c1ccc3cn[nH]c3c1)C(=O)N2]

A. tert-butyl 2-oxoindolin-5-ylcarbamate

A THF (20 mL) solution of 5-aminoindolin-2-one (200 mg, 1.3 mmol) and di-t-butyl dicarbonate (300 mg, 1.4 mmol) at rt under N$_2$, was treated with Et$_3$N (0.37 mL, 2.7 mmol). The stirring was continued at rt overnight; the reaction mixture was concentrated under reduced pressure, taken into DCM and washed (H$_2$O 2x, brine). The organic layer was dried (Na$_2$SO$_4$) and concentrated under reduced pressure. Trituration with hexanes provided the title compound as a white solid (260 mg, 77%). NMR (400 MHz, CDCl$_3$) δ ppm 7.43 (br. s., 2H), 7.07 (dd, J=8.84, 1.26 Hz, 1H), 6.77 (d, J=8.59 Hz, 1H), 6.39 (br. s., 1H), 3.52 (s, 2H), 1.52 (s, 9H); MS ESI 249.0 (80) [M+H]$^+$, calcd for [C$_{13}$H$_{16}$N$_2$O$_3$+H]$^+$ 249.3.

B. (E)-tert-butyl 3-((1H-indazol-6-yl)methylene)-2-oxoindolin-5-ylcarbamate

The title compound was synthesized according to the method described for Example A11B from tert-butyl 2-oxoindolin-5-ylcarbamate (100 mg, 0.403 mmol) and precipitation with CH$_2$Cl$_2$ to obtain the title compound (70 mg, 46%). $^1$H NMR (400 MHz, CD$_3$OD) δ 8.92 (s, 1H), 8.09 (s, 1H), 7.89-7.80 (m, 4H), 7.18 (d, J=7.0 Hz, 1H), 6.80 (d, J=8.3 Hz, 1H), 1.56 (s, 911); MS ESI 377.3 [M+H]$^+$, calcd for [C$_{21}$H$_{20}$N$_4$O$_3$+H]$^+$ 377.16.

Example A13

(E)-N-(3-((1H-indazol-6-yl)methylene)-2-oxoindolin-6-yl)acetamide

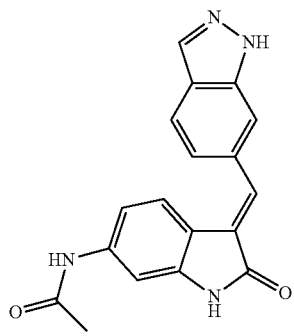 [SMILES: CC(=O)Nc1ccc2c(c1)NC(=O)/C2=C/c1ccc2cn[nH]c2c1]

The title compound was synthesized according to the method described for Example A11B except substituting N-(2-oxoindolin-6-yl)acetamide (25 mg, 0.131 mmol), to obtain 12 mg, 29%. $^1$H NMR (400 MHz, d$_6$-DMSO) δ 13.25 (s, 1H), 10.59 (s, 1H), 10.08 (s, 1H), 8.15 (s, 1H), 7.88 (s, 2H), 7.62 (s, 1H), 7.54 (d, J=6.9 Hz, 1H), 7.50 (s, 1H), 7.41 (d, J=7.9 Hz, 1H), 6.87 (d, J=7.0 Hz, 1H), 2.04 (s, 3H); MS ESI 319.1 [M+H]$^+$, calcd for [C$_{18}$H$_{14}$N$_4$O$_2$+H]$^+$ 319.12.

Example A14

(E)-3-((1H-benzo[d][1,2,3]triazol-5-yl)methylene)-5-(trifluoromethoxy)indolin-2-one

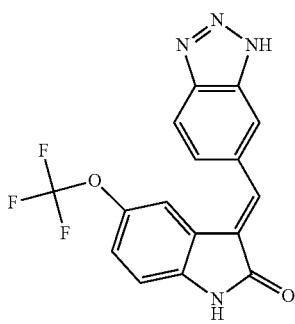 [SMILES: O=C1Nc2ccc(OC(F)(F)F)cc2/C1=C\c1ccc2nn[nH]c2c1]

A scintillation vial was charged with 5-(trifluoromethoxy)indolin-2-one (27 mg, 0.124 mmol), 1H-benzo[d][1,2,3]triazole-5-carbaldehyde (20 mg, 0.136 mmol), piperidine (2 uL, 0.012 mmol) and MeOH (2 mL). The reaction was then heated to 60° C. for 2 hrs. The MeOH was removed in vacuo and the residue purified by column chromatography (silica gel, 95:4:1, CH$_2$Cl$_2$/MeOH/AcOH) to give the title compound as a yellow solid (10 mg, 23%). $^1$H NMR (400 MHz, CD$_3$OD) δ 8.23 (s, 1H), 8.04 (d, J=4.5 Hz, 1H), 8.02 (s, 1H), 7.77 (d, J=9.3 Hz, 1H), 7.42 (s, 1H), 7.21-7.18 (m, 1H), 6.99 (s, 1H); MS ESI 347.0 [M+H]$^+$, calcd for [C$_{16}$H$_9$F$_3$N$_4$O$_2$+H]$^+$ 347.08.

Example A15

(E)-3-((1H-indazol-6-yl)methylene)-2-oxoindolin-5-aminium 2,2,2-trifluoroacetate

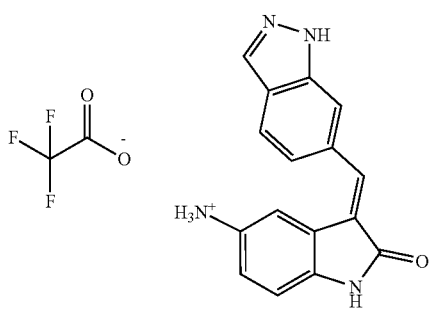 [SMILES: O=C(O)C(F)(F)F ; [NH3+]c1ccc2c(c1)/C(=C\c1ccc3cn[nH]c3c1)C(=O)N2]

To (E)-tert-butyl 3-((1H-indazol-6-yl)methylene)-2-oxoindolin-5-ylcarbamate (15 mg, 0.040 mmol) in CH$_2$Cl$_2$ (2 mL) was added TFA (0.1 mL). After 1.5 hrs the solvent was removed and the product precipitated with ether and filtered washing with ether to give 9 mg, 56% of the title compound as a brown solid. $^1$H NMR (400 MHz, d$_6$-DMSO) δ 13.41 (s, 1H), 10.79 (s, 1H), 9.25-8.90 (bs, 3H), 9.01 (s, 1H), 8.14 (s, 1H), 8.00-7.96 (m, 2H), 7.82 (d, J=8.5 Hz, 1H), 7.56 (s, 1H), 7.09-7.07 (m, 1H), 6.86 (d, J=8.1 Hz, 1H); MS ESI 277.0 [M]$^+$, calcd for [C$_{16}$H$_{13}$N$_4$O]$^+$ 277.11.

Example A16

(E)-3-((1H-indazol-6-yl)methylene)-5-fluoroindolin-2-one

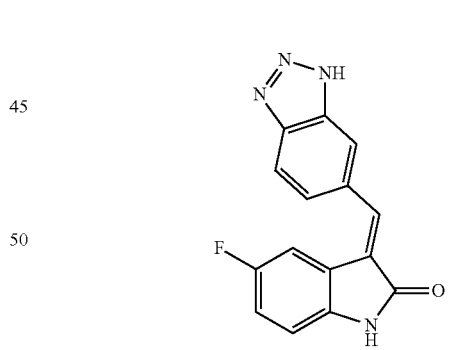

A scintillation vial was charged with 5-fluoroindolin-2-one (40 mg, 0.265 mmol), 1H-indazole-6-carbaldehyde (43 mg, 0.292 mmol), piperidine (3 uL, 0.027 mmol) and MeOH (2 mL). The reaction was then heated to 60° C. for 2 hrs. LC-MS analysis of the filtered yellow solid indicated a 9:1 mixture of geometric isomers. The mixture was resolved through prep-HPLC purification to give 11 mg, 15% of the major isomer (E) as the title compound. The minor fraction was also isolated; see Example A32. $^1$H NMR (400 MHz, d$_6$-DMSO) δ 13.31 (s, 1H), 10.66 (s, 1H), 8.18 (s, 1H), 7.92 (d, J=8.7 Hz, 1H), 7.91 (s, 1H), 7.86 (s, 1H), 7.42 (d, J=8.5 Hz, 1H), 7.29 (d, J=9.5 Hz, 1H), 7.10 (t, J=6.8 Hz, 1H), 6.88 (dd, J1=8.8 Hz, J2=4.7, 1H); MS ESI 280.0 [M+H]$^+$, calcd for [C$_{16}$H$_{10}$FN$_3$O+H]$^+$ 280.09.

Example A17

(E)-N-(3-((1H-benzo[d][1,2,3]triazol-5-yl)methylene)-2-oxoindolin-6-yl)acetamide

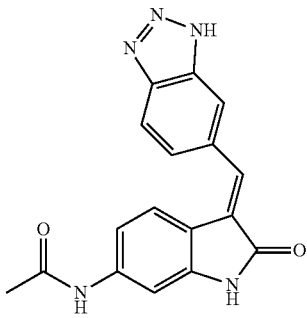 [SMILES: CC(=O)Nc1ccc2c(c1)NC(=O)/C2=C/c1ccc2nn[nH]c2c1]

The title compound was synthesized according to the method described for Example A11B except substituting N-(2-oxoindolin-6-yl)acetamide (30 mg, 0.158 mmol) and 1H-benzo[d][1,2,3]triazole-6-carbaldehyde (26 mg, 0.174 mmol) to obtain 22 mg, 44%. $^1$H NMR (400 MHz, d$_6$-DMSO) δ ~16 (s, 1H), 10.60 (s, 1H), 10.10 (s, 1H), 8.23 (s, 1H), 8.01 (s, 1H), 7.73 (d, J=8.0 Hz, 1H), 7.64 (s, 1H), 7.51 (s, 1H), 7.47 (d, J=8.0 Hz, 1H), 6.86 (d, J=7.4 Hz, 1H), 2.02 (s, 3H); MS ESI 320.1 [M+H]$^+$, calcd for [C$_{17}$H$_{13}$N$_5$O$_2$+H]$^+$ 320.11.

Example A18

((E)-N-(3-((1H-indazol-5-yl)methylene)-2-oxoindolin-6-yl)acetamide

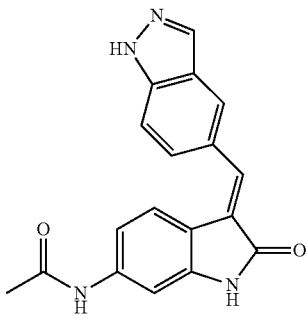 [SMILES: CC(=O)Nc1ccc2c(c1)NC(=O)/C2=C/c1ccc2[nH]ncc2c1]

The title compound was synthesized according to the method described for Example A11B except substituting N-(2-oxoindolin-6-yl)acetamide (40 mg, 0.210 mmol) and 1H-indazole-5-carbaldehyde (34 mg, 0.231 mmol) to obtain 41 mg, 61%. $^1$H NMR (400 MHz, d$_6$-DMSO) δ 13.31 (s, 1H), 10.55 (s, 1H), 10.07 (s, 1H), 8.19 (s, 1H), 8.15 (s, 1H), 7.71-7.64 (m, 2H), 7.61 (s, 1H), 7.57 (d, J=8.4 Hz, 1H), 7.48 (s, 1H), 6.89 (d, J=8.3 Hz, 1H), 2.04 (s, 3H); MS ESI 319.1 [M+H]$^+$, calcd for [C$_{18}$H$_{14}$N$_4$O$_2$+H]$^+$ 319.12.

Example A19

(E)-3-((1H-benzo[d]imidazol-5-yl)methylene)indolin-2-one

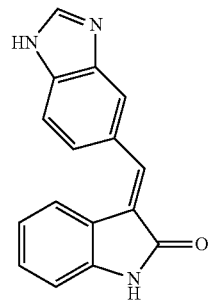

Indolin-2-one (80 mg, 0.60 mmol), 1H-benzo[d]imidazole-5-carbaldehyde (97 mg, 0.66 mmol) and piperidine (2 drops) in EtOH (2 mL) were heated with stirring in a sealed tube under microwave irradiation at 90° C. for 15 min. A yellow precipitate was filtered and rinsed with EtOH. Recrystallization from EtOH afforded the title compound as a yellow powder (15.5 mg, 10%). $^1$H NMR (400 MHz, DMSO-d$_6$) δ ppm 12.71 (br. s., 1H), 10.59 (s, 1H), 8.35 (s, 1H), 7.99 (s, 1H), 7.78 (s, 1H), 7.65-7.75 (m, 2H), 7.59 (d, J=8.34 Hz, 1H), 7.22 (t, J=7.58 Hz, 1H), 6.82-6.91 (m, 2H); MS ESI [M+H]$^+$ 262.0, calcd for [C16H11N3O+H]$^+$ 262.3.

Example A20

N'-[(3E)-3-(1H-indazol-6-ylmethylidene)-2-oxo-2,3-dihydro-1H-indol-5-yl]-N,N-dimethylsulfamide

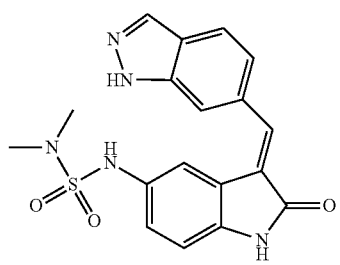 [SMILES: CN(C)S(=O)(=O)Nc1ccc2c(c1)/C(=C\c1ccc3cn[nH]c3c1)C(=O)N2]

To a solution of N,N-dimethyl-N-(2-oxo-2,3-dihydro-1H-indol-5-yl)sulfamide (28 mg, 0.11 mmol) was added 1H-indazole-6-carbaldehyde (18 mg, 0.12 mmol), piperidine (2 uL, 0.012 mmol) and MeOH (2 mL). The reaction was then heated to 85° C. for 30 min. The MeOH was removed in vacuo and the residue purified by column chromatography (silica gel, 95:5, CH$_2$Cl$_2$/MeOH) to give 14 mg, 33% of the title compound as an orange solid. $^1$H NMR (400 MHz, CDCl$_3$) δ 8.13 (s, 1H), 7.91 (s, 1H), 7.84 (s, 1H), 7.64 (s, 1H), 7.45 (d, J=8.3 Hz, 1H), 7.07 (d, J=8.1 Hz, 1H), 6.86 (d, J=8.3 Hz, 1H), 2.59 (s, 6H); MS ESI 384.1 [M+H]$^+$, calcd for [C$_{18}$H$_{17}$N$_5$O$_3$S+H]$^+$ 384.1.

Example A21

N'-[(3E)-3-(1H-benzotriazol-5-ylmethylidene)-2-oxo-2,3-dihydro-1H-indol-5-yl]-N,N-dimethylsulfamide

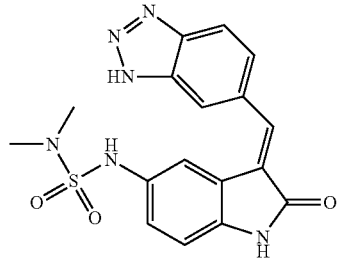 [SMILES: CN(C)S(=O)(=O)Nc1ccc2c(c1)/C(=C\c1ccc3nn[nH]c3c1)C(=O)N2]

According to the method described in example A20, except substituting 1H-benzo[d][1,2,3]triazole-5-carbaldehyde (18 mg, 0.12 mmol), the title compound was obtained as an orange solid (16 mg, 38%). $^1$H NMR (400 MHz, CDCl$_3$) δ 8.20 (s, 1H), 8.02 (d, J=8.3 Hz, 1H), 7.92 (s, 1H), 7.78 (d, J=8.3 Hz, 1H), 7.59 (s, 1H), 7.09 (d, J=8.1 Hz, 1H), 6.87 (d, J=8.6 Hz, 1H), 2.61 (s, 6H); MS ESI 385.1 [M+H]$^+$, calcd for [C$_{17}$H$_{16}$N$_6$O$_3$S+H]$^+$ 385.1.

Example A22

(E)-N-(3-((1H-indazol-6-yl)methylene)-2-oxoindolin-5-yl)acetamide

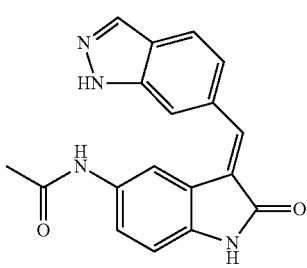 [SMILES: CC(=O)Nc1ccc2c(c1)/C(=C\c1ccc3cn[nH]c3c1)C(=O)N2]

To a solution of N-(2-oxoindolin-5-yl)acetamide (19 mg, 0.1 mmol) was added 1H-indazole-6-carbaldehyde (16 mg, 0.12 mmol), piperidine (2 uL, 0.011 mmol) and MeOH (2 mL). The reaction was then heated to 85° C. for 30 min. The MeOH was removed in vacuo and the solid triturated with ether to give 11 mg, 34% of the title compound as an orange solid. $^1$H NMR (400 MHz, CD$_3$OD) δ 8.13 (s, 1H), 8.06 (s, 1H), 7.92-7.88 (m, 2H), 7.84 (s, 1H), 7.49 (d, J=8.6 Hz, 1H), 7.35 (d, 1H), 6.88 (d, J=8.3 Hz, 1H), 2.04 (s, 3H); MS ESI 319.1 [M+H]$^+$, calcd for [C$_{18}$H$_{17}$N$_5$O$_3$S+H]$^+$ 319.11.

Example A23

(E)-N-(3-((1H-benzo[d][1,2,3]triazol-5-yl)methylene)-2-oxoindolin-5-yl)acetamide

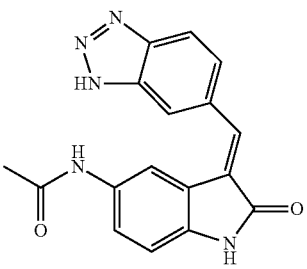 [SMILES: CC(=O)Nc1ccc2c(c1)/C(=C\c1ccc3nn[nH]c3c1)C(=O)N2]

According to the method of Example A22, except substituting 1H-benzo[d][1,2,3]triazole-5-carbaldehyde (16 mg, 0.12 mmol), the title compound was obtained as an orange solid (7 mg, 22%). $^1$H NMR (400 MHz, DMSO-d$_6$) δ 10.54 (s, 1H), 9.73 (s, 1H), 8.32-8.22 (m, 1H), 8.05-7.75 (m, 2H), 7.92 (s, 1H), 7.80-7.7 (m, 2H), 7.47 (d, 1H), 6.82 (d, J=8.3 Hz, 1H), 1.92 (s, 3H); MS ESI 320.0 [M+H]$^+$, calcd for [C$_{17}$H$_{13}$N$_5$O$_2$+H]$^+$ 320.1.

Example A24

(E)-N-(3-((1H-benzo[d][1,2,3]triazol-5-yl)methylene)-2-oxoindolin-5-yl)methanesulfonamide

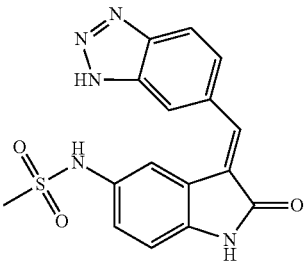 [SMILES: CS(=O)(=O)Nc1ccc2c(c1)/C(=C\c1ccc3nn[nH]c3c1)C(=O)N2]

According to the method of Example A20, except substituting N-(2-oxoindolin-5-yl)methanesulfonamide (12 mg, 0.053 mmol) and 1H-benzo[d][1,2,3]triazole-5-carbaldehyde (9 mg, 0.058 mmol), the title compound was obtained as an orange solid (8 mg, 42%). $^1$H NMR (400 MHz, CDCl$_3$) δ 8.22 (s, 1H), 8.00 (d, J=8.6 Hz, 1H), 7.93 (s, 1H), 7.80 (d, J=8.4 Hz, 1H), 7.61 (s, 1H), 7.14 (d, J=8.4 Hz, 1H), 6.91 (d, J=8.3 Hz, 1H), 2.86 (s, 3H); MS ESI 356.0 [M+H]$^+$, calcd for [C$_{16}$H$_{13}$N$_5$O$_3$S+H]$^+$ 356.1.

Example A25

(E)-N-(3-((1H-indazol-6-yl)methylene)-2-oxoindolin-5-yl)methanesulfonamide

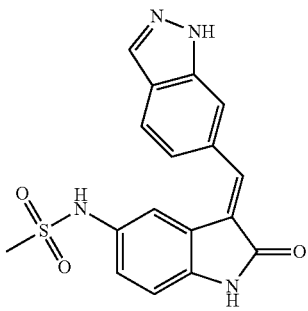 [SMILES: CS(=O)(=O)Nc1ccc2c(c1)/C(=C\c1ccc3cn[nH]c3c1)C(=O)N2]

According to the method of Example A20, except substituting N-(2-oxoindolin-5-yl)methanesulfonamide (10 mg, 0.044 mmol), the title compound was obtained as an orange solid (2 mg, 13%). $^1$H NMR (400 MHz, DMSO-$d_6$) δ 13.29 (s, 1H), 10.61 (s, 1H), 8.17 (s, 1H), 7.86-7.87 (m, 2H), 7.79 (s, 1H), 7.61 (s, 1H), 7.43 (d, J=7.8 Hz, 1H), 7.11 (d, J=7.8 Hz, 1H), 6.86 (d, J=8.0 Hz, 1H), 2.86 (s, 3H); MS ESI 355.1 [M+H]$^+$, calcd for [C$_{16}$H$_{13}$N$_5$O$_3$S+H]$^+$ 355.1.

Example A26

(E)-1-(3-((1H-indazol-6-yl)methylene)-2-oxoindolin-5-yl)-3-isopropylurea

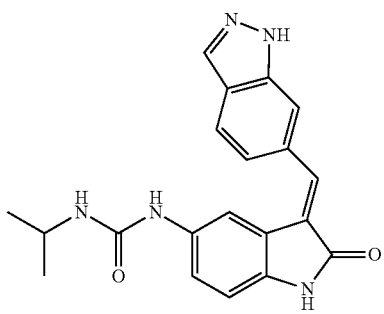 [SMILES: CC(C)NC(=O)Nc1ccc2c(c1)/C(=C\c1ccc3cn[nH]c3c1)C(=O)N2]

According to the method of Example A20, except substituting 1-isopropyl-3-(2-oxoindolin-5-yl)urea (23 mg, 0.099 mmol), the title compound was obtained as an orange solid (8 mg, 22%). $^1$H NMR (400 MHz, DMSO-$d_6$) δ 13.29 (s, 1H), 10.41 (s, 1H), 8.16 (s, 1H), 8.00 (s 1H), 7.87 (m, 2H), 7.72 (s, 1H), 7.60 (s, 1H), 7.45 (d, J=9.4 Hz, 1H), 7.37 (d, J=7.8 Hz, 1H), 6.74 (d, J=8.1 Hz, 1H), 5.76 (d, J=8.6 Hz, 1H), 3.75-3.70 (m, 1H), 1.03-1.00 (m, 6H); MS ESI 362.1 [M+H]$^+$, calcd for [C$_{20}$H$_{19}$N$_5$O$_2$+H]$^+$ 362.2.

Example A27

(E)-1-(3-((1H-benzo[d][1,2,3]triazol-5-yl)methylene)-2-oxoindolin-5-yl)-3-isopropylurea

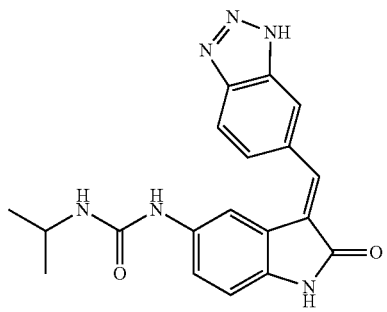 [SMILES: CC(C)NC(=O)Nc1ccc2c(c1)/C(=C\c1ccc3nn[nH]c3c1)C(=O)N2]

According to the method of Example A20, except substituting 1-isopropyl-3-(2-oxoindolin-5-yl)urea (23 mg, 0.099 mmol) and 1H-benzo[d][1,2,3]triazole-5-carbaldehyde (15 mg, 0.11 mmol), the title compound was obtained as an orange solid (6 mg, 16%). $^1$H NMR (400 MHz, DMSO-$d_6$) δ 10.44 (s, 1H), 8.01 (s 1H), 7.75 (s, 1H), 7.57-7.59 (m, 2H), 7.31 (d, J=7.6 Hz, 1H), 6.74 (d, J=8.4 Hz, 1H), 5.76 (d, J=7.6 Hz, 1H), 3.75-3.70 (m, 1H), 1.03-1.00 (d, 6H); MS ESI 363.1 [M+H]$^+$, calcd for [C$_{20}$H$_{19}$N$_5$O$_2$+H]$^+$ 363.2.

Example A28

(E and Z)-3-(3-((1H-indazol-6-yl)methylene)-2-oxoindolin-6-yl)pyridinium 2,2,2-trifluoroacetate

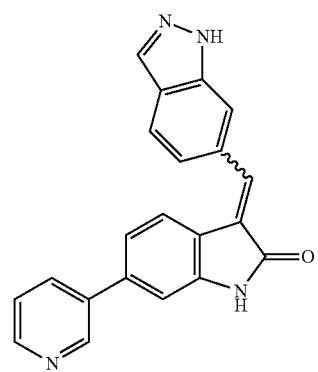 [SMILES: O=C1Nc2cc(-c3cccnc3)ccc2C1=Cc1ccc2cn[nH]c2c1]

6-(Pyridin-3-yl)indolin-2-one (25 mg, 0.12 mmol) and 1H-indazole-6-carbaldehyde (17.4 mg, 0.12 mmol) were heated with stirring in a sealed tube under microwave irradiation at 90° C. for 15 min. The crude mixture was concentrated and purified by prepTLC (SiO$_2$ 20% MeOH/DCM) followed by HPLC. Subsequent recrystalization from MeCN provided the title compound as a dark orange solid (6.2 mg, 12%) in a (2:1) mixture of E and Z isomers. E-isomer: $^1$H NMR (400 MHz, CD$_3$OD) 8.97 (br. s., 1H), 8.67 (br. s., 1H), 8.45 (d, J=7.83 Hz, 1H), 8.15 (s, 1H), 7.76-8.01 (m, 5H), 7.50 (d, J=8.34 Hz, 1H), 7.22-7.29 (m, 2H); Z-isomer: $^1$H NMR (400

MHz, CD₃OD) δ ppm 9.01 (br. s., 1H), 8.67 (br. s., 1H), 8.54 (d, J=7.33 Hz, 1H), 8.09 (s, 1H), 7.76-8.01 (m, 6H), 7.43 (d, J=7.58 Hz, 1H), 7.22-7.29 (m, 1H); MS ESI 339.1 (100) [M+H]⁺, calcd for [C₂₁H₁₄N₄O+H]⁺ 339.4.

Example A29

(E)-3-((1H-benzo[d][1,2,3]triazol-5-yl)methylene)-6-(pyridin-3-yl)indolin-2-one

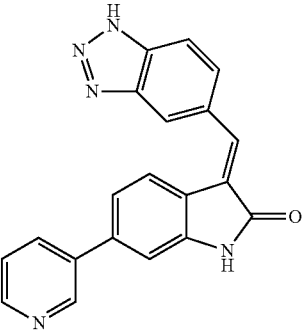 [SMILES: O=C1Nc2cc(-c3cccnc3)ccc2/C1=C\c1ccc2[nH]nnc2c1]

According to the method of Example A19, utilizing 6-(pyridin-3-yl)indolin-2-one (37.1 mg, 0.18 mmol) and 1H-benzo[d][1,2,3]triazole-5-carbaldehyde (25.8 mg, 0.18 mmol), the title compound was obtained as an orange solid (20 mg, 34%). ¹H NMR (400 MHz, DMSO-d6) δ ppm 15.96 (br.s. 1H), 10.83 (s, 1H), 8.86 (br. s., 1H), 8.57-8.61 (m, 1H), 8.45 (br. s., 0.5H), 8.18 (br. s., 1H), 8.05 (d, J=7.83 Hz, 1H), 7.95 (br. s., 1H), 7.86 (s, 0.5H), 7.75 (br. s., 1H), 7.64 (d, J=7.33 Hz, 1H), 7.49 (dd, J=7.71, 4.93 Hz, 1H), 7.22 (d, J=7.58 Hz, 1H), 7.17 (s, 1H); ¹H NMR (400 MHz, DMF-d7) δ ppm 10.77 (br. s., 1H), 8.94 (br. s., 1H), 8.61-8.65 (m, 1H), 8.42 (s, 1H), 8.13 (t, J=7.96 Hz, 1H), 7.93 (s, 1H), 7.90 (d, J=8.84 Hz, 1H), 7.78 (d, J=7.83 Hz, 1H), 7.52 (dd, J=7.71, 4.67 Hz, 1H), 7.33 (s, 1H), 7.30 (d, J=7.83 Hz, 1H); MS ESI 340.1 (100) [M+H]⁺, calcd for [C₂₀H₁₃N₅O+H]⁺ 340.4.

Example A30

(E)-3-((1H-indazol-5-yl)methylene)-6-(pyridin-3-yl)indolin-2-one

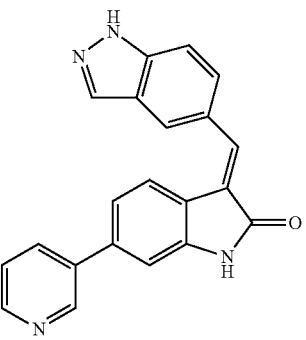 [SMILES: O=C1Nc2cc(-c3cccnc3)ccc2/C1=C\c1ccc2[nH]ncc2c1]

According to the method of Example A19, utilizing 6-(pyridin-3-yl)indolin-2-one (25 mg, 0.12 mmol) and 1H-indazole-5-carbaldehyde (17.4 mg, 0.12 mmol), the title compound was obtained as an orange solid (7 mg, 17%). ¹H NMR (400 MHz, DMSO-d₆) δ ppm 13.32 (br. s., 1H), 10.81 (s, 1H), 9.04 (s, 1H), 8.89 (d, J=1.26 Hz, 1H), 8.57 (dd, J=4.55, 1.26 Hz, 1H), 8.52 (d, J=7.83 Hz, 1H), 8.25 (s, 1H), 8.06-8.11 (m, 1H), 8.04 (s, 1H), 7.87 (d, J=7.83 Hz, 1H), 7.62 (d, J=8.84 Hz, 1H), 7.49 (dd, J=7.33, 4.55 Hz, 1H), 7.38 (dd, J=7.83, 1.26 Hz, 1H), 7.11 (d, J=1.01 Hz, 1H); MS ESI 339.1 (100) [M+H]⁺, calcd for [C₂₁H₁₄N₄O+H]⁺ 339.4.

Example A31

(E)-3-((1H-indazol-5-yl)methylene)-5-bromoindolin-2-one

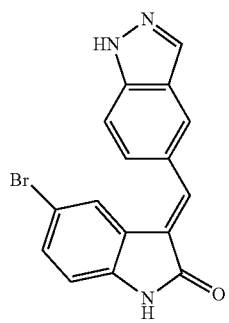 [SMILES: O=C1Nc2ccc(Br)cc2/C1=C\c1ccc2[nH]ncc2c1]

The title compound was synthesized according to the method described for Example A11B except substituting 5-bromooxindole (40 mg, 0.189 mmol) and 1H-indazole-5-carbaldehyde (30 mg, 0.208 mmol) to obtain the title compound (6.8 mg, 4.0%) as a yellow solid. ¹H NMR (400 MHz, CD₃OD) δ 8.19 (s, 1H), 8.17 (s, 1H), 7.95 (s, 1H), 7.77 (s, 1H), 7.76-7.68 (m, 2H), 7.38 (d, J=8.59 Hz, 1H), 6.87 (d, J=8.59 Hz, 1H); MS ESI 340.1 [M+H]⁺, calcd for [C₁₆H₁₀BrN₃O+H]⁺ 340.01.

Example A32

(Z)-3-((1H-indazol-6-yl)methylene)-5-fluoroindolin-2-one

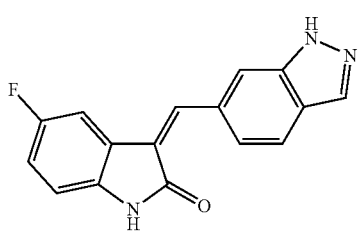 [SMILES: O=C1Nc2ccc(F)cc2/C1=C/c1ccc2cn[nH]c2c1]

The title compound was isolated through resolution of mixed fractions of (E) and (Z) isomers from Example A16 by preparatory-HPLC to obtain 6.1 mg (8.0%) of a yellow solid. ¹H NMR (400 MHz, CD₃OD) δ 8.94 (s, 1H), 8.07 (s, 1H), 7.94-7.85 (m, 2H), 7.80 (d, J=8.59 Hz, 1H), 7.49 (d, J=8.84

Hz, 1H), 6.97 (t, J=9.20 Hz, 1H), 6.87-6.81 (m, 1H); MS ESI 280.0 [M+H]+, calcd for [C$_{16}$H$_{10}$FN$_3$O+H]+ 280.09.

Example A33

(E)-3-((1H-benzo[d][1.2.3]triazol-5-yl)methylene)-1-methylindolin-2-one

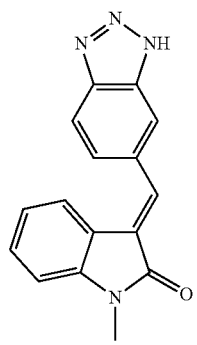 [SMILES: CN1C(=O)/C(=C/c2ccc3nn[nH]c3c2)c2ccccc21]

The title compound was synthesized according to the method described for Example A11B, except substituting 1-methylindolin-2-one (18 mg, 0.124 mmol) and 1H-benzo[d][1,2,3]triazole-6-carbaldehyde (20 mg, 0.136 mmol) and then purified by preparatory HPLC to obtain 3.4 mg, 10% of a yellow solid. $^1$H NMR (400 MHz, CD$_3$OD) δ 8.23 (bs, 1H), 8.00 (bs, 1H), 7.95 (s, 1H), 7.84-7.75 (m, 1H), 7.59 (d, J=7.58 Hz, 1H), 7.34 (t, J=8.00 Hz, 1H), 7.04 (d, J=7.83 Hz, 1H), 6.92 (d, J=7.58 Hz, 1H), 3.35 (s, 3H); MS ESI 277.0 [M+H]+, calcd for [C$_{16}$H$_{12}$N$_4$O+H]+ 277.11.

Example A34

(E)-3-((1H-indazol-6-yl)methylene)-1-methylindolin-2-one

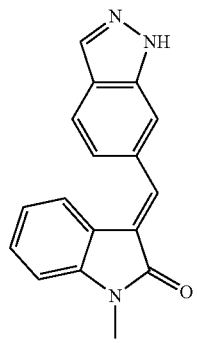 [SMILES: CN1C(=O)/C(=C/c2ccc3cn[nH]c3c2)c2ccccc21]

The desired product was synthesized according to the method described for Example A11B, except substituting 1-methylindolin-2-one (37 mg, 0.249 mmol) and 1H-indazole-6-carbaldehyde (40 mg, 0.274 mmol) and then purified by preparatory HPLC to obtain the title compound (12 mg, 17%) as a yellow solid. $^1$H NMR (400 MHz, CD$_3$OD) δ 8.13 (s, 1H), 7.96-7.86 (m, 3H), 7.67 (d, J=7.83 Hz, 1H), 7.46 (d, J=8.08 Hz, 1H), 7.33 (t, J=7.71 Hz, 1H), 7.02 (d, J=7.83 Hz, 1H), 6.93 (t, J=7.71 Hz, 1H), 3.31 (s, 3H); MS ESI 276.1 [M+H]+, calcd for [C$_{17}$H$_{13}$N$_3$O+H]+ 276.11.

Example A35

(E)-3-((1H-indazol-6-yl)methylene)-5-bromoindolin-2-one

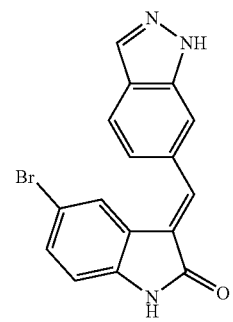 [SMILES: O=C1Nc2ccc(Br)cc2/C1=C\c1ccc2cn[nH]c2c1]

The title compound was synthesized according to the method described for Example A11B except substituting 5-bromooxindole (40 mg, 0.189 mmol) and 1H-indazole-6-carbaldehyde (30 mg, 0.208 mmol) to obtain 1.0 mg (1.6%) of a yellow solid. $^1$H NMR (400 MHz, CD$_3$OD) δ 8.16 (s, 1H), 7.98-7.92 (m, 2H), 7.87 (s, 1H), 7.73 (s, 1H), 7.44 (d, J=8.34 Hz, 1H), 7.39 (d, J=8.59 Hz, 1H), 6.87 (d, J=8.34 Hz, 1H); MS ESI 340.1 [M+H]+, calcd for [C$_{16}$H$_{10}$BrN$_3$O+H]+ 340.01.

Example A36

(E)-3-((1H-indazol-6-yl)methylene)-6-chloroindolin-2-one

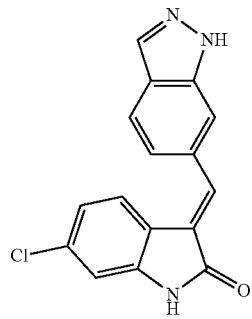 [SMILES: O=C1Nc2cc(Cl)ccc2/C1=C\c1ccc2cn[nH]c2c1]

The title compound was synthesized according to the method described for Example A11B except substituting 6-chlorooxindole (30 mg, 0.179 mmol) and 1H-indazole-6-carbaldehyde (29 mg, 0.197 mmol) to obtain 22 mg (42%) of a yellow solid. $^1$H NMR (400 MHz, d$_6$-DMSO) δ 13.30 (s, 1H), 10.79 (s, 1H), 8.16 (s, 1H), 7.90-7.87 (m, 2H), 7.83 (s, 1H), 7.56 (d, J=8.00 Hz, 1H), 7.41 (d, J=8.80 Hz, 1H), 6.93-6.88 (m, 2H); MS ESI 296.0 [M+H]+, calcd for [C$_{16}$H$_{10}$ClN$_3$O+H]+ 296.06.

Example A37

(E)-tert-butyl 3-((1H-indazol-6-yl)methylene)-2-oxoindolin-6-ylcarbamate

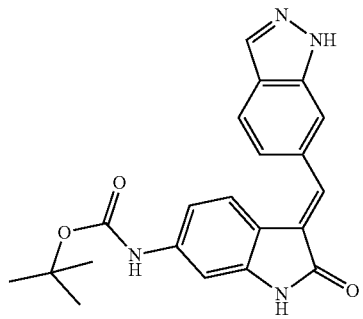 [SMILES: CC(C)(C)OC(=O)Nc1ccc2c(c1)NC(=O)/C2=C/c1ccc2cn[nH]c2c1]

A. tert-butyl 2-oxoindolin-6-ylcarbamate

A THF (2.5 mL) solution of 6-aminoindolin-2-one (100 mg, 0.675 mmol) and di-t-butyl dicarbonate (155 mg, 0.709 mmol) at rt under N₂, was treated with Et₃N (0.28 mL, 2.03 mmol). The solvent was removed in vacuo and the residue purified by column chromatography (silica gel, CH₂Cl₂/MeOH, 98:2 to 95:5) to give 76 mg, 45% of a tan solid. ¹H NMR (400 MHz, CDCl₃) δ 7.21 (s, 1H), 7.10 (d, J=8.08 Hz, 1H), 6.88 (d, J=7.58 Hz, 1H), 3.45 (s, 2H), 1.51 (s, 9H); MS ESI 249.0 [M+H]⁺, calcd for [C₁₃H₁₆N₂O₃+H]⁺ 249.12.

B. (E)-tert-butyl 3-((1H-indazol-6-yl)methylene)-2-oxoindolin-6-ylcarbamate The synthetic method followed that described in Example A11B, with a modified purification procedure. The MeOH was removed in vacuo and the residue was treated with 95:5 CH₂Cl₂/MeOH. The resulting precipitate was filtered and washed with 95:5 CH₂Cl₂/MeOH to obtain the title compound as a yellow-brown solid (40 mg, 35%). ¹H NMR (400 MHz, CD₃OD) δ 8.11 (s, 1H), 7.89-7.83 (m, 2H), 7.71 (s, 1H), 7.52 (d, J=8.40 Hz, 1H), 7.44 (d, J=9.60 Hz, 1H), 7.29 (s, 1H), 6.73 (d, J=8.40 Hz, 1H), 1.51 (s, 9H); MS ESI 377.2 [M+H]⁺, calcd for [C₂₁H₂₀N₄O₃+H]⁺ 377.16.

Example A38

(E)-3-((1H-indazol-6-yl)methylene)-2-oxoindolin-6-aminium 2,2,2-trifluoroacetate

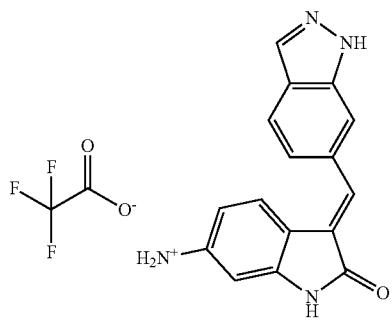 [SMILES: O=C([O-])C(F)(F)F ; [NH3+]c1ccc2c(c1)NC(=O)/C2=C/c1ccc2cn[nH]c2c1]

The title compound was synthesized according to the method described for Example A15 except substituting (E)-tert-butyl 3-((1H-indazol-6-yl)methylene)-2-oxoindolin-6-ylcarbamate (31 mg, 0.0823 mmol) to obtain 14 mg (44%) of a brown solid. ¹H NMR (400 MHz, CD₃OD) δ 8.09 (s, 1H), 7.85 (d, J=8.59 Hz, 1H), 7.82 (s, 1H), 7.55 (s, 1H), 7.49-7.37 (m, 2H), 6.34 (d, J=1.77 Hz, 1H), 6.23 (dd, J=8.46, 1.89 Hz, 1H); MS ESI 277.0 [M+H]⁺ calcd for [C₁₆H₁₂N₄O+H]⁺ 277.11.

Example A39

(E)-3-((3-iodo-1H-indazol-6-yl)methylene)indolin-2-one

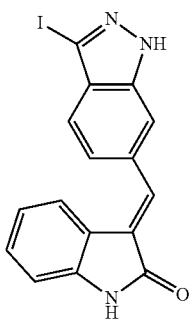 [SMILES: O=C1Nc2ccccc2/C1=C\c1ccc2c(I)n[nH]c2c1]

The title compound was synthesized from 3-iodo-1H-indazole-6-carbaldehyde (15 mg, 0.0551 mmol) and oxindole (8 mg, 0.0616 mmol) according to the method described for Example A11B and purified by column chromatography (silica gel, CH₂Cl₂/MeOH, 98:2 to 96:4) to obtain 6.9 mg, 33% of a yellow solid. ¹H NMR (400 MHz, CD₃OD) δ 7.89-7.82 (m, 2H), 7.63-7.49 (m, 3H), 7.23 (t, J=8.21 Hz, 1H), 6.91 (d, J=7.07 Hz, 1H), 6.89-6.83 (m, 1H); MS ESI 388.0 [M+H]⁺, calcd for [C₁₆H₁₀IN₃O+H]⁺ 387.99.

Example A40

(E & Z)-3-((3-amino-1H-indazol-5-yl)methylene)indolin-2-one

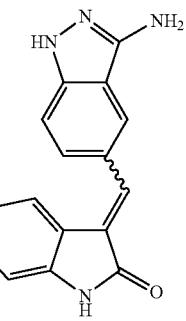

A. 5-(1,3-dioxolan-2-yl)-2-fluorobenzonitrile

To a solution of 2-fluoro-5-formylbenzonitrile (450 mg, 3 mmol) in toluene (10 mL) was added ethylene glycol (2 mL) and p-toluene sulfonic acid (25 mg). The solution was heated to 70° C. overnight. The solution was cooled to room temperature. Ethyl acetate (100 mL) was added and the solution was washed with sat. sodium bicarbonated (10 mL), water (10 mL) and brine (10 mL), dried over MgSO₄ and concentrated to a clear oil (567 mg, 98%). $^1$H NMR (400 MHz, CDCl$_3$) δ 7.78 (dd 1H, J=6.3, 2.3 Hz), 7.74-7.70 (m, 1H), 7.27-7.24 (m, 1H), 5.80 (s, 1H), 4.14-4.08 (m, 4H).

B. 5-(1,3-dioxolan-2-yl)-1H-indazol-3-amine

To a solution of 5-(1,3-dioxolan-2-yl)-2-fluorobenzonitrile (567 mg, 3 mmol) in n-butanol (5 mL) was added hydrazine hydrate (1.47 mL, 30 mmol). The solution was heated to 110° C. for 2 h and cooled to room temperature. The solution was stirred overnight and the resulting precipitate was collected to give the title compound as a white solid (220 mg, 36%). $^1$H NMR (400 MHz, DMSO-d$_6$) δ 11.44 (s, 1H), 7.78 (s, 1H), 7.28-7.26 (m, 1H), 7.21-7.19 (m, 1H), 5.72 (s, 1H), 5.37 (bs), 4.08-4.02 (m, 2H), 3.98-3.92 (m, 2H); MS ESI 206.0 [M+H]$^+$, calcd for [C$_{10}$H$_{11}$N$_3$O$_2$+H]$^+$ 206.1.

C. 3-amino-1H-indazole-5-carbaldehyde

To a solution of 5-(1,3-dioxolan-2-yl)-1H-indazol-3-amine (75 mg, 0.36 mmol) in THF (5 mL) and H$_2$O (0.5 mL) was added p-toluene sulfonic acid (25 mg) and the reaction was stirred overnight at room temperature. Ethyl acetate (75 mL) was added and the solution was washed with sat. sodium bicarbonate (5 mL), brine (2×5 mL), dried over MgSO$_4$ and concentrated to give the title compound as an orange solid (52 mg, 89%). $^1$H NMR (400 MHz, CD$_3$OD) δ 9.68 (s, 1H), 8.94 (s, 1H), 8.18 (d, 1H, J=7.6 Hz), 7.68 (d, 1H, J=8.4 Hz).

D. tert-butyl 5-formyl-1H-indazol-3-ylcarbamate

To a solution of 3-amino-1H-indazole-5-carbaldehyde (50 mg, 0.31 mmol) in DMF (3 mL) was added di-tert-butyl dicarbonate (135 mg, 0.62 mmol) and triethylamine (0.17 mL, 1.2 mmol). The mixture was stirred overnight and concentrated. The residue was dissolved into ethyl acetate (50 mL), washed with H$_2$O and dried over MgSO$_4$. The title compound was purified by silica gel chromatography (EtOAc/Hex 1:1) as a red solid (25 mg, 30%). $^1$H NMR (400 MHz, CD$_3$OD) δ 10.07 (s, 1H), 8.26-8.02 (m, 3H), 1.73-1.71 (m, 9H).

E. (E)-tert-butyl 5-((2-oxoindolin-3-ylidene)methyl)-1H-indazol-3-ylcarbamate To a solution of oxindole (13 mg, 0.01 mmol) and tert-butyl 5-formyl-1H-indazol-3-ylcarbamate (25 mg, 0.01 mmol) in ethanol (1 mL) was added piperidine (1 drop). The mixture was heated to 80° C. for 2 h and cooled to rt. The solution was loaded onto a silica gel column and the title compound was eluted with EtOAc/Hex 4:1 as a red solid (14 mg, 37%). $^1$H NMR (400 MHz, CD$_3$OD) δ 8.14-8.02 (m, 2H), 7.90-7.83 (m, 2H), 7.63 (s, 1H), 7.24 (bs, 1H), 7.00-6.91 (m, 2H), 1.71 (s, 9H).

F. (E and Z)-3-((3-amino-1H-indazol-5-yl)methylene)indolin-2-one

To a solution of (E)-tert-butyl 5-((2-oxoindolin-3-ylidene)methyl)-1H-indazol-3-ylcarbamate (14 mg, 0.04 mmol) in CH$_2$Cl$_2$ (1 mL) was added TFA (0.25 mL) and the reaction was stirred for 3 h. The solution was concentrated to dryness and purified by preparatory HPLC to give the title compound as a 3:2 mixture of E/Z isomers. ESI 277.0 [M+H]$^+$, calcd for [C$_{16}$H$_{12}$N$_4$O+H]$^+$ 277.1.

E-isomer: Short Retention Time by reverse phase HPLC; $^1$H NMR (400 MHz, CD$_3$OD) δ 8.93 (s, 1H), 8.50 (d, 1H, J=8.6 Hz), 7.82 (s, 1H), 7.64 (d, 1H, J=7.7 Hz), 7.41 (d, 1H, J=8.6 Hz), 7.26-7.21 (m 1H), 6.94-6.88 (m, 2H).

Z-isomer: Long Retention Time by reverse phase HPLC; $^1$H NMR (400 MHz, CD$_3$OD) δ 8.22 (s, 1H), 7.87 (d, 1H, J=8.9 Hz), 7.82 (s, 1H), 7.70 (d, 1H, J=7.0 Hz), 7.50 (d, 1H, J=8.8 Hz), 7.26-7.21 (m 1H), 7.05 (t, 1H, J=7.6 Hz) 6.94-6.88 (m, 1H).

Example A41

(E and Z)-3-((3-((E)-2-(pyridin-2-yl)vinyl)-1H-indazol-6-yl)methylene)indolin-2-one

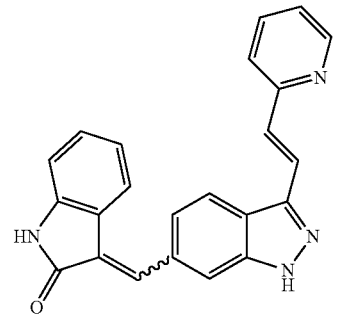 [SMILES: O=C1Nc2ccccc2C1=Cc1ccc2c(/C=C/c3ccccn3)n[nH]c2c1]

A. 3-iodo-1-(tetrahydro-2H-pyran-2-yl)-1H-indazole-6-carbaldehyde

An oven-dried round bottom flask under Ar was charged with 3-iodo-1H-indazole-6-carbaldehyde (50 mg, 0.184 mmol), THF (1.5 mL) and CH$_2$Cl$_2$ (1.0 mL). Methanesulfonic acid (1.4 uL, 0.0221 mmol) was added and the solution cooled with an ice-water bath. A solution of 3,4-dihydro-2H-pyran (41 uL, 0.460 mmol) in CH$_2$Cl$_2$ (0.5 mL) was then added dropwise over 15 minutes and the reaction stirred overnight. The solvents were removed in vacuo and the residue purified by column chromatography (silica gel, 99:1 to 98:2 CH$_2$Cl$_2$/MeOH) to give the title compound as a white powder (16 mg, 25%). $^1$H NMR (400 MHz, CDCl$_3$) δ 10.18 (s, 1H), 8.13 (s, 1H), 7.77 (d, J=8.4 Hz, 1H), 7.62 (d, J=8.4 Hz, 1H), 5.84-5.77 (m, 1H), 4.07-4.02 (m, 1H), 3.83-3.75 (m, 1H), 2.62-2.51 (m, 1H), 2.20-2.10 (m, 2H), 1.86-1.70 (m, 3H); MS ESI 378.9 [M+Na]$^+$, calcd for [C$_{13}$H$_{13}$IN$_2$O$_2$+Na]$^+$ 378.99.

B. Synthesis of (E)-3-(2-(pyridin-2-yl)vinyl)-1-(tetrahydro-2H-pyran-2-yl)-1H-indazole-6-carbaldehyde In a scintillation vial a solution of 3-iodo-1-(tetrahydro-2H-pyran-2-yl)-1H-indazole-6-carbaldehyde (24 mg, 0.0673 mmol), 2-vinylpyridine (9.4 uL, 0.0875 mmol), DIPEA (24 uL, 0.135 mmol) and DMF (1.0 mL) was purged with Ar for 20 min. Pd(OAc)$_2$ (1.5 mg, 0.0067 mmol) and P(o-tolyl)$_3$ (6.1 mg, 0.0202 mmol) were then added and the vial was capped and heated to 100° C. overnight. The solution was cooled to room temperature and extracted with EtOAc, washing with NH$_4$Cl$_{(sat.)}$, H$_2$O, and brine. The organic layer was dried over MgSO$_4$, the solvent removed in vacuo, and the residue purified by column chromatography (silica gel, 96:4 CH$_2$Cl$_2$/MeOH) to give 17 mg, 77% of a yellow oil which was 70% pure by NMR. This crude material was used for the subsequent synthetic step. $^1$H NMR (400 MHz, CD$_3$OD) δ 10.16 (s, 1H), 8.59 (s, 1H), 8.34 (s, 1H), 8.27 (d, J=8.4 Hz, 1H), 7.95-7.83 (m, 4H), 7.75 (m, 1H), 7.68 (d, J=16.0 Hz, 1H), 6.00 (d, J=9.6 Hz, 1H), 4.05-4.01 (m, 1H), 3.93-3.86 (m, 1H), 2.65-2.56 (m, 1H), 2.27-2.10 (m, 2H), 1.92-1.66 (m, 3H); MS ESI 334.1 [M+H]$^+$, calcd for [C$_{20}$H$_{19}$N$_3$O$_2$+H]$^+$ 334.16.

C. (E)-3-((3-((E)-2-(pyridin-2-yl)vinyl)-1-(tetrahydro-2H-pyran-2-yl)-1H-indazol-6-yl)methylene)indolin-2-one To a solution of (E)-3-(2-(pyridin-2-yl)vinyl)-1-(tetrahydro-2H-pyran-2-yl)-1H-indazole-6-carbaldehyde (25 mg, 0.0749 mmol), oxindole (10 mg, 0.0749 mmol), and MeOH (1 mL) was added piperidine (1 uL) and the reaction heated to 60° C. for 3 hours. The reaction was cooled to room temperature and the product yellow solid was precipitated with MeOH (1 mL) and then filtered to give 11 mg. The filtrate was purified by column chromatography (silica gel, 99:1 to 98:2 CH$_2$Cl$_2$/MeOH) to give an additional 6 mg of product (17 mg total, 50%). $^1$H NMR (400 MHz, CDCl$_3$) δ 8.69-8.62 (m, 1H), 8.14 (d, J=8.3 Hz, 1H), 8.00-7.91 (m, 3H), 7.77 (d, J=8.1 Hz, 1H), 7.72 (t, J=8.3 Hz, 1H), 7.63 (d, J=16.9 Hz, 1H), 7.53 (m, 2H), 7.44 (b.s., 1H), 7.25-7.17 (m, 2H), 6.92-6.86 (m, 2H), 5.77 (d, J=10.6 Hz, 1H), 4.09 (d, J=9.6 Hz, 1H), 3.84-3.74 (m, 1H), 2.67-2.53 (m, 1H), 2.24-2.13 (m, 2H), 1.85-1.66 (m, 3H); MS ESI 449.2 [M+H]$^+$, calcd for [C$_{28}$H$_{24}$N$_4$O$_2$+H]$^+$ 449.20.

D. (E and Z)-3-((3-((E)-2-(pyridin-2-yl)vinyl)-1H-indazol-6-yl)methylene)-indolin-2-one To a solution of (E)-3-((3-((E)-2-(pyridin-2-yl)vinyl)-1-(tetrahydro-2H-pyran-2-yl)-1H-indazol-6-yl)methylene)indolin-2-one (17 mg, 0.0379 mmol) in MeOH (3 mL) was added p-TsOH.H$_2$O (30 mg). The reaction was heated to reflux for 5 hours at which time LC-MS indicated complete consumption of starting material. The MeOH was removed in vacuo and the product extracted into EtOAc washing with NaHCO$_3$ $_{(sat)}$, H$_2$O, and brine. The organic layer was dried over MgSO$_4$ and the solvent removed to give an orange solid. The solid was titurated 2× with 5:1 hexanes/Et$_2$O while decanting off the solvent to give the orange solid (10 mg, 71%). The compound was a 3:1 mixture of (E)/(Z) isomers by analysis of the proton NMR. $^1$H NMR (400 MHz, d6-DMSO) δ 13.60, 13.50 (s, 1H), 10.71, 10.65 (s, 1H), 9.01, 7.92 (s, 1H), 8.61 (m, 1H), 8.33, 8.25 (d, J=8.5 Hz, 1H), 8.08-7.53 (m, 7H), 7.34-7.17 (m, 2H), 6.93-6.82 (m, 2H); MS ESI 365.2 [M+H]$^+$, calcd for [C$_{23}$H$_{16}$N$_4$O+H]$^+$ 365.14.

Example A42

(E)-3-((1H-indazol-6-yl)methylene)-7-fluoroindolin-2-one

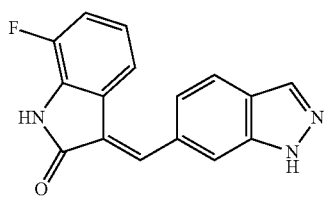 [SMILES: O=C1Nc2c(F)cccc2/C1=C\c1ccc2cn[nH]c2c1]

According to the method described in example A6, except substituting 7-fluorooxindole (15 mg, 0.1 mmol) the title compound was prepared as a brown solid (20 mg, 71%). $^1$H NMR (400 MHz, CD$_3$OD) δ 8.14 (s, 1H), 7.69 (s, 1H), 7.25 (d, 1H, J=8 Hz), 7.90 (s, 1H), 7.48 (dd, 2H, J=8 Hz, 4 Hz), 7.08 (t, 1H, J=8 Hz), 6.89-6.84 (m, 1H); MS ESI [M+H]$^+$, calcd for [C$_{16}$H$_{10}$FN$_3$O+H]$^+$ 280.09; found m/z 280.1.

Example A43

(E)-3-((1H-indazol-6-yl)methylene)-7-chloroindolin-2-one

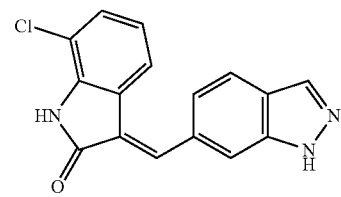 [SMILES: O=C1Nc2c(Cl)cccc2/C1=C\c1ccc2cn[nH]c2c1]

According to the method described in example A6, except substituting 7-chlorooxindole (17 mg, 0.1 mmol), the title compound was prepared as a dark yellow solid (29 mg, 97%). $^1$H NMR (400 MHz, DMSO) δ 13.33 (s, 1H), 11.07 (s, 1H), 8.16 (s, 1H), 7.90 (m, 3H), 7.55 (d, 1H, J=8 Hz), 7.42 (d, 1H, J=8 Hz), 7.32 (d, 1H, J=8 Hz), 6.88 (t, 1H, J=8 Hz); MS ESI [M+H]$^+$, calcd for [C$_{16}$H$_{10}$ClN$_3$O+H]$^+$ 296.06; found m/z 296.1.

Example A44

(E)-3-((1H-indazol-6-yl)methylene)-7-bromoindolin-2-one

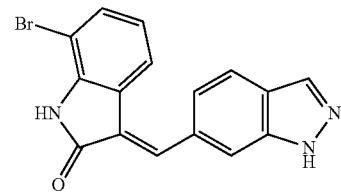

According to the method described in example A6, except substituting 7-bromooxindole (21 mg, 0.1 mmol), the title compound was prepared as a yellow solid (6.8 mg, 20%). $^1$H NMR (400 MHz, CD$_3$OD) δ 8.15 (s, 1H), 7.96 (s, 1H), 7.93 (d, 1H, J=8 Hz), 7.89 (s, 1H), 7.62 (d, 1H, J=8 Hz), 7.46 (d, 1H, J=8 Hz), 7.41 (d, 1H, J=8 Hz), 6.81 (t, 1H, J=8 Hz); MS ESI [M+H]$^+$, calcd for [C$_{16}$H$_{10}$BrN$_3$O+H]$^+$ 340.01; found m/z 340.0.

Example A45

(E and Z)-3-((1H-indazol-6-yl)methylene)-2-oxoindoline-7-carbonitrile

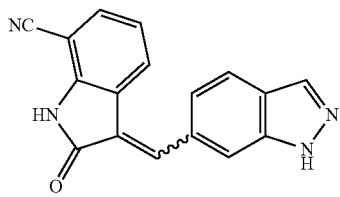 [SMILES: N#Cc1cccc2c1NC(=O)C2=Cc1ccc2cn[nH]c2c1]

According to the method described in example A6, except substituting 7-cyanooxindole (32 mg, 0.2 mmol), the title compound was prepared as a mixture of isomers (Z:E=41:59) and red solid (40 mg, 70%). Z isomer: $^1$H NMR (400 MHz, DMSO) δ 8.95 (s, 1H), 8.17 (m, 1H), 8.14 (m, 1H), 8.08 (d, 1H, J=7.6 Hz), 7.99 (d, 1H, J=7.6 Hz), 7.85-7.83 (m, 1H), 7.62-7.58 (m, 1H), 7.16 (t, 1H, J=7.6 Hz). E isomer: $^1$H NMR (400 MHz, DMSO) δ 8.17 (m, 1H), 7.94-7.90 (m, 3H), 7.85-7.83 (m, 1H), 7.62-7.58 (m, 1H), 7.43 (d, 1H, J=8 Hz), 6.99 (t, 1H, J=8 Hz); MS ESI [M+H]$^+$, calcd for [C$_{17}$H$_{10}$N$_4$O+H]$^+$ 287.09; found m/z 287.1.

Example A46

(E and Z)-methyl 3-((1H-indazol-6-yl)methylene)-2-oxoindoline-7-carboxylate

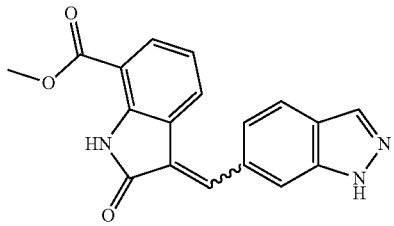 [SMILES: COC(=O)c1cccc2c1NC(=O)C2=Cc1ccc2cn[nH]c2c1]

According to the method described in example A6, except substituting methyl oxindole-7-carboxylate (23 mg, 0.12 mg), the title compound was prepared as a mixture of isomers (Z:E=62:38) and yellow solid (36 mg, 91%). Z isomer: $^1$H NMR (400 MHz, DMSO) δ 13.45 (s, 1H), 10.47 (s, 1H), 8.95 (s, 1H), 8.14 (m, 2H), 8.14 (d, 1H, J=7.6 Hz), 8.06 (d, 1H, J=7.6 Hz), 7.84 (d, 1H, J=8.8 Hz), 7.76 (d, 1H, J=8 Hz), 7.15 (t, 1H, J=8 Hz), 3.89 (s, 3H). E isomer: $^1$H NMR (400 MHz, CD$_3$OD) δ 8.20 (s, 1H), 8.16 (s, 1H), 8.00-7.95 (m, 2H), 7.92-7.89 (m, 2H), 7.50 (d, 1H, J=8.8 Hz), 7.01 (t, 1H, J=8 Hz), 3.99 (s, 3H); MS ESI [M+H]$^+$, calcd for [C$_{18}$H$_{13}$N$_3$O$_3$+H]$^+$ 320.10; found m/z 320.1.

Example A47

(E and Z)-3-((1H-indazol-6-yl)methylene)-7-(trifluoromethyl)indolin-2-one

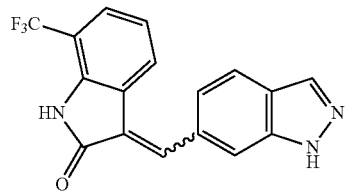 [SMILES: O=C1Nc2c(cccc2C(F)(F)F)C1=Cc1ccc2cn[nH]c2c1]

According to the method described in example A6, except substituting 7-(trifluoromethyl)indolin-2-one (40 mg, 0.2 mmol), the title compound was prepared as a mixture of isomers (Z:E=1:5) and yellow solid (4.6 mg, 7%). Z isomer: $^1$H NMR (400 MHz, CD$_3$OD) δ 9.00 (s, 1H), 8.10 (s, 1H), 7.93 (d, 1H, J=8 Hz), 7.89 (s, 1H), 7.85 (d, 1H, J=8 Hz), 7.50-7.45 (m, 2H), 7.19 (t, 1H, J=8 Hz). E isomer: $^1$H NMR (400 MHz, CD$_3$OD) δ 8.15 (s, 1H), 8.02 (s, 1H), 7.93 (d, 1H, J=8 Hz), 7.89 (s, 1H), 7.85 (d, 1H, J=8 Hz), 7.50-7.45 (m, 2H), 7.00 (t, 1H, J=8 Hz); MS ESI [M+H]$^+$, calcd for [C$_{17}$H$_{10}$F$_3$N$_3$O+H]$^+$ 330.08; found m/z 330.1.

Example A48

(E)-1-(3-((1H-indazol-6-yl)methylene)-2-oxoindolin-7-yl)-3-isopropyl-urea

A. 1-isopropyl-3-(2-oxoindolin-7-yl)urea

To a suspension of 7-aminoindolin-2-one (60 mg, 0.41 mmol) in THF (3 mL) was added DIPEA (0.28 mL, 1.62 mmol), and 2-isocyanatopropane (0.05 mL, 0.49 mmol). The mixture was stirred at rt overnight then filtered. The filter cake was washed with diethyl ether to give the title compound as a pale solid (57.3 mg, 61%). $^1$H NMR (400 MHz, CD$_3$OD) δ 7.09-7.04 (m, 2H), 6.99-6.95 (m, 1H), 3.57 (s, 2H), 2.64 (m, 1H), 1.20 (d, 6H, J=6.4 Hz). MS ESI [M+H]$^+$, calcd for [C$_{12}$H$_{15}$N$_3$O$_2$+H]$^+$ 234.12; found m/z 234.0.

B. (E)-1-(3-((1H-indazol-6-yl)methylene)-2-oxoindolin-7-yl)-3-isopropyl-urea

According to the method described in example A6, except substituting 1-isopropyl-3-(2-oxoindolin-7-yl)urea (57 mg, 0.24 mmol), the title compound was prepared as a yellow solid (61.4 mg, 70%). $^1$H NMR (400 MHz, DMSO) δ 13.29

(s, 1H), 10.16 (s, 1H), 8.15 (s, 1H), 8.00 (s, 1H), 7.89 (s, 2H), 7.78 (s, 1H), 7.41 (d, 1H, J=8 Hz), 7.35 (d, 1H, J=8 Hz), 7.28 (d, 1H, J=8 Hz), 6.77 (t, 1H, J=8 Hz), 6.09 (d, 1H, J=7.6 Hz), 3.77 (m, 1H), 1.12 (s, 3H), 1.10 (s, 3H); MS ESI [M+H]$^+$, calcd for [C$_{20}$H$_{19}$N$_5$O$_2$+H]$^+$ 362.16; found m/z 362.2.

Example A49

(E)-N-(3-((1H-indazol-6-yl)methylene)-2-oxoindolin-7-yl)acetamide

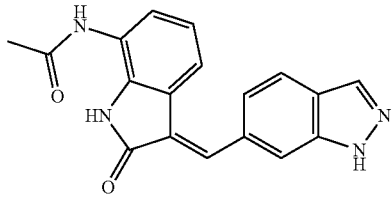 [SMILES: CC(=O)Nc1cccc2c1NC(=O)/C2=C/c1ccc2cn[nH]c2c1]

A. N-(2-oxoindolin-7-yl)acetamide

According to the method described in example A48a, 7-aminoindol-2-one (80 mg, 0.54) was reacted with acetic anhydride (66 mg, 0.65 mmol) to give the title compound as a white solid (82 mg, 80%). $^1$H NMR (400 MHz, CD$_3$OD) δ 7.13 (d, 2H, J=8 Hz), 6.99 (t, 1H, J=8 Hz), 3.57 (s, 2H), 2.16 (s, 3H). MS ESI [M+H]$^+$, calcd for [C$_{10}$H$_{10}$N$_2$O$_2$+H]$^+$ 191.08; found m/z 191.0.

B. (E)-N-(3-((1H-indazol-6-yl)methylene)-2-oxoindolin-7-yl)acetamide

According to the method described in example A6, except substituting N-(2-oxoindolin-7-yl)acetamide (18 mg, 0.095 mmol), the title compound was prepared as a yellow solid (6.8 mg, 20%). $^1$H NMR (400 MHz, CD$_3$OD) δ 8.16 (s, 1H), 7.94 (m, 3H), 7.54 (d, 1H, J=8 Hz), 7.48 (d, 1H, J=8 Hz), 7.26 (d, 1H, J=8 Hz), 6.89 (t, 1H, J=8 Hz), 2.19 (s, 3H). MS ESI [M+H]$^+$, calcd for [C$_{18}$H$_{14}$N$_4$O$_2$+H]$^+$ 319.12. found m/z 391.1.

Example A50

(E and Z)—N-(3-((1H-indazol-6-yl)methylene)-2-oxoindolin-7-yl)formamide

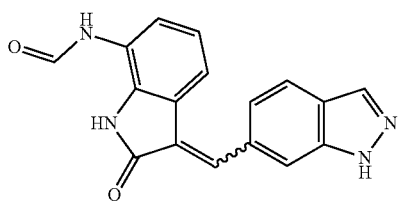 [SMILES: O=CNc1cccc2c1NC(=O)C2=Cc1ccc2cn[nH]c2c1]

A) N-(2-oxoindolin-7-yl)formamide

To a suspension of 7-aminooxindole (32 mg, 0.22 mmol) in CH$_2$Cl$_2$ (1 mL) was added EDC (83 mg, 0.43 mmol) and formic acid (12 mg, 0.26 mmol). The reaction mixture was stirred at rt for 2 h and then filtered. The filter cake was washed with diethyl ether to give the title compound as a grey solid (27 mg, 71%). $^1$H NMR (400 MHz, CD$_3$OD) δ 8.23 (s, 1H), 7.20 (d, 1H, J=8 Hz), 7.15 (d, 1H, J=8 Hz), 7.02 (t, 1H, J=8 Hz), 3.59 (s, 2H); MS ESI [M+H]$^+$, calcd for [C$_9$H$_8$N$_2$O$_2$+H]$^+$ 177.07. found m/z 177.0.

B. N-(3-((1H-indazol-6-yl)methylene)-2-oxoindolin-7-yl)formamide

According to the method described in example A1, except substituting N-(2-oxoindolin-7-yl)formamide (20 mg, 0.11 mmol), the title compound was prepared as a mixture of isomers (Z:E=35:65) and dark brown solid (12 mg, 35%). Z isomer: $^1$H NMR (400 MHz, DMSO) δ 9.88 (s, 1H), 8.98 (s, 1H), 8.61 (m, 1H), 8.12 (s, 1H), 8.02 (s, 1H), 7.97 (d, 1H, J=8 Hz), 7.82 (s, 1H), 7.61 (d, 1H, J=7.2 Hz), 7.25 (m, 1H), 7.01 (t, 1H, J=8 Hz). E isomer: $^1$H NMR (400 MHz, DMSO) δ 9.88 (s, 1H), 8.26 (s, 1H), 8.12 (s, 1H), 7.90 (m, 2H), 7.82 (s, 1H), 7.53 (m, 1H), 7.42 (m, 2H), 6.84 (t, 1H, J=8 Hz); MS ESI [M+H]$^+$, calcd for [C$_{17}$H$_{12}$N$_4$O$_2$+H]$^+$ 305.10. found m/z 305.1.

Example A51

(E)-3-(1-(1H-indazol-6-yl)ethylidene)indolin-2-one

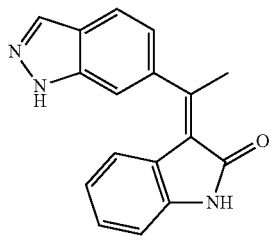 [SMILES: C/C(=C1\C(=O)Nc2ccccc21)c1ccc2cn[nH]c2c1]

A. 1-(1H-indazol-6-yl)ethanol

To a solution of 1H-indazole-6-carbaldehyde (200 mg, 1.37 mmol) in THF (7 mL) at −78° C. was added methyl magnesium bromide (1.4 mL, 4.11 mmol) dropwise under argon. The solution was warmed to rt and quenched with saturated ammonium chloride (2 mL). The mixture was extracted into ethyl acetate (3×10 mL), dried over MgSO$_4$ and concentrated. The yellow oil was purified by silica gel chromatography (EtOAc/Hex 4:1) to yield the title compound as a clear oil (135 mg, 60%). $^1$H NMR (400 MHz, CDCl$_3$) δ 8.07 (s, 1H), 7.76 (s, 1H), 7.50-7.47 (m, 2H), 5.05 (q, 1H, J=7.4 Hz), 1.57 (d, 3H, J=7.2 Hz); MS ESI [M+H]$^+$, calcd for [C$_9$H$_{10}$N$_2$O+H]$^+$ 163.1; found m/z 163.0.

B. 1-(1H-indazol-6-yl)ethanone

To a solution of 1-(1H-indazol-6-yl)ethanol (100 mg, 0.6 mmol) in acetone (50 mL) was added PDC (1.11 g, 3 mmol). The mixture was stirred overnight at rt. The mixture was filtered through silica gel and purified by silica gel chromatography (4:1 EtOAc/Hex) to give the title compound as a brown solid (70 mg, 72%). $^1$H NMR (400 MHz, CDCl$_3$) δ 8.45 (s, 1H), 8.23 (s, 1H), 8.09-8.08 (m, 1H), 7.56-7.54 (m, 1H), 2.72 (s, 3H).

C. (E)-3-(1-(1H-indazol-6-yl)ethylidene)indolin-2-one

A solution of oxindole (16 mg, 0.12 mmol), pyrrolidine (10 µL, 0.12 mmol) and 1-(1H-indazol-6-yl)ethanone (20 mg, 0.12 mmol) in toluene was refluxed in a Dean-Stark trap for 2 h. The solution was then stirred at 50° C. for 72 h. Two equivalents of pyrrolidine were added and the solution was heated to reflux for 48 h. The solution was concentrated and the red residue was purified by preparatory HPLC to give the title compound as an orange solid (5 mg, 16%). $^1$H NMR (400 MHz, CDCl$_3$) δ 8.13 (s, 1H), 7.78 (s, 1H), 7.70 (d, 1H, J=8.5 Hz), 7.34 (d, 1H, J=8.5 Hz), 7.03 (t, 1H, J=7.6 Hz), 6.81 (d, 1H, J=7.7 Hz), 6.50 (t, 1H, J=7.6 Hz), 6.05 (d, 1H, J=7.7 Hz), 2.82 (s, 3H); MS ESI [M+H]$^+$, calcd for [C$_{17}$H$_{13}$N$_3$O+H]$^+$ 276.1; found m/z 276.0.

Example A52

(E)-3-((4-chloro-1H-indazol-6-yl)methylene)indolin-2-one

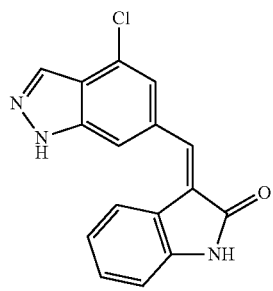 [SMILES: O=C1Nc2ccccc2/C1=C\c1cc(Cl)c2cn[nH]c2c1]

A. (4-chloro-1H-indazol-6-yl)methanol

A solution of 4-chloro-1H-indazole-6-carboxylic acid (100 mg, 0.5 mmol) in THF (1 mL) was cooled to 0° C. under argon. Borane (1.4 mL, 1.4 mmol) was added dropwise and the solution was stirred overnight at rt. The reaction was quenched with ice cold sat. sodium bicarbonate, extracted with ethyl acetate (3×10 mL), dried over MgSO$_4$ and concentrated to give the title compound as a white solid (60 mg, 66%). MS ESI [M+H]$^+$, calcd for [C$_8$H$_7$ClN$_2$O+H]$^+$ 183.0; found m/z 183.0.

B. 4-chloro-1H-indazole-6-carbaldehyde

To a solution of (4-chloro-1H-indazol-6-yl)methanol (30 mg, 0.18 mmol) in acetone (5 mL) was added PDC (100 mg, 0.27 mmol). The mixture was stirred overnight at rt. The mixture was filtered through celite, the filter cake was washed with ethyl acetate. The solution was washed with water (2×10 mL), brine (10 mL), dried over MgSO$_4$ and concentrated to a brown solid (30 mg, 100%). $^1$H NMR (400 MHz, CD$_3$OD) δ 10.1 (s, 1H), 8.21 (s, 1H), 8.08 (s, 1H), 7.62 (s, 1H).

C. (E)-3-((4-chloro-1H-indazol-6-yl)methylene)indolin-2-one

The compound was synthesized according to the method described for Example A1. Oxindole (8 mg, 0.06 mmol) was reacted with 4-chloro-1H-indazole-6-carbaldehyde (11 mg, 0.06 mmol) to give the title compound as an orange solid (3 mg, 13%). $^1$H NMR (400 MHz, CD$_3$OD) δ 8.21 (s, 1H), 7.87 (s, 1H), 7.82 (s, 1H), 7.59 (d, 1H, J=7.8 Hz), 7.48 (s, 1H), 7.28 (t, 1H, J=7.9 Hz), 6.95 (d, 1H, J=7.7 Hz), 6.90 (t, 1H, J=8.2 Hz); MS ESI [M+H]$^+$, calcd for [C$_{16}$H$_{10}$ClN$_3$O+H]$^+$ 296.1; found m/z 296.1.

Example A53a

(E)-3-((4-bromo-1H-indazol-6-yl)methylene)indolin-2-one and A53b: (Z)-3-((4-bromo-1H-indazol-6-yl)methylene)indolin-2-one

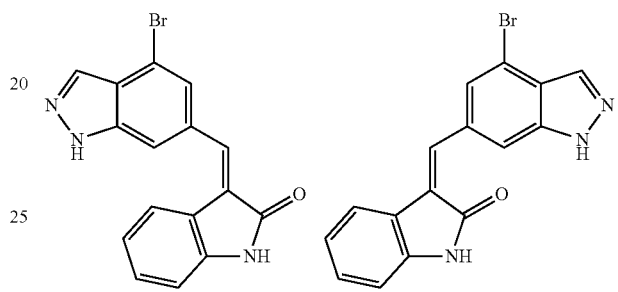

A. (4-bromo-1H-indazol-6-yl)methanol

According to the method of A52A, 4-bromo-1H-indazole-6-carboxylic acid (1 g, 4 mmol) was reacted with borane (6 ml, 6 mmol) to give the title compound as a pale yellow solid (800 mg, 88%). MS ESI [M+H]$^+$, calcd for [C$_8$H$_7$BrN$_2$O+H]$^+$ 227.0, 229.0; found m/z 226.9, 228.9.

B. 4-bromo-1H-indazole-6-carbaldehyde

According to the method of A52B, (4-bromo-1H-indazol-6-yl)methanol was oxidized with PDC to give the title compound as a beige solid (413 mg, 53%). MS ESI [M+H]$^+$, calcd for [C$_8$H$_5$BrN$_2$O+H]$^+$ 225.0, 227.0; found m/z 224.9, 226.9.

C. 3-((4-bromo-1H-indazol-6-yl)methylene)indolin-2-one

According to the method described for Example A1, oxindole (15 mg, 0.11 mmol) was reacted with 4-bromo-1H-indazole-6-carbaldehyde (25 mg, 0.11 mmol) to give the title compound as an orange solid. The E and Z stereoisomers were separated by HPLC.

(E-isomer 7 mg, 19%, HPLC retention time, 11 min). $^1$H NMR (400 MHz, CD$_3$OD) δ 8.11 (s, 1H), 7.87 (s, 1H), 7.80 (s, 1H), 7.63 (s, 1H), 7.56 (d, 1H, J=7.7 Hz), 7.28 (t, 1H, J=7.8 Hz), 6.93 (d, 1H, J=7.7 Hz), 6.89 (t, 1H, J=7.7 Hz); MS ESI [M+H]$^+$, calcd for [C$_{16}$H$_{10}$BrN$_3$O+H]$^+$ 339.0, 341.0; found m/z 340.0, 342.0.

(Z-isomer, 3 mg, 8%, HPLC retention time, 11.8 min) $^1$H NMR (400 MHz, DMSO-d$_6$) δ 13.75 (s, 1H), 10.72 (s, 1H), 8.85 (s, 1H), 8.41 (s, 1H), 8.07 (s, 1H), 7.96 (s, 1H), 7.73 (d, 1H, J=7.5 Hz), 7.22 (t, 1H, J=7.5 Hz), 7.02 (t, 1H, J=7.4 Hz), 6.85 (d, 1H, J=7.8 Hz); MS ESI [M+H]⁺, calcd for [C₁₆H₁₀BrN₃O+H]⁺ 339.0, 341.0; found m/z 340.0, 342.0.

Example A54a (E)-3-((4-(pyridin-4-yl)-1H-indazol-6-yl)methylene)indolin-2-one and A54b: (E)-3-((4-(pyridin-4-yl)-1H-indazol-6-yl)methylene)indolin-2-one

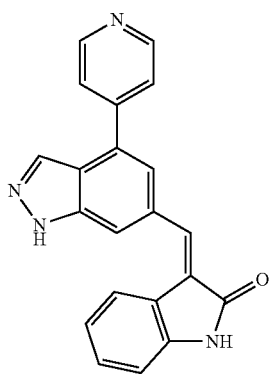 [SMILES: O=C1Nc2ccccc2/C1=C\c1cc(-c2ccncc2)c2cn[nH]c2c1]

A. 4-bromo-1-((2-(trimethylsilyl)ethoxy)methyl)-1H-indazole-6-carbaldehyde

To a solution of 4-bromo-1H-indazole-6-carbaldehyde (225 mg, 1 mmol) in CH₂Cl₂ (10 mL) and aqueous KOH (2 mL, 50% wt) at 0° C. was added TBAB (3 mg, 0.01 mmol) and SEMCl (200 mg, 1.2 mmol). The mixture was stirred at 0° C. for 4 h, warmed to rt and extracted with ethyl acetate (100 mL). The organic phase was washed with water (2×10 mL) and brine (10 mL), dried over MgSO₄ and concentrated. The residue was purified by silica gel chromatography (1:1 EtOAc/Hex) to give the title compound as a pale yellow solid (280 mg, 82%). ¹H NMR (400 MHz, CD₃OD) δ 10.02 (s, 1H), 8.21-8.19 (m, 2H), 7.80 (s, 1H), 5.78 (s, 2H), 3.70-3.65 (m, 2H), 0.95-0.92 (m, 2H), −0.05 (s, 9H).

B. 4-(pyridin-4-yl)-1-((2-(trimethylsilyl)ethoxy)methyl)-1H-indazole-6-carbaldehyde To a solution of 4-bromo-1-((2-(trimethylsilyl)ethoxy)methyl)-1H-indazole-6-carbaldehyde (50 mg, 0.14 mmol) and pyridine boronic acid (20 mg, 0.16 mmol) in 10:1 DMF/water (1 mL) was added K₂CO₃ (36 mg, 0.26 mmol) and tetrakistriphenylphosphine palladium (7.5 mg, 0.007 mmol). The mixture was heated to 120° C. under microwave irradiation for 20 min. Ethyl acetate (20 mL) was added and the solution was washed with water (2×5 mL) and brine (5 mL), dried over MgSO₄ and concentrated. The residue was purified by silica gel chromatography (3:1 EtOAc/Hex) to give the title compound as a pale yellow solid (31 mg, 62%). MS ESI [M+H]⁺, calcd for [C₁₉H₂₃N₃O₂Si+H]⁺ 354.2; found m/z 354.2.

C. 3-((4-(pyridin-4-yl)-1H-indazol-6-yl)methylene)indolin-2-one

To a solution of oxindole (12 mg, 0.08 mmol) and 4-(pyridin-4-yl)-1-((2-(trimethylsilyl)ethoxy)methyl)-1H-indazole-6-carbaldehyde (31 mg, 0.087 mmol) in ethanol (2 mL) was added pyrrolidine (20 μL). The mixture was heated to 70° C. for 3 h. The solution was concentrated to dryness and treated with 4M HCl (1 mL) in ethanol (3 mL) at 70° C. for 4 h. The solution was cooled to rt and extracted with ethyl acetate (50 mL), dried over MgSO₄ and concentrated to give the title compound as a mixture of E/Z isomers which were separated by preparatory HPLC.

(E-isomer 5.4 mg, 18%, HPLC retention time, 6.6 min). ¹H NMR (400 MHz, CD₃OD) δ 8.94-8.91 (m, 2H), 8.44 (s, 1H), 8.39 (d, 2H, J=6.4 Hz), 8.16 (s, 1H), 7.93 (s, 1H), 7.86 (s, 1H), 7.59 (d, 1H, J=7.9 Hz), 7.26 (t, 1H, J=7.8 Hz), 6.95 (d, 1H, 7.7 Hz), 6.86 (t, 1H, J=7.8 Hz); MS ESI [M+H]⁺, calcd for [C₂₁H₁₄N₄O+H]⁺ 339.1; found m/z 339.1.

(Z-isomer, 3.3 mg, 12%, HPLC retention time, 7.2 min) ¹H NMR (400 MHz, CD₃OD) δ 8.92 (d, 2H, J=5.6 Hz), 8.76 (s, 1H), 8.73 (s, 1H), 8.48 (d, 2H, J=6.7 Hz), 8.43 (s, 1H), 7.99 (s, 1H), 7.71 (d, 1H, J=7.8 Hz), 7.28 (t, 1H, J=7.5 Hz), 7.08 (t, 1H, J=7.9 Hz), 6.90 (d, 1H, J=7.9 Hz); MS ESI [M+H]⁺, calcd for [C₂₁H₁₄N₄O+H]⁺ 339.1; found m/z 339.1.

Example A55

(E and Z)-3-((4-((E)-2-(pyridin-4-yl)vinyl)-1H-indazol-6-yl)methylene)indolin-2-one

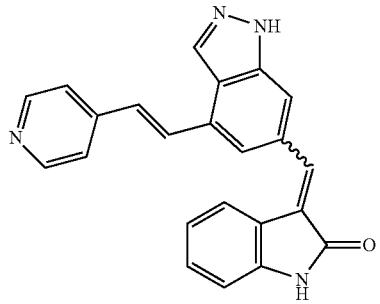 [SMILES: O=C1Nc2ccccc2C1=Cc1cc(/C=C/c2ccncc2)c2cn[nH]c2c1]

A. (E)-4-(2-(pyridin-4-yl)vinyl)-1-((2-(trimethylsilyl)ethoxy)methyl)-1H-indazole-6-carbaldehyde A solution of 4-(pyridine-4-yl)-1-((2-(trimethylsilyl)ethoxy)methyl)-1H-indazole-6-carbaldehyde (50 mg, 0.14 mmol) and 4-pyridylethylene (20 μL, 0.19 mmol) in acetonitrile (1.5 mL) was purged with argon. Palladium acetate (2 mg, 0.007 mmol), tri-o-tolylphosphine (4 mg, 0.014 mmol) and DIPEA (50 μL) was added and the mixture was heated to 70° C. for 16 h. Ethyl acetate (50 mL) was added and the mixture was washed with water (2×5 mL), brine (5 mL), dried over MgSO₄ and concentrated. The residue was purified by silica gel chromatography (98:2 EtOAc/MeOH) to give the title compound as a yellow solid (28 mg, 53%). MS ESI [M+H]⁺, calcd for [C₂₁H₂₅N₃O₂Si+H]⁺ 380.2; found m/z 380.2.

B. (E and Z)-3-((4-((E)-2-(pyridin-4-yl)vinyl)-1H-indazol-6-yl)methylene)-indolin-2-one According to the method of A54C, oxindole (10 mg, 0.07 mmol) was reacted with (E)-4-(2-(pyridin-4-yl)vinyl)-1-((2-(trimethylsilyl)ethoxy)methyl)-1H-indazole-6-carb-aldehyde (27 mg, 0.06 mmol) and then treated with HCl to give the title compound as a 3:1 mixture of E/Z isomers (4 mg, 28%). MS ESI [M+H]⁺, calcd for [C₂₃H₁₆N₄O+H]⁺ 365.1; found m/z 365.2. E-isomer ¹H NMR (400 MHz, DMSO-d₆) δ 8.82-8.79 (m, 2H), 8.20-8.12 (m, 3H), 7.96 (s, 1H), 7.81-7.74

(m, 3H), 7.64 (s, 1H), 7.52 (d, 1H, J=8.1 Hz), 7.23 (t, 1H, J=7.8 Hz), 6.89 (d, 1H, J=8.0 Hz), 6.88-6.86 (m, 1H); Z-isomer $^1$H NMR (400 MHz, DMSO-d$_6$) δ 8.97 (s, 1H), 8.67 (s, 1H), 8.60-8.58 (m, 2H), 8.27 (s, 1H), 8.01 (s, 1H), 7.91 (d, 1H, J=16.8 Hz), 7.77 (d, 1H, J=7.5 Hz), 7.74 (d, 2H, J=5.5 Hz), 7.49 (d, 1H, J=16 Hz), 7.23 (t, 1H, J=7.8 Hz), 7.02 (t, 1H, J=7.6 Hz), 6.86 (d, 1H, J=7.6 Hz).

Example A56

(E)-3-((1H-indazol-6-yl)methylene)-7-aminoindolin-2-one

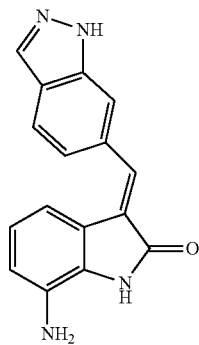 [SMILES: Nc1cccc2c1NC(=O)/C2=C/c1ccc2cn[nH]c2c1]

A 13 mg (0.0877 mmol) solution of 7-aminooxindole (T. Nakashima & I. Suzuki, Chem. Pharm. Bull. (1969) 11, 2293) and 1H-indazole-6-carbaldehyde (14 mg, 0.0965 mmol) in MeOH (1.0 mL) was treated with piperidine (~1 uL, 0.00877 mmol) and the reaction was heated to 60° C. for 4 hours. The MeOH was then removed in vacuo and the residue treated with 95:5 CH$_2$Cl$_2$/MeOH. The resulting precipitate was filtered and washed with 95:5 CH$_2$Cl$_2$/MeOH to obtain the title compound as a orange powder (6.7 mg, 28%). NMR (400 MHz, CD$_3$OD) δ 8.14 (s, 1H), 7.94-7.87 (m, 3H), 7.46 (d, J=8.19 Hz, 1H), 7.31 (d, J=7.63 Hz, 1H), 6.90 (d, J=7.89 Hz, 1H), 6.81 (t, J=7.79 Hz, 1H); MS ESI 277.0 [M+H]$^+$, calcd for [C$_{16}$H$_{12}$N$_4$O+H]$^+$ 277.11.

Example A57

(E)-3-((3-((E)-2-(pyridin-4-yl)vinyl)-1H-indazol-6-yl)methylene)-indolin-2-one

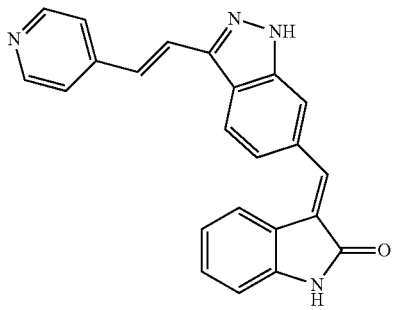 [SMILES: O=C1Nc2ccccc2/C1=C\c1ccc2c(/C=C/c3ccncc3)n[nH]c2c1]

A. (E)-3-(2-(pyridin-4-yl)vinyl)-1-((2-(trimethylsilyl)ethoxy)methyl)-1H-indazole-6-carbaldehyde A solution of 3-iodo-1-((2-(trimethylsilyl)ethoxy)methyl)-1H-indazole-6-carbaldehyde (2.0 g, 4.98 mmol), 4-vinylpyridine (0.69 mL, 6.47 mmol), diisopropylethylamine (1.74 mL, 9.96 mmol) and DMF (50 mL) was purged with Ar gas for 20 min at which time Pd(OAc)$_2$ (112 mg, 0.500 mmol) and P(o-tol)$_3$ (457 mg, 1.50 mmol) were added and the reaction heated to 100° C. for 20 hours. The reaction was cooled to room temperature and partitioned between EtOAc and NH$_4$Cl. The aqueous layer was extracted with EtOAc (3×) and the combined organics washed with water (2×) and brine (2×). The organic layer was dried over MgSO$_4$ and the EtOAc removed in vacuo. The residue was purified by column chromatography (silica gel, 97:3 CH$_2$Cl$_2$/MeOH) to give 927 mg, 49% of the title compound which was used without further purification. MS ESI 380.2 [M+H]$^+$, calcd for [C$_{21}$H$_{25}$N$_3$O$_2$Si+H]$^+$ 380.18.

B. (E)-3-((3-((E)-2-(pyridin-4-yl)vinyl)-1-((2-(trimethylsilyl)ethoxy)methyl)-1H-indazol-6-yl)methylene)indolin-2-one To a solution of (E)-3-(2-(pyridin-4-yl)vinyl)-1-((2-(trimethylsilyl)ethoxy)methyl)-1H-indazole-6-carbaldehyde (927 mg, 2.44 mmol), oxindole (325 mg, 2.44 mmol) and MeOH (20 mL) was added piperidine (24 uL, 0.244 mmol) and the reaction heated to 60° C. for 4 hours. A yellow precipitate crashed out of the reaction medium which was filtered and washed with MeOH to give the title compound (960 mg, 79%) as a yellow solid. MS ESI 495.3 [M+H]$^+$, calcd for [C$_{29}$H$_{30}$N$_4$O$_2$Si+H]$^+$ 495.22.

C. (E)-3-((3-((E)-2-(pyridin-4-yl)vinyl)-1H-indazol-6-yl)methylene)-indolin-2-one A dry-round bottom was charged with (E)-3-((3-((E)-2-(pyridin-4-yl)vinyl)-1-((2-(trimethylsilyl)ethoxy)methyl)-1H-indazol-6-yl)methylene)indolin-2-one (906 mg, 1.83 mmol), and CH$_2$Cl$_2$ (100 mL) under an atmosphere of N$_2$. Boron trifluoride etherate (2.3 mL, 18.3 mmol) was added dropwise and the reaction was stirred for 4 hours at which time LC-MS indicated complete conversion to the partially de-protected material (E)-3-((1-(hydroxymethyl)-3-((E)-2-(pyridin-4-yl)vinyl)-1H-indazol-6-yl)methylene)-indolin-2-one. The CH$_2$Cl$_2$ was removed in vacuo, and then 150 mL of a 2:1 mixture of EtOH/2M HCl was added and the reaction heated to 50° C. for 3 hours at which time LC-MS indicated complete conversion to the title compound. The reaction was cooled with an ice-bath and neutralized with NH$_4$OH to pH~8, the EtOH was removed and the suspension filtered washing with water. The dried solid was collected and then titurated and filtered several times with 90:10 CH$_2$Cl$_2$/MeOH which gave, after drying, the title compound (353 mg, 53%) as an orange solid. $^1$H NMR (400 MHz, d$^6$-DMSO) δ 13.57 (s, 1H), 10.64 (s, 1H), 8.57 (d, J=5.16 Hz, 2H), 8.38 (d, J=8.13 Hz, 1H), 7.92 (s, 1H), 7.87 (d, J=16.7 Hz, 1H), 7.80 (s, 1H), 7.71 (d, J=5.16 Hz, 2H), 7.62-7.53 (m, 3H), 7.23 (t, J=8.29 Hz, 1H), 6.91-6.82 (m, 2H); MS ESI 365.1 [M+H]$^+$, calcd for [C$_{23}$H$_{16}$N$_4$O+H]$^+$ 365.14.

Example A58

(E)-3-((E)-(3-styryl-1H-indazol-6-yl)methylene)indolin-2-one

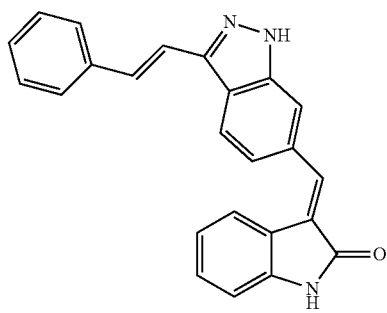 [SMILES: O=C1Nc2ccccc2/C1=C\c1ccc2c(/C=C/c3ccccc3)n[nH]c2c1]

A. (E)-3-styryl-1-((2-(trimethylsilyl)ethoxy)methyl)-1H-indazole-6-carbaldehyde A solution of 3-iodo-1-((2-(trimethylsilyl)ethoxy)methyl)-1H-indazole-6-carbaldehyde (100 mg, 0.249 mmol), styrene (37 uL, 0.324 mmol), diisopropylethylamine (87 uL, 0.324 mmol) and DMF (2.5 mL) was purged with Ar gas for 20 min at which time Pd(OAc)$_2$ (2.8 mg, 0.0125 mmol) and P(o-tol)$_3$ (11 mg, 0.0374 mmol) were added and the reaction heated to 100° C. for 20 hours. The reaction was cooled to room temperature and partitioned between EtOAc and NH$_4$Cl. The aqueous layer was extracted 3× with EtOAc and the combined organics washed with water (2×) and brine (2×). The organic layer was dried over MgSO$_4$ and the EtOAc removed in vacuo. The residue was purified by column chromatography (silica gel, 5:1 hexanes/EtOAc) to give the title compound (63 mg, 67%) which was used without further purification. MS ESI 379.2 [M+H]$^+$, calcd for [C$_{22}$H$_{26}$N$_2$O$_2$Si+H]$^+$ 379.18.

B. (E)-3-styryl-1H-indazole-6-carbaldehyde

A solution of (E)-3-styryl-1-((2-(trimethylsilyl)ethoxy)methyl)-1H-indazole-6-carbaldehyde (63 mg, 0.166 mmol) in THF (2.0 mL) was treated with TBAF (0.83 mL of a 1M solution in THF) and refluxed overnight. The solvent was removed and the residue re-dissolved into EtOAc. The organics were washed with water (2×), brine (2×) and then dried (MgSO$_4$). The solvent was removed and the residue purified by column chromatography (silica gel, 98:2 CH$_2$Cl$_2$/MeOH) to give the title compound (27 mg, 66%) which was used without further purification. MS ESI 249.0 [M+H]$^+$, calcd for [C$_{16}$H$_{12}$N$_2$O+H]$^+$ 249.10.

C. (E)-3-((E)-(3-styryl-1H-indazol-6-yl)methylene)indolin-2-one

A solution of (E)-3-styryl-1H-indazole-6-carbaldehyde (27 mg, 0.109 mmol) and oxindole (15 mg, 0.109 mmol) in MeOH (1.0 mL) was treated with piperidine (1 uL, 0.011 mmol) and the reaction stirred at 60° C. for 4 hours. The MeOH was removed and the residue purified by prep-HPLC to give 4.7 mg, 12% of a yellow powder. $^1$H NMR (400 MHz, CD$_3$OD) δ 8.26 (d, J=8.38 Hz, 2H), 7.91-7.86 (m, 2H), 7.71-7.64 (m, 3H), 7.60-7.49 (m, 2H), 7.42 (t, J=7.41 Hz, 2H), 7.31 (t, J=7.49 Hz, 1H), 7.26 (t, J=7.89 Hz, 1H), 6.94 (d, J=7.75 Hz, 1H), 6.89 (t, J=6.86 Hz, 1H); MS ESI 364.2 [M+H]$^+$, calcd for [C$_{24}$H$_{17}$N$_3$O+H]$^+$ 364.14.

Example A59

(E and Z)-3-((3-((E)-2-methoxystyryl)-1H-indazol-6-yl)methylene)-indolin-2-one

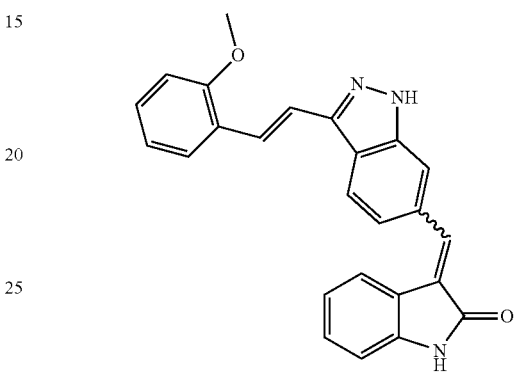

The synthetic method followed of that described in Example A58 starting from 2-methoxystyrene (43 uL, 0.324 mmol) and 3-iodo-1-((2-(trimethylsilyl)ethoxy)methyl)-1H-indazole-6-carbaldehyde (100 mg, 0.249 mmol). Obtained 4.6 mg (4.7% yield over 3 steps) of a yellow powder after prep-HPLC purification. Was isolated as a 75:25 mixture of (E)/(Z) isomers. $^1$H NMR (400 MHz, CD$_3$OD) δ 8.91, 7.89 (s, 1H), 8.19, 8.09 (d, J=7.43 Hz, 1H), 7.95-7.85 (m, 2H), 7.71-7.67 (m, 2H), 7.58-7.46 (m, 2H), 7.33-7.23 (m, 2H), 7.09-6.98 (m, 2H), 6.96-6.87 (m, 2H), 3.97 (s, 3H); MS ESI 394.2 [M+H]$^+$, calcd for [C$_{25}$H$_{19}$N$_3$O$_2$+H]$^+$ 394.16.

Example A60

(E)-3-((3-((E)-2-chlorostyryl)-1H-indazol-6-yl)methylene)indolin-2-one

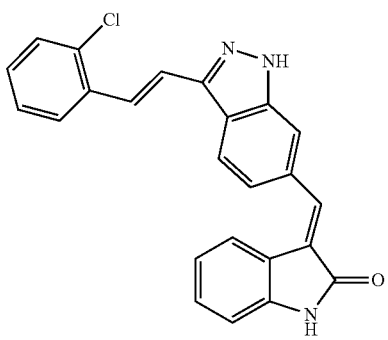 [SMILES: O=C1Nc2ccccc2/C1=C\c1ccc2c(/C=C/c3ccccc3Cl)n[nH]c2c1]

According to the method described in Example A58 2-chlorostyrene (42 uL, 0.324 mmol) and 3-iodo-1-((2-(trimethylsilyl)ethoxy)methyl)-1H-indazole-6-carbaldehyde (100 mg, 0.249 mmol) were reacted to obtain, after prep-HPLC purification, the title compound (2.0 mg, 2.0%) as a yellow powder. ¹H NMR (400 MHz, CD₃OD) δ 8.20 (d, J=8.51, 1H), 7.99-7.88 (m, 4H), 7.68 (d, J=7.32 Hz, 1H), 7.60-7.46 (m, 3H), 7.39 (t, J=7.68 Hz, 1H), 7.33-7.23 (m, 2H), 6.94 (d, J=8.02 Hz, 1H), 6.90 (t, J=7.77 Hz, 1H); MS ESI 398.2 [M+H]⁺, calcd for [C₂₄H₁₆ClN₃O+H]⁺ 398.11.

Example A61

(E)-methyl 3-(6-((E)-(2-oxoindolin-3-ylidene)methyl)-1H-indazol-3-yl)acrylate

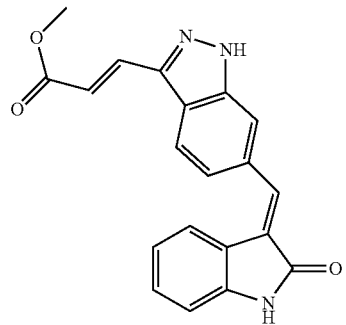 [SMILES: COC(=O)/C=C/c1n[nH]c2cc(/C=C3/C(=O)Nc4ccccc43)ccc12]

The synthetic method followed that described in Example A58, starting from methylacrylate (41 uL, 0.457 mmol) and 3-iodo-1-((2-(trimethylsilyl)ethoxy)methyl)-1H-indazole-6-carbaldehyde (153 mg, 0.381 mmol). In the final step a yellow solid precipitated from the reaction medium which was filtered and washed with MeOH to give the title compound (3.8 mg, 2.9%). ¹H NMR (400 MHz, d⁶-DMSO) δ 13.87 (s, 1H), 10.65 (s, 1H), 8.25 (d, J=8.74 Hz, 1H), 7.95 (s, 1H), 7.93 (d, J=16.7 Hz, 1H), 7.78 (s, 1H), 7.57-7.54 (m, 2H), 7.24 (t, J=7.28 Hz, 1H), 6.90-6.80 (m, 3H), 3.77 (s, 3H); MS ESI 346.2 [M+H]⁺, calcd for [C₂₀H₁₅N₃O₃+H]⁺ 346.12.

Example A62

(E)-5-bromo-3-((3-((E)-2-(pyridin-4-yl)vinyl)-1H-indazol-6-yl)-methylene)indolin-2-one

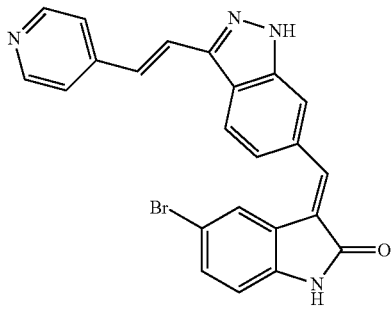 [SMILES: O=C1Nc2ccc(Br)cc2/C1=C\c1ccc2c(/C=C/c3ccncc3)n[nH]c2c1]

A. (E)-5-bromo-3-((3-((E)-2-(pyridin-4-yl)vinyl)-1-((2-(trimethylsilyl)ethoxy)-methyl)-1H-indazol-6-yl)methylene)indolin-2-one The title compound was prepared from 5-bromooxindole (36 mg, 0.171 mmol) and (E)-3-(2-(pyridin-4-yl)vinyl)-1-((2-(trimethylsilyl)ethoxy)methyl)-1H-indazole-6-carbaldehyde (65 mg, 0.171 mmol) as described in Example A57 part B to give, after silica gel column chromatography (Eluent: 98:2 CH₂Cl₂/MeOH) the title compound as a yellow oil (75 mg, 77%). MS ESI 573.4 [M+H]⁺, calcd for [C₂₉H₂₉BrN₄O₂Si+H]⁺ 573.13.

B. (E)-5-bromo-3-((3-((E)-2-(pyridin-4-yl)vinyl)-1H-indazol-6-yl)methylene)-indolin-2-one A solution of (E)-5-bromo-3-((3-((E)-2-(pyridin-4-yl)vinyl)-1-((2-(trimethylsilyl)-ethoxy)methyl)-1H-indazol-6-yl)methylene)indolin-2-one (75 mg, 0.131 mmol) in 12 mL of a 2:1:1 mixture of MeOH/EtOH/4M HCl was heated to 80° C. for 24 hours. LC-MS indicated a mixture of the title compound plus a partially deprotected methoxymethyl indazole compound (see Example A63). The solvents were removed and the mixture was purified by prep-HPLC to give 7.3 mg (13%) of the title compound as a yellow solid. ¹H NMR (400 MHz, d⁶-DMSO) δ 13.87 (s, 1H), 10.82 (s, 1H), 8.76 (d, J=5.78 Hz, 2H), 8.45 (d, J=8.00 Hz, 1H), 8.23-8.13 (m, 3H), 8.04 (s, 1H), 7.96 (s, 1H), 7.73 (d, J=16.6 Hz, 1H), 7.64 (s, 1H), 7.60 (d, J=7.81 Hz, 1H), 7.43 (d, J=7.31 Hz, 1H), 6.87 (d, J=8.11 Hz, 1H); MS ESI 443.3 [M+H]⁺, calcd for [C₂₃H₁₅BrN₄O+H]⁺ 443.05.

Example A63

(E)-5-bromo-3-((1-(methoxymethyl)-3-((E)-2-(pyridin-4-yl)vinyl)-1H-indazol-6-yl)methylene)indolin-2-one

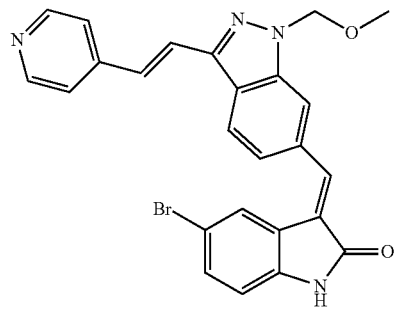 [SMILES: COCn1nc(/C=C/c2ccncc2)c2ccc(/C=C3/C(=O)Nc4ccc(Br)cc43)cc21]

The title compound (4.0 mg, 7.0% of a yellow powder) was isolated by prep-HPLC as a bi-product from the final deprotection step in Example A62. ¹H NMR (400 MHz, d⁶-DMSO) δ 10.84 (s, 1H), 8.75 (d, J=4.81 Hz, 2H), 8.48 (d, J=8.54 Hz, 1H), 8.24 (s, 1H), 8.18-8.10 (m, 3H), 7.88 (s, 1H), 7.75 (d, J=16.8 Hz, 1H), 7.67-7.61 (m, 2H), 7.43 (d, J=7.53 Hz, 1H), 6.87 (d, J=8.28 Hz, 1H), 5.83 (s, 2H), 3.33 (s, 3H); MS ESI 487.3 [M+H]⁺, calcd for [C₂₅H₁₉BrN₄O₂+H]⁺ 487.08.

Example A64

(E and Z)-3-((3-(2-(pyridin-4-yl)ethyl)-1H-indazol-6-yl)methylene)-indolin-2-one

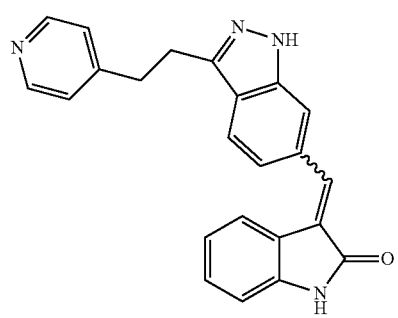 [SMILES: O=C1Nc2ccccc2C1=Cc1ccc2c(CCc3ccncc3)n[nH]c2c1]

A. 4-(2-(pyridin-4-yl)ethyl)-1-((2-(trimethylsilyl)ethoxy)methyl)-1H-indazole-6-carbaldehyde A solution of (E)-3-(2-(pyridin-4-yl)vinyl)-1-((2-(trimethylsilyl)ethoxy)methyl)-1H-indazole-6-carbaldehyde (see Example A2 for preparation) (58 mg, 0.153 mmol) in EtOAc (5.0 mL) was purged with Ar gas for 10 min at which time 6 mg of 10% Pd/C (Degussa type) was added. The reaction was then purged briefly with $H_{2\ (g)}$ and then stirred under an atmosphere of $H_{2\ (g)}$ for 5 hours. The reaction was then filtered through a pad of celite, washed with EtOAc, and the solvent removed to give the title compound (54 mg, 93%) as a yellow oil. MS ESI 382.2 [M+H]$^+$, calcd for [$C_{21}H_{27}N_3O_2Si+H$]$^+$ 382.20.

B. 3-((3-(2-(pyridin-4-yl)ethyl)-1-((2-(trimethylsilyl)ethoxy)methyl)-1H-indazol-6-yl)-methylene)indolin-2-one A solution of 3-(2-(pyridin-4-yl)ethyl)-1-((2-(trimethylsilyl)ethoxy)methyl)-1H-indazole-6-carbaldehyde (54 mg, 0.142 mmol), oxindole (19 mg, 0.142 mmol) in MeOH (2.0 mL) was treated with piperidine (1.5 uL, 0.0142 mmol) and the reaction heated to 60° C. and stirred for 4 hours at which time the solvent was removed and the residue purified by column chromatography (silica gel, 96:4 CH$_2$Cl$_2$/MeOH) to give the title compound (57 mg, 80%) as a yellow film. MS ESI 497.2 [M+H]$^+$, calcd for [$C_{29}H_{32}N_4O_2Si+H$]$^+$ 497.24.

C. (E and Z)-3-((3-(2-(pyridin-4-yl)ethyl)-1H-indazol-6-yl)methylene)indolin-2-one A solution of 3-((3-(2-(pyridin-4-yl)ethyl)-1-((2-(trimethylsilyl)ethoxy)-methyl)-1H-indazol-6-yl)methylene)indolin-2-one (57 mg, 0.115 mmol) in THF (3 mL) was treated with TBAF (0.58 mL of a 1.0 M solution in THF) and the reaction heated at reflux for 20 hours. The solvent was removed and the residue re-dissolved into EtOAc. The organics were washed with water (2×), brine (2×) and then dried (MgSO$_4$). The solvent was removed and the residue purified by column chromatography (silica gel, 93:7 CH$_2$Cl$_2$/MeOH) to give a yellow solid which was impure by LC-MS. The mixture was further purified by prep-HPLC to give 11.3 mg, 27% of the title compound as a 76:24 mixture of (E)/(Z) geometric isomers. $^1$H NMR (400 MHz, CD$_3$OD) δ 8.79, 7.87 (s, 1H), 8.69, 8.66 (d, J=6.52 Hz, 2H), 7.98-7.73 (m, 4H), 7.74, 7.62 (d, J=8.36 Hz, 1H), 7.66, 7.44 (d, J=8.44 Hz, 1H), 7.25, 7.05 (t, J=7.79 Hz, 1H), 6.95-6.84 (m, 2H), 3.53, 3.51 (s, 4H); MS ESI 367.2 [M+H]$^+$, calcd for [$C_{23}H_{18}N_4O+H$]$^+$ 367.16.

Example A65

(E & Z)-3-((3-((E)-4-(trifluoromethyl)styryl)-1H-indazol-6-yl)-methylene)-indolin-2-one

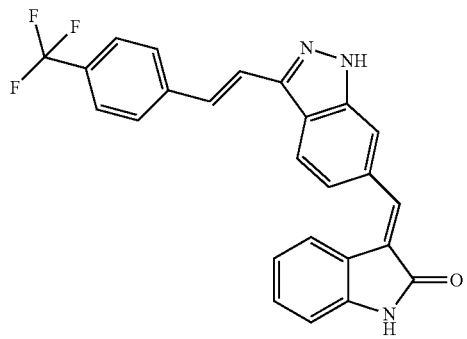 [SMILES: O=C1Nc2ccccc2/C1=C\c1ccc2c(/C=C/c3ccc(C(F)(F)F)cc3)n[nH]c2c1]

A. (E)-3-((3-(4-(trifluoromethyl)styryl)-1-((2-(trimethylsilyl)ethoxy)methyl)-1H-indazol-6-yl)methylene)indolin-2-one The synthetic method followed that described in Example A57, parts A and B starting from 4-trifluoromethylstyrene (48 uL, 0.324 mmol) and 3-iodo-1-((2-(trimethylsilyl)ethoxy)methyl)-1H-indazole-6-carbaldehyde (100 mg, 0.249 mmol) to obtain the title compound (49 mg, 35%). MS ESI 562.2 [M+H]$^+$, calcd for [$C_{31}H_{30}F_3N_3O_2Si+H$]$^+$ 562.21.

B. (E and Z)-3-((3-((E)-4-(trifluoromethyl)styryl)-1H-indazol-6-yl)-methylene)-indolin-2-one The synthetic method followed that described in Example A64, part C starting from (E)-3-((3-(4-(trifluoromethyl)styryl)-1-((2-(trimethylsilyl)ethoxy)methyl)-1H-indazol-6-yl)methylene)indolin-2-one (49 mg, 0.087 mmol). Following prep-HPLC purification, the title compound was obtained of a yellow powder (4.5 mg, 12%) which consisted of a 72:28 mixture of (E)/(Z) isomers. $^1$H NMR (400 MHz, CD$_3$OD) δ 8.92, 7.89 (two s, 1H), 8.27, 8.16 (two d, J=8.45 Hz, 1H), 7.98-7.83 (m, 3H), 7.70-7.56 (m, 5H), 7.26, 7.06 (two t, J=8.24 Hz, 1H), 7.64 (s, 1H), 6.95-6.86 (m, 2H); MS ESI 432.2 [M+H]$^+$, calcd for [$C_{25}H_{16}F_3N_3O+H$]$^+$ 432.13.

Example A66

(E and Z)-3-((3-((E)-3-(4-methylpiperazin-1-yl)-3-oxoprop-1-enyl)-1H-indazol-6-yl)methylene)indolin-2-one

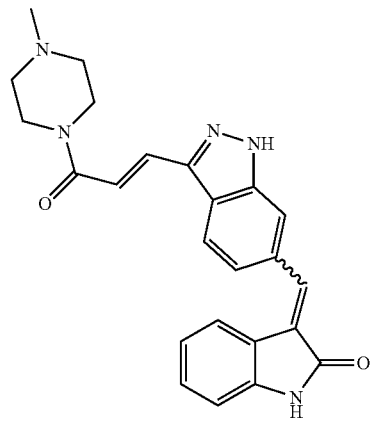 [SMILES: CN1CCN(C(=O)/C=C/c2n[nH]c3cc(C=C4C(=O)Nc5ccccc54)ccc23)CC1]

A. 1-(4-methylpiperazin-1-yl)prop-2-en-1-one

A dry round-bottom flask was charged with 1-methylpiperazine (0.15 mL, 1.36 mmol), diisopropylethylamine (0.65 mL, 3.72 mmol) and CH$_2$Cl$_2$ (6 mL) and then the solution was cooled with an ice-water bath. Acryloyl chloride (0.10 mL, 1.24 mmol) was then added dropwise and the reaction was allowed to warm to room temperature. After 3 hours TLC indicated reaction completion. The CH$_2$Cl$_2$ was removed and the residue taken up in EtOAc, washed with NaHCO$_3$ $_{(sat.)}$ (1×), brine (2×) and then dried over MgSO$_4$. The EtOAc was removed in vacuo which yielded after drying, the title compound as an orange-brown oil. (400 MHz, CDCl$_3$) 6.57 (dd, J$_1$=16.8 Hz, J$_2$=10.5 Hz, 1H), 6.29 (d, J=16.8 Hz, 1H), 5.70

(d, J=10.5 Hz, 1H), 3.73 (bs, 2H), 3.60 (bs, 2H), 2.46-2.41 (m, 4H), 2.34 (s, 3H); MS ESI 155.0 [M+H]⁺, calcd for [C₈H₁₄N₂O+H]⁺

B. (E and Z)-3-((3-((E)-3-(4-methylpiperazin-1-yl)-3-oxoprop-1-enyl)-1H-indazol-6-yl)methylene)indolin-2-one The synthetic method followed of that described in Example A2 with a modified purification. A yellow oil was obtained which was titurated and sonicated with 1:5 Et₂O/hexanes which after decanting off the solvent gave 4.7 mg (8.5% yield over 3 steps) of an orange-yellow powder as a 73:27 mixture of (E)/(Z) isomers. ¹H NMR (400 MHz, CD₃OD) δ 8.93, 7.97 (s, 1H), 8.17, 8.06 (d, J=8.33 Hz, 1H), 7.98-7.87 (m, 2H), 7.69-7.58 (m, 2H), 7.46, 7.42 (d, J=15.5 Hz, 1H), 7.25 (t, J=7.77 Hz, 1H), 7.07-6.85 (m, 2H), 3.95-3.78 (m, 4H), 2.68-2.55 (bs, 4H), 2.41 (s, 3H); MS ESI 414.2 [M+H]⁺, calcd for [C₂₄H₂₃N₅O₂+H]⁺ 414.19.

Example A67

(E)-3-((1H-indazol-6-yl)methylene)-1H-pyrrolo[2,3-b]pyridin-2(3H)-one

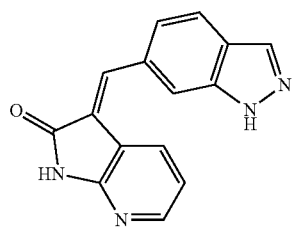 [SMILES: O=C1Nc2ncccc2/C1=C\c1ccc2cn[nH]c2c1]

To a mixture of 1H-pyrrolo[2,3-b]pyridin-2(3H)-one (26.8 mg, 0.2 mmol) and 1H-indazole-6-carbaldehyde (29.2 mg, 0.2 mmol) in MeOH (2 mL) was added 1 drop of piperidine via syringe needle. The resulting mixture was refluxed for 2 h (oil temp. 70° C.) and then cooled to rt. The resulting precipitate was collected by suction filtration to give the title compound as a yellow solid (37 mg, 71%). ¹H NMR (400 MHz, DMSO-d6) δ 13.31 (s, 1H, NH), 11.25 (s, 1H, NH), 8.16 (s, 1H), 8.10 (d, J=5.2 Hz, 1H), 7.93-7.87 (m, 4H), 7.44 (d, J=8.8 Hz, 1H), 6.90 (dd, J=7.6 Hz, 5.6 Hz, 1H); MS ESI 263.0 [M+H]⁺, calcd for [C₁₅H₁₀N₄O+H]⁺ 263.1.

Example A68

(E)-3-((1H-indazol-5-yl)methylene)-1H-pyrrolo[2,3-b]pyridin-2(3H)-one

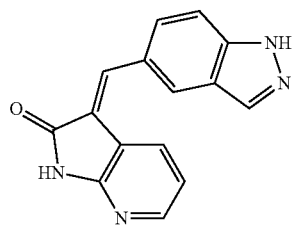 [SMILES: O=C1Nc2ncccc2/C1=C\c1ccc2[nH]ncc2c1]

The title compound (50 mg, 95%) was synthesized as an orange solid according to the method described for Example A67 using 1H-pyrrolo[2,3-b]pyridin-2(3H)-one (26.8 mg, 0.2 mmol) and 1H-indazole-5-carbaldehyde (29.2 mg, 0.2 mmol). ¹H NMR (400 MHz, DMSO-d6) δ 13.36 (s, 1H, NH), 11.20 (s, 1H, NH), 8.21 (s, 2H), 8.09 (d, J=5.2 Hz, 1H), 7.94 (d, J=8.0 Hz, 1H), 7.89 (s, 1H), 7.72 (d, J=8.8 Hz, 1H), 7.68 (d, J=8.4 Hz, 1H), 6.91 (dd, J=8.0 Hz, 5.6 Hz, 1H); MS ESI 263.0 [M+H]⁺, calcd for [C₁₅H₁₀N₄O+H]⁺ 263.1.

Example A69

(E and Z)-3-((1H-indazol-6-yl)methylene)-5-bromo-1H-pyrrolo[2,3-b]pyridin-2(3H)-one

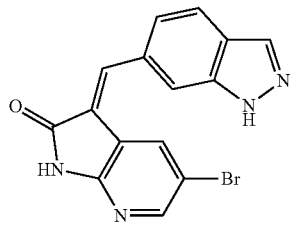 [SMILES: O=C1Nc2ncc(Br)cc2/C1=C\c1ccc2cn[nH]c2c1]

The title compound (50 mg, 95%) was synthesized as a green solid according to the method described for Example A67 using 5-bromo-1H-pyrrolo[2,3-b]pyridin-2(3H)-one (21.3 mg, 0.1 mmol) and 1H-indazole-6-carbaldehyde (14.6 mg, 0.1 mmol). ¹H NMR indicated 56:44 mixture of E/Z isomers. E isomer: ¹H NMR (400 MHz, DMSO-d6) δ 13.38 (s, 1H, NH), 11.45 (s, 1H, NH), 8.38 (d, J=2.0 Hz, 1H), 8.25 (d, J=2.0 Hz, 1H), 8.19 (s, 1H), 8.01 (s, 1H), 7.93 (s, 1H), 7.90 (d, J=2.0 Hz, 1H), 7.45 (dd, J=8.4 Hz, 2.0 Hz, 1H); Z isomer: δ 13.46 (s, 1H, NH), 11.45 (s, 1H, NH), 8.94 (s, 1H), 8.21 (d, J=2.0 Hz, 1H), 8.19 (s, 1H), 8.15 (s, 1H), 7.99 (dd, J=8.8 Hz, 1.6 Hz, 1H), 7.94 (d, J=8.4 Hz, 1H), 7.85 (d, J=8.0 Hz, 1H); MS ESI 341.0 [M+H]⁺, calcd for [C₁₅H₉BrN₄O+H]⁺ 341.1.

Example A70

(E)-3-(6-((E)-(2-oxoindolin-3-ylidene)methyl)-1H-indazol-3-yl)acrylic acid

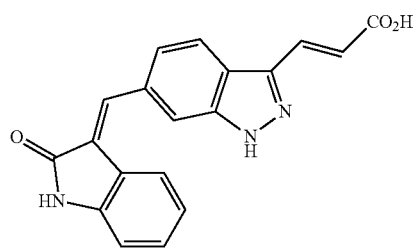 [SMILES: O=C(O)/C=C/c1n[nH]c2cc(/C=C3/C(=O)Nc4ccccc43)ccc12]

a) (E)-3-(6-cyano-1H-indazol-3-yl)acrylic acid

To a mixture of 3-formyl-1H-indazole-6-carbonitrile (34 mg, 0.2 mmol) and malic acid (104 mg, 1 mmol) in pyridine (3 mL) was added 2 drops of piperidine. The resulting mixture was refluxed for 1 h (oil temp. 130° C.) before cooling to 0° C. the reaction was quenched with ice, followed by 2M HCl (30 mL). The resulting mixture was extracted with EtOAc (30 mL+15 mL). The combined extracts were washed with 2 M HCl and dried (Na$_2$SO$_4$). Evaporation of the solvents gave the title compound (29 mg, 68%) as an orange solid. $^1$H NMR (400 MHz, DMSO-d6) δ 14.13 (s, 1H, NH), 12.55 (brs, 1H, CO$_2$H), 8.31 (d, J=8.0 Hz, 1H), 8.24 (s, 1H), 7.86 (d, J=16.4 Hz, 1H), 7.56 (d, J=8.0 Hz, 1H), 6.75 (d, J=16.4 Hz, 1H); MS ESI 214.0 [M+H]$^+$, calcd for [C$_{11}$H$_8$N$_2$O$_3$+H]$^+$ 214.1.

b) (E)-3-(6-formyl-1H-indazol-3-yl)acrylic acid

To a solution of (E)-3-(6-cyano-1H-indazol-3-yl)acrylic acid (25 mg, 0.12 mmol) in acetic acid/pyridine (2 mL/4 mL) was added a solution of sodium hypophophite (42 mg, 0.48 mmol) in H$_2$O (2 mL), followed by Raney-Nickel 2400 (slurry in H$_2$O, 0.1 mL). The resulting mixture was heated at 55° C. (oil temp.) for 1 h before cooling to rt. H$_2$O (20 mL) was added and the mixture was extracted with EtOAc (30 mL×2). The combined extracts were washed with 2M HCl (10 mL×2), H$_2$O (10 mL×2), brine (10 mL) and dried (Na$_2$SO$_4$). Removal of the solvent gave the title compound (18 mg, 72%) as a beige solid. $^1$H NMR (400 MHz, DMSO-d6) δ 14.12 (s, 1H, NH), 12.24 (brs, 1H, CO$_2$H), 10.01 (s, 1H, CHO), 8.26 (d, J=8.8 Hz, 1H), 8.22 (s, 1H), 7.87 (d, J=16.0 Hz, 1H), 7.71 (d, J=8.8 Hz, 1H), 6.76 (d, J=16.4 Hz, 1H); MS ESI 217.0 [M+H]$^+$, calcd for [C$_{11}$H$_8$N$_2$O$_3$+H]$^+$ 217.1.

c) (E)-3-(6-((E)-(2-oxoindolin-3-ylidene)methyl)-1H-indazol-3-yl)acrylic acid

The title compound (7 mg, 21%) was synthesized as an orange solid according to the method described for Example A67 using oxindole (13.3 mg, 0.1 mmol) and (E)-3-(6-formyl-1H-indazol-3-yl)acrylic acid (21.6 mg, 0.1 mmol). NMR (400 MHz, DMSO-d6) δ 13.80 (br. s, 1H, NH), 10.64 (s, 1H, CO$_2$H), 8.20 (d, J=8.4 Hz, 1H), 7.94 (s, 1H), 7.85 (d, J=16.4 Hz, 1H), 7.78 (s, 1H), 7.58-7.53 (m, 2H), 7.24 (t, J=7.6 Hz, 1H), 6.88 (d, J=8.0 Hz, 1H), 6.84 (t, J=7.8 Hz, 1H), 6.75 (d, J=16.0 Hz, 1H); MS ESI 332.1 [M+H]$^+$, calcd for [C$_{19}$H$_{13}$N$_3$O$_3$+H]$^+$ 322.1.

Example A71

(E)-3-(6-((E & Z)-(2-oxo-1H-pyrrolo[2,3-b]pyridin-3(2H)-ylidene)-methyl)-1H-indazol-3-yl)acrylic acid

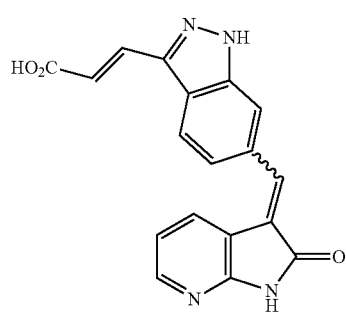 [SMILES: O=C(O)/C=C/c1n[nH]c2cc(C=C3C(=O)Nc4ncccc43)ccc12]

The title compound (13 mg, 39%) was synthesized as an orange solid according to the method described for Example A67 using 1H-pyrrolo[2,3-b]pyridin-2(3H)-one (13.4 mg, 0.1 mmol) and (E)-3-(6-formyl-1H-indazol-3-yl)acrylic acid (21.6 mg, 0.1 mmol). The $^1$H NMR indicated a 5:2 mixture of E/Z isomers. $^1$H NMR (400 MHz, DMSO-d6) δ 11.25 (br. s, 1H), 8.21 (d, J=8.4 Hz, 1H), 8.12-8.07 (m, 2H), 7.6 (s, 1H), 7.93 (s, 1H), 7.82 (d, J=16.0 Hz, 1H), 7.55 (d, J=8.4 Hz, 1H), 6.90 (dd, J=8.4 Hz, 3.2 Hz, 1H), 6.75 (d, J=16.0 Hz, 1H); MS ESI 332.1 [M+H]$^+$, calcd for [C$_{18}$H$_{12}$N$_4$O$_3$+H]$^+$ 332.1.

Example A72

(E)-3-((3-((E)-2-(pyridin-2-yl)vinyl)-1H-indazol-6-yl)methylene)-1H-pyrrolo[2,3-b]pyridin-2(3H)-one

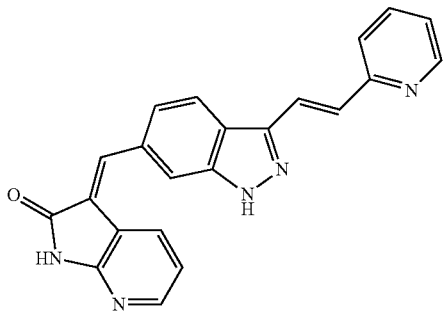 [SMILES: O=C1Nc2ncccc2/C1=C\c1ccc2c(/C=C/c3ccccn3)n[nH]c2c1]

The title compound (7 mg, 21%) was synthesized as yellow solid according to the method described for Example A67 using 1H-pyrrolo[2,3-b]pyridin-2(3H)-one (9.3 mg, 0.07 mmol) and (E)-3-(2-(pyridin-2-yl)vinyl)-1H-indazole-6-carbaldehyde (17 mg, 0.068 mmol). $^1$H NMR (400 MHz, DMSO-d6) δ 13.53 (s, 1H, NH), 11.27 (s, 1H, NH), 8.62 (d, J=4.0 Hz, 1H), 8.35 (d, J=8.4 Hz, 1H), 8.12 (d, J=5.2 Hz, 1H), 8.02-7.89 (m, 4H), 7.82 (t, J=8.0 Hz, 1H), 7.69 (d, J=7.6 Hz, 1H), 7.63 (d, J=16.8 Hz, 1H), 7.56 (d, J=8.4 Hz, 1H), 7.28 (t, J=6.0 Hz, 1H), 6.91 (dd, J=7.6 Hz, 5.6 Hz, 1H); MS ESI 366.1 [M+H]$^+$, calcd for [C$_{22}$H$_{15}$N$_5$O+H]$^+$ 366.1.

Example A73

(E and Z)-3-(1H-indazol-6-ylimino)indolin-2-one

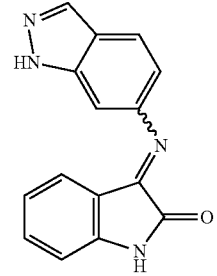 [SMILES: O=C1Nc2ccccc2C1=Nc1ccc2cn[nH]c2c1]

To a mixture of isatin (147 mg, 1 mmol) and 6-aminoindazole (133 mg, 1 mmol) in EtOH (5 mL) was added 2 drops of acetic acid. The resulting mixture was capped and microwaved 60 min at 120° C. After cooling to rt, the precipitate was collected by suction filtration to give 135 mg (48%) of title compound as yellow solid. $^1$H NMR indicated a 85:15 mixture of E/Z isomers. $^1$H NMR (400 MHz, DMSO-d6) δ 13.04 (s, 1H, NH), 11.00 (s, 1H, NH), 8.09 (s, 1H), 8.36 (d, J=8.4 Hz, 1H), 7.32 (t, J=8.0 Hz, 1H), 7.07 (s, 1H), 6.89 (t, J=8.0 Hz, 1H), 7.77 (d, J=8.4 Hz, 1H), 6.66 (t, J=7.6 Hz, 1H), 6.32 (d, J=7.6 Hz, 1H); MS ESI 263.0 [M+H]$^+$, calcd for [C$_{15}$H$_{10}$N$_4$O+H]$^+$ 263.1.

Example A74

(E and Z)-3-(1H-indazol-6-ylimino)-5-methylindolin-2-one

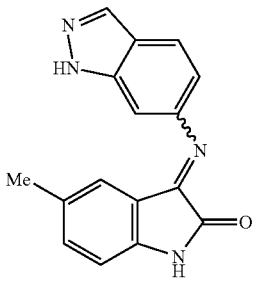 [SMILES: Cc1ccc2c(c1)C(=Nc1ccc3cn[nH]c3c1)C(=O)N2]

To a mixture of 5-methylisatin (80.5 mg, 0.5 mmol) and 6-aminoindazole (66.5 mg, 0.5 mmol) in EtOH (2 mL) was added 1 drops of acetic acid. The resulting mixture was capped and microwaved 30 min at 120° C. After cooling to rt, it was stirred for 5 min at rt and the resulting precipitate was collected by suction filtration to give the title compound (35 mg, 28%) as an orange red solid. $^1$H NMR indicated a 80:20 mixture of E/Z isomers. $^1$H NMR (400 MHz, DMSO-d6) δ 13.03 (s, 1H, NH), 10.89 (s, 1H, NH), 8.10 (s, 1H), 7.84 (d, J=8.8 Hz, 1H), 7.15 (d, J=7.2 Hz, 1H), 7.07 (s, 1H), 6.81-6.74 (m, 2H), 6.17 (s, 1H), 2.49 (s, 3H, CH$_3$); MS ESI 277.0 [M+H]$^+$, calcd for [C$_{16}$H$_{12}$N$_4$O+H]$^+$ 277.1.

Example A75

(E and Z)-3-(1H-indazol-6-ylimino)-5-fluoroindolin-2-one

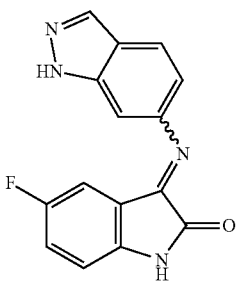 [SMILES: O=C1Nc2ccc(F)cc2C1=Nc1ccc2cn[nH]c2c1]

The title compound (76 mg, 54%) was synthesized as a dark red solid according to the method described for Example A74 using 5-fluoroisatin (82.5 mg, 0.5 mmol) and 6-aminoindazole (66.5 mg, 0.5 mmol). NMR analysis indicated a 79:21 mixture of E/Z isomers. $^1$H NMR (400 MHz, DMSO-d6) δ 13.08 (s, 1H, NH), 11.03 (s, 1H, NH), 8.11 (s, 1H), 7.87 (d, J=8.4 Hz, 1H), 7.22 (dt, J=9.2 Hz, 2.8 Hz, 1H), 6.90 (dd, J=8.4 Hz, 4.4 Hz, 1H), 6.82-6.77 (m, 1H), 5.98 (dd, J=8.0 Hz, 2.0 Hz, 1H); MS ESI 281.0 [M+H]$^+$, calcd for [C$_{15}$H$_9$FN$_4$O+H]$^+$ 281.1.

Example A76

(E and Z)-3-(1H-indazol-6-ylimino)-6-bromoindolin-2-one

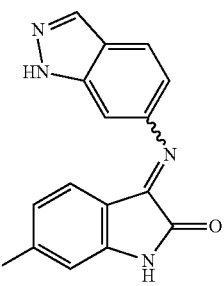

The title compound (82 mg, 48%) was synthesized as a orange red solid according to the method described for Example A74 using 6-bromoisatin (113 mg, 0.5 mmol), 6-aminoindazole (73 mg, 0.55 mmol). $^1$H NMR indicated a 83:17 mixture of E/Z isomers. $^1$H NMR (400 MHz, DMSO-d6) δ 13.07 (s, 1H, NH), 10.93 (brs, 1H, NH), 8.09 (s, 1H), 7.84 (d, J=8.4 Hz, 1H), 7.08 (s, 1H), 7.05 (d, J=1.6 Hz, 1H), 6.92 (dd, J=8.0 Hz, 1.6 Hz, 1H), 6.77 (dd, J=8.4 Hz, 1.2 Hz, 1H), 6.27 (d, J=8.0 Hz, 1H); MS ESI 341.1 [M+H]$^+$, calcd for [C$_{15}$H$_9$BrN$_4$O+H]$^+$ 341.1.

Example A77

(E and Z)-3-(1H-indazol-5-ylimino)indolin-2-one

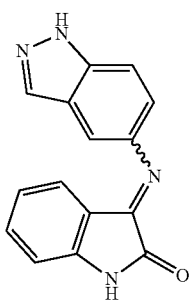 [SMILES: O=C1Nc2ccccc2C1=Nc1ccc2[nH]ncc2c1]

The title compound (165 mg, 63%) was synthesized as a yellow solid according to the method described for Example A74 using isatin (147 mg, 1 mmol), 5-aminoindazole (133 mg, 1 mmol) and 2 drops of HOAc. $^1$H NMR indicated a 5:1 mixture of E/Z isomers. $^1$H NMR (400 MHz, DMSO-d6) δ 13.17 (s, 1H, NH), 11.00 (s, 1H, NH), 8.07 (s, 1H), 7.64 (d, J=8.8 Hz, 1H), 7.35 (s, 1H), 7.31 (t, J=7.6 Hz, 1H), 7.07 (dd, J=9.2 Hz, 1.6 Hz, 1H), 6.88 (d, J=8.0 Hz, 1H), 6.67 (t, J=8.0 Hz, 1H), 6.45 (d, J=7.6 Hz, 1H); MS ESI 263.0 [M+H]⁺, calcd for [C₁₅H₁₀N₄O+H]⁺ 263.1.

Example A78

(E and Z)-3-(1H-indazol-5-ylimino)-5-methylindolin-2-one

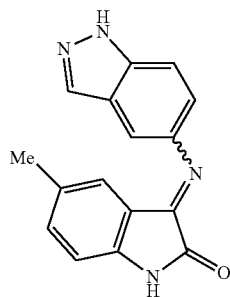 [SMILES: Cc1ccc2c(c1)C(=Nc1ccc3[nH]ncc3c1)C(=O)N2]

The title compound (83 mg, 60%) was synthesized as a brown solid according to the method described for Example A74 using 5-methylisatin (80.5 mg, 0.5 mmol), 5-aminoindazole (66.5 mg, 0.5 mmol). ¹H NMR indicated a 78:22 mixture of E/Z isomers. ¹H NMR (400 MHz, DMSO-d6) δ 13.15 (s, 1H, NH), 10.86 (s, 1H, NH), 8.08 (s, 1H), 7.64 (d, J=8.4 Hz, 1H), 7.36 (s, 1H), 7.14 (d, J=8.4 Hz, 1H), 7.07 (dd, J=8.8 Hz, 1H), 6.79 (d, J=8.0 Hz, 1H) 6.33 (s, 1H), 1.89 (s, 3H); MS ESI 277.0 [M+H]⁺, calcd for [C₁₆H₁₂N₄O+H]⁺ 277.1.

Example A79

(E and Z)-3-(1H-indazol-5-ylimino)-5-fluoroindolin-2-one

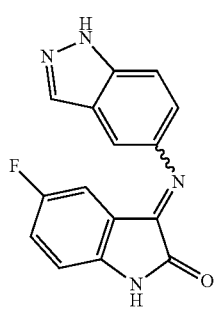 [SMILES: O=C1Nc2ccc(F)cc2C1=Nc1ccc2[nH]ncc2c1]

The title compound (62 mg, 43%) was synthesized as a brick red solid (instead of stirring at it, 1 mL of H₂O was added to crash out the product) according to the method described for Example A74 using 5-fluoroisatin (82.5 mg, 0.5 mmol), 5-aminoindazole (66.5 mg, 0.5 mmol). 1H NMR indicated a 3:1 mixture of E/Z isomers. ¹H NMR (400 MHz, DMSO-d6) δ 13.22 (s, 1H), 11.00 (s, 1H), 8.10 (s, 1H), 6.67 (d, J=8.8 Hz, 1H), 7.39 (s, 1H), 7.22 (dt, J=9.2 Hz, 2.4 Hz, 1H), 7.10 (dd, J=8.8 Hz, 1.6 Hz, 1H), 6.90 (dd, J=8.8 Hz, 4.4 Hz, 1H), 6.14 (dd, J=8.8 Hz, 2.8 Hz, 1H); MS ESI 281.0 [M+H]⁺, calcd for [C₁₅H₉FN₄O+H]⁺ 281.1.

Example A80

(E)-3-((1H-indazol-6-yl)methylene)-5-chloroindolin-2-one

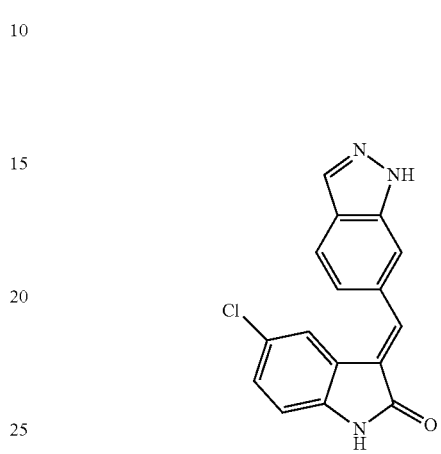

The title compound was prepared according to the procedure described in Example A1, except substituting 5-chlorooxindole (21 mg, 0.13 mmol) to give 6.3 mg of a yellow solid (29%). ¹H NMR (400 MHz, CD₃OD) δ 8.17 (s, 1H), 7.96 (s, 1H), 7.94 (d, J=8.0 Hz, 1H), 7.88 (s, 1H), 7.59 (d, J=4.0 Hz, 1H), 7.45 (d, J=8.0 Hz, 1H), 7.25 (dd, J=8.0, 4.0 Hz, 1H), 6.92 (d, J=4.0 Hz, 1H); MS ESI 296.0 [M+H]⁺, calcd for [C₁₆H₁₀ClN₃O+H]⁺ 296.06.

Example A81

(E and Z)-3-((1H-indazol-6-yl)methylene)-5-methylindolin-2-one

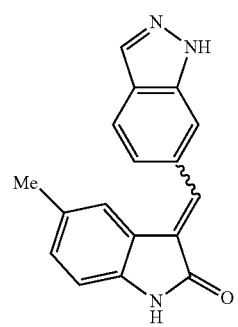 [SMILES: Cc1ccc2c(c1)C(=Cc1ccc3cn[nH]c3c1)C(=O)N2]

The title compound was prepared according to the procedure described in Example A1, except substituting 5-methyloxindole (18 mg, 0.12 mmol) to give 15 mg of a yellow solid (43%). A mixture of (E)- and (Z)-isomers (89:11 by NMR) was obtained. ¹H NMR (400 MHz, CD₃OD) δ 8.14 (s, 1H), 7.91 (d, J=8.0 Hz, 1H), 7.89 (s, 1H), 7.84 (s, 1H), 7.48 (s, 1H), 7.45 (d, J=8.0 Hz, 1H), 7.07 (d, J=8.0 Hz, 1H), 6.82 (d, J=8.0 Hz, 1H), 2.18 (s, 3H); MS ESI 276.1 [M+H]⁺, calcd for [C₁₇H₁₃N₃O+H]⁺ 276.11.

Example A82

(E and Z)-3-((1H-indazol-6-yl)methylene)-5-(trifluoromethyl)-indolin-2-one

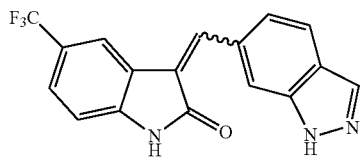 [SMILES: O=C1Nc2ccc(C(F)(F)F)cc2C1=Cc1ccc2cn[nH]c2c1]

The title compound was prepared according to the procedure described in Example A1, except substituting 5-trifluoromethyl-oxindole (28 mg, 0.14 mmol) to give 2.2 mg of a yellow solid (7%). A mixture of (E and Z)-isomers (40:60 by NMR) was obtained. ¹H NMR (400 MHz, d₆-DMSO) δ 13.43 (br s, 1H), 11.07 (br s, 1H), 8.98 (s, 1H), 8.21 (s, 1H), 8.14 (s, 1H), 8.05 (d, J=8.5 Hz, 1H), 7.93 (d, J=12.4 Hz, 1H), 7.84 (d, J=8.4 Hz, 1H), 7.57 (d, J=8.0 Hz, 1H), 7.00 (d, J=8.0 Hz, 1H); MS ESI 330.1 [M+H]⁺, calcd for [C₁₇H₁₀F₃N₃O+H]⁺ 330.08.

Example A83

(E and Z)-3-((1H-indazol-6-yl)methylene)-5-methoxyindolin-2-one

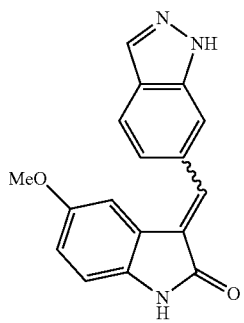 [SMILES: COc1ccc2c(c1)C(=Cc1ccc3cn[nH]c3c1)C(=O)N2]

The title compound was prepared according to the procedure described in Example A1, except substituting 5-methoxyoxindole (22 mg, 0.14 mmol) to give 12.3 mg as a yellow solid (31%). A mixture of (E)- and (Z)-isomers (84:16 by NMR) was obtained. ¹H NMR (400 MHz, CD₃OD) δ 8.14 (s, 1H), 7.95-7.87 (m, 3H), 7.46 (d, J=8.8 Hz, 1H), 7.23 (s, 1H), 6.84 (s, 2H), 3.62 (s, 3H); MS ESI 292.1 [M+H]⁺, calcd for [C₁₇H₁₃N₃O₂+H]⁺ 292.10.

Example A84

(E)-5-chloro-3-((3-((E)-2-(pyridin-4-yl)vinyl)-1H-indazol-6-yl)methylene)indolin-2-one

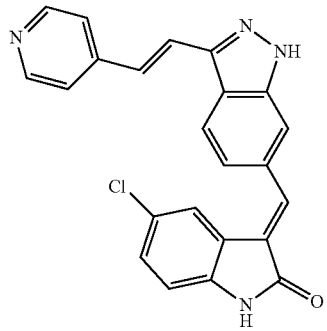 [SMILES: O=C1Nc2ccc(Cl)cc2/C1=C\c1ccc2c(/C=C/c3ccncc3)n[nH]c2c1]

According to the procedure for the synthesis of (E)-3-((3-((E)-2-(pyridin-4-yl)vinyl)-1H-indazol-6-yl)methylene)indolin-2-one (Example A57), except substituting 5-chlorooxindole (14 mg, 0.08 mmol), the title compound was prepared as an orange solid (13.5 mg, 42%). ¹H NMR (400 MHz, d₆-DMSO) δ 13.63 (br s, 1H), 10.78 (br. s, 1H), 8.56 (d, J=4.0 Hz, 2H), 8.40 (d, J=10.0 Hz, 1H), 7.91 (s, 1H), 7.89 (d, J=13.2 Hz, 2H), 7.72 (d, J=3.5 Hz, 2H), 7.57 (d, J=12.0 Hz, 1H), 7.52 (d, J=12.0 Hz, 2H), 7.30 (d, J=10.0 Hz, 1H), 6.90 (d, J=11.5 Hz, 1H); MS ESI 399.2 [M+H]⁺, calcd for [C₂₃H₁₅ClN₄O+H]⁺ 399.09.

Example A85

(E)-5-methyl-3-((3-((E)-2-(pyridin-4-yl)vinyl)-1H-indazol-6-yl)methylene)indolin-2-one

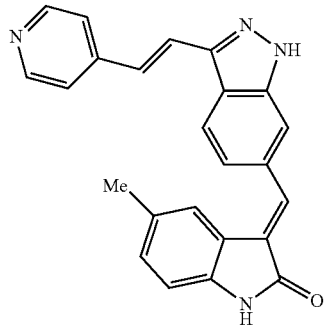 [SMILES: Cc1ccc2c(c1)/C(=C\c1ccc3c(/C=C/c4ccncc4)n[nH]c3c1)C(=O)N2]

According to procedure for the synthesis of (E)-3-((3-((E)-2-(pyridin-4-yl)vinyl)-1H-indazol-6-yl)methylene)indolin-2-one, except substituting 5-methyloxindole (9 mg, 0.06 mmol) to give the title compound as an orange solid (5.9 mg, 26%). ¹H NMR (400 MHz, d₆-DMSO) δ 13.58 (br s, 1H), 10.53 (br s, 1H), 8.57 (br s, 2H), 8.36 (d, J=8.0 Hz, 1H), 7.93-7.46 (m, 8H), 7.06 (d, J=8.0 Hz, 1H), 6.79 (d, J=5.8 Hz, 1H), 2.16 (s, 3H); MS ESI 379.2 [M+H]$^+$, calcd for [C$_{24}$H$_{18}$N$_4$O+H]$^+$ 379.15.

Example A86

(E)-5-methoxy-3-((3-((E)-2-(pyridin-4-yl)vinyl)-1H-indazol-6-yl)methylene)indolin-2-one

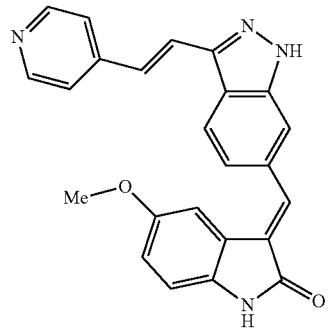 [SMILES: COc1ccc2c(c1)/C(=C\c1ccc3c(/C=C/c4ccncc4)n[nH]c3c1)C(=O)N2]

According to procedure for the synthesis of (E)-3-((3-((E)-2-(pyridin-4-yl)vinyl)-1H-indazol-6-yl)methylene)indolin-2-one, except substituting 5-methoxyoxindole (11 mg, 0.068 mmol) to give the title compound as an orange solid (13.6 mg, 51%). $^1$H NMR (400 MHz, d$_6$-DMSO) δ 13.58 (br s, 1H), 10.45 (br s, 1H), 8.57 (d, J=6.0 Hz, 2H), 8.37 (d, J=8.5 Hz, 1H), 7.93 (s, 1H), 7.87 (d, J=16.6 Hz, 1H), 7.79 (s, 1H), 7.71 (d, J=6.0 Hz, 2H), 7.57 (d, J=2.3 Hz, 1H), 7.54 (d, J=6.3 Hz, 1H), 7.18 (d, J=10.0 Hz, 1H), 6.86 (dd, J=8.8, 2.5 Hz, 1H) 6.80 (d, J=8.3 Hz, 1H), 3.6 (s, 3H); MS ESI 395.2 [M+H]$^+$, calcd for [C$_{24}$H$_{18}$N$_4$O$_2$+H]$^+$ 395.14.

Example A87

(E and Z)-5-methoxy-3-((3-((E)-2-(pyridin-2-yl)vinyl)-1H-indazol-6-yl)methylene)indolin-2-one

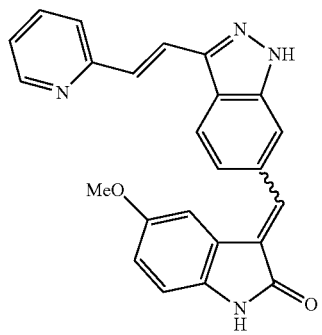 [SMILES: COc1ccc2c(c1)C(=Cc1ccc3c(/C=C/c4ccccn4)n[nH]c3c1)C(=O)N2]

According to procedure for the synthesis of (E)-3-((3-((E)-2-(pyridin-2-yl)vinyl)-1H-indazol-6-yl)methylene)indolin-2-one (Example A41), except substituting 5-methoxyoxindole (14 mg, 0.086 mmol), the title compound was prepared as an orange solid (8.8 mg, 26%). A mixture of (E)- and (Z)-isomers (80:20 by NMR) was obtained. $^1$H NMR (400 MHz, CD$_3$OD) δ 8.59-57 (m, 1H), 8.28 (d, J=8.5 Hz, 1H), 7.95 (d, J=16.6 Hz, 1H), 7.92-7.89 (m, 2H), 7.86 (dd, J=7.5, 1.8 Hz, 1H), 7.75 (d, J=8.0 Hz, 1H), 7.65 (d, J=16.6 Hz, 1H), 7.59 (dd, J=8.8, 1.3 Hz, 1H), 7.33 (ddd, J=7.5, 5.0, 1.3 Hz, 1H), 7.27 (t, J=1.3 Hz, 1H), 6.86-6.85 (m, 2H), 3.85 (s, 3H); MS ESI 395.2 [M+H]$^+$, calcd for [C$_{24}$H$_{18}$N$_4$O$_2$+H]$^+$ 395.14.

Example A88

2-((E)-2-(6-((E)-(5-methoxy-2-oxoindolin-3-ylidene)methyl)-1H-indazol-3-yl)vinyl)pyridine 1-oxide

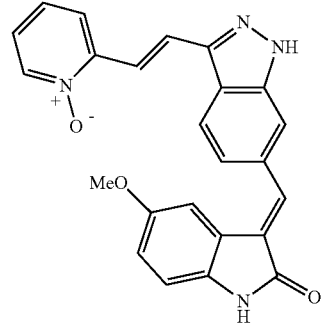

A round bottom flask was charged with (E)-5-methoxy-3-((3-((E)-2-(pyridin-2-yl)vinyl)-1H-indazol-6-yl)methylene)indolin-2-one (25 mg, 0.063 mmol), mCPBA (13 mg, 0.076 mmol), and dichloromethane (4 mL). The reaction was stirred at rt for 24 hrs. Solvent was removed in vacuo and the residue was loaded onto a silica gel column. Elution with 90:10 CH$_2$Cl$_2$/MeOH gave 9 mg (35%) of the title compound as an orange solid. $^1$H NMR (400 MHz, CD$_3$OD) δ 8.41 (d, J=6.0 Hz, 1H), 8.31 (d, J=8.5 Hz, 1H), 8.19 (d, J=16.3 Hz, 1H), 8.14 (d, J=8.0 Hz, 1H), 8.04 (d, J=17.1 Hz, 1H), 7.91 (d, J=16.1 Hz, 2H), 7.67-7.60 (m, 2H), 7.47-7.43 (m, 1H), 7.25 (s, 1H), 6.85 (s, 2H), 3.64 (s, 3H); MS ESI 411.2 [M+H]$^+$, calcd for [C$_{24}$H$_{18}$N$_4$O$_3$+H]$^+$ 411.14.

Example A89

(E and Z)-3-((3-(1H-pyrrol-2-yl)-1H-indazol-6-yl)methylene)indolin-2-one

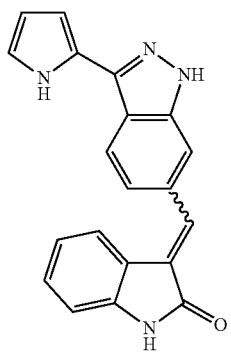 [SMILES: O=C1Nc2ccccc2C1=Cc1ccc2c(-c3ccc[nH]3)n[nH]c2c1]

A. 3-(1H-pyrrol-2-yl)-1H-indazole-6-carbaldehyde

A mixture of 3-iodo-1-((2-(trimethylsilyl)ethoxy)methyl)-1H-indazole-6-carbaldehyde (50 mg, 0.12 mmol), 1-(tert-butoxycarbonyl)-1H-pyrrol-2-ylboronic acid (40 mg, 0.19 mmol), Pd(PPh$_3$)$_4$ (15 mg, 0.012 mmol) and 2M Na$_2$CO$_3$ (0.19 mL, 0.37 mmol) in DME/H$_2$O (2 mL/1 mL) was degassed by evacuation and blanketed with Ar. The reaction mixture was sealed and heated with stirring under microwave irradiation at 125° C. for 60 min. The crude reaction mixture was concentrated under reduced pressure. The residue was purified by flash chromatography on silica gel using EtOAc (2%) in DCM as the eluent to provide a pale yellow solid (39 mg, 71%). The solid was dissolved in THF (8 mL) and treated with 1M TBAF (0.44 mL, 0.44 mmol); the resulting reaction mixture was heated under reflux for 16 h. The crude reaction mixture was concentrated under reduced pressure. Ethyl acetate (5 mL) was added and the solution was washed with brine (2×10 mL), dried over MgSO$_4$, filtered and concentrated. The crude product was purified by flash chromatography on silica gel using EtOAc (20%) in DCM as the eluent to provide the title compound a pale yellow solid (4.3 mg, 24%). $^1$H NMR (400 MHz, CDCl$_3$) δ ppm 10.11 (s, 1H), 8.16 (d, J=8.0 Hz, 1H), 8.09 (s, 1H), 7.72 (d, J=8.0 Hz, 1H), 6.92 (s, 1H), 6.79 (d, J=2.2 Hz, 1H), 6.28 (s, 1H); MS ESI 212.0 (100) [M+H]$^+$, calcd for [C$_{12}$H$_9$N$_3$O+H]$^+$ 212.07.

B. (E and Z)-3-((3-(1H-pyrrol-2-yl)-1H-indazol-6-yl)methylene)indolin-2-one

According to the procedure described in A1, except substituting 3-(1H-pyrrol-2-yl)-1H-indazole-6-carbaldehyde (6.9 mg, 0.033 mmol), the title compound was prepared as a yellow solid (6.8 mg, 64%). A mixture of (E)- and (Z)-isomers (83:17 by NMR) was obtained. $^1$H NMR (400 MHz, CD$_3$OD) δ 8.13 (d, J=8.5 Hz, 1H), 7.96 (d, J=19.1 Hz, 2H), 7.69 (d, J=7.8 Hz, 1H), 7.49 (d, J=8.3 Hz, 1H), 7.24 (t, J=7.5, 1.0 Hz, 1H), 6.94-6.91 (m, 2H), 6.88 (t, J=7.8 Hz, 1H), 6.80 (d, J=2.5 Hz, 1H), 6.29 (t, J=3.5 Hz, 1H); MS ESI 327.1 [M+H]$^+$, calcd for [C$_{20}$H$_{14}$N$_4$O+H]$^+$ 327.12.

Example A90

(E and Z)-3-((3-(1H-indol-2-yl)-1H-indazol-6-yl)methylene)indolin-2-one

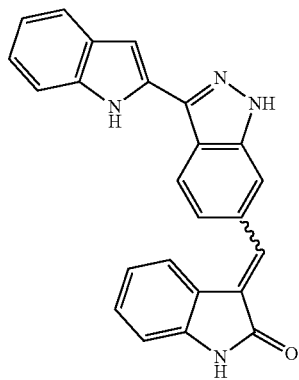 [SMILES: O=C1Nc2ccccc2C1=Cc1ccc2c(-c3cc4ccccc4[nH]3)n[nH]c2c1]

A. 3-(1H-indol-2-yl)-1H-indazole-6-carbaldehyde

According to the procedure for the synthesis of 3-(1H-pyrrol-2-yl)-1H-indazole-6-carbaldehyde, except substituting 1-(tert-butoxycarbonyl)-1H-indol-2-ylboronic acid (39 mg, 0.15 mmol), the title compound was prepared as a beige solid (4.4 mg, 14%). $^1$H NMR (400 MHz, CDCl$_3$) δ ppm 10.18 (s, 1H), 9.09 (s, 1H), 8.29 (d, J=8.8 Hz, 1H), 8.06 (s, 1H), 7.85 (d, J=8.0 Hz, 1H), 7.73 (d, J=7.8 Hz, 1H), 7.47 (d, J=8.0 Hz, 1H), 7.0520-7.15 (m, 2H); MS ESI 262.1 (100) [M+H]$^+$, calcd for [C$_{16}$H$_{11}$N$_3$O+H]$^+$ 262.09.

B. (E and Z)-3-((3-(1H-indol-2-yl)-1H-indazol-6-yl)methylene)indolin-2-one

According to the procedure for the synthesis of (E)-3-((1H-indazol-6-yl)methylene)indolin-2-one, except substituting 3-((3-(1H-indol-2-yl)-1H-indazol-6-yl)methylene)indolin-2-one (4.6 mg, 0.018 mmol), the title compound was prepared as a yellow solid (2.2 mg, 33%). A mixture of (E)- and (Z)-isomers (66:34 by NMR) was obtained. $^1$H NMR (400 MHz, CD$_3$OD) δ 8.30 (d, J=8.5 Hz, 1H), 7.93 (d, J=4.3 Hz, 1H), 7.92 (s, 1H), 7.71 (d, J=8.0 Hz, 1H), 7.65 (d, J=7.8 Hz, 1H), 7.59 (dd, J=7.5, 1.0 Hz, 1H), 7.48 (dd, J=8.0, 0.8 Hz, 1H), 7.26 (t, J=7.3 Hz, 1H), 7.19-7.14 (m, 2H), 7.09-7.03 (m, 1H), 6.95 (d, J=7.5 Hz, 1H), 6.90 (td, J=7.5, 1.0 Hz, 1H); MS ESI 377.2 [M+H]$^+$, calcd for [C$_{24}$H$_{16}$N$_4$O+H]$^+$ 377.13.

Example A91

(E)-3-((3-(thiophen-2-yl)-1H-indazol-6-yl)methylene)indolin-2-one

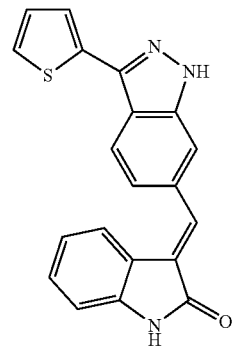 [SMILES: O=C1Nc2ccccc2/C1=C\c1ccc2c(-c3cccs3)n[nH]c2c1]

A. 3-(thiophen-2-yl)-1H-indazole-6-carbaldehyde

A mixture of 1H-indazole-6-carbaldehyde (50 mg, 0.18 mmol), thiophen-2-ylboronic acid (47 mg, 0.37 mmol), Pd(PPh$_3$)$_4$ (21 mg, 0.018 mmol) and 2M Na$_2$CO$_3$ (0.28 mL, 0.55 mmol) in DME/H$_2$O (2 mL/1 mL) was heated under reflux for 16 hours. The crude reaction mixture was concentrated under reduced pressure and purified by flash chromatography on silica gel using EtOAc (10 to 20%) in DCM as the eluent to provide the title compound as a pale yellow solid (29 mg, 70%). $^1$H NMR (400 MHz, CD$_3$OD) δ ppm 10.09 (s, 1H), 8.15 (d, J=8.5 Hz, 1H), 8.09 (s, 1H), 7.72 (d, J=8.5 Hz, 1H), 7.69 (d, J=3.8 Hz, 1H), 7.48 (d, J=5.0 Hz, 1H), 7.19 (dd, J=4.8, 3.8 Hz, 1H); MS ESI 229.0 (100) [M+H]$^+$, calcd for [C$_{12}$H$_8$N$_2$OS+H]$^+$ 229.04.

B. (E)-3-((3-(thiophen-2-yl)-1H-indazol-6-yl)methylene)indolin-2-one

According to the procedure for the synthesis of (E)-3-((1H-indazol-6-yl)methylene)indolin-2-one, except substituting 3-(thiophen-2-yl)-1H-indazole-6-carbaldehyde (29 m 0.13 mmol), the title compound was prepared as a yellow solid (19.7 mg, 45%). $^1$H NMR (400 MHz, d$_6$-DMSO) δ 10.64 (br s, 1H), 8.22 (d, J=8.5 Hz, 1H), 7.92 (s, 1H), 7.79 (s, 2H), 7.61

(d, J=7.5 Hz, 1H), 7.59 (d, J=5.0 Hz, 1H), 7.53 (d, J=8.0 Hz, 1H), 7.26-7.20 (m, 2H), 6.89 (d, J=7.5 Hz, 1H), 6.85 (t, J=7.5 Hz, 1H); MS ESI 344.1 [M+H]$^+$, calcd for [C$_{20}$H$_{13}$N$_3$OS+H]$^+$ 344.08.

Example A92

(E)-3-((3-(thiazol-2-yl)-1H-indazol-6-yl)methylene)indolin-2-one

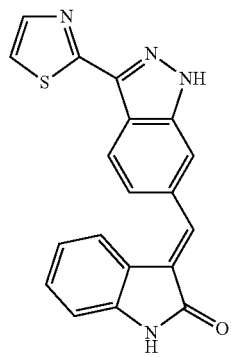 [SMILES: O=C1Nc2ccccc2/C1=C\c1ccc2c(-c3nccs3)n[nH]c2c1]

A. 3-(thiazol-2-yl)-1H-indazole-6-carbaldehyde

A mixture of 3-iodo-1-((2-(trimethylsilyl)ethoxy)methyl)-1H-indazole-6-carbaldehyde (100 mg, 0.25 mmol), 2-(tributylstannyl)thiazole (85 mg, 0.23 mmol), Pd$_2$(dba)$_3$ (23 mg, 0.025 mmol), P(o-Tol)$_3$ (15 mg, 0.05 mmol), and Et$_3$N (0.05 mL, 0.30 mmol) in DMF (2 mL) was degassed by evacuation and refilling with Ar. The reaction mixture was sealed and heated with stirring under microwave irradiation at 125° C. for 2 h. Ethyl acetate (5 mL) was added and the solution was washed with brine (2×20 mL), dried over MgSO$_4$, filtered and concentrated. The crude product was purified by flash chromatography on silica gel using EtOAc (10%) in hexanes as the eluent to provide a pale yellow solid (33 mg, 37%). The solid was dissolved in THF (10 mL) and 1M TBAF (0.47 mL, 0.47 mmol) was added. The resulting reaction mixture was heated under reflux for 16 h. The crude reaction mixture was concentrated under reduced pressure. Ethyl acetate (5 mL) was added and the solution was washed with brine (2×10 mL), dried over MgSO$_4$, filtered and concentrated. The crude product was purified by flash chromatography on silica gel using EtOAc (40%) in hexanes as the eluent to provide the title compound a pale yellow solid (4.6 mg, 8%). $^1$H NMR (400 MHz, CDCl$_3$) δ ppm 10.18 (s, 1H), 8.70 (d, J=8.5 Hz, 1H), 8.08 (s, 1H), 8.01 (d, J=3.0 Hz, 1H), 8.86 (d, J=8.5 Hz, 1H), 7.43 (d, J=3.3 Hz, 1H); MS ESI 230.0 (100) [M+H]$^+$, calcd for [C$_{11}$H$_7$N$_3$OS+H]$^+$ 230.03.

B. (E)-3-((3-(thiazol-2-yl)-1H-indazol-6-yl)methylene)indolin-2-one

According to the procedure for the synthesis of (E)-3-((1H-indazol-6-yl)methylene)indolin-2-one, except substituting 3-(thiazol-2-yl)-1H-indazole-6-carbaldehyde (4.6 mg, 0.02 mmol), the title compound was prepared as a yellow solid (2.3 mg, 36%). $^1$H NMR (400 MHz, d$_6$-DMSO) δ 13.75 (br. s, 1H), 10.64 (br. s, 1H), 8.44 (d, J=8.5 Hz, 1H), 8.03 (d, J=3.3 Hz, 1H), 7.96 (s, 1H), 7.80-7.78 (m, 2H), 7.60 (d, 7.3 Hz, 1H), 7.58 (d, J=7.5 Hz, 1H), 7.25 (td, J=7.5, 1.0 Hz, 1H), 6.88 (d, J=7.8 Hz, 1H), 6.85 (td, J=7.5, 1.0 Hz, 1H); MS ESI 345.1 [M+H]$^+$, calcd for [C$_{19}$H$_{12}$N$_4$OS+H]$^+$ 345.07.

Example A93

(E and Z)-3-((3-(pyridin-3-yl)-1H-indazol-6-yl)methylene)indolin-2-one

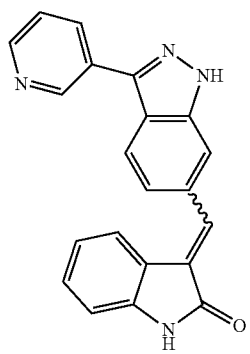 [SMILES: O=C1Nc2ccccc2C1=Cc1ccc2c(-c3cccnc3)n[nH]c2c1]

A. 3-(pyridin-3-yl)-1H-indazole-6-carbaldehyde

A mixture of 3-iodo-1H-indazole-6-carbaldehyde (50 mg, 0.18 mmol), pyridin-3-ylboronic acid (27 mg, 0.22 mmol), PdCl$_2$(PPh$_3$)$_2$ (13 mg, 0.018 mmol) and 2M Na$_2$CO$_3$ (0.10 mL, 0.18 mmol) in DME/H$_2$O/EtOH (1.4 mL/0.4 mL/0.2 mL) was degassed by evacuation and refilling with Ar. The reaction mixture was sealed and heated with stirring under microwave irradiation at 125° C. for 60 min. The crude reaction mixture was concentrated under reduced pressure. Ethyl acetate (5 mL) was added and the solution was washed with brine (2×20 mL), dried over MgSO$_4$, filtered and concentrated. The crude product was purified by flash chromatography on silica gel using MeOH (5%) in DCM as the eluent to provide the title compound a pale yellow solid (24 mg, 59%). $^1$H NMR (400 MHz, CDCl$_3$) δ ppm 10.17 (s, 1H), 8.88 (d, J=2.3 Hz, 1H), 8.69 (d, J=4.8 Hz, 1H), 8.16 (d, J=8.5 Hz, 1H), 8.10 (s, 1H), 7.92 (d, J=8.0 Hz, 1H), 7.82 (d, J=8.5 Hz, 1H), 7.45 (dd, J=8.0, 5.0 Hz, 1H); MS ESI 224.0 (100) [M+H]$^+$, calcd for [C$_{13}$H$_9$N$_3$O+H]$^+$ 224.07.

B. (E and Z)-3-((3-(pyridin-3-yl)-1H-indazol-6-yl)methylene)indolin-2-one

According to the procedure for the synthesis of (E)-3-((1H-indazol-6-yl)methylene)indolin-2-one, except substituting 3-(pyridin-3-yl)-1H-indazole-6-carbaldehyde (24 mg, 0.11 mol), the title compound was prepared as a yellow solid (9.2 mg, 25%). A mixture of (E)- and (Z)-isomers (83:17 by NMR) was obtained. $^1$H NMR (400 MHz, d$_6$-DMSO) δ 10.65 (br s, 1H), 9.23 (s, 1H), 8.62 (d, J=5.0 Hz, 1H), 8.41 (d, J=7.5 Hz, 1H), 8.21 (d, J=8.5 Hz, 1H), 7.97 (s, 1H), 7.80 (s, 1H), 7.62 (d, J=7.5, 1H), 7.58-7.53 (m, 2H), 7.24 (t, J=7.8 Hz, 1H), 6.89 (d, J=7.8 Hz, 1H), 6.85 (t, J=7.3 Hz, 1H); MS ESI 339.1 [M+H]$^+$, calcd for [C$_{21}$H$_{14}$N$_4$O+H]$^+$ 339.12.

Example A94

(E and Z)-5-chloro-3-((3-(pyridin-3-yl)-1H-indazol-6-yl)methylene)-indolin-2-one

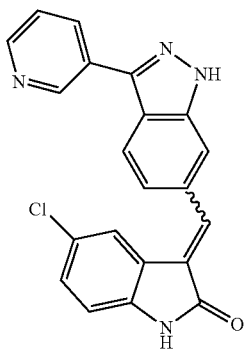 [SMILES: O=C1Nc2ccc(Cl)cc2C1=Cc1ccc2c(-c3cccnc3)n[nH]c2c1]

According to the procedure for the synthesis of 3-((3-(pyridin-3-yl)-1H-indazol-6-yl)methylene)indolin-2-one, except substituting 5-chlorooxindole (5.3 mg, 0.031 mmol) the title compound was prepared as a yellow solid (6.5 mg, 54%). A mixture of (E)- and (Z)-isomers (68:32 by NMR) was obtained. $^1$H NMR (400 MHz, d$_6$-DMSO) δ 13.77 (br s, 1H), 10.80 (br s, 1H), 9.24 (d, J=1.5 Hz, 1H), 8.63 (dd, J=4.8, 1.8 Hz, 1H), 8.41 (dt, J=7.8, 1.8 Hz, 1H), 8.28 (d, J=8.5 Hz, 1H), 8.21-8.16 (m, 1H), 7.98 (s, 1H), 7.89 (s, 1H), 7.57 (t, J=4.5, 1H), 7.55-7.52 (m, 1H), 7.31 (dd, J=8.3, 2.3 Hz, 1H), 6.91 (d, J=8.3 Hz, 1H); MS ESI 373.1 [M+H]$^+$, calcd for [C$_{21}$H$_{13}$ClN$_4$O+H]$^+$ 373.08.

Example A95

(E and Z)-3-((3-(quinolin-3-yl)-1H-indazol-6-yl)methylene)indolin-2-one

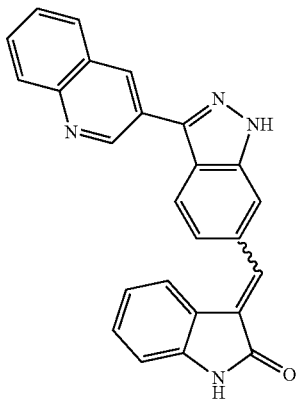 [SMILES: O=C1Nc2ccccc2C1=Cc1ccc2c(-c3cnc4ccccc4c3)n[nH]c2c1]

A. 3-(quinolin-3-yl)-1H-indazole-6-carbaldehyde

According to the procedure for the synthesis of 3-(pyridin-3-yl)-1H-indazole-6-carbaldehyde, except substituting quinolin-3-ylboronic acid (38 mg, 0.22 mmol), the title compound was obtained as a beige solid (15 mg, 30%). $^1$H NMR (400 MHz, CDCl$_3$) δ ppm 10.19 (s, 1H), 9.61 (d, J=2.0 Hz, 1H), 8.73 (d, J=2.0 Hz, 1H), 8.27 (d, J=8.3 Hz, 1H), 8.21 (d, J=8.3 Hz, 1H), 8.13 (s, 1H), 7.98 (d, J=8.3 Hz, 1H), 7.87 (dd, J=8.5, 1.3 Hz, 1H), 7.80 (ddd, J=8.3, 7.0, 1.5 Hz, 1H), 7.66 (ddd, J=8.3, 7.0, 1.3 Hz, 1H); MS ESI 274.0 (100) [M+H]$^+$, calcd for [C$_{17}$H$_{11}$N$_3$O+H]$^+$ 274.09.

B. (E and Z)-3-((3-(quinolin-3-yl)-1H-indazol-6-yl)methylene)indolin-2-one

According to the procedure for the synthesis of (E)-3-((1H-indazol-6-yl)methylene)-indolin-2-one, except substituting 3-(quinolin-3-yl)-1H-indazole-6-carbaldehyde (8 mg, 0.03 mol), the title compound was obtained as a yellow solid (4.3 mg, 38%). A mixture of (E)- and (Z)-isomers (94:6 by NMR) was obtained. $^1$H NMR (400 MHz, d$_6$-DMSO) δ 13.75 (br s, 1H), 10.66 (br. s, 1H), 9.61 (d, J=2.0 Hz, 1H), 9.04 (d, J=2.3 Hz, 1H), 8.47 (d, J=8.8 Hz, 1H), 8.22 (d, J=7.8 Hz, 1H), 8.08 (d, J=8.0 Hz, 1H), 8.01 (s, 1H), 7.83 (s, 1H), 7.80 (td, J=6.8, 1.3 Hz, 1H), 7.68 (t, J=7.8, 1H), 7.64 (d, J=7.8 Hz, 1H), 7.61 (d, J=7.8 Hz, 1H), 7.25 (t, J=7.8 Hz, 1H), 6.90 (d, J=8.3 Hz, 1H), 6.86 (t, J=7.8 Hz, 1H); MS ESI 389.1 [M+H]$^+$, calcd for [C$_{25}$H$_{16}$N$_4$O+H]$^+$ 389.13.

Example A96

(E and Z)-3-((3-(6-(4-methylpiperazin-1-yl)pyridin-3-yl)-1H-indazol-6-yl)methylene)indolin-2-one

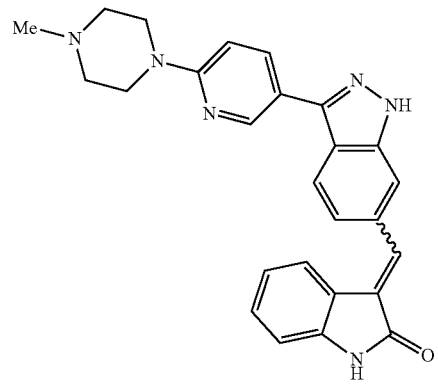 [SMILES: CN1CCN(c2ccc(-c3n[nH]c4cc(C=C5C(=O)Nc6ccccc65)ccc34)cn2)CC1]

A. 3-(6-(4-methylpiperazin-1-yl)pyridin-3-yl)-1H-indazole-6-carbaldehyde

According to the procedure for the synthesis of 3-(pyridin-3-yl)-1H-indazole-6-carbaldehyde, except substituting 1-methyl-4-(5-(4,4,5,5-tetramethyl-1,3,2-dioxa-borolan-2-yl)pyridin-2-yl)piperazine (67 mg, 0.22 mmol), the title compound was obtained as a beige solid (57 mg, 99%). $^1$H NMR (400 MHz, CD$_3$OD) δ ppm 10.11 (s, 1H), 8.73 (d, J=2.3 Hz, 1H), 8.16 (dd, J=8.8, 2.3 Hz, 1H), 8.14 (s, 1H), 8.09 (d, J=8.3 Hz, 1H), 7.72 (d, J=8.5 Hz, 1H), 7.05 (d, J=8.8 Hz, 1H), 3.83-3.78 (m, 4H), 3.01 (t, J=5.0 Hz, 4H), 2.67 (s, 3H); MS ESI 322.1 (100) [M+H]$^+$, calcd for [C$_{18}$H$_{19}$N$_5$O+H]$^+$ 322.16.

B. (E and Z)-3-((3-(6-(4-methylpiperazin-1-yl)pyridin-3-yl)-1H-indazol-6-yl)methylene)-indolin-2-one According to the procedure for the synthesis of (E)-3-((1H-indazol-6-yl)methylene)-indolin-2-one, except substituting 3-(6-(4-methylpiperazin-1-yl)pyridin-3-yl)-1H-indazole-6-carbaldehyde (40 mg, 0.12 mol), the title compound was prepared as a yellow solid (4.9 mg, 9%). A mixture of (E)- and (Z)-isomers (79:21 by NMR) was obtained. $^1$H NMR (400 MHz, d$_6$-DMSO) δ 13.34 (br. s, 1H), 10.64 (br. s, 1H), 8.76 (d, J=2.3 Hz, 1H), 8.14 (dd, J=8.8, 2.5 Hz, 2H), 7.91 (s, 1H), 7.79 (s, 1H), 7.62 (d, J=7.8, 1H), 7.48 (d, J=8.0 Hz, 1H), 7.24 (t, J=7.5 Hz, 1H), 6.99 (d, J=9.0 Hz, 1H), 6.89 (d, J=7.8 Hz, 1H), 6.85 (t, J=7.3 Hz, 1H), 3.57 (t, J=4.5 Hz, 4H), 2.42 (t, J=5.0 Hz, 4H), 2.23 (s, 3H); MS ESI 437.2 [M+H]$^+$, calcd for [C$_{26}$H$_{24}$N$_6$O+H]$^+$ 437.20.

Example A97

(E and Z)-5-methoxy-3-((3-(6-(4-methylpiperazin-1-yl)pyridin-3-yl)-1H-indazol-6-yl)methylene)indolin-2-one

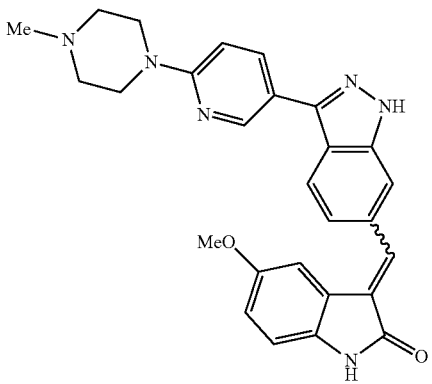 [SMILES: COc1ccc2c(c1)C(=Cc1ccc3c(-c4ccc(N5CCN(C)CC5)nc4)n[nH]c3c1)C(=O)N2]

According to the procedure for the synthesis of 3-((3-(6-(4-methylpiperazin-1-yl)pyridin-3-yl)-1H-indazol-6-yl)methylene)indolin-2-one (Example A97), except substituting 5-methoxyoxindole (28 mg, 0.087 mol), the title compound was prepared as a yellow solid (14.4 mg, 35%). A mixture of (E)- and (Z)-isomers (83:17 by NMR) was obtained. $^1$H NMR (400 MHz, CD$_3$OD) 8.74 (d, J=2.3 Hz, 1H), 8.14 (dd, J=8.8, 2.3 Hz, 1H), 8.07 (d, J=8.5 Hz, 1H), 7.87 (d, J=10.0 Hz, 2H), 7.49 (d, J=8.3 Hz, 1H), 7.26 (s, 1H), 7.01 (d, J=8.8, 1H), 6.83 (s, 2H), 3.75-3.69 (br. m, 4H), 3.62 (s, 3H), 2.82-2.76 (br. m, 4H), 2.51 (s, 3H); MS ESI 467.2 [M+H]$^+$, calcd for [C$_{27}$H$_{26}$N$_6$O$_2$+H]$^+$ 467.21.

Example A98

(E and Z)-3-((3-(1H-pyrazol-5-yl)-1H-indazol-6-yl)methylene)-indolin-2-one

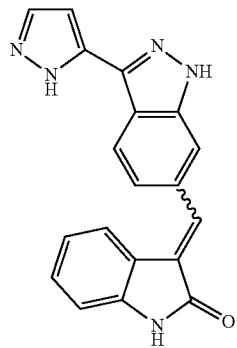 [SMILES: O=C1Nc2ccccc2C1=Cc1ccc2c(-c3ccn[nH]3)n[nH]c2c1]

A. 3-(1H-pyrazol-5-yl)-1H-indazole-6-carbaldehyde

According to the procedure for the synthesis of 3-(pyridin-3-yl)-1H-indazole-6-carbaldehyde, except substituting 1H-pyrazole-5-boronic acid (25 mg, 0.22 mmol), the title compound was prepared as a beige solid (5.3 mg, 13%). $^1$H NMR (400 MHz, CD$_3$OD) δ ppm 10.13 (s, 1H), 8.44-8.32 (br. m, 1H), 8.14 (s, 1H), 7.78 (d, J=1.8 Hz, 1H), 7.75 (d, J=8.3 Hz, 1H), 6.90 (d, J=2.0 Hz, 1H); MS ESI 213.0 (100) [M+H]$^+$, calcd for [C$_{11}$H$_8$N$_4$O+H]$^+$ 213.07.

B. (E and Z)-3-((3-(1H-pyrazol-5-yl)-1H-indazol-6-yl)methylene)indolin-2-one

According to the procedure for the synthesis of (E)-3-((1H-indazol-6-yl)methylene)indolin-2-one, except substituting 3-(1H-pyrazol-5-yl)-1H-indazole-6-carbaldehyde (5.3 mg, 0.025 mmol), the title compound was prepared as a yellow solid (4.4 mg, 54%). A mixture of (E)- and (Z)-isomers (78:22 by NMR) was obtained. $^1$H NMR (400 MHz, CD$_3$OD) δ 8.35 (br. s, 1H), 7.92-7.89 (m, 2H), 7.79-7.77 (m, 1H), 7.68 (d, J=7.8 Hz, 1H), 7.53 (d, J=8.5 Hz, 1H), 7.25 (t, J=7.5 Hz, 1H), 6.94-6.86 (m, 3H); MS ESI 328.1 [M+H]$^+$, calcd for [C$_{19}$H$_{13}$N$_5$O+H]$^+$ 328.11.

Example A99

(E and Z)-3-((4-(pyridin-3-yl)-1H-indazol-6-yl)methylene)indolin-2-one

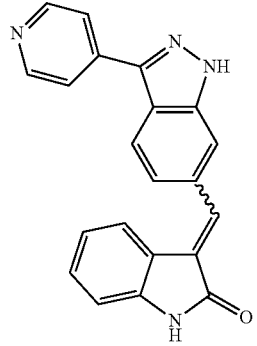 [SMILES: O=C1Nc2ccccc2C1=Cc1ccc2c(-c3ccncc3)n[nH]c2c1]

A. 3-(pyridin-4-yl)-1H-indazole-6-carbaldehyde

According to the procedure for the synthesis of 3-(pyridin-3-yl)-1H-indazole-6-carbaldehyde, except substituting pyridin-4-ylboronic acid (27 mg, 0.22 mmol), the title compound was obtained as a beige solid (3.7 mg, 9%). $^1$H NMR (400 MHz, CD$_3$OD) δ ppm 10.15 (s, 1H), 8.69 (d, J=6.3 Hz, 2H), 8.32 (d, J=8.8 Hz, 1H), 8.22 (s, 1H), 8.10 (d, J=6.3 Hz, 2H), 7.84 (d, J=6.3 Hz, 1H); MS ESI 224.0 (100) [M+H]$^+$, calcd for [C$_{13}$H$_9$N$_3$O+H]$^+$ 224.07.

B. (E and Z)-3-((4-(pyridin-3-yl)-1H-indazol-6-yl)methylene)indolin-2-one

According to the procedure for the synthesis of (E)-3-((1H-indazol-6-yl)methylene)-indolin-2-one, except substituting 3-(pyridin-4-yl)-1H-indazole-6-carbaldehyde (3.9 mg, 0.017 mol), the title compound was prepared as a yellow solid (4.8 mg, 81%). A mixture of (E)- and (Z)-isomers (64:36 by NMR) was obtained. $^1$H NMR (400 MHz, CD$_3$OD) δ 8.69 (d, J=6.0 Hz, 2H), 8.30 (d, J=8.5 Hz, 1H), 8.13 (d, J=6.0 Hz, 1H), 7.97 (s, 1H), 7.90 (s, 1H), 7.67 (d, J=8.0 Hz, 1H), 7.63 (d, J=8.9 Hz, 1H), 7.26 (t, J=8.0 Hz, 1H), 6.94 (d, J=8.0 Hz, 1H), 6.89 (t, J=7.8 Hz, 1H); MS ESI 339.1 [M+H]+, calcd for [C21H14N4O+H]+ 339.12.

Example A100

(E and Z)-3-((3-(pyrimidin-5-yl)-1H-indazol-6-yl)methylene)-indolin-2-one

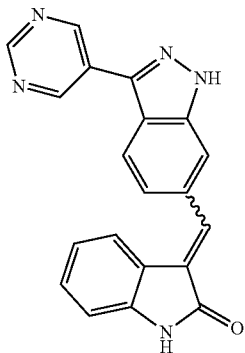 [SMILES: O=C1Nc2ccccc2C1=Cc1ccc2c(-c3cncnc3)n[nH]c2c1]

A. 3-(pyrimidin-5-yl)-1H-indazole-6-carbaldehyde

According to the procedure for the synthesis of 3-(1H-pyrrol-2yl)-1H-indazole-6-carbaldehyde, except substituting pyrimidin-5-ylboronic acid (34 mg, 0.15 mmol), the title compound was obtained as a beige solid (8.1 mg, 30%). $^1$H NMR (400 MHz, CD$_3$OD) δ ppm 10.15 (s, 1H), 9.44 (s, 2H), 9.21 (s, 1H), 8.26 (d, J=8.5 Hz, 1H), 8.23 (t, J=1.3 Hz, 1H), 7.84 (dd, J=8.5, 1.3 Hz, 1H); MS ESI 225.0 (100) [M+H]+, calcd for [C12H8N4O+H]+ 225.07.

B. (E and Z)-3-((3-(pyrimidin-5-yl)-1H-indazol-6-yl)methylene)indolin-2-one According to the procedure for the synthesis of (E)-3-((1H-indazol-6-yl)methylene)indolin-2-one, except substituting 3-(pyrimidin-5-yl)-1H-indazole-6-carbaldehyde (8.5 mg, 0.038 mol), the title compound was prepared as a yellow solid (1.2 mg, 9%). A mixture of (E)- and (Z)-isomers (63:37 by NMR) was obtained. $^1$H NMR (400 MHz, CD$_3$OD) δ 9.47 (s, 2H), 9.22 (s, 1H), 8.24 (d, J=8.5 Hz, 1H), 7.97 (s, 1H), 7.90 (s, 1H), 7.66 (d, J=7.8 Hz, 1H), 7.63 (d, J=8.5 Hz, 1H), 7.26 (t, J=8.0 Hz, 1H), 6.49 (d, J=8.0 Hz, 1H), 6.88 (t, J=7.8 Hz, 1H); MS ESI 340.1 [M+H]+, calcd for [C20H13N5O+H]+ 340.11.

Example A101

(E)-3-((3-((E)-2-(pyridin-4-yl)vinyl)-1H-indazol-6-yl)methylene)-1H-pyrrolo[2,3-b]pyridin-2(3H)-one

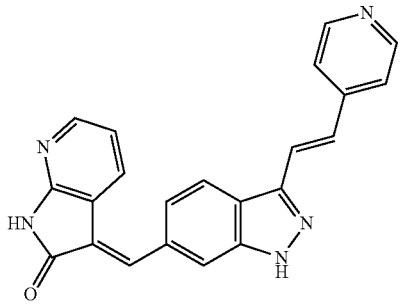 [SMILES: O=C1Nc2ncccc2/C1=C\c1ccc2c(/C=C/c3ccncc3)n[nH]c2c1]

The title compound (64 mg, 64%) was synthesized as orange red solid according to the method described for Example A11B from 1H-pyrrolo[2,3-b]pyridin-2(3H)-one (26.8 mg, 0.2 mmol) and E)-3-(2-(pyridin-4-yl)vinyl)-1H-indazole-6-carbaldehyde (49.8 mg, 0.2 mmol). $^1$H NMR (400 MHz, DMSO-d6) δ 13.60 (s, 1H, NH), 11.28 (s, 1H, NH), 8.57 (d, J=5.6 Hz, 2H), 8.39 (d, J=8.4 Hz, 1H), 8.12 (d, J=4.8 Hz, 1H), 7.95 (s, 2H), 7.90 (d, J=6.4 Hz, 1H, partially overlapping with the peak at 7.87 ppm), 7.87 (d, J=16.4 Hz, 1H, partially overlapping with the peak at 7.90 ppm), 7.71 (d, J=5.6 Hz, 2H), 7.57 (d, J=8.0 Hz, 1H, partially overlapping with the peak at 7.56 ppm), 7.56 (d, J=16.4 Hz, 1H, partially overlapping with the peak at 7.57 ppm), 6.91 (dd, J=7.6 Hz, 5.2 Hz, 1H); MS ESI 366.1 [M+H]+, calcd for [C22H15N5O+H]+ 366.1.

Example A102

(E)-3-((3-cyclopropyl-1H-indazol-6-yl)methylene)indolin-2-one

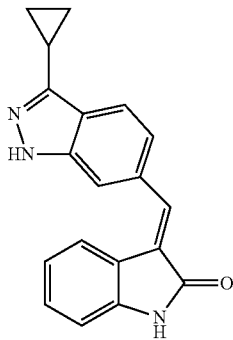 [SMILES: O=C1Nc2ccccc2/C1=C\c1ccc2c(C3CC3)n[nH]c2c1]

A. 3-cyclopropyl-1-((2-(trimethylsilyl)ethoxy)methyl)-1H-indazole-6-carbaldehyde A degassed mixture of 3-iodo-1-((2-(trimethylsilyl)ethoxy)methyl)-1H-indazole-6-carbaldehyde (51 mg, 0.12 mmol), cyclopropylboronic acid (21 mg, 0.24 mmol), powdered K$_3$PO$_4$ (103 mg, 0.48 mmol) and Pd(PPh$_3$)$_4$ (10 mg, 0.009 mmol) in PhMe (2 mL) and H$_2$O (0.1 mL) was heated with stirring in a sealed tube under Ar at 95-100° C. for 1 d. The crude mixture was concentrated and purified by prepTLC (SiO$_2$ 5:1 hexanes/EtOAc) to provide the title compound as a clear oil (40 mg, quant): $^1$H NMR (400 MHz, CDCl$_3$) δ ppm 10.13 (s, 1H), 8.02 (s, 1H), 7.87 (d, J=8.28 Hz, 1H), 7.70 (d, J=8.28 Hz, 1H), 5.71 (s, 2H), 3.54 (d, J=8.53 Hz, 2H), 2.19-2.28 (m, 1H), 1.06-1.12 (m, 4H), 0.89 (d, J=8.28 Hz, 2H), −0.07 (s, 9H); MS ESI 317.1 [M+H]+, calcd for [C17H24N2O2Si+H]+ 317.5.

B. (E)-3-((3-cyclopropyl-1-((2-(trimethylsilyl)ethoxy)methyl)-1H-indazol-6-yl)methyl-ene)indolin-2-one According to the method of Example A19, indolin-2-one (17 mg, 0.13 mmol) and 3-cyclopropyl-1-((2-(trimethylsilyl)ethoxy)methyl)-1H-indazole-6-carbaldehyde (40 mg, 0.13 mmol) were reacted to obtain crude product. The crude mixture was purified by prepTLC (SiO$_2$ 2% MeOH in DCM) to provide the title compound as a yellow solid (48 mg, 88%). MS ESI 432.2 [M+H]+, calcd for [C$_{25}$H$_{29}$N$_3$O$_2$Si+H]+ 432.6.

C. (E)-3-((3-cyclopropyl-1H-indazol-6-yl)methylene)indolin-2-one

A mixture of (E)-3-((3-cyclopropyl-1-((2-(trimethylsilyl)ethoxy)methyl)-1H-indazol-6-yl)methylene)indolin-2-one (47 mg, 0.11 mmol) and tetrabutylammonium fluoride (1.0 M in THF, 10 mL, 10 mmol) in anh. THF (30 mL) was refluxed under Ar for 18 h. The reaction mixture was then concentrated to a brown oil, which was diluted with H$_2$O, extracted (2% MeOH in DCM), washed (H$_2$O (2×), brine), dried (Na$_2$SO$_4$, and MgSO$_4$) and concentrated under reduced pressure. The material was suspended in DCM, collected by filtration and washed with xs. DCM to afford the title compound as a yellow solid (7.0 mg, 21%). $^1$H NMR (400 MHz, CD$_3$OD) δ ppm 7.90 (d, J=8.53 Hz, 1H), 7.86 (s, 1H), 7.78 (s., 1H), 7.65 (d, J=8.03 Hz, 1H), 7.42 (d, J=8.78 Hz, 1H), 7.23 (t, J=8.03 Hz, 1H), 6.92 (d, J=7.78 Hz, 1H), 1H), 6.87 (t, J=7.65 Hz, 1H), 2.26-2.36 (m, 1H), 1.04-1.11 (m, 4H); MS ESI 302.1 [M+H]+, calcd for [C$_{19}$H$_{15}$N$_3$O+H]+ 302.3.

Example A103

(E)-3-((3-((E)-2-(4-methylthiazol-5-yl)vinyl)-1H-indazol-6-yl)methyl-ene)indolin-2-one

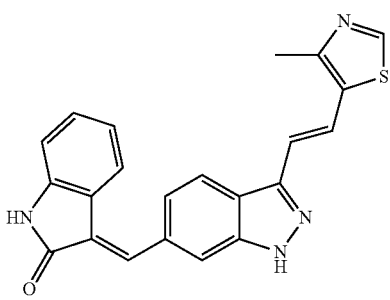 [SMILES: Cc1ncsc1/C=C/c1n[nH]c2cc(/C=C3/C(=O)Nc4ccccc43)ccc12]

A. (E)-3-(2-(4-methylthiazol-5-yl)vinyl)-1-((2-(trimethylsilyl)ethoxy)methyl)-1H-indazole-6-carbaldehyde A degassed mixture of 3-iodo-1-((2-(trimethylsilyl)ethoxy)methyl)-1H-indazole-6-carbaldehyde (70 mg, 0.17 mmol), 4-methyl-5-vinylthiazole (44 mg, 0.35 mmol), N-ethyl-N-isopropylpropan-2-amine (DIPEA, 45 mg, 0.35 mmol), Pd(OAc)$_2$ (3.9 mg, 0.017 mmol) and P(o-MeC$_6$H$_4$)$_3$ (16 mg, 0.052 mmol) in anhydrous MeCN (2 mL) were heated with stirring in a sealed tube under Ar at 90° C. for 1 d. The crude mixture was later concentrated under reduced pressure and purified by prepTLC (SiO$_2$ 5:1 hexanes/EtOAc) to provide the title compound (30 mg, 43%): $^1$H NMR (400 MHz, CDCl$_3$) δ ppm 10.17 (s, 1H), 8.64 (s, 1H), 8.12 (s, 1H), 8.06 (d, J=8.28 Hz, 1H), 7.83 (d, 1H), 7.64 (d, J=16.06 Hz, 1H), 7.12 (d, J16.31 Hz, 1H), 5.82 (s, 2H), 3.62 (t, J=8.28 Hz, 2H), 2.62 (s, 3H), 0.92 (t, J=8.28 Hz, 2H), −0.05 (s, 9H); MS ESI 400.2 [M+H]+, calcd for [C$_{20}$H$_{25}$N$_3$O$_2$SSi+H]+ 400.6.

B. (E)-3-(2-(4-methylthiazol-5-yl)vinyl)-1H-indazole-6-carbaldehyde

A mixture of (E)-3-(2-(4-methylthiazol-5-yl)vinyl)-1-((2-(trimethylsilyl)ethoxy)-methyl)-1H-indazole-6-carbaldehyde (30 mg, 0.075 mmol) and tetrabutyl-ammonium fluoride (1.0 M in THF, 0.37 mL, 0.37 mmol) in anh. THF (10 mL) was refluxed under Ar for 1 d. The reaction mixture was then concentrated under reduced pressure and purified by prepTLC (SiO$_2$ 10% MeOH/DCM) to provide the title compound (15 mg, 74%) as a tan solid (7.0 mg, 21%). MS ESI 270.0 [M+H]+, calcd for [C$_{14}$H$_{11}$N$_3$OS+H]+ 270.3.

C. (E)-3-((3-((E)-2-(4-methylthiazol-5-yl)vinyl)-1H-indazol-6-yl)methylene)-indolin-2-one According to the method of Example A19, indolin-2-one (7.5 mg, 0.056 mmol) and 3(E)-3-(2-(4-methylthiazol-5-yl)vinyl)-1H-indazole-6-carbaldehyde (15 mg, 0.059 mmol) were reacted to obtain crude product. The crude mixture was concentrated under reduced pressure and triturated with DCM, followed by MeCN to provide the title compound as a yellow solid (3.0 mg, 13%). 1H NMR (400 MHz, DMF-d$_7$) δ ppm 13.67 (br. s., 1H), 10.66 (br. s., 1H), 9.01 (s, 1H), 8.41 (d, J=8.03 Hz, 1H), 7.86 (s, 1H), 7.78 (d, J=16.1 Hz, 1H), 7.73 (d, J=8.03 Hz, 1H), 7.61 (d, J=8.28 Hz, 1H), 7.26-7.35 (m, 2H), 7.02 (d, J=7.78 Hz, 1H), 6.90 (t, J=7.28 Hz, 1H), 2.62 (s, 3H); MS ESI 385.1 [M+H]+, calcd for [C$_{22}$H$_{16}$N$_4$OS+H]+ 385.4.

Example A104

(E and Z)-3-((3-((E)-2-(pyrazin-2-yl)vinyl)-1H-indazol-6-yl)methylene)-indolin-2-one

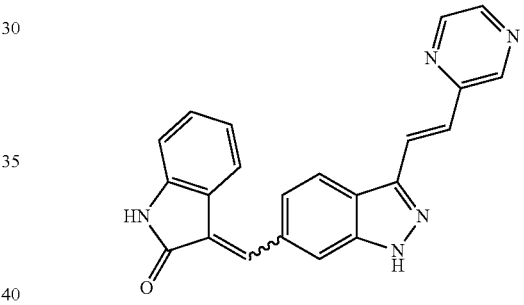

A. (E)-3-(2-(pyrazin-2-yl)vinyl)-1-((2-(trimethylsilyl)ethoxy)methyl)-1H-indazole-6-carbaldehyde A degassed mixture of 3-iodo-1-((2-(trimethylsilyl)ethoxy)methyl)-1H-indazole-6-carbaldehyde (70 mg, 0.17 mmol), 2-vinylpyrazine (27 mg, 0.25 mmol), N-ethyl-N-isopropylpropan-2-amine (DIPEA, 45 mg, 0.35 mmol), Pd(OAc)$_2$ (3.9 mg, 0.017 mmol) and P(o-MeC$_6$H$_4$)$_3$ (16 mg, 0.052 mmol) in anh MeCN (2.5 mL) was heated with stirring in a sealed tube under microwave irradiation at 120° C. for 40 min. The crude mixture was later concentrated under reduced pressure and purified by prepTLC (SiO$_2$ 2:1 hexanes/EtOAc) to provide the title compound as a colorless solid (28 mg, 43%): $^1$H NMR (400 MHz, CDCl$_3$) δ ppm 10.18 (s, 1H), 8.73 (s, 1H), 8.60 (br. s., 1H), 8.47 (d, J=2.26 Hz, 1H), 8.14-8.18 (m, 2H), 8.07 (d, J=16.06 Hz, 1H), 7.84 (d, J=8.53 Hz, 1H), 7.61 (d, J=16.31 Hz, 1H), 5.85 (s, 2H), 3.61 (t, J=8.28 Hz, 2H), 0.94 (t, J=8.53 Hz, 2H), −0.05 (s, 9H); MS ESI 381.2 [M+H]+, calcd for [C$_{20}$H$_{24}$N$_4$O$_2$Si+H]+ 381.5.

B. (E)-3-((3((E)-2-(pyrazin-2-yl)vinyl)-1-((2-(trimethylsilyl)ethoxy)methyl)-1H-indazol-6-yl)methylene)indolin-2-one The title compound was synthesized according to the method of Example A19, utilizing indolin-2-one (10.0 mg, 0.075 mmol) and (E)-3-(2-(pyrazin-2-yl)vinyl)-1-((2-(trimethylsilyl)ethoxy)methyl)-1H-indazole-6-carbaldehyde (28 mg, 0.074 mmol). The crude mixture was concentrated under reduced pressure and purified by prepTLC (SiO$_2$ 2% MeOH/DCM) to provide the title compound to as a yellow material (20 mg, 55%); MS ESI 496.3 [M+H]$^+$, calcd for [C$_{28}$H$_{29}$N$_5$O$_2$Si+H]$^+$ 496.6.

C. (E & Z)-3-((3-((E)-2-yl)pyrazin-2-yl)vinyl)-1H-indazol-6-yl)methylene)indolin-2-one A degassed mixture of (E)-3-((3-((E)-2-(pyrazin-2-yl)vinyl)-1-((2-(trimethylsilyl)-ethoxy)methyl)-1H-indazol-6-yl)methylene)indolin-2-one (20 mg, 0.040 mmol) and tetrabutylammonium fluoride (1.0 M in THF, 0.6 mL, 0.6 mmol) in anh. THF (10 mL) was refluxed under Ar for 1 d. The reaction mixture was then concentrated under reduced pressure and purified by prepTLC (SiO$_2$ 12% MeOH/DCM) and trituration with DCM to provide the title compound as a 1.5:1.0 (E:Z) mixture of isomers: a yellow solid (1.7 mg, 12%). 1H NMR (400 MHz, DMF-d$_7$) δ ppm 9.33 (s, 0.35H), 9.16 (d, J=1.51 Hz, 1.0H), 8.84-8.87 (m, 1.1H), 8.70 (t, J=2.26 Hz, 1.0H), 8.60 (d, J=8.78 Hz, 0.6H), 8.51 (d, J=8.28 Hz, 0.45H), 8.37-8.46 (m, 1.6H), 8.26 (d, J=5.52 Hz, 1.0H), 8.04 (s, 0.6H), 8.02 (d, J=7.53 Hz, 0.39H), 7.92-7.98 (m, 1.7H), 7.79 (d, J=8.03 Hz, 0.60H), 7.41-7.49 (m, 1.1H), 7.05-7.25 (m, 2.1H); MS ESI 366.2 [M+H]$^+$, calcd for [C$_{22}$H$_{15}$N$_5$O+H]$^+$ 366.4.

Example A105

(E and Z)-3-((3-((E)-2-(1-methyl-1H-imidazol-2-yl)vinyl)-1H-indazol-6-yl)methylene)indolin-2-one

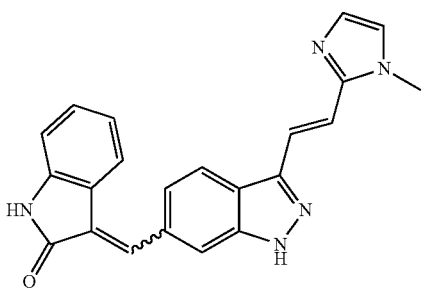 [SMILES: Cn1ccnc1/C=C/c1n[nH]c2cc(C=C3C(=O)Nc4ccccc43)ccc12]

A. (E)-3-(2-(1-methyl-1H-imidazol-2-yl)vinyl)-1-((2-(trimethylsilyl)ethoxy)-methyl)-1H-indazole-6-carbaldehyde The title compound was synthesized according to the method of Example A103, utilizing 1-methyl-2-vinyl-1H-imidazole (35 mg, 0.32 mmol) and 3-iodo-1-((2-(trimethylsilyl)ethoxy)methyl)-1H-indazole-6-carbaldehyde (100 mg, 0.23 mmol). Purified by prepTLC (SiO$_2$ 10% MeOH/DCM) to provide the title compound (15 mg, 74%) as a tan oil (41.6 mg, 47%). $^1$H NMR (400 MHz, CD$_3$OD) δ ppm 10.09 (s, 1H), 8.22 (t, J=1.00 Hz, 1H), 8.13 (d, J=8.53 Hz, 1H), 7.78 (dd, J=8.53, 1.25 Hz, 1H), 7.68 (d, J=16.06 Hz, 1H), 7.43 (d, J=16.06 Hz, 1H), 7.13 (d, J=1.25 Hz, 1H), 7.05 (d, J=1.00 Hz, 1H), 5.84 (s, 2H), 4.89 9s, 3H), 3.63 (t, J=8.03 Hz, 1H), 0.87 (t, J=8.03 Hz, 2H), −0.10 (s, 9H); MS ESI 383.2 [M+H]$^+$, calcd for [C$_{20}$H$_{26}$N$_4$O$_2$Si+H]$^+$ 383.5.

B. (E)-3-((3-((E)-2-(1-methyl-1H-imidazol-2-yl)vinyl)-1-((2-(trimethylsilyl)-ethoxy)methyl)-1H-indazol-6-yl)methylene)indolin-2-one Synthesized according to the method of Example A19, utilizing indolin-2-one (14.5 mg, 0.11 mmol) and (E)-3-(2-(1-methyl-1H-imidazol-2-yl)vinyl)-1-((2-(trimethylsilyl)-ethoxy)methyl)-1H-indazole-6-carbaldehyde (41.6 mg, 0.11 mmol). The crude mixture was concentrated under reduced pressure and purified by prepTLC (SiO$_2$ 10% MeOH/DCM) to provide the title compound to as a yellow material (35.4 mg, 65%); MS ESI 498.4 [M+H]$^+$, calcd for [C$_{28}$H$_{31}$N$_5$O$_2$Si+H]$^+$ 498.7.

C. (E and Z)-3-((3-((E)-2-(1-methyl-1H-imidazol-2-yl)vinyl)-1H-indazol-6-yl)methylene)-indolin-2-one hydrochloride A sealed, degassed mixture of (E)-3-((3-((E)-2-(1-methyl-1H-imidazol-2-yl)vinyl)1-((2-(trimethylsilyl)ethoxy)methyl)-1H-indazol-6-yl)methylene)indolin-2-one (35.4 mg, 0.071 mmol) in EtOH (4 mL) and aq HCl (4 M, 1 mL) was heated at 75-80° C. under Ar for 1 d. The reaction mixture was cooled to rt, diluted with MeCN (10 mL) and Et2O (5 mL) and stored at −20° C. overnight. The precipitate was collected by filtration, washed with MeCN to provide the title compound as a 1.5:1.0 (E:Z) mixture of isomers: a yellow solid (14.5 mg, 51%). $^1$H NMR (400 MHz, CD$_3$OD) δ ppm 8.93 (s, 0.44H), 8.25 (d, J=8.28 Hz, 1.00H), 8.13 (d, J=8.53 Hz, 0.65H), 8.02-8.06 (m, 0.45H), 8.02 (s, 1.78H), 7.92-8.00 (m, 1.78H), 7.86-7.91 (m, 1.47H), 7.58-7.71 (m, 5.0H), 7.53 (d, J=16.81 Hz, 1.29H), 7.25 (t, J=7.65 Hz, 1.52H), 7.05 (t, J=7.78 Hz, 0.66H), 6.94 (d, J=7.78 Hz, 1.01H), 6.83-6.91 (m, 1.73H), 4.04 (s, 2.46H), 4.03 (s, 1.41H); MS ESI 368.1 [M+H]$^+$, calcd for [C$_{22}$H$_{17}$N$_5$O+H]$^+$ 368.4.

Example A106

(E and Z)-3-[(3-{(E)-2-[4-((dimethylamino)methyl)-phenyl]-ethenyl}-1H-indazol-6-yl)methylidene]-1,3-dihydro-2H-indol-2-one 2,2,2-trifluoroacetate

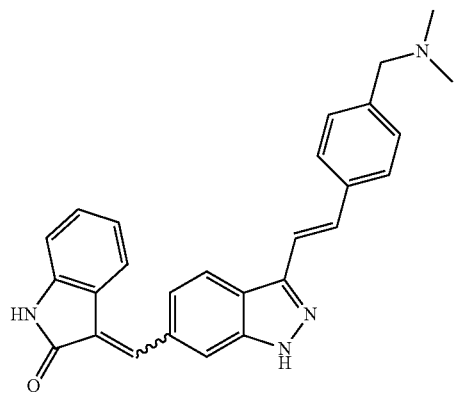 [SMILES: CN(C)Cc1ccc(/C=C/c2n[nH]c3cc(C=C4C(=O)Nc5ccccc54)ccc23)cc1]

A. (E)-3-(4-((dimethylamino)methyl)styryl)-1-((2-(trimethylsilyl)ethoxy)methyl)-1H-indazole-6-carbaldehyde The title compound was synthesized according to the method of Example A103, utilizing N,N-dimethyl-1-(4-vinylphenyl)methanamine (42 mg, 0.26 mmol) and 3-iodo-1-((2-(trimethylsilyl)ethoxy)methyl)-1H-indazole-6-carbaldehyde (70 mg, 0.17 mmol). Purified by prepTLC (SiO$_2$ 10% MeOH/DCM) to provide the title compound to as a pale orange gum (33.4 mg, 44%). $^1$H NMR (400 MHz, CD$_3$OD) δ ppm 10.13 (s, 1H), 8.27 (m, 2H), 7.81 (d, J=9.29 Hz, 1H), 7.69 (d, J=8.28 Hz, 2H), 7.61 (d, J=16.6 Hz, 1H), 7.50 (d, J=16.6 Hz, 1H), 7.43 (d, J=8.28 Hz, 2H), 5.86 (s, 2H), 3.82 (s, 2H), 3.62 (t, J=8.03 Hz, 1H), 2.50 (s, 6H), 0.87 (t, J=8.03 Hz, 2H), −0.09 (s, 9H); MS ESI 436.3 [M+H]$^+$, calcd for [C$_{25}$H$_{33}$N$_3$O$_2$Si+H]$^+$ 436.6.

B. (E)-3-((3-(4-((dimethylamino)methyl)styryl)-1-((2-(trimethylsilyl)ethoxy)-methyl)-1H-indazol-6-yl)methylene)indolin-2-one Synthesized according to the method of Example A19, utilizing indolin-2-one (10.4 mg, 0.0.78 mmol) and (E)-3-(4-((dimethylamino)methyl)styryl)-1-((2-(trimethylsilyl)-ethoxy)methyl)-1H-indazole-6-carbaldehyde (33.4 mg, 0.077 mmol). The crude mixture was concentrated under reduced pressure and purified by prepTLC (SiO$_2$ 10% MeOH/DCM) to provide the title compound to as a 1.5-2.0:1.0 (E:Z) mixture of isomers: a yellow solid (29.1 mg, 67%): $^1$H NMR (400 MHz, CD$_3$OD) δ ppm 9.09-9.14 (s, 0.31H), 8.22 (d, J=8.28 Hz, 0.84H), 8.09 (d, J=8.53 Hz, 0.34H), 7.83-7.87 (m, 1.25H), 7.61-7.69 (m, 4.02H), 7.56-7.60 (m, 1.69H), 7.50 (s, 0.61H), 7.36-7.48 (m, 3.85H), 7.24 (t, J=7.78 Hz, 1.48H), 7.03 (t, J=7.28 Hz, 0.48H), 6.92 (d, J=7.53 Hz, 1.01H), 6.81-6.89 (m, 1.49H), 5.80 (s, 0.60H), 5.78 (s, 1.52H), 3.59-3.65 (m, 2.20H), 2.37-2.42 (m, 7.40H), 0.89 (t, J=8.28 Hz, 3.05H), −0.09 (s, 9H); MS ESI 551.4 [M+H]$^+$, calcd for [C$_{33}$H$_{38}$N$_4$O$_2$Si+H]$^+$ 551.8.

C. (E and Z)-3-[(3-{(E)-2-[4-((dimethylamino)methyl)phenyl]-ethenyl}-1H-indazol-6-yl)methylidene]-1,3-dihydro-2H-indol-2-one 2,2,2-trifluoroacetate The title compound was synthesized according to the method of Example A105-C utilizing (E)-3-((3-(4-((dimethylamino)methyl)styryl)-1-((2-(trimethylsilyl)ethoxy)-methyl)-1H-indazol-6-yl)methylene)indolin-2-one (29.1 mg, 0.052 mmol). The crude reaction mixture was concentrated under reduced pressure to dryness, triturated with Et$_2$O and DCM. Later the material was purified by prepTLC (SiO$_2$ 30% MeOH/DCM) followed by prep HPLC to provide the title compound as a 1.7:1.0 (E:Z) mixture of isomers: a yellow solid (1.8 mg, 6%); $^1$H NMR (400 MHz, D$_2$O) δ ppm 7.93-8.36 and 5.96-7.33 (m, 13H), 3.82 (br. s., 2H), 2.62 (br. s., 6H); MS ESI 421.2 [M+H]$^+$, calcd for [C$_{27}$H$_{24}$N$_4$O+H]$^+$ 421.5.

Example A107

(E and Z)-3-((3-((E)-3-(4-methylpiperazine-1-carbonyl)styryl)-1H-indazol-6-yl)methylene)indolin-2-one 2,2,2-trifluoroacetate

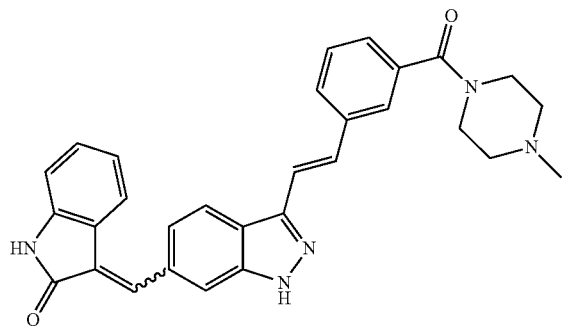 [SMILES: CN1CCN(C(=O)c2cccc(/C=C/c3n[nH]c4cc(C=C5C(=O)Nc6ccccc65)ccc34)c2)CC1]

A. (E)-3-(3-(4-methylpiperazine-1-carbonyl)styryl)-1-((2-(trimethylsilyl)ethoxy)-methyl)-1H-indazole-6-carbaldehyde The title compound was synthesized according to the method of Example A103, utilizing 1-[(3-ethenylphenyl)carbonyl]-4-methylpiperazine (76 mg, 0.33 mmol) and 3-iodo-1-((2-(trimethylsilyl)ethoxy)methyl)-1H-indazole-6-carbaldehyde (100 mg, 0.25 mmol). Purified by prepTLC (SiO$_2$ 10% MeOH/DCM) to provide the title compound to as a colorless material (30.1 mg, 24%). $^1$H NMR (400 MHz, CD$_3$OD) δ ppm 10.14 (s, 1H), 8.27 (s, 1H), 7.80 (m, 1H), 7.71 (s, 1H), 7.65 (d, J=16.6 Hz, 1H), 7.56-7.60 (m, 1H), 7.57 (s, 1H), 7.48-7.55 (m, 2H), 7.35 (d, J=7.28 Hz, 1H), 5.86 (s, 2H), 3.69-3.90 (m, 2H), 3.63 (t, J=7.91 Hz, 2H), 3.43-3.56 (m, 2H), 2.40-2.64 (m, 4H), 2.35 (s, 3H), 0.88 (t, J=7.91 Hz, 2H), −0.09 (m, 9H); MS ESI 505.4 [M+H]$^+$, calcd for [C$_{28}$H$_{36}$N$_4$O$_3$Si+H]$^+$ 505.7.

B. (3E & 3Z)-3-((3-((E)-3-(4-methylpiperazine-1-carbonyl)styryl)-1-((2-(trimethylsilyl)ethoxy)methyl)-1H-indazol-5-yl)methylene)indolin-2-one The title compound was synthesized according to the method of Example A19, utilizing indolin-2-one (7.9 mg, 0.059 mmol) and (E)-3-(3-(4-methylpiperazine-1-carbonyl)styryl)-1-((2-(trimethylsilyl)methyl)-1H-indazole-6-carbaldehyde (30.1 mg, 0.060 mmol). The crude mixture was concentrated under reduced pressure and purified by prepTLC (SiO$_2$ 10% MeOH/DCM) to provide the title compound as a ~2.5:1 (E:Z) mixture of isomers: a yellow solid (21.6 mg, 59%): $^1$H NMR (400 MHz, CD$_3$OD) δ ppm 9.06 (s, 0.22H), 8.20 (d, J=8.28 Hz, 0.72H), 8.07 (d, J=8.53 Hz, 0.27H), 7.94-7.96 (m, 0.98H), 7.92 (d, J=9.0 Hz, 0.82H), 7.84 (s, 0.82H), 7.72-7.79 (m, 2.53H), 7.45-7.66H), 7.31-7.36 (m, 1.29H), 7.18-7.25 (m, 1.30H), 7.01 (t, J=7.40 Hz, 0.42H), 6.90 (d, J=7.78 Hz, 0.83H), 5.78 (s., 0.57H), 5.77 (s, 1.24H), 3.75-3.90 (m, 2.28H), 3.58-3.68 (m, 2.63H), 3.45-3.57 (m, 2.43H), 2.39-2.62 (m, 4.67H), 2.36 (s, 3.53H), 0.84-0.93 (t, J=7.91 Hz, 2.63H), −0.09 (s, 9.81H); MS ESI 505.4 [M−CH$_2$CH$_2$SiMe$_3$−Me+H]$^+$, calcd for [C$_{30}$H$_{26}$N$_5$O$_3$.+H]$^+$ 505.6.

C. (E and Z)-3-((3-((E)-3-(4-methylpiperazine-1-carbonyl)styryl)-1H-indazol-6-yl)methylene)indolin-2-one 2,2,2-trifluoroacetate A degassed mixture of (3E)-3-((3-((E)-3-(4-methylpiperazine-1-carbonyl)styryl)-1-((2-(trimethylsilyl)ethoxy)methyl)-1H-indazol-5-yl)methylene)indolin-2-one (21.6 mg, 0.035 mmol), tetrabutylammonium fluoride (1.0 M in THF, 0.05 mL, 0.05 mmol) and activated molecular sieves (4 A) in anh. THF (5 mL) was refluxed under Ar for 1 d. The reaction mixture diluted with MeOH, filtered, concentrated under reduced pressure and purified by prepHPLC to provide the title compound as a ~4:1 (E:Z) mixture of isomers: a yellow solid (2.8 mg, 14%). $^1$H NMR (400 MHz, CD$_3$OD) δ ppm 8.88 (s, 0.28H), 8.26 (d, J=8.28 Hz, 1.00H), 8.15 (d, J=8.28 Hz, 0.29H), 7.98 (d, J=8.28 Hz, 0.37H), 7.88-7.91 (m, 1.65H), 7.82-7.87 (m, 1.51H), 7.79 (s, 1.14H), 7.52-7.71 (m, 5.35H), 7.42 (d, J=7.53 Hz, 1.13H), 7.25 (t, J=7.78 Hz, 1.19H), 7.05 (d, J=7.53 Hz, 0.28H), 6.94 (d, J=8.03 Hz, 1.01H), 6.84-6.91 (m, 1.15H), 3.36-3.81 (m, 4.22H), 3.06-3.28 (m, ~4H), 2.98 (s, 3.42H); MS ESI 490.3 [M+H]$^+$, calcd for [C$_{30}$H$_{27}$N$_5$O$_2$+H]$^+$ 490.6.

A108 (E and Z)-3-((3-((E)-2-(6-(4-methylpiperazin-1-yl)pyridin-3-yl)vinyl)-1H-indazol-6-yl)methylene)indolin-2-one

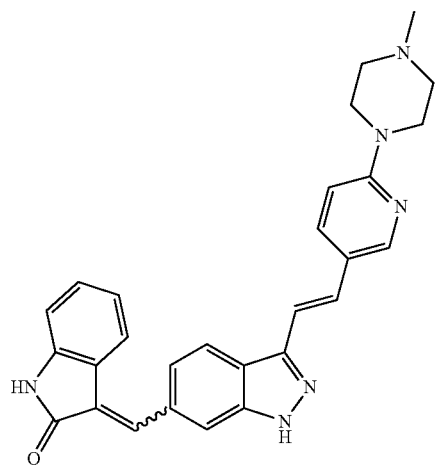 [SMILES: CN1CCN(c2ccc(/C=C/c3n[nH]c4cc(C=C5C(=O)Nc6ccccc65)ccc34)cn2)CC1]

A. 1-Methyl-4-(5-vinylpyridin-2-yl)piperazine

A sealed, degassed mixture of powdered KOH (123 mg, 2.2 mmol) and 1,2-dibromoethane (0.05 mL, 0.6 mmol) in anh THF (2 mL) under Ar was heated under microwave irradiation at 95° C. for 70 min. The reaction mixture was then cooled to rt and treated with Pd(OAc)$_2$ (5.0 mg, 0.022 mmol), PPh$_3$ (11.5 mg, 0.044 mmol), 1-methyl-4-(5-(4,4,5,5-tetramethyl-1,3,2-dioxaborolan-2-yl)pyridin-2-yl)piperazine (120 mg, 0.39 mmol) and degassed MeOH (2 mL). The sealed reaction mixture was heated again under microwave irradiation at 95° C. for 60 min. The crude mixture was concentrated under reduced pressure and purified by prepTLC (SiO$_2$ 10% MeOH/DCM) to provide the title compound a colorless gum (0.18 g, quant): $^1$H NMR (400 MHz, CD$_3$OD) δ ppm 8.07 (d, J=2.26 Hz, 1H), 7.73 (dd, J=8.91, 2.38 Hz, 1H), 6.82 (d, J=9.03 Hz, 1H), 6.62 (dd, J=17.82, 11.04 Hz, 1H), 5.63 (d, 1H), 5.12 (d, J=10.79 Hz, 4H), 3.52-3.66 (m, 4H), 2.50-2.61 (m, 4H), 2.35 (s, 3H); MS ESI 204.0 [M+H]$^+$, calcd for [C$_{12}$H$_{17}$N$_3$+H]$^+$ 204.3.

B. (E)-3-(2-(6-(4-methylpiperazin-1-yl)pyridin-3-yl)vinyl)-1-((2-(trimethylsilyl)-ethoxy)methyl)-1H-indazole-6-carbaldehyde The title compound was synthesized according to the method of Example A103, utilizing 1-methyl-4-(5-vinylpyridin-2-yl)piperazine (65 mg, 0.32 mmol) and 3-iodo-1-((2-(trimethylsilyl)ethoxy)methyl)-1H-indazole-6-carbaldehyde (100 mg, 0.25 mmol). Purified by prepTLC (SiO$_2$ 10% MeOH/DCM) to provide the title compound to as a pale orange material (46 mg, 39%). $^1$H NMR (400 MHz, CD$_3$OD) δ ppm 10.14 (s, 1H), 8.34 (d, J=2.26 Hz, 1.0H), 8.24-8.28 (m, 2H), 8.00 (dd, J=8.91, 2.38 Hz, 1H), 7.80 (d, J=8.78 Hz, 1H), 7.51 (d, J=16.56 Hz, 1H), 7.36 (d, J=16.56 Hz, 1H), 6.97 (d, J=9.29 Hz, 1H), 5.85 (s, 2H), 3.77-3.87 (m, 4H), 3.63 (t, J=7.91 Hz, 2H), 3.06-3.15 (m, 4H), 2.75 (s, 3H), 0.88 (t, J=8.03 Hz, 2H), −0.09 (s, 9H); MS ESI 478.3 [M+H]$^+$, calcd for [C$_{26}$H$_{35}$N$_5$O$_2$Si+H]$^+$ 478.7.

C. (E & Z)-3-((3-((E)-2-(6-(4-methylpiperazin-1-yl)pyridin-3-yl)vinyl)-1H-indazol-6-yl)methylene)-1-((2-(trimethylsilyl)ethoxy)methyl)indolin-2-one The title compound was synthesized according to the method of Example A19, utilizing indolin-2-one (8.3 mg, 0.062 mmol) and (E)-3-(2-(6-(4-methylpiperazin-1-yl)pyridin-3-yl)vinyl)-1-((2-(trimethylsilyl)ethoxy)methyl)-1H-indazole-6-carbaldehyde (46 mg, 0.096 mmol). The crude mixture was concentrated under reduced pressure and purified by prepTLC (SiO$_2$ 10% MeOH/DCM) to provide the title compound as a (E:Z) mixture of isomers: a yellow solid (22.5 mg, 40%); MS ESI 593.4 [M+H]$^+$, calcd for [C$_{34}$H$_{40}$N$_6$O$_2$Si+H]$^+$ 593.8.

D. (E & Z)-3-((3-((E)-2-(6-(4-methylpiperazin-1-yl)pyridin-3-yl)vinyl)-1H-indazol-6-yl)methylene)indolin-2-one dihydrochloride The title compound was prepared according to the method of Example A105-C utilizing (E & Z)-3-((3-((E)-2-(6-(4-methylpiperazin-1-yl)pyridin-3-yl)vinyl)-1H-indazol-6-yl)-methylene)-1-((2-(trimethylsilyl)ethoxy)methyl)indolin-2-one (22.5 mg, 0.038 mmol). The crude reaction mixture was stored at −20° C. overnight. The precipitate was collected by filtration, washed with MeCN to provide the title compound as a ~4:1 (E:Z) mixture of isomers: a yellow solid (6.9 mg, 34%). $^1$H NMR (400 MHz, CD$_3$OD) δ ppm 8.87 (s, 0.16H), 8.56 (d, J=9.54 Hz, 1.0H), 8.33 (s, 0.95H), 8.26 (d, J=8.28 Hz, 0.72H), 8.14 (d, J=9.54 Hz, 0.23H), 7.98 (d, J=8.53 Hz, 0.20H), 7.85-7.91 (m, 1.56H), 7.68 (d, J=7.03 Hz, 0.25H), 7.65 (d, J=7.78 Hz, 0.86H), 7.50-7.61 (m, 3.31H), 7.25 (t, J=7.53 Hz, 1.03H), 7.05 (t, J=8.03 Hz, 0.24H), 6.94 (d, J=7.53 Hz, 0.73H), 6.84-6.91 (m, 0.93H), 4.49 (br. s., 1.66H), 3.73

(br. s., 3.84H), 3.34-3.52 (m, 1.47H), 3.03 (s, 2.78H); MS ESI 463.2 [M+H]⁺, calcd for [C$_{28}$H$_{26}$N$_6$O+H]⁺ 462.5.

Example A109

(E and Z)-5-bromo-3-((3-((E)-2-(pyridin-4-yl)vinyl)-1H-indazol-6-yl)methyl-ene)-1H-pyrrolo[2,3-b]pyridin-2(3H)-one

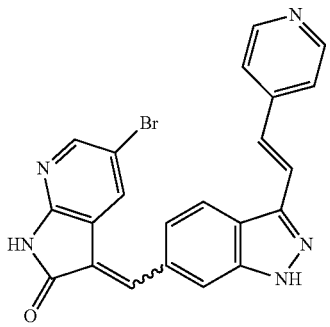 [SMILES: O=C1Nc2ncc(Br)cc2C1=Cc1ccc2c(/C=C/c3ccncc3)n[nH]c2c1]

The title compound (64 mg, 64%) was synthesized as a greenish yellow solid according to the method described for Example A67 (oil temp 75° C., reflux 2 h) using 5-bromo-1H-pyrrolo[2,3-b]pyridin-2(3H)-one (42.6 mg, 0.2 mmol) and (E)-3-(2-(pyridin-4-yl)vinyl)-1H-indazole-6-carbaldehyde (49.8 mg, 0.2 mmol). ¹H NMR indicated 7:6 mixture of E/Z isomers. ¹H NMR (400 MHz, DMSO-d6) δ 8.57 (d, J=5.2 Hz, 2H), 8.34 (d, J=8.4 Hz, 1H), 8.26 (d, 1H), 8.22 (s, 1H), 8.12 (d, J=8.8 Hz, 1H), 8.03 (s, 1H), 7.93 (d, 1H), 7.89 (d, J=16.8 Hz, 1H), 7.72 (t, J=4.8 Hz, 2H), 7.55 (d, J=16.0 Hz, 1H); MS ESI 444.3 [M+H]⁺, calcd for [C$_{22}$H$_{14}$BrN$_5$O+H]⁺ 444.0.

Example A110

(E and Z)-ethyl 3-(6-((E)-(2-oxo-1H-pyrrolo[2,3-b]pyridin-3(2H-ylidene)methyl)-1H-indazol-3-yl)acrylate

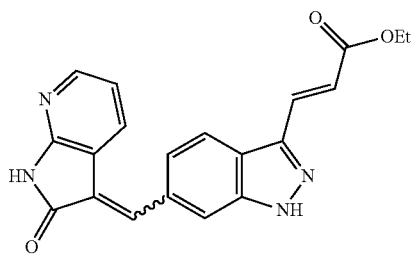 [SMILES: CCOC(=O)/C=C/c1n[nH]c2cc(C=C3C(=O)Nc4ncccc43)ccc12]

The title compound (46 mg, 64%) was synthesized as a brown solid according to the method described for Example A67 (oil temp 75° C., reflux 2 h) using 1H-pyrrolo[2,3-b]pyridin-2(3H)-one (26.8 mg, 0.2 mmol) and (E)-ethyl 3-(6-formyl-1H-indazol-3-yl)acrylate (48.8 mg, 0.2 mmol). ¹H NMR indicated 7:3 mixture of E/Z isomers. ¹H NMR (400 MHz, DMSO-d6) δ 13.30 (br. s, 1H, NH), 11.20 (br. s, 1H, NH), 8.26 (d, J=8.8 Hz, 1H), 8.11 (d, J=5.5 Hz, 1H, partially overlapping with the peak at 8.09 ppm), 8.09 (d, J=6.4 Hz, 1H, partially overlapping with the peak at 8.11 ppm), 7.95 (d, J=17.2 Hz, 1H, partially overlapping with the peak at 7.93 ppm), 7.93 (s, 1H, partially overlapping with the peak at 7.95 ppm), 7.87 (d, J=7.6 Hz, 1H), 7.56 (d, J=8.0 Hz, 1H), 6.90 (dd, J=7.6 Hz, 4.8 Hz, 1H), 6.81 (d, J=16.4 Hz, 1H), 4.23 (q, J=6.8 Hz, 2H), 1.29 (t, J=6.8 Hz, 3H); MS ESI 361.1 [M+H]⁺, calcd for [C$_{20}$H$_{16}$N$_4$O$_3$+H]⁺ 361.1.

Example A111

(E)-ethyl 3-(6-((E)-(5-methoxy-2-oxoindolin-3-ylidene)methyl)-1H-indazol-3-yl)acrylate

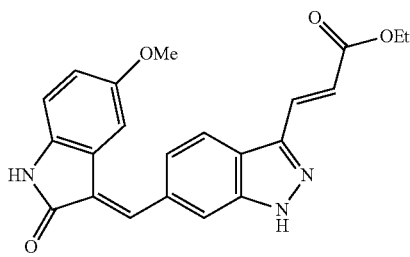 [SMILES: CCOC(=O)/C=C/c1n[nH]c2cc(/C=C3/C(=O)Nc4ccc(OC)cc43)ccc12]

The title compound (60 mg, 77%) was synthesized as an orange red solid according to the method described for Example A67 (oil temp 75° C., reflux 2 h) using 5-methoxyoxindole (26.8 mg, 0.2 mmol) and (E)-ethyl 3-(6-formyl-1H-indazol-3-yl)acrylate (48.8 mg, 0.2 mmol). ¹H NMR (400 MHz, DMSO-d6) δ 13.80 (brs, 1H, NH), 10.44 (s, 1H, NH), 8.26 (d, J=8.4 Hz, 1H), 7.96 (s, 1H), 7.92 (d, J=16.4 Hz, 1H), 7.77 (s, 1H), 7.56 (d, J=8.4 Hz, 1H), 7.14 (d, 1H), 6.90-6.80 (m, 3H), 4.23 (q, J=7.2 Hz, 2H), 3.58 (s, 3H), 2.29 (t, J=7.2 Hz, 3H); MS ESI 390.3 [M+H]⁺, calcd for [C$_{22}$H$_{19}$N$_3$O$_4$+H]⁺ 390.1.

Example A112

(E)-5-methoxy-3-((3-(6-morpholinopyridin-3-yl)-1H-indazol-6-yl)-methylene)indolin-2-one

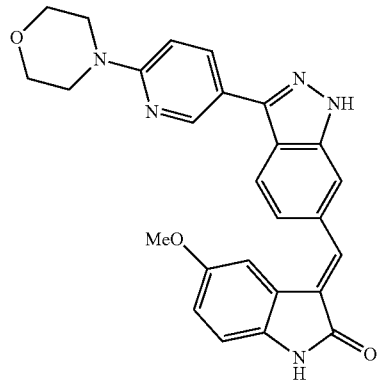 [SMILES: COc1ccc2c(c1)/C(=C\c1ccc3c(-c4ccc(N5CCOCC5)nc4)n[nH]c3c1)C(=O)N2]

A. 3-(6-morpholinopyridin-3-yl)-1H-indazole-6-carbaldehyde

According to procedure for the synthesis of 3-(pyridin-3-yl)-1H-indazole-6-carbaldehyde, except substituting 2-(4-morpholino)pyridine-5-boronic acid pinacol ester (64 mg, 0.22 mmol), the title compound was prepared as a yellow powder (35 mg, 62%). $^1$H NMR (400 MHz, $d_6$-DMSO) δ ppm 13.71 (br s, 1H), 10.14 (s, 1H), 8.77 (d, J=1.9 Hz, 1H), 8.02-8.18 (m, 2H), 8.15 (dd, J=8.9 Hz, 2.5, 1H), 7.64 (d, J=8.6 Hz, 1H), 7.00 (d, J=8.8 Hz, 1H), 3.73 (t, J=4.5 Hz, 4H), 3.53 (t, J=5.1 Hz, 4H); MS ESI 309.1 (100) [M+H]$^+$, calcd for [$C_{17}H_{16}N_4O_2$+H]$^+$ 309.13.

B. (E)-5-methoxy-3-((3-(6-morpholinopyridin-3-yl)-1H-indazol-6yl)methylene)-indolin-2-one According to procedure for the synthesis of (E)-3-((1H-indazol-6-yl)methylene)indolin-2-one, except substituting 3-(6-morpholinopyridin-3-yl)-1H-indazole-6-carbaldehyde (35 mg, 0.11 mmol), the title compound was prepared as an orange powder (22 mg, 42%). $^1$H NMR (400 MHz, $d_6$-DMSO) δ 13.37 (br s, 1H), 10.43 (br s, 1H), 8.79 (d, J=2.2 Hz, 1H), 8.17 (d, J=8.6 Hz, 2H), 7.93 (s, 1H), 7.79 (s, 1H), 7.49 (d, J=8.0 Hz, 1H), 7.21 (d, J=1.8 Hz, 1H), 7.00 (d, J=9.0 Hz, 1H), 6.85 (dd, J=8.5, 2.0 Hz, 1H), 6.80 (d, J=8.6 Hz, 1H), 3.73 (t, J=4.6 Hz, 4H), 5.59 (s, 3H), 3.53 (t, J=4.8 Hz, 4H); MS ESI 454.3 [M+H]$^+$, calcd for [$C_{26}H_{23}N_5O_2$+H]$^+$ 454.18.

Example A113

(E)-3-((3-((E)-2-(pyridin-3-yl)vinyl)-1H-indazol-6-yl)methylene)-indolin-2-one

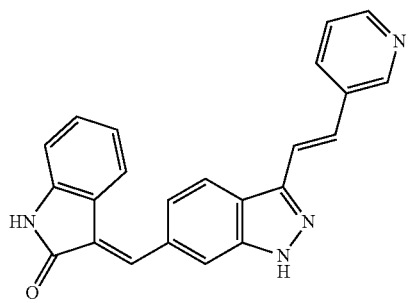 [SMILES: O=C1Nc2ccccc2/C1=C\c1ccc2c(/C=C/c3cccnc3)n[nH]c2c1]

The title compound (61 mg, 84%) was synthesized as a yellow solid according to the method described for Example A67 (oil temp 75° C., reflux 90 min) using oxindole (26.6 mg, 0.2 mmol) and (E)-3-(2-(pyridin-3-yl)vinyl)-1H-indazole-6-carbaldehyde (49.8 mg, 0.2 mmol). $^1$H NMR (400 MHz, DMSO-d6) δ 13.46 (s, 1H, NH), 10.64 (s, 1H, NH), 8.91 (s, 1H), 8.48 (d, J=4.4 Hz, 1H), 8.36 (d, J=8.4 Hz, 1H), 8.20 (d, J=8.4 Hz, 1H), 7.90 (s, 1H), 7.80 (s, 1H), 7.73 (d, J=16.8 Hz, 1H), 7.61 (d, J=7.2 Hz, 1H, partially overlapping with the peak at 7.60 ppm), 7.60 (d, J=17.2 Hz, 1H, partially overlapping with the peak at 7.61 ppm), 7.54 (d, J=8.4 Hz, 1H), 7.43 (dd, J=7.8 Hz, 4.8 Hz, 1H), 7.24 (t, J=7.8 Hz, 1H), 6.89 (d, J=7.6 Hz, 1H), 6.85 (t, J=7.8 Hz, 1H); MS ESI 365.1 [M+H]$^+$, calcd for [$C_{23}H_{16}N_4$+H]$^+$ 365.1.

Example A114

(E and Z)-3-((3-((E)-2-(pyridin-3-yl)vinyl)-1H-indazol-6-yl)methylene)-1H-pyrrolo[2,3-b]pyridin-2(3H)-one

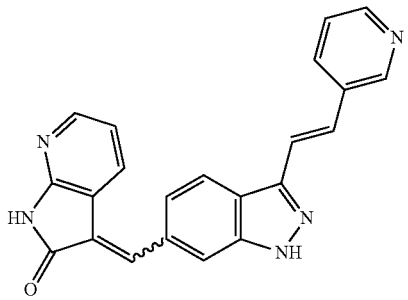 [SMILES: O=C1Nc2ncccc2C1=Cc1ccc2c(/C=C/c3cccnc3)n[nH]c2c1]

The title compound (59 mg, 81%) was synthesized as an orange solid according to the method described for Example A67 (oil temp 75° C., reflux 90 min) using 1H-pyrrolo[2,3-b]pyridin-2(3H)-one (26.8 mg, 0.2 mmol) and (E)-3-(2-(pyridin-3-yl)vinyl)-1H-indazole-6-carbaldehyde (49.8 mg, 0.2 mmol). $^1$H NMR indicated 5:2 mixture of Z/E isomers. $^1$H NMR (400 MHz, DMSO-d6) δ 13.60 (s, 1H, NH), 11.30 (s, 1H, NH), 8.95 (s, 1H), 8.91 (d, 1H), 8.47 (d, J=4.4 Hz, 1H), 8.31 (d, J=8.4 Hz, 1H), 8.19 (d, J=7.2 Hz, 1H), 8.13-8.07 (m, 4H), 7.72 (d, J=16.8 Hz, 1H), 7.59 (d, J=17.2 Hz, 1H), 7.42 (dd, J=8.0 Hz, 4.4 Hz, 1H), 7.50 (dd, J=7.2 Hz, 5.6 Hz, 1H); MS ESI 444.3 [M+H]$^+$, calcd for [$C_{22}H_{15}N_5O$+H]$^+$ 366.1.

Example A115

(E and Z)-5-methoxy-3-((3-((E)-2-(pyridin-3-yl)vinyl)-1H-indazol-6-yl)methylene)indolin-2-one

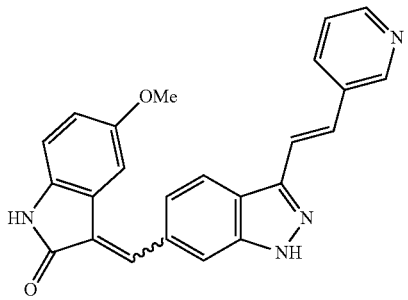 [SMILES: COc1ccc2c(c1)C(=Cc1ccc3c(/C=C/c4cccnc4)n[nH]c3c1)C(=O)N2]

The title compound (53 mg, 67%) was synthesized as an orange red solid according to the method described for Example A67 (oil temp 75° C., reflux 90 min) using 5-methyoxyoxindole (32.6 mg, 0.2 mmol) and (E)-3-(2-(pyridin-3-yl)vinyl)-1H-indazole-6-carbaldehyde (49.8 mg, 0.2 mmol). $^1$H NMR indicated 4:1 mixture of E/Z isomers. $^1$H NMR (400 MHz, DMSO-d6) δ 13.50 (br. s, 1H, NH), 10.44 (s, 1H, NH), 8.91 (d, 1H), 8.48 (d, J=4.8 Hz, 1H), 8.36 (d, J=8.4 Hz, 1H), 8.20 (d, J=7.6 Hz, 1H), 7.92 (s, 1H), 7.79 (s, 1H), 7.73 (d, J=16.8 Hz, 1H), 7.59 (d, J=16.4 Hz, 1H), 7.54 (d, J=8.8 Hz, 1H), 7.43 (dd, J=8.0 Hz, 5.2 Hz, 1H), 7.19 (d, 1H), 6.86 (dd, J=8.4 Hz, 2.0 Hz, 1H), 6.81 (d, J=8.4 Hz, 1H), 3.78 (s, 3H); MS ESI 395.2 [M+H]$^+$, calcd for [$C_{24}H_{18}N_4O_2$+H]$^+$ 395.1.

Example A116

(E)-3-((3-(6-(dimethylamino)pyridin-3-yl)-1H-indazol-6-yl)methyl-ene)-5-methoxyindolin-2-one

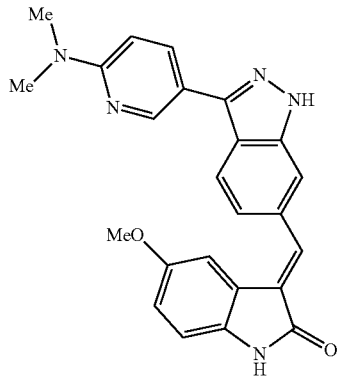 [SMILES: COc1ccc2c(c1)/C(=C\c1ccc3c(-c4ccc(N(C)C)nc4)n[nH]c3c1)C(=O)N2]

A. 3-(6-(dimethylamino)pyridin-3-yl)-1H-indazole-6-carbaldehyde

According to the procedure for the synthesis of 3-(pyridin-3-yl)-1H-indazole-6-carbaldehyde, except substituting 2-(dimethylamino)pyridine-5-boronic acid hydrate (41 mg, 0.22 mmol), the title compound was prepared as a yellow powder (14 mg, 29%). $^1$H NMR (400 MHz, d$_6$-DMSO) δ ppm 10.13 (s, 1H), 8.72 (d, J=2.4 Hz, 1H), 8.17-8.16 (m, 2H), 8.09 (dd, J=8.4, 2.1 Hz, 1H), 7.62 (d, J=8.9 Hz, 1H), 6.79 (d, J=8.8 Hz, 1H), 3.09 (s, 6H); MS ESI 267.0 (100) [M+H]$^+$, calcd for [C$_{15}$H$_{14}$N$_4$O+H]$^+$ 267.12.

B. (E)-3-((3-(6-(dimethylamino)pyridin-3-yl)-1H-indazol-6-yl)methylene)-5-methoxyindolin-2-one According to the procedure for the synthesis of (E)-3-((1H-indazol-6-yl)-methylene)-indolin-2-one, except substituting 3-(6-(dimethylamino)pyridin-3-yl)-1H-indazole-6-carbaldehyde (14 mg, 0.053 mol), the title compound was prepared as a red solid (2.9 mg, 13%). $^1$H NMR (400 MHz, d$_6$-DMSO) δ 13.30 (br. s, 1H), 10.43 (br s, 1H), 8.75 (s, 1H), 8.15 (d, J=8.7 Hz, 1H), 8.11 (d, J=8.4 Hz, 1H), 7.92 (s, 1H), 7.78 (s, 1H), 7.47 (d, J=7.7 Hz, 1H), 7.22 (s, 1H), 6.86-6.79 (m, 3H), 3.60 (s, 3H), 3.10 (s, 6H); MS ESI 412.2 [M+H]$^+$, calcd for [C$_{24}$H$_{21}$N$_5$O$_2$+H]$^+$

Example A117

4-((E)-2-(6-((E)-(5-methoxy-2-oxoindolin-3-ylidene)methyl)-1H-indazol-3-yl)vinyl)pyridine 1-oxide

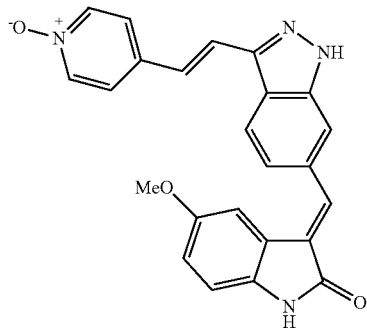

According to the procedure for the synthesis of 2-((E)-2-(6-((E)-(5-methoxy-2-oxoindolin-3-ylidene)methyl)-1H-indazol-3-yl)vinyl)pyridine 1-oxide (Example A88), except substituting (E)-5-methoxy-3-((3-((E)-2-(pyridin-4-yl)vinyl)-1H-indazol-6-yl)methyl-ene)indolin-2-one (8.1 mg, 0.021 mmol), the title compound was prepared as an orange solid (1.3 mg, 15%.). $^1$H NMR (400 MHz, DMSO-d6) δ 13.55 (br. s, 1H), 10.45 (s, 1H), 8.35 (d, J=8.6 Hz, 1H), 8.20 (d, J=6.8 Hz, 2H), 7.93 (s, 1H), 7.79-7.72 (m, 4H), 7.55 (d, J=14.3 Hz, 1H), 7.54 (d, J=8.9 Hz, 1H), 7.17 (d, J=2.7 Hz, 1H), 6.86 (dd, J=8.5, 2.7 Hz, 1H), 6.80 (d, J=8.5 Hz, 1H), 3.60 (s, 3H); MS ESI 411.2 [M+H]$^+$, calcd for [C$_{24}$H$_{18}$N$_4$O$_3$+H]$^+$ 411.14.

Example A118

(E and Z)-5-methoxy-3-((3-((E)-3-(4-methylpiperazin-1-yl)-3-oxoprop-1-enyl)-1H-indazol-6-yl)methylene)indolin-2-one

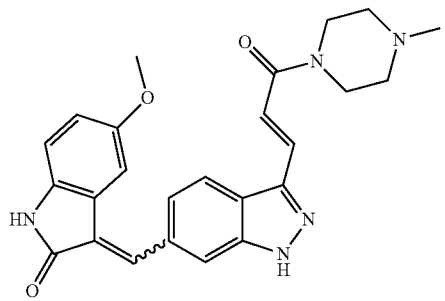 [SMILES: COc1ccc2c(c1)C(=Cc1ccc3c(/C=C/C(=O)N4CCN(C)CC4)n[nH]c3c1)C(=O)N2]

The synthetic method followed that described in Example A66 starting from 5-methoxyoxindole (10 mg, 0.0583 mmol) and (E)-3-(3-(4-methylpiperazin-1-yl)-3-oxoprop-1-enyl)-1-((2-(trimethylsilyl)ethoxy)methyl)-1H-indazole-6-carbaldehyde (25 mg, 0.0583 mmol) to give 2.5 mg of the title compound as an 85:15 mixture of (E)/(Z) isomers. $^1$H NMR (400 MHz, CD$_3$OD) 8.95, 7.80 (s, 1H), 8.21-8.16 (m, 1H), 7.97-7.87 (m, 2H), 7.59 (d, J=7.52 Hz, 1H), 7.45 (d, J=15.7 Hz, 1H), 7.32, 7.22 (s, 1H), 6.85 (s, 2H), 3.84, 3.63 (s, 3H), 3.90-3.75 (m, 4H), 2.62-2.48 (br. s, 4H), 2.34 (s, 3H); MS ESI 444.2 [M+H]$^+$, calcd for [C$_{25}$H$_{25}$N$_5$O$_3$+H]$^+$ 444.20.

Example A119

(E)-3-((3-((E)-2-(3-chloropyridin-4-yl)vinyl)-1H-indazol-6-yl)methyl-ene)-5-methoxyindolin-2-one

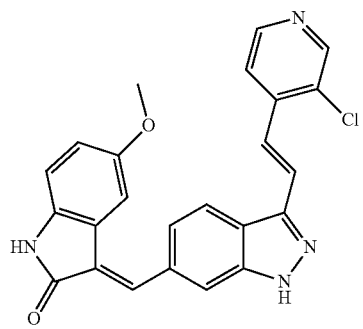 [SMILES: COc1ccc2c(c1)/C(=C\c1ccc3c(/C=C/c4ccncc4Cl)n[nH]c3c1)C(=O)N2]

A. 3-chloro-4-vinylpyridine

A dry round-bottom flask containing with methyltriphenylphosphonium iodide (632 mg, 1.77 mmol) and THF (25 mL) was cooled with an ice-water bath and the suspension treated with n-BuLi (1.0 mL of a 1.6M solution in hexanes) and the reaction stirred for 0.5 hours. The solution was cooled to −78° C. and 3-chloroisonicotinaldehyde (250 mg, 1.77 mmol) was added portion-wise and then the reaction was allowed to warm to room temperature over 4 hours. The reaction was quenched with AcOH (0.10 mL) and the THF removed in vacuo. The residue was dissolved in EtOAc and then washed with water (2×), and brine (2×), the organic layer dried (MgSO$_4$) and the EtOAc was removed. The residue was purified by column chromatography, silica gel (99:1 to 98:2 CH$_2$Cl$_2$/MeOH) to give the title compound (135 mg, 55%) as a yellow oil. MS ESI 140.0 [M+H]$^+$, calcd for [C$_7$H$_6$ClN+H]$^+$ 140.03.

B. (E)-3-((3-((E)-2-(3-chloropyridin-4-yl)vinyl)-1H-indazol-6-yl)methylene)-5-methoxyindolin-2-one The synthetic method followed that described in Example A57 starting from 3-chloro-4-vinylpyridine (42 mg, 0.299 mmol) and 3-iodo-1-((2-(trimethylsilyl)ethoxy)methyl)-1H-indazole-6-carbaldehyde (100 mg, 0.249 mmol) with a modified purification procedure. The title compound was purified by prep-HPLC to give 4.0 mg of an orange-red powder. $^1$H NMR (400 MHz, CD$_3$OD) δ 8.97 (s, 1H), 8.67 (s, 1H), 8.50 (d, J=5.20 Hz, 1H), 8.11-7.84 (m, 6H), 7.33 (s, 1H), 6.86-6.78 (m, 2H), 3.85 (s, 3H); MS ESI 429.2 [M+H]$^+$, calcd for [C$_{24}$H$_{17}$ClN$_4$O$_2$+H]$^+$ 429.11.

Example A120

N-((E)-2-oxo-3-((3-((E)-2-(pyridin-4-yl)vinyl)-1H-indazol-6-yl)-methylene)indolin-7-yl)acetamide

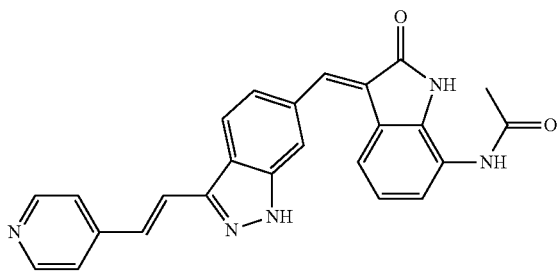 [SMILES: CC(=O)Nc1cccc2c1NC(=O)/C2=C/c1ccc2c(/C=C/c3ccncc3)n[nH]c2c1]

A. N-((E)-2-oxo-3-((3-((E)-2-thyridin-4-yl)vinyl)-1-((2-(trimethylsilyl)ethoxy)-methyl)-1H-indazol-6-yl)methylene)indolin-7-yl)acetamide According to the method of A57B, N-(2-oxoindolin-7-yl)acetamide (30 mg, 0.16 mmol) was reacted with (E)-3-(2-(pyridin-4-yl)vinyl)-1-((2-(trimethylsilyl)ethoxy)methyl)-1H-indazole-6-carbaldehyde (60 mg, 0.16 mmol) to give the title compound as an orange solid (64 mg, 72%). MS ESI 552.3 [M+H]$^+$, calcd for [C$_{31}$H$_{33}$N$_5$O$_3$Si+H]$^+$ 552.2.

B. N-((E)-2-oxo-3-((3-((E)-2-(pyridin-4-yl)vinyl)-1H-indazol-6-yl)methylene)-indolin-7-yl)acetamide According to the method of A57C, N-((E)-2-oxo-3-((3-((E)-2-(pyridin-4-yl)vinyl)-1-((2-(trimethylsilyl)ethoxy)methyl)-1H-indazol-6-yl)methylene)indolin-7-yl)acetamide (64 mg, 0.11 mmol) was treated with boron trifluoride etherate, followed by 2 N HCl to give the title compound as an orange solid (33 mg, 71%). $^1$H NMR (400 MHz, d$^6$-DMSO) δ 10.33 (s, 1H), 9.42 (s, 1H), 8.85 (d, J=6.2 Hz, 2H), 8.46-8.30 (m, 4H), 7.98 (s, 1H), 7.87-7.78 (m, 2H), 7.80 (s, 1H), 7.63 (d, J=8.2 Hz, 1H), 7.42-7.35 (m, 2H), 6.81 (t, J=8.1 Hz, 1H), 2.05 (s, 3H); MS ESI 422.1 [M+H]$^+$, calcd for [C$_{25}$H$_{19}$N$_5$O$_2$+H]$^+$ 422.2.

Example A121 tert-butyl(E)-2-oxo-3-((3-((E)-2-(pyridin-4-yl)vinyl)-1H-indazol-6-yl)methylene)indolin-5-ylcarbamate

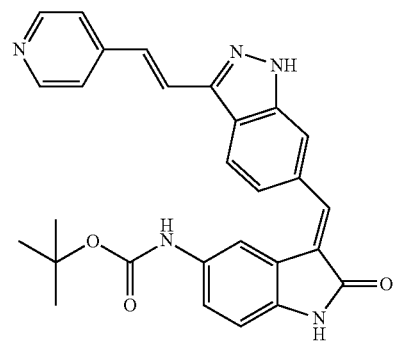

The title compound (102 mg, 76%) was synthesized as orange-yellow solid according to the method described for Example A11B from tert-butyl 2-oxoindolin-5-ylcarbamate (70 mg, 0.282 mmol) and (E)-3-(2-(pyridin-4-yl)vinyl)-1H-indazole-6-carbaldehyde (70 mg, 0.282 mmol). $^1$H NMR (400 MHz, d6-DMSO) δ 13.53 (s, 1H), 10.47 (s, 1H), 9.14 (s, 1H), 8.55 (d, J=6.5 Hz, 2H), 8.33 (d, J=8.8 Hz, 1H), 7.88-7.83 (m, 3H), 7.74 (s, 2H), 7.69 (d, J=6.5 Hz, 2H), 7.56-7.50 (m, 2H), 6.75 (d, J=8.2 Hz, 1H), 1.34 (s, 9H); MS ESI 480.3 [M+H]$^+$, calcd for [C$_{28}$H$_{25}$N$_5$O$_3$+H]$^+$ 480.20.

Example A122

(E)-5-amino-3-((3-((E)-2-(pyridin-4-yl)vinyl)-1H-indazol-6-yl)-methylene)indolin-2-one bis(2,2,2-trifluoroacetate)

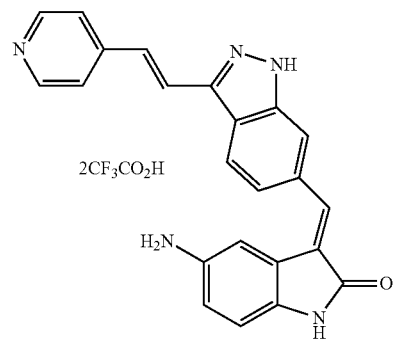 [SMILES: Nc1ccc2c(c1)/C(=C\c1ccc3c(/C=C/c4ccncc4)n[nH]c3c1)C(=O)N2]

tert-Butyl(E)-2-oxo-3-((3-((E)-2-(pyridin-4-yl)vinyl)-1H-indazol-6-yl)-methyl-ene)indolin-5-ylcarbamate (13 mg, 0.027 mmol) was dissolved into CH$_2$Cl$_2$ (1.0 mL) and then trifluoroacetic acid (0.1 mL) was added and the reaction stirred for 1 hour. The solvent was removed and the residue titurated with ether/EtOAc to give after drying 4.6 mg, 29% of the title compound as an orange powder. $^1$H NMR (400 MHz, CD$_3$OD) δ 8.68 (d, J=5.8 Hz, 2H), 8.31 (d, J=8.7 Hz, 1H), 8.21-8.12 (m, 3H), 7.97 (s, 1H), 7.88 (s, 1H), 7.70 (d, J=16.8 Hz, 1H), 7.62-7.57 (m, 2H), 7.18 (d, J=8.8 Hz, 1H), 6.99 (d, J=8.6 Hz, 1H); MS ESI 380.1 [M+H]$^+$, calcd for [C$_{23}$H$_{17}$N$_5$O+H]$^+$ 380.15.

Example A123

(E)-3-((1H-indazol-6-yl)methylene)-5-hydroxyindolin-2-one

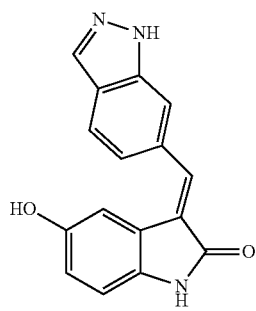 [SMILES: O=C1Nc2ccc(O)cc2/C1=C\c1ccc2cn[nH]c2c1]

A. 5-Hydroxyindolin-2-one

An oven-dried flask was charged with BBr$_3$.SMe$_2$ (2.80 g, 9.20 mmol) and 1,2-dichloroethane (15 mL). 5-Methoxyindolin-2-one (0.30 g, 1.84 mmol) was then added and the mixture was heated to reflux for 18 hours. The reaction was then cooled to room temperature and quenched with MeOH (1.0 mL). The mixture was then extracted into EtOAc washing with brine (3×). The organic layer was dried over MgSO$_4$, filtered and the solvent removed in vacuo; the resulting residue was then purified by column chromatography (silica gel, 94:6 to 92:8, CH$_2$Cl$_2$/MeOH) to give 144 mg, 53% of a beige powder. MS ESI 149.9 [M+H]$^+$, calcd for [C$_8$H$_7$NO$_2$+H]$^+$ 150.06

B. (E)-3-((1H-indazol-6-yl)methylene)-5-hydroxyindolin-2-one

The title compound was synthesized according to the method described for Example A11B from 5-Hydroxyindolin-2-one (16 mg, 0.107 mmol) and precipitation with 98:2 CH$_2$Cl$_2$/MeOH to obtain the title compound (18 mg, 60%). $^1$H NMR (400 MHz, CD$_3$OD) δ 8.14 (s, 1H), 7.92 (d, J=8.0 Hz, 1H), 7.87 (s, 1H), 7.85 (s, 1H), 7.44 (d, J=8.0 Hz, 1H), 7.15 (s, 1H), 6.75 (d, J=8.2 Hz, 1H), 6.69 (d, J=8.2 Hz, 1H); MS ESI 278.0 [M+H]$^+$, calcd for [C$_{16}$H$_{11}$N$_3$O$_2$+H]$^+$ 278.09.

Example A124

(E)-5-hydroxy-3-((3-((E)-2-(pyridin-4-yl)vinyl)-1H-indazol-6-yl)methylene)indolin-2-one 2,2,2-trifluoroacetate

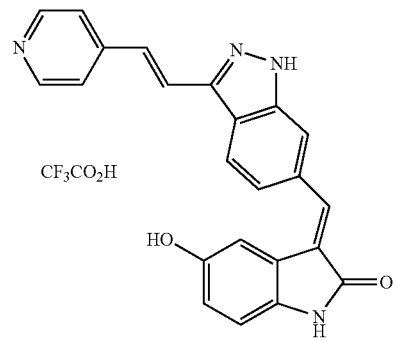 [SMILES: "CF3CO2H" ; O=C1Nc2ccc(O)cc2/C1=C\c1ccc2c(/C=C/c3ccncc3)n[nH]c2c1]

The title compound was synthesized according to the method described in Example A57 from 5-Hydroxyindolin-2-one (10 mg, 0.107 mmol) with a modified purification procedure. The title compound was purified by preparatory HPLC to give 10 mg, 30% of a yellow solid. $^1$H NMR (400 MHz, CD$_3$OD) δ 8.73 (d, J=6.5 Hz, 2H), 8.35 (d, J=8.8 Hz, 1H), 8.27 (d, J=6.5 Hz, 2H), 8.24 (d, J=16.4 Hz, 1H), 7.94 (s, 1H), 7.88 (s, 1H), 7.83 (d, J=16.4 Hz, 1H), 7.61 (d, J=8.1 Hz, 1H), 7.13 (s, 1H), 6.77 (d, J=8.2 Hz, 1H), 6.71 (d, J=8.2 Hz, 1H); MS ESI 381.1 [M+H]$^+$, calcd for [C$_{23}$H$_{16}$N$_4$O$_2$+H]$^+$ 381.13.

Example A125

(E and Z)—N-(2-(dimethylamino)ethyl)-N-methyl-3-(6-((E)-(5-methyl-2-oxoindolin-3-ylidene)methyl)-1H-indazol-3-yl)acrylamide

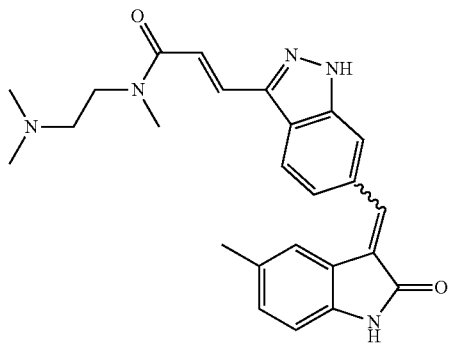 [SMILES: Cc1ccc2c(c1)C(=Cc1ccc3c(/C=C/C(=O)N(C)CCN(C)C)n[nH]c3c1)C(=O)N2]

A. (E)-N-(2-(dimethylamino)ethyl)-3-(6-formyl-1-((2-(trimethylsilyl)ethoxy)methyl)-1H-indazol-3-yl)-N-methylacrylamide A dry round-bottom flask was charged with N1,N1,N2-trimethylethane-1,2-diamine (0.32 mL, 2.50 mmol), diisopropylethylamine (0.87 mL, 5.00 mmol) and CH$_2$Cl$_2$ (12 mL) and the solution cooled with an ice-water bath. Acryloyl chloride (0.20 mL, 2.50 mmol) was added dropwise and the reaction allowed to warm to room temperature. After 3 hours the solvent was removed and the residue purified by column chromatography (silica gel, 88:10:2, CH$_2$Cl$_2$/MeOH/7M NH$_3$ in MeOH) to give 50 mg of a crude oil to which was added 3-iodo-1-((2-(trimethylsilyl)ethoxy)methyl)-1H-indazole-6-carbaldehyde (105 mg, 0.262 mmol), DMF (5 mL) and diisopropylethylamine (0.091 mL, 0.524 mmol). The mixture was degassed by bubbling Argon through the solution for 15 min. Pd(OAc)$_2$ (3.0 mg, 0.013 mmol) and P(o-tolyl)$_3$ (12 mg, 0.039 mmol) were then added and the reaction heated to 110° C. for 18 hours. The mixture was cooled to room temperature, NaHCO$_{3(sat.)}$ (5 mL) was added, and the product extracted (3×) with EtOAc. The organic layer was washed with water (2×) and brine (2×), and then dried over MgSO$_4$. After removal of solvent the residue was purified by column chromatography (silica gel, 93:6:1, CH$_2$Cl$_2$/MeOH/7M NH$_3$ in MeOH) to give 41 mg, 41% of a red-orange oil. MS ESI 431.2 [M+H]$^+$, calcd for [C$_{22}$H$_{34}$N$_4$O$_3$Si+H]$^+$ 431.25.

B. (E and Z)—N-(2-(dimethylamino)ethyl)-N-methyl-3-(6-((E)-(5-methyl-2-oxoindolin-3-ylidene)methyl)-1H-indazol-3-yl)acrylamide The title compound was synthesized according to the method described in Example A57 from 5-methylindolin-2-one (8.0 mg, 0.0535 mmol) and (E)-N-(2-(dimethylamino)ethyl)-3-(6-formyl-1-((2-(trimethylsilyl)ethoxy)methyl)-1H-indazol-3-yl)-N-methylacrylamide (23 mg, 0.0535 mmol) with a modified purification procedure. The product was extracted into EtOAc after the final deprotection step and washed with NaHCO$_{3(sat)}$ (2×), brine (2×) and the organic layer dried over MgSO$_4$. After removal of solvent the resulting film was titurated with Et$_2$O/hexanes to give after drying 9.4 mg, 41% yield of a yellow solid which was a 77:23 mixture of (E)/(Z) isomers. $^1$H NMR (400 MHz, CD$_3$OD) δ 8.94, 7.91 (s, 1H), 8.20, 8.16 (d, J=8.7 Hz, 1H), 7.98-7.93 (m, 1H), 7.84 (s, 1H), 7.59, 7.43 (d, J=8.2 Hz, 1H), 7.52-7.42 (m, 2H), 7.08 (d, J=7.2 Hz, 1H), 6.82, 6.78 (d, J=7.6 Hz, 1H), 3.77-3.68 (m, 2H), 3.60, 3.13 (s, 3H), 2.68-2.61 (m, 2H), 2.37 (s, 6H), 2.19 (s, 3H); MS ESI 430.3 [M+H]$^+$, calcd for [C$_{25}$H$_{27}$N$_5$O$_2$+H]$^+$ 430.22.

Example A126

(E)-N-(2-(dimethylamino)ethyl)-3-(6-((E)-(5-methoxy-2-oxoindolin-3-ylidene)methyl)-1H-indazol-3-yl)-N-methylacrylamide 2,2,2-trifluoroacetate

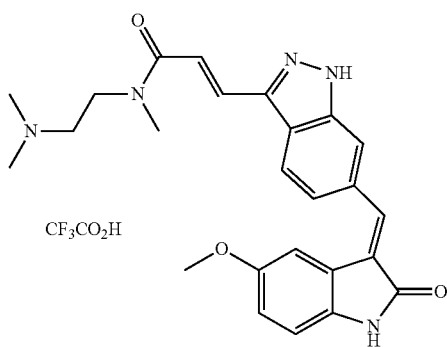 [SMILES: "CF3CO2H" ; COc1ccc2c(c1)/C(=C\c1ccc3c(/C=C/C(=O)N(C)CCN(C)C)n[nH]c3c1)C(=O)N2]

The title compound was synthesized according to the method described in Example A57 from 5-methoxyindolin-2-one (8.0 mg, 0.0535 mmol) and (E)-N-(2-(dimethylamino)ethyl)-3-(6-formyl-1-((2-(trimethylsilyl)ethoxy)methyl)-1H-indazol-3-yl)-N-methylacrylamide (23 mg, 0.0535 mmol) with a modified purification procedure. The final compound was purified by preparatory-HPLC to give 4.0 mg, 17% of a yellow powder. $^1$H NMR (400 MHz, CD$_3$OD) δ 8.17 (d, J=8.6 Hz, 1H), 8.02 (d, J=15.7 Hz, 1H), 7.94 (s, 1H), 7.88 (s, 1H), 7.59 (d, J=8.1 Hz, 1H), 7.44 (d, J=15.5 Hz, 1H), 7.21 (s, 1H), 6.86 (s, 2H), 3.95-3.90 (m, 2H), 3.63 (s, 3H), 3.46-3.42 (m, 2H), 3.36 (s, 3H), 3.03 (s, 6H); MS ESI 446.3 [M+H]$^+$, calcd for [C$_{25}$H$_{27}$N$_5$O$_3$+H]$^+$ 446.22.

Example A127

(E)-5-isopropyl-3-((3-((E)-2-(pyridin-4-yl)vinyl)-1H-indazol-6-yl)methylene)indolin-2-one 2,2,2-trifluoroacetate

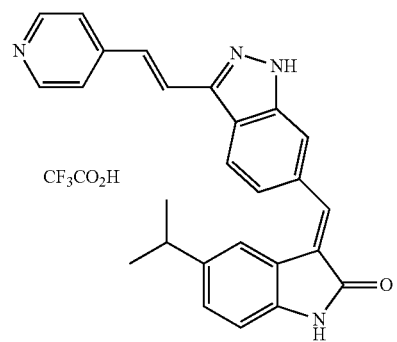 [SMILES: "CF3CO2H" ; CC(C)c1ccc2c(c1)/C(=C\c1ccc3c(/C=C/c4ccncc4)n[nH]c3c1)C(=O)N2]

A. 5-isopropylindolin-2-one

A mixture of 5-bromoindolin-2-one (106 mg, 0.500 mmol), isopropenylboronic acid pinacol ester (0.14 mL, 0.750 mmol), K$_3$PO$_4$ (212 mg, 1.00 mmol), water (1 mL) and n-BuOH (4 mL) was briefly sonicated in a microwave vial and then purged with argon for 15 min. Tris(dibenzyldeneacetone)dipalladium (9.2 mg, 0.010 mmol) and dicyclohexyl (2',4',6'-triisopropylbiphenyl-2-yl)phosphine (19 mg, 0.040 mmol) were added, the vial sealed and heated in microwave reactor at 110° C. for 1 hour. The solvent was removed and the residue purified by column chromatography (silica gel, 2:1, hexanes/EtOAc) to give 40 mg, 46% of 5-isopropenylindolin-2-one as a beige solid; 5-isopropenylindolin-2-one (15 mg, 0.0866 mmol) was then dissolved into MeOH and the solution purged with N$_{2\,(g)}$. 2 mg of 10% Pd/C (Degussa type) was then added and the mixture purged briefly with H$_{2\,(g)}$. The mixture was stirred under 1 atm of H$_{2\,(g)}$ for 3 hours and then filtered through a pad of celite. The solvent was removed to give 15 mg, 99% of the product as an off-white solid. MS ESI 176.0 [M+H]$^+$, calcd for [C$_{11}$H$_{13}$NO+H]$^+$ 176.11.

B. (E)-5-isopropyl-3-((3-((E)-2-(pyridin-4-yl)vinyl)-1H-indazol-6-yl)methylene)indolin-2-one 2,2,2-trifluoroacetate The title compound was synthesized according to the method described in Example A57 from 5-isopropylindolin-2-one (7.0 mg, 0.040 mmol) and (E)-3-(2-(pyridin-4-yl)vinyl)-1-((2-(trimethylsilyl)ethoxy)methyl)-1H-indazole-6-carbaldehyde (15 mg, 0.040 mmol) with a modified purification procedure. The final compound was purified by preparatory-HPLC to give 3.1 mg, 19% yield of a yellow powder. ¹H NMR (400 MHz, CD₃OD) δ 8.72 (d, J=6.7 Hz, 2H), 8.36 (d, J=8.1 Hz, 1H), 8.26 (d, J=6.7 Hz, 2H), 8.24 (d, J=16.3 Hz, 1H), 7.96 (s, 1H), 7.87 (s, 1H), 7.78 (d, J=16.3 Hz, 1H), 7.64 (d, J=6.7 Hz, 1H), 7.53 (s, 1H), 7.15 (d, J=6.5 Hz, 1H), 6.86 (d, J=7.9 Hz, 1H), 2.77-2.72 (m, 1H), 1.12 (d, J=6.9 Hz, 6H); MS ESI 407.2 [M+H]⁺, calcd for [C₂₆H₂₂N₄O+H]⁺ 407.19.

Example A128

(E and Z)-2-oxo-3-((3-((E)-2-(pyridin-4-yl)vinyl)-1H-indazol-6-yl)methylene)indoline-5-carbonitrile

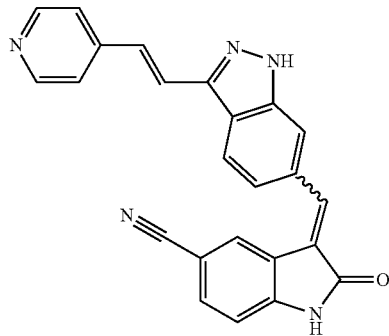 [SMILES: N#Cc1ccc2c(c1)C(=Cc1ccc3c(/C=C/c4ccncc4)n[nH]c3c1)C(=O)N2]

The title compound was synthesized according to the method described in Example A57 from 2-oxoindoline-5-carbonitrile (10 mg, 0.063 mmol) and (E)-3-(2-(pyridin-4-yl)vinyl)-1-((2-(trimethylsilyl)ethoxy)methyl)-1H-indazole-6-carbaldehyde (25 mg, 0.063 mmol) with a modified purification procedure. The product was precipitated with EtOAc and filtered washing with EtOAc to give 4.5 mg, 30% of a yellow powder which was a 65:35 mixture of (E)/(Z) isomers. ¹H NMR (400 MHz, d6-DMSO) δ 14.04, 13.94 (s, 1H), 11.24, 11.22 (s, 1H), 9.01, 8.42 (s, 1H), 8.83 (d, J=5.5 Hz, 2H), 8.50-8.17 (m, 3H), 8.03 (s, 1H), 7.99 (s, 1H), 7.86 (s, 1H), 7.81-7.65 (m, 3H), 7.07, 7.01 (d, J=8.4 Hz, 1H); MS ESI 390.1 [M+H]⁺, calcd for [C₂₄H₁₅N₅O+H]⁺ 390.14.

Example A129

(E and Z)—N-(2-(dimethylamino)ethyl)-N-methyl-2-oxo-3-((3-((E)-2-(pyridin-4-yl)vinyl)-1H-indazol-6-yl)methylene)indoline-5-sulfonamide

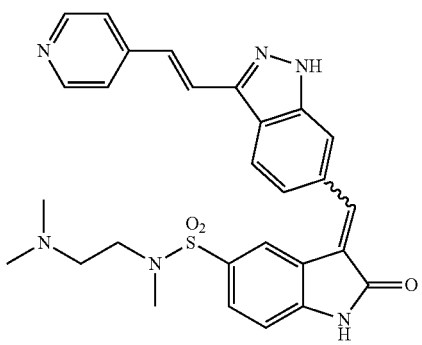 [SMILES: CN(C)CCN(C)S(=O)(=O)c1ccc2c(c1)C(=Cc1ccc3c(/C=C/c4ccncc4)n[nH]c3c1)C(=O)N2]

A. N-(2-(dimethylamino)ethyl)-N-methyl-2-oxoindoline-5-sulfonamide

To a solution of N1,N1,N2-trimethylethane-1,2-diamine (26 uL, 0.20 mmol) in THF (2 mL) was added 2-oxoindoline-5-sulfonyl chloride (30 mg, 0.130 mmol) and the reaction stirred for 3 hours. The solvent was removed and the crude material used for the next step. MS ESI 298.0 [M+H]⁺, calcd for [C₁₃H₁₉N₃O₃S+H]⁺ 298.12.

B. (E and Z)—N-(2-(dimethylamino)ethyl)-N-methyl-2-oxo-3-((3-((E)-2-(pyridin-4-yl)vinyl)-1H-indazol-6-yl)methylene)indoline-5-sulfonamide The title compound was synthesized according to the method described in Example A57 from N-(2-(dimethylamino)ethyl)-N-methyl-2-oxoindoline-5-sulfonamide and (E)-3-(2-(pyridin-4-yl)vinyl)-1-((2-(trimethylsilyl)ethoxy)methyl)-1H-indazole-6-carbaldehyde (25 mg, 0.065 mmol) with a modified purification procedure. The product was extracted into EtOAc, and washed with NaHCO₃₍sat₎ (2×), brine (2×) and the organic layer dried over MgSO₄. After removal of solvent the resulting yellow solid was titurated with Et₂O/hexanes to give after drying 1.5 mg, 4.1% yield of a yellow solid which was a 77:23 mixture of (E)/(Z) isomers. ¹H NMR (400 MHz, CD₃OD) δ 9.01, 8.03 (s, 1H), 8.55-8.45 (m, 2H), 8.30-8.05 (m, 3H), 7.96-7.76 (m, 2H), 7.75-7.65 (m, 3H), 7.58-7.51 (m, 1H), 7.10, 7.07 (d, J=8.6 Hz, 1H), 3.05-2.99 (m, 2H), 2.90, 2.72 (m, 2H), 2.80, 2.63 (s, 3H), 2.57, 2.34 (s, 6H); MS ESI 529.2 [M+H]⁺, calcd for [C₂₈H₂₈N₆O₃S+H]⁺ 529.20.

Example A130

(E and Z)-5-(3-(dimethylamino)propylamino)-3-((3-((E)-2-(pyridin-4-yl)-vinyl)-1H-indazol-6-yl)methylene)indolin-2-one

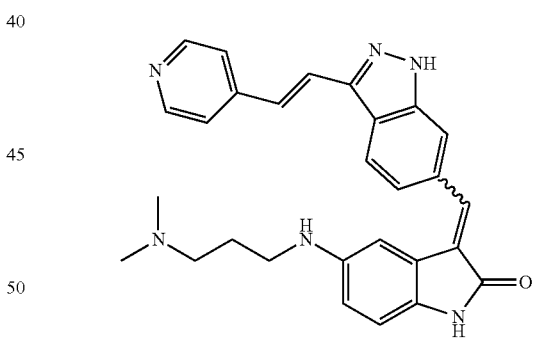

A mixture of mono(4-((E)-2-(6-((E)-(5-ammonio-2-oxoindolin-3-ylidene)methyl)-1H-indazol-3-yl)vinyl)pyridinium)di(2,2,2-trifluoroacetate) (10 mg, 0.016 mmol), K₂CO₃ (11 mg, 0.082 mmol) and DMF (1.0 mL) was cooled to 0° C. and then 3-bromo-N,N-dimethylpropan-1-amine hydrobromide (4.0 mg, 0.0164 mmol) was added. The reaction was allowed to warm to room temperature and stirred for 18 hours. EtOAc (10 mL) was added and the mixture washed with brine (3×). The organic layer was dried over MgSO₄ and the solvent removed to give a red gum which was titurated with ether/EtOAc (~10:1) three times while decanting the mother liquor to give after drying 2.4 mg, 32% of a red powder which was a 85:15 mixture of (E)/(Z) isomers. ¹H NMR (400 MHz, CD₃OD) δ 9.03, 7.93 (s, 1H), 8.55-8.49 (m, 2H), 8.23 (d, J=8.3 Hz, 1H), 7.82-7.73 (m, 2H), 7.68-7.64 (m, 2H), 7.59-7.50 (m, 2H), 7.11, 7.10 (s, 1H), 6.71-6.64 (m, 2H), 4.54-4.50 (m, 2H), 2.40-2.34 (m, 2H), 2.25, 2.22 (s, 6H), 2.18-2.10 (m, 2H); MS ESI 465.2 [M+H]$^+$, calcd for [$C_{28}H_{28}N_6O$+H]$^+$ 465.24.

Example A131

(E and Z)-3-((3-((E)-2-(pyridin-4-yl)vinyl)-1H-indazol-5-yl)-methylene)indolin-2-one hydrochloride

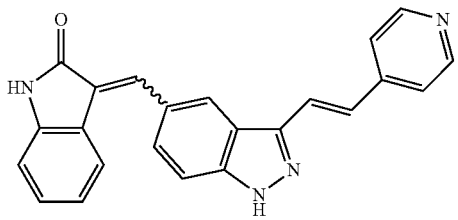 [SMILES: O=C1Nc2ccccc2C1=Cc1ccc2[nH]nc(/C=C/c3ccncc3)c2c1]

A. 3-iodo-1H-indazole-5-carbaldehyde

To a solution of 1H-indazole-5-carbaldehyde (315.2 mg, 2.16 mmol), $K_2CO_3$ (598.8 mg, 4.33 mmol) in DMF (2.5 mL) was added dropwise a solution of $I_2$ (938 mg, 3.7 mmol) in DMF (2.5 mL) and the reaction allowed to stir for three hours. An aqueous solution consisting of $Na_2S_2O_4$ (511 mg)/$K_2CO_3$ (35 mg)/$H_2O$ (3.5 mL) was then added and the solution stirred for two hours. Water (30 mL) and aqueous sodium hydrogen sulfate (1M, 10 mL) was added and the product was extracted with ethyl acetate (350 mL); this organic layer was washed with brine (3×25 mL). The aqueous layer was then extracted with dichloromethane (3×75 mL), this second organic layer was also washed with brine (25 mL). TLC indicated product present in both, so the residues were combined and purified by chromatography (10 g silica SPE tube, Silicycle, 5% ethyl acetate in dichloromethane) to yield a beige solid (203 mg, 35%). A precipitate that formed in the original aqueous layer was collected by vacuum filtration to give after drying a beige solid (first crop 135.6 mg, 23%; second crop 147 mg, 25%). $^1$H NMR (400 MHz, CDCl$_3$ plus a drop of CD$_3$OD) δ 10.03 (s, 1H), 8.00 (s, 1H), 7.95 (d, J=8.8 Hz, 1H), 7.54 (d, J=8.8 Hz, 1H).

B. 3-iodo-1-((2-(trimethylsilyl)ethoxy)methyl)-1H-indazole-5-carbaldehyde

To a suspension of 3-iodo-1H-indazole-6-carbaldehyde (126.6 mg, 0.46 mmol) in CH$_2$Cl$_2$ (5 mL) and 50% aq. KOH (1.0 mL) was added tetrabutylammonium bromide (3.4 mg, 0.01 mmol) and the solution cooled to 0° C. (2-(Chloromethoxy)ethyl)trimethylsilane (0.10 mL, 0.56 mmol) was then added dropwise and the reaction stirred at 0° C. for 1.5 hours. The solution was then transferred to a sep. funnel containing ethyl acetate (200 mL) and the organic layer was washed with water (2×20 mL) and brine (20 mL), dried (Na$_2$SO$_4$) and the solvent removed in vacuo. The resulting residue was adsorbed onto silica using dichloromethane-methanol to dissolve, and evaporated to dryness. Chromatography (10 g silica SPE tube, Silicycle, 50-100% dichloromethane in hexane, 10% ethyl acetate in dichloromethane) to give 88 mg, 47%. $^1$H NMR: (400 MHz, CDCl$_3$) δ 10.12 (s, 1H), 8.05 (m, 2H), 7.67 (d, J=9.2 Hz, 1H), 5.77 (s, 2H), 3.60 (m, 2H), 0.90 (m, 2H), −0.048 (s, 9H).

C. (E)-3-(2-(pyridin-4-yl)vinyl)-1-((2-(trimethylsilyl)ethoxy)methyl)-1H-indazole-5-carbaldehyde To a suspension of 3-iodo-1-((2-(trimethylsilyl)ethoxy)methyl)-1H-indazole-5-carbaldehyde (87 mg, 0.22 mmol), NaOAc (36 mg, 0.44 mmol), "Bu$_4$NCl (61 mg, 0.44 mmol), and Pd(OAc)$_2$ (8.0 mg, 0.036 mmol) in DMF (2 mL) under argon was added 4-vinylpyridine (0.05 mL, 0.46 mmol). The resulting mixture was heated in a sealed vial at 100° C. for 14 hours. Ethyl acetate (200 mL) was added and the solution was washed with water (20 mL) and brine (3×20 mL), dried over Na$_2$SO$_4$ and concentrated. The residue was chromatographed (5 g silica SPE tube, Silicycle, 1-2% MeOH in CH$_2$Cl$_2$, repeated for mixed fractions) gave the title compound as a yellow solid (43 mg, 52%). $^1$H NMR (400 MHz, CDCl$_3$ plus a drop of CD$_3$OD) δ 10.07 (s, 1H), 8.52 (m, 3H), 7.97 (d, J=8.4 Hz, 1H), 7.67 (d, J=8.8 Hz, 1H); 7.60 (d, J=16.4 Hz, 1H); 7.48 (m, 3H); 5.73 (s, 2H), 3.56 (m, 2H), 0.86 (m, 2H), −0.12 (s, 9H).

D. (E and Z)-3-((3-((E)-2-(pyridin-4-yl)vinyl)-1-((2-(trimethylsilyl)ethoxy)-methyl)-1H-indazol-5-yl)methylene)indolin-2-one A solution of piperidine (0.2M in EtOH, 0.10 mL, 0.02 mmol) was added to a suspension of oxindole (16.5 mg, 0.12 mmol) and (E)-3-(2-(pyridin-4-yl)vinyl)-1-((2-(trimethylsilyl)ethoxy)methyl)-1H-indazole-5-carbaldehyde (42.5 mg, 0.11 mmol) in EtOH (4 mL). The reaction was then heated to 75° C. for 15 hrs. The solvent was evaporated in vacuo. MeOH was added and the resulting suspension was sonicated, but the solution was still cloudy even after EtOAc was added. The solid was removed by filtration and the solvent evaporated in vacuo. Chromatography (5 g silica SPE tube, Silicycle, 2% MeOH in CH$_2$Cl$_2$) gave a yellow solid (35 mg, 64%, 55:45 mixture of E/Z isomers). $^1$H NMR (400 MHz, CDCl$_3$ plus a drop of CD$_3$OD) δ 9.77 (s, 0.45H), 8.63 (m, 1.9H), 8.42 (s, 0.55H), 8.18 (s, 0.45H), 8.14 (dd, J=8.8, 1.2 Hz, 0.45H), 8.00 (s, 1H), 7.83-7.42 (m, 7H), 7.26 (t, J=7.6 Hz, 1H), 7.09 (t, J=7.6 Hz, 0.45H), 6.94-6.88 (m, 1.6H), 5.80 (s, 0.55H), 5.77 (s, 0.45H), 3.64 (m, 2H), 0.95 (m, 2H), −0.02 (s, 5H), −0.03 (s, 4H).

E. (E and Z)-3-((3-((E)-2-(pyridin-4-yl)vinyl)-1H-indazol-5-yl)methylene)-indolin-2-one hydrochloride According to the method of A57C and D, 3-((3-((E)-2-(pyridin-4-yl)vinyl)-1-((2-(trimethylsilyl)ethoxy)methyl)-1H-indazol-5-yl)methylene)indolin-2-one (13.1 mg, 0.026 mmol) was treated with boron trifluoride etherate, followed by 2 N HCl (water/EtOH) treatment. Suction filtration gave a solid which was rinsed with 1:1 EtOH:water (2×1 mL). Pumping under high vacuum gave an orange solid (7.3 mg, 69%, 55:45 mixture of E/Z isomers, HCl salt). $^1$H NMR (400 MHz, CD$_3$OD) δ 9.83 (s, 0.4H), 8.73 (m, 2H), 8.59 (s, 0.6H), 8.33-8.20 (m, 3.5H), 7.95 (m, 1H), 7.91-7.87 (m, 1H), 7.80-

7.63 (m, 3H), 7.25 (t, J=8.4 Hz, 1H), 7.07 (t, J=7.6 Hz, 0.4H), 6.96-6.87 (m, 1.6H); MS ESI 365.2 [M+H]+, calcd for [C23H16N4O+H]+ 365.14.

Example A132

(E and Z)-5-methoxy-3-((3-((E)-2-(6-(4-methylpiperazin-1-yl)pyridin-3-yl)vinyl)-1H-indazol-6-yl)methylene)indolin-2-one dihydrochloride

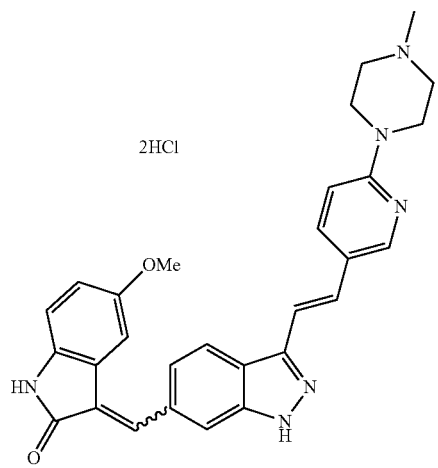 [SMILES: COc1ccc2c(c1)C(=Cc1ccc3c(/C=C/c4ccc(N5CCN(C)CC5)nc4)n[nH]c3c1)C(=O)N2]

A. 5-methoxy-3-(E & Z)-((3-((E)-2-(6-(4-methylpiperazin-1-yl)-pyridin-3-yl)vinyl)-1-((2-(trimethylsilyl)ethoxy)methyl)-1H-indazol-6-yl)methylene)indolin-2-one The title compound was synthesized according to the method of Example A19, utilizing 5-methoxyindolin-2-one (14.7 mg, 0.090 mmol) and (E)-3-(2-(6-(4-methylpiperazin-1-yl)pyridine-3-yl)vinyl)-1-((2-(trimethylsilyl)ethoxy)methyl)-1H-indazole-6-carbaldehyde (Example A108-B: 41 mg, 0.086 mmol). The crude mixture was concentrated under reduced pressure and purified by prepTLC (SiO2 5% MeOH/DCM) to provide the title compound as a (E:Z) mixture of isomers: a yellow solid (11.5 mg, 21%); 1H NMR (400 MHz, CD3OD) δ ppm 8.29 (d, J=2.26 Hz, 1H), 8.22 (d, J=8.03 Hz, 1H), 7.92-7.97 (m, 2H), 7.86 (s, 1H), 7.57 (d, J=8.53 Hz, 1H), 7.50 (d., J=16.6 Hz, 1H), 7.30 (d., J=16.6 Hz, 1H), 7.20 (br. s, 1H), 6.89 (d, J=9.03 Hz, 1H), 6.84 (s, 2H), 5.77 (s, 2H), 3.58-3.67 (m, 9H), 2.55-2.62 (m, 4H), 2.37 (s, 3H), 0.88 (t, J=8.16 Hz, 2H), −0.09 (s, 9H); MS ESI [M+2H—CH2CH2SiMe3]+ 523.4, calcd for [C35H42N6O3Si+H]+ 623.8.

B. (E and Z)-5-methoxy-3-((3-((E)-2-(6-(4-methylpiperazin-1-yl)pyridin-3-yl)vinyl)-1H-indazol-6-yl)methylene)indolin-2-one dihydrochloride To a DCM (50 mL) solution of 5-methoxy-3-(E & Z)-((3-((E)-2-(6-(4-methylpiperazin-1-yl)-pyridin-3-yl)vinyl)-1-((2-(trimethylsilyl)ethoxy)methyl)-1H-indazol-6-yl)methylene)indolin-2-one (0.85 g, 1.36 mmol) was added BF3OEt2 (1.7 mL, 13.6 mmol) at 0° C. The cooling bath was removed and the reaction mixture was stirred for 4 h. After removal of the solvent under reduced pressure, the residue was heated in EtOH (40 mL) and 2 M aq HCl (20 mL) at 60° C. overnight. The reaction was then stored at 5° C. overnight. A red precipitate was collected and washed separately with EtOAc, MeCN and Et2O to provide the title compound as a 3.3:1 (E:Z) mixture of isomers: an orange-red powder (0.32 g, 42%). 1H NMR (400 MHz, CD3OD) δ ppm 8.87 (s, 0.3H), 8.53-8.61 (m, 1.0H), 8.28-8.32 (m, 1H), 8.26 (d, J=8.53 Hz, 0.7H), 8.13 (d, J=8.28 Hz, 0.3H), 8.00 (t, J=7.99 Hz, 0.3H), 7.95-8.02 (m, 1.5H), 7.83-7.90 (m, 3.3H), 7.30 (d, J=2.3 Hz, 0.3H), 7.24 (s, 0.7H), 6.84 (s, 1.4H), 6.76-6.84 (m, 0.4H), 4.39-4.59 (br.s, 2H), 3.64-3.85 (br.s., 4H), 3.63 (s, 3H), 3.32-3.60 (br.s., 2H), 3.03 (s, 3H); MS ESI [M+H]+ 493.3, calcd for [C29H28N6O2+H]+ 493.6.

Example A133

(Z)-3-((1H-indazol-6-yl)methylene)-4-bromoindolin-2-one

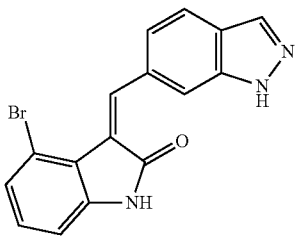 [SMILES: O=C1Nc2cccc(Br)c2/C1=C/c1ccc2cn[nH]c2c1]

The title compound was synthesized according to the method of Example A19, utilizing 4-bromoindolin-2-one (50 mg, 0.23 mmol) and 1H-indazole-6-carbaldehyde (34.5 mg, 0.23 mmol). On completion the reaction mixture was stored at rt overnight. Filtration and rinsing with xs EtOH provided the title compound as an orange solid (30 mg, 38%). 1H NMR (400 MHz, DMSO-d6) δ ppm 13.36 (br. s., 1H), 10.91 (br. s., 1H), 8.78 (s, 1H), 8.73 (s, 1H), 8.13 (s, 1H), 7.80 (d, J=8.28 Hz, 1H), 7.65 (d, J=8.28 Hz, 1H), 7.22 (d, J=8.28 Hz, 1H), 7.16 (t, J=7.78 Hz, 1H), 6.88 (d, J=7.78 Hz, 1H); MS ESI [M+H]+ 340.1/341.9, calcd for [C16H10BrN3O+H]+ 340.0/342.0.

Example A 134

(E)-3-((1H-indazol-6-yl)methylene)-5-chloro-1H-pyrrolo[3,2-b]pyridin-2(3H)-one

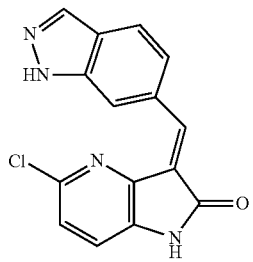 [SMILES: O=C1Nc2ccc(Cl)nc2/C1=C\c1ccc2cn[nH]c2c1]

The title compound (40 mg, 67%) was synthesized as an orange solid according to the method described for Example A67 (oil temp 75° C., reflux 30 min) using 5-chloro-1H-pyrrolo[3,2-b]pyridin-2(3H)-one (33.7 mg, 0.2 mmol) and 1H-indazole-6-carbaldehyde (29.2 mg, 0.2 mmol). 1H NMR (400 MHz, DMSO-d6) δ 13.56 (s, 1H), 10.90 (s, 1H), 8.93 (s, 1H), 8.37 (d, J=8.4 Hz, 1H), 8.17 (s, 1H), 7.93 (s, 1H), 7.89 (d, J=8.4 Hz, 1H), 7.39 (d, J=8.4 Hz, 1H), 7.35 (d, J=8.0 Hz, 1H); MS ESI 297.0 [M+H]$^+$, calcd for [C$_{15}$H$_9$ClN$_4$O+H]$^+$ 297.1.

Example A135

(E)-3-((1H-indazol-6-yl)methylene)-5,6-dimethoxy-indolin-2-one

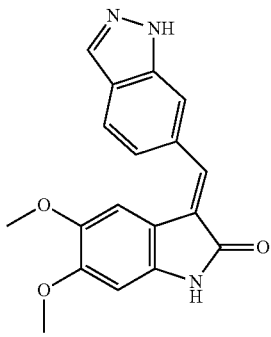 [SMILES: COc1cc2c(cc1OC)/C(=C\c1ccc3cn[nH]c3c1)C(=O)N2]

The title compound (43 mg, 67%) was synthesized as an orange yellow solid according to the method described for Example A67 (oil temp 75° C., reflux 90 min) using 5,6-dimethoxyindolin-2-one (38.6 mg, 0.2 mmol) and 1H-indazole-6-carbaldehyde (29.2 mg, 0.2 mmol). $^1$H NMR (400 MHz, DMSO-d6) δ 13.26 (s, 1H), 10.36 (s, 1H), 8.14 (s, 1H), 7.95-7.85 (m, 2H), 7.57 (s, 1H), 7.46-7.37 (m, 1H), 7.24 (s, 1H), 6.52 (s, 1H), 3.78 (s, 3H), 3.53 (s, 3H); MS ESI 322.1 [M+H]$^+$, calcd for [C$_{18}$H$_{15}$N$_3$O$_3$+H]$^+$ 322.1.

Examples A136(a)

(E)-3-((3-(4-((dimethylamino)methyl)styryl)-1H-indazol-6-yl)-methylene)-5-methoxyindolin-2-one 2,2,2-trifluoroacetate and A136(b): (Z)-3-((3-(4-((dimethylamino)methyl)styryl)-1H-indazol-6-yl)-methylene)-5-methoxyindolin-2-one 2,2,2-trifluoroacetate

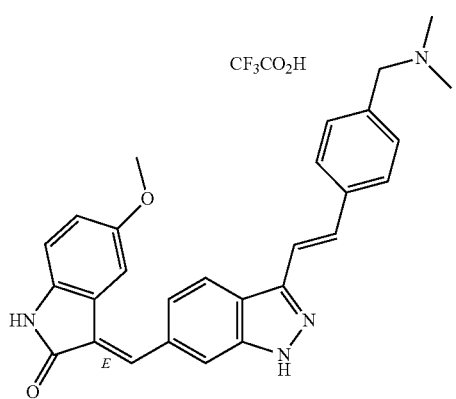

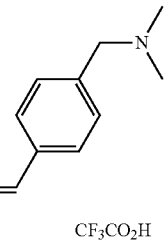

Piperidine (0.01 mL, 0.1 mmol) was added to a solution of 5-methoxyoxindole (52 mg, 0.32 mmol) and (E)-3-(4-((dimethylamino)methyl)styryl)-1-((2-(trimethylsilyl)ethoxy)methyl)-1H-indazole-6-carbaldehyde (contaminated with TBAF from previous deprotection attempt, 95.5 mg, 0.22 mmol) in EtOH (5 mL). The reaction was then heated to 75° C. for 25 hrs. The solvent was evaporated in vacuo. Chromatography (5 g silica SPE tube, Silicycle, 5-10% MeOH in CH$_2$Cl$_2$) gave a brown oil (105 mg, contained product and TBAF by NMR). The residue was dissolved in EtOAc (100 mL) and washed with brine (3×15 mL), dried over Na$_2$SO$_4$ and the solvent was evaporated in vacuo to give 3-((3-(4-((dimethylamino)methyl)styryl)-1-((2-(trimethylsilyl)ethoxy)methyl)-1H-indazol-6-yl)methylene)-5-methoxyindolin-2-one as a brown oil (110 mg, used without further purification).

According to the method of A57C, 3-((3-(4-((dimethylamino)methyl)styryl)-1-((2-(trimethylsilyl)ethoxy)methyl)-1H-indazol-6-yl)methylene)-5-methoxyindolin-2-one (19 mg, 0.033 mmol) was treated with boron trifluoride etherate, followed by 2 N HCl (water/EtOH) treatment. The solvents were removed in vacuo using additional EtOH to azeotropically remove water. The residue was dissolved in MeOH/EtOAc and filtered to remove solid, then the solvent was evaporated in vacuo. Purification by prep-HPLC gave the title compound (E isomer, first eluting fraction, 94% by HPLC) as an orange solid (11 mg, 60% yield,). $^1$H NMR (400 MHz, CD$_3$OD) δ ppm 8.26 (d, J=8.5 Hz, 1H), 7.88 (d, J=9.3 Hz, 2H), 7.80 (d, J=8.3 Hz, 2H), 7.61 (s, 2H), 7.51-7.58 (m, 3H), 7.26 (s, 1H), 6.84 (s, 2H), 4.34 (s, 2H), 3.63 (s, 3H), 2.89 (s, 6H); MS ESI 451.2 [M+H]$^+$, calcd for [C$_{28}$H$_{26}$N$_4$O$_2$+H]$^+$ 451.22. The second eluting fraction was the Z-isomer (5 mg, 30%). $^1$H NMR (400 MHz, CD$_3$OD) δ ppm 8.89 (s, 1H), 8.15 (d, J=9.0 Hz, 1H), 7.99 (dd, J=9.0, 1.3 Hz, 1H), 7.90 (s, 1H), 7.81 (d, J=8.3 Hz, 2H), 7.57-7.61 (m, 2H), 7.53 (d, J=8.3 Hz, 2H), 7.33 (d, J=2.0 Hz, 1H), 6.85 (dd, J=8.4, 2.4 Hz, 1H), 6.80 (d, J=8.4 Hz, 1H), 4.34 (s, 2H), 3.84 (s, 3H), 2.89 (s, 6H); MS ESI 451.2 [M+H]$^+$, calcd for [C$_{28}$H$_{26}$N$_4$O$_2$+H]$^+$ 451.22.

Example A137

(E and Z)-5-chloro-3-((3-((E)-2-(pyridin-4-yl)vinyl)-1H-indazol-6-yl)methylene)-1H-pyrrolo[3,2-b]pyridin-2(3H)-one

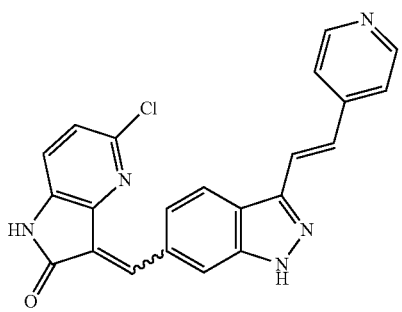 [SMILES: O=C1Nc2ccc(Cl)nc2C1=Cc1ccc2c(/C=C/c3ccncc3)n[nH]c2c1]

The title compound (E/Z=3:1, 63 mg, 84%) was synthesized as an orange solid according to the method described for Example A67 (oil temp 70° C., reflux 60 min) using 5-chloro-1H-pyrrolo[3,2-b]pyridin-2(3H)-one (33.7 mg, 0.2 mmol) and (E)-3-(2-(pyridin-4-yl)vinyl)-1H-indazole-6-carbaldehyde (49.8 mg, 0.2 mmol). $^1$H NMR (400 MHz, DMSO-d6) E isomer: δ 13.83 (s, 1H), 10.92 (s, 1H), 8.91 (s, 1H), 8.57 (d, J=6.0 Hz, 3H), 8.37 (d, J=8.8 Hz, 1H), 7.95 (s, 1H), 7.90 (d, J=16.4 Hz, 1H), 7.75-7.70 (m, 2H), 7.57 (d, J=16.8 Hz, 1H), 7.41 (d, J=8.0 Hz, 1H), 7.36 (d, J=8.4 Hz, 1H); Z isomer: δ 13.80 (s, 1H), 11.03 (s, 1H), 9.15 (s, 1H), 8.57 (d, J=6.0 Hz, 2H, buried under the doublet at 8.57), 8.34 (d, J=8.4 Hz, 1H, partially overlapping with the doublet at 8.37), 8.25 (d, J=9.2 Hz, 1H), 8.20 (s, 1H), 7.86 (d, J=14.4 Hz, 1H, partially overlapping with the doublet at 7.90), 7.75-7.70 (m, buried under the multiplet 7.75-7.70), 7.56 (d, J=16.8 Hz, 1H), 7.32 (d, J=8.0 Hz, 1H), 7.28 (d, J=8.0 Hz, 1H); MS ESI 400.0 [M+H]$^+$, calcd for [C$_{22}$H$_{14}$ClN$_5$O+H]$^+$ 400.1.

Example A138

(E)-5,6-dimethoxy-3-((3-((E)-2-(pyridin-4-yl)vinyl)-1H-indazol-6-yl)methylene)indolin-2-one

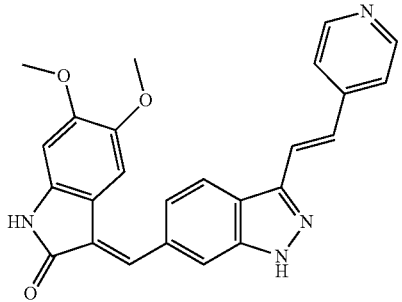 [SMILES: COc1cc2c(cc1OC)/C(=C\c1ccc3c(/C=C/c4ccncc4)n[nH]c3c1)C(=O)N2]

The title compound (36 mg, 42%) was synthesized as an orange red solid according to the method described for Example A67 (oil temp 75° C., reflux 90 min) using 5,6-dimethoxyindolin-2-one (38.6 mg, 0.2 mmol) and (E)-3-(2-(pyridin-4-yl)vinyl)-1H-indazole-6-carbaldehyde (49.8 mg, 0.2 mmol). $^1$H NMR (400 MHz, DMSO-d6) δ 13.54 (s, 1H), 10.39 (s, 1H), 8.60-8.53 (m, 2H), 8.35 (d, J=7.2 Hz, 1H), 7.94 (s, 1H), 7.87 (d, J=16.4 Hz, 1H), 7.75-7.67 (m, 2H), 7.63-7.50 (m, 3H), 7.25 (s, 1H), 6.53 (s, 1H), 3.80 (s, 3H), 3.55 (s, 3H); MS ESI 425.2 [M+H]$^+$, calcd for [C$_{25}$H$_{20}$N$_4$O$_3$+H]$^+$ 425.1.

Example A139

(E and Z)-5-bromo-3-((3-((E)-2-(pyridin-3-yl)vinyl)-1H-indazol-6-yl)methylene)indolin-2-one

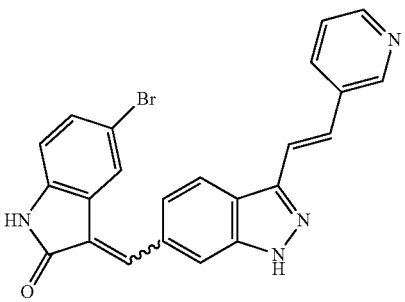 [SMILES: O=C1Nc2ccc(Br)cc2C1=Cc1ccc2c(/C=C/c3cccnc3)n[nH]c2c1]

The title compound (E:Z=1:4, 73 mg, 83%) was synthesized as a dark yellow solid according to the method described for Example A67 (oil temp 75° C., reflux 2 h) using 5-bromoindolin-2-one (44.5 mg, 0.21 mmol) and (E)-3-(2-(pyridin-3-yl)vinyl)-1H-indazole-6-carbaldehyde (49.8 mg, 0.2 mmol). $^1$H NMR (400 MHz, DMSO-d6): δ 13.60 (s, 1H), 10.84 (s, 1H), 8.99 (s, 1H), 8.91 (s, 1H), 8.48 (d, J=4.4 Hz, 1H), 8.30 (d, J=8.4 Hz, 1H), 8.19 (d, J=8.0 Hz, 1H), 8.16-8.10 (m, 3H), 8.04 (s, 1H), 7.71 (d, J=16.8 Hz, 1H), 7.59 (d, J=17.2 Hz, 1H), 7.43 (dd, J=7.6 Hz, J=4.8 Hz, 1H), 7.39 (dd, J=8.0 Hz, J=1.2 Hz, 1H); MS ESI 443.3 [M+H]$^+$, calcd for [C$_{23}$H$_{15}$BrN$_4$O+H]$^+$ 443.1.

Example A140

(E and Z)-5-bromo-3-((3-((E)-2-(pyridin-3-yl)vinyl)-1H-indazol-6-yl)methylene)-1H-pyrrolo[2,3-b]pyridin-2(3H)-one

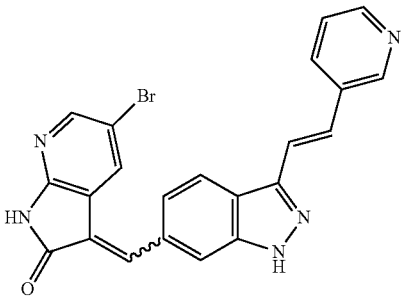 [SMILES: O=C1Nc2ncc(Br)cc2C1=Cc1ccc2c(/C=C/c3cccnc3)n[nH]c2c1]

The title compound (E/Z=5:4, 75 mg, 84%) was synthesized as a yellow solid according to the method described for Example A67 (oil temp 75° C., reflux 2 h) using 5-bromo-1H-pyrrolo[2,3-b]pyridin-2(3H)-one (44.5 mg, 0.21 mmol) and (E)-3-(2-(pyridin-3-yl)vinyl)-1H-indazole-6-carbaldehyde (49.8 mg, 0.2 mmol). $^1$H NMR (400 MHz, DMSO-d6) δ 13.64 (s, 0.45H), 13.56 (s, 0.48H), 11.50 (s, 0.91H), 8.94 (s, 0.43H), 8.91 (s, 0.97H), 8.48 (d, J=3.6 Hz, 0.99H), 8.43-8.37 (m, 0.98H), 8.33 (d, J=8.0 Hz, 0.52H), 8.28-8.17 (m, 2.36H), 8.11 (d, J=8.8 Hz, 0.50H), 8.03 (s, 0.56H), 7.94 (s, 1.02H), 7.77-7.69 (2 doublets partially overlapping, J=17.2 Hz, 1.07H, vinylic proton), 7.64-7.54 (m, 1.54H), 7.45-7.41 (2 doublets overlapping, J=8.8 Hz, 1.00H); MS ESI 444.3 [M+H]$^+$, calcd for [C$_{22}$H$_{14}$BrN$_5$O+H]$^+$ 444.1.

Example A141 methyl 4-((E)-2-(6-((Z)-(2-oxoindolin-3-ylidene)methyl)-1H-indazol-3-yl)vinyl)benzoate

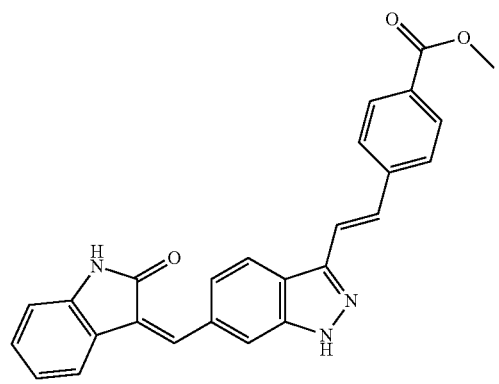 [SMILES: COC(=O)c1ccc(/C=C/c2n[nH]c3cc(/C=C4\C(=O)Nc5ccccc54)ccc23)cc1]

The title compound (40 mg, 83%) was synthesized as an orange solid according to the method described for Example A67 (oil temp 75° C., reflux 150 min) using indolin-2-one (26.6 mg, 0.2 mmol) and (E)-methyl 4-(2-(6-formyl-1H-indazol-3-yl)vinyl)benzoate (61.2 mg, 0.2 mmol). $^1$H NMR (400 MHz, DMSO-d6) δ 13.60 (s, 1H), 10.70 (s, 1H), 9.00 (s, 1H), 8.29 (d, J=8.0 Hz, 1H), 8.08 (d, J=8.4 Hz, 1H), 8.00 (s, 1H), 7.98 (d, J=8.0 Hz, 2H), 7.88 (d, J=8.0 Hz, 2H), 7.77 (d, J=8.4 Hz, 1H, partially overlapping with the doublet at 7.74), 7.74 (d, J=17.2 Hz, 1H, partially overlapping with the doublet at 7.77), 7.63 (d, J=17.2 Hz, 1H), 7.23 (t, J=7.6 Hz, 1H), 7.01 (t, J=7.6 Hz, 1H), 6.84 (d, J=7.6 Hz, 1H), 3.86 (s, 3H); MS ESI 422.3 [M+H]$^+$, calcd for [$C_{26}H_{19}N_3O_3$+H]$^+$ 422.1.

Example A142 methyl 4-((E)-2-(6-((E and Z)-(5-methoxy-2-oxoindolin-3-ylidene)methyl)-1H-indazol-3-yl)vinyl)benzoate

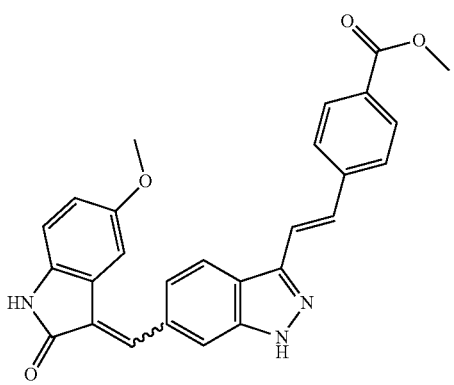 [SMILES: COC(=O)c1ccc(/C=C/c2n[nH]c3cc(C=C4C(=O)Nc5ccc(OC)cc54)ccc23)cc1]

The title compound (E/Z=2:1, 60 mg, 67%) was synthesized as an orange red solid according to the method described for Example A67 (oil temp 75° C., reflux 150 min) using 5-methoxyindolin-2-one (32.6 mg, 0.2 mmol) and (E)-methyl 4-(2-(6-formyl-1H-indazol-3-yl)vinyl)benzoate (61.2 mg, 0.2 mmol). $^1$H NMR (400 MHz, DMSO-d6) E isomer: δ 13.25 (s, br, 1H), 10.45 (s, 1H), 8.37 (d, J=8.0 Hz, 1H), 7.98 (d, J=8.4 Hz, 2H), 7.93 (s, 1H), 7.89 (d, J=8.0 Hz, 2H), 7.79 (s, 1H), 7.76 (d, J=16.8 Hz, 1H), 7.64 (d, J=16.8 Hz, 1H), 7.54 (d, J=8.4 Hz, 1H), 7.19 (d, J=2.0 Hz, 1H), 6.86 (dd, J=8.4 Hz, 2.0 Hz, 1H), 6.80 (d, J=8.0 Hz, 1H), 3.86 (s, 3H), 3.6 (s, 3H); Z isomer: δ 13.25 (s, br, 1H), 10.50 (s, 1H), 9.02 (s, 1H), 8.29 (d, J=8.4 Hz, 1H), 8.09 (d, J=8.4 Hz, 1H), 7.99 (s, 1H), 7.98 (d, J=8.4 Hz, 2H, buried by doublet at 7.98), 7.89 (d, J=8.0 Hz, 2H, buried by doublet at 7.89), 7.74 (d, J=16.8 Hz, 1H), 7.63 (d, J=16.4 Hz, 1H), 7.47 (d, J=2.0 Hz, 1H), 6.80 (d, 1H, buried by doublet at 6.80), 6.74 (d, 8J=8.4 Hz, 1H), 3.86 (s, 3H), 3.78 (s, 3H); MS ESI 452.3 [M+H]$^+$, calcd for [$C_{27}H_{21}N_3O_4$+H]$^+$ 452.2.

Example A143 methyl 4-((E)-2-(6-((E and Z)-(2-oxo-1H-pyrrolo[2,3-b]pyridin-3(2H)-ylidene)methyl)-1H-indazol-3-yl)vinyl)benzoate

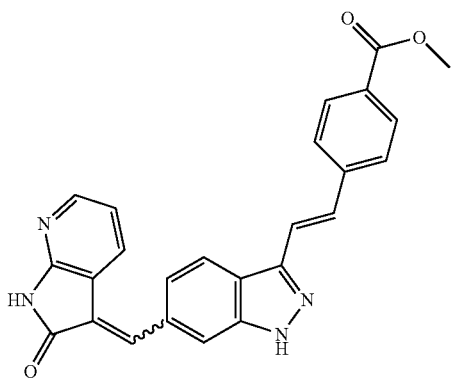 [SMILES: COC(=O)c1ccc(/C=C/c2n[nH]c3cc(C=C4C(=O)Nc5ncccc54)ccc23)cc1]

The title compound (E/Z=9:1, 62 mg, 73%) was synthesized as a yellow solid according to the method described for Example A67 (oil temp 75° C., reflux 120 min) using 1H-pyrrolo[2,3-b]pyridin-2(3H)-one (26.8 mg, 0.2 mmol) and (E)-methyl 4-(2-(6-formyl-1H-indazol-3-yl)vinyl)benzoate (61.2 mg, 0.2 mmol). $^1$H NMR (400 MHz, DMSO-d6) δ 15.53 (s, 1H), 11.27 (s, 1H), 8.38 (d, J=8.0 Hz, 1H), 8.11 (d, J=4.4 Hz, 1H), 7.98 (d, J=8.4 Hz, 2H), 7.95-7.87 (m, 5H), 7.76 (d, J=16.8 Hz, 1H), 7.64 (d, J=17.2 Hz, 1H), 7.55 (d, J=8.4 Hz, 1H), 6.91 (dd, J=7.2 Hz, J=5.6 Hz, 1H), 3.86 (s, 3H); MS ESI 423.2 [M+H]$^+$, calcd for [$C_{25}H_{18}N_4O_3$+H]$^+$ 423.1.

Example A144

4-((E)-2-(6-((E)-(2-oxoindolin-3-ylidene)methyl)-1H-indazol-3-yl)vinyl)benzoic acid

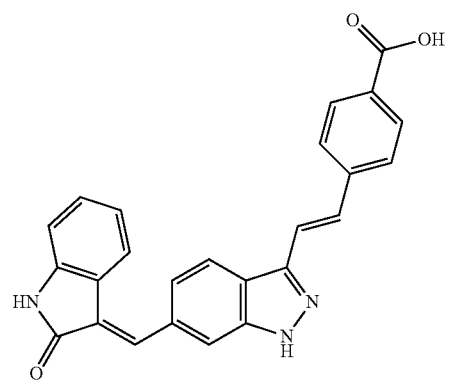 [SMILES: O=C1Nc2ccccc2/C1=C\c1ccc2c(/C=C/c3ccc(C(=O)O)cc3)n[nH]c2c1]

The title compound (17 mg, 21%) was synthesized as an orange solid according to the method described for Example A67 (oil temp 75° C., reflux 90 min) using indolin-2-one (26.6 mg, 0.2 mmol) and (E)-4-(2-(6-formyl-1H-indazol-3- yl)vinyl)benzoic acid (58.4 mg, 0.2 mmol). ¹H NMR (400 MHz, DMSO-d6) δ 13.49 (s, 1H), 12.90 (s, br, 1H), 10.64 (s, 1H), 8.37 (d, J=8.4 Hz, 1H), 7.97 (d, J=8.4 Hz, 2H), 7.91 (s, 1H), 7.86 (d, J=8.0 Hz, 2H), 7.80 (s, 1H), 7.74 (d, J=16.8 Hz, 1H), 7.63 (d, J=15.6 Hz, 1H partially overlapping with the singlet at 7.62), 7.62 (s, 1H partially overlapping with the doublet at 7.63), 7.24 (t, J=7.4 Hz, 1H), 6.91-6.82 (m, 2H); MS ESI 408.2 [M+H]⁺, calcd for [C$_{25}$H$_{17}$N$_3$O$_3$+H]⁺ 408.1.

Example A145

4-((E)-2-(6-((E)-(5-methoxy-2-oxoindolin-3-ylidene)methyl)-1H-indazol-3-yl)vinyl)benzoic acid

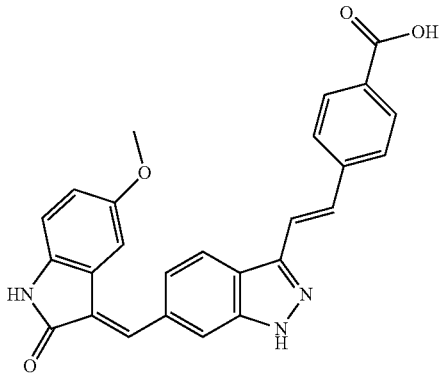 [SMILES: COc1ccc2c(c1)/C(=C\c1ccc3c(/C=C/c4ccc(C(=O)O)cc4)n[nH]c3c1)C(=O)N2]

The title compound (20 mg, 23%) was synthesized as an orange red solid according to the method described for Example A67 (oil temp 75° C., reflux 90 min) using 5-methoxylindolin-2-one (32.6 mg, 0.2 mmol) and (E)-4-(2-(6-formyl-1H-indazol-3-yl)vinyl)benzoic acid (58.4 mg, 0.2 mmol). ¹H NMR (400 MHz, DMSO-d6) δ 13.50 (s, 1H), 12.90 (s, br, 1H), 10.45 (s, 1H), 8.37 (d, J=8.4 Hz, 1H), 7.96 (d, J=8.0 Hz, 2H), 7.92 (s, 1H), 7.86 (d, J=8.0 Hz, 2H), 7.79 (s, 1H), 7.74 (d, J=16.8 Hz, 1H), 7.63 (d, J=16.4 Hz, 1H), 7.54 (d, J=8.4 Hz, 1H), 7.19 (s, 1H), 6.86 (dd, J=8.8 Hz, J=2.4 Hz, 1H), 6.80 (d, J=8.4 Hz, 1H), 3.60 (s, 3H); MS ESI 438.2 [M+H]⁺, calcd for [C$_{26}$H$_{19}$N$_3$O$_4$+H]⁺ 438.1.

Example A146

4-((E)-2-(6-((E/Z)-(2-oxo-1H-pyrrolo[2,3-b]pyridin-3(2H)-ylidene)methyl)-1H-indazol-3-yl)vinyl)benzoic acid

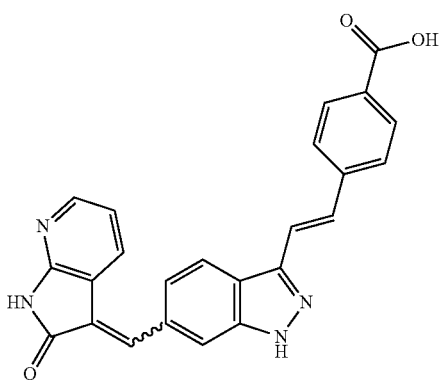 [SMILES: O=C1Nc2ncccc2C1=Cc1ccc2c(/C=C/c3ccc(C(=O)O)cc3)n[nH]c2c1]

The title compound (E/Z=10:3, 54 mg, 66%) was synthesized as a yellow solid according to the method described for Example A67 (oil temp 75° C., reflux 450 min) using 1H-pyrrolo[2,3-b]pyridin-2(3H)-one (26.8 mg, 0.2 mmol) and (E)-

4-(2-(6-formyl-1H-indazol-3-yl)vinyl)benzoic acid (58.4 mg, 0.2 mmol). ¹H NMR (400 MHz, DMSO-d6) δ 13.52 (s, 1H), 11.27 (s, 1H), 8.32 (d, J=8.8 Hz, 1H), 8.11 (t, J=5.2 Hz, 2H), 7.97-7.89 (m, 4H), 7.84 (d, J=8.4 Hz, 2H), 7.73 (d, J=16.8 Hz, 1H), 7.63 (d, J=16.4 Hz, 1H), 7.53 (d, J=8.4 Hz, 1H), 6.91 (dd, J=7.2 Hz, J=5.2 Hz, 1H); MS ESI 409.2 [M+H]⁺, calcd for [C$_{24}$H$_{16}$N$_4$O$_3$+H]⁺ 409.1.

Example A147

(E)-3-((3-(pyridin-3-ylethynyl)-1H-indazol-6-yl)methylene)indolin-2-one

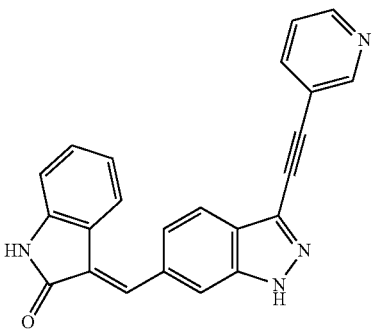 [SMILES: O=C1Nc2ccccc2/C1=C\c1ccc2c(C#Cc3cccnc3)n[nH]c2c1]

The title compound (30 mg, 83%) was synthesized as a yellow solid according to the method described for Example A67 (oil temp 75° C., reflux 2 h) using indolin-2-one (13.3 mg, 0.1 mmol) and 3-(pyridin-3-ylethynyl)-1H-indazole-6-carbaldehyde (24.7 mg, 0.1 mmol). ¹H NMR (400 MHz, DMSO-d6) δ 13.80 (s, 1H), 10.64 (s, 1H), 8.90 (s, 1H), 9.64 (d, J=4.4 Hz, 1H), 8.12 (d, J=8.0 Hz, 1H), 8.03 (d, J=8.0 Hz, 1H), 7.96 (s, 1H), 7.80 (s, 1H), 7.60-7.50 (m, 3H), 7.24 (t, J=7.8 Hz, 1H), 6.89 (d, J=7.6 Hz, 1H) 6.84 (t, J=7.8 Hz, 1H); MS ESI 363.1 [M+H]⁺, calcd for [C$_{23}$H$_{14}$N$_4$O+H]⁺ 363.1.

Example A148

(E)-5-methoxy-3-((3-(pyridin-3-ylethynyl)-1H-indazol-6-yl)methylene)indolin-2-one

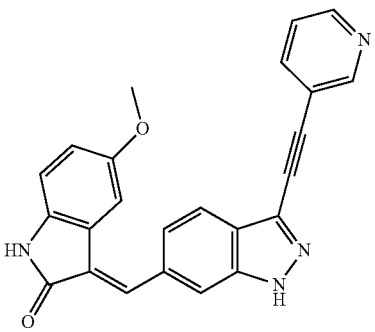 [SMILES: COc1ccc2c(c1)/C(=C\c1ccc3c(C#Cc4cccnc4)n[nH]c3c1)C(=O)N2]

The title compound (34 mg, 53%) was synthesized as a orange red solid according to the method described for Example A67 (oil temp 75° C., reflux 2 h) using 5-methoxylindolin-2-one (29 mg, 0.18 mmol) and 3-(pyridin-3-ylethynyl)-1H-indazole-6-carbaldehyde (40 mg, 0.163 mmol), followed by additional 90 min with additional 5-methoxylindolin-2-one (5.8 mg, 0.036 mmol). ¹H NMR (400 MHz, DMSO-d6) δ 13.80 (s, br, 1H, NH), 10.46 (s, 1H, NH), 8.90 (s, 1H), 8.63 (d, J=4.4 Hz, 1H), 8.12 (dt, J=8.0 Hz, 1H), 8.04 (d, J=8.4 Hz, 1H), 7.98 (s, 1H), 7.79 (s, 1H), 7.58 (d, J=8.4 Hz, 1H), 7.52 (dd, J=8.0 Hz, J=4.8 Hz, 1H), 7.13 (d, J=1.6 Hz, 1H), 6.86 (dd, J=8.0 Hz, J=2.4 Hz, 1H), 6.80 (d, J=8.4 Hz, 1H), 3.59 (s, 3H); MS ESI 393.2 [M+H]$^+$, calcd for [C$_{24}$H$_{16}$N$_4$O$_2$+H]$^+$ 393.1.

Example A149

(E and Z)-3-((3-((4-(dimethylamino)phenyl)ethynyl)-1H-indazol-6-yl)methylene)indolin-2-one

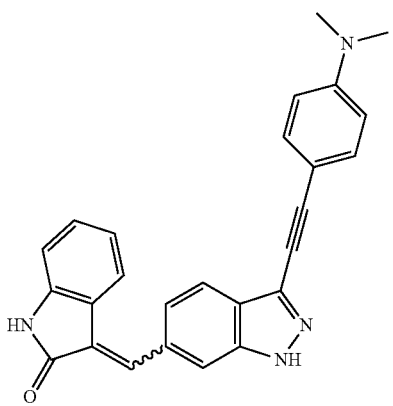 [SMILES: CN(C)c1ccc(C#Cc2n[nH]c3cc(C=C4C(=O)Nc5ccccc54)ccc23)cc1]

To a solution of 3-iodo-1H-indazole-6-carbaldehyde (136 mg, 0.5 mmol), Pd(PPh$_3$)$_2$Cl$_2$ (14 mg, 0.02 mmol) and CuI (7.6 mg, 0.04 mmol) in DMF (3 mL) was added Et$_3$N (5 mL), followed by 4-ethynyl-N,N-dimethylaniline (109 mg, 0.75 mmol). The resulting mixture was heated at 100° C. (oil temp.) for 45 min. After removal of Et$_3$N, the residue was loaded directly onto a silical gel column. Flash chromatography (eluent: hex to hex/ethyl acetate=5:1 to 1:1, to ethyl acetate) gave the crude 3-((4-(dimethylamino)phenyl)ethynyl)-1H-indole-6-carbaldehyde as greenish brown solid, which was redissolved in MeOH (20 mL). 2-Oxindole (53.2 mg, 0.4 mmol) and piperidine (10 drops) were added and the resulting mixture was refluxed (oil temp 75° C.) for 2 h. Additional 2-oxindole (13.3 mg) was added and the mixture was refluxed for another hour. After cooling to rt, the reaction mixture was suction filtered and the filter cake was rinsed with MeOH (10 mL). The filtrate was concentrated to about 0.5 mL and diluted with EtOAc (8 mL). Hexane (15 mL) was added and the resulting precipitate was collected by suction filtration to give the title compound (63 mg, 31% over 2 steps) as a golden solid (E:Z=9:1). $^1$H NMR (400 MHz, DMSO-d6) δ 13.40 (s, br, 1H), 10.64 (s, 1H), 7.93 (d, J=8.4 Hz, 1H), 7.91 (s, 1H), 7.79 (s, 1H), 7.57 (d, J=7.2 Hz, 1H), 7.53 (d, J=8.8 Hz, 1H), 7.47 (d, J=8.8 Hz, 2H), 7.24 (t, J=7.6 Hz, 1H), 6.89 (d, J=7.6 Hz, 1H), 6.84 (t, J=7.4 Hz, 1H), 6.75 (d, J=8.8 Hz, 2H), 2.97 (s, 6H); MS ESI 405.2 [M+H]$^+$, calcd for [C$_{26}$H$_{20}$N$_4$O+H]$^+$ 405.2.

Example A150

(E and Z)-5-bromo-3-((3-(6-(4-methylpiperazin-1-yl)pyridin-3-yl)-1H-indazol-6-yl)methylene)indolin-2-one

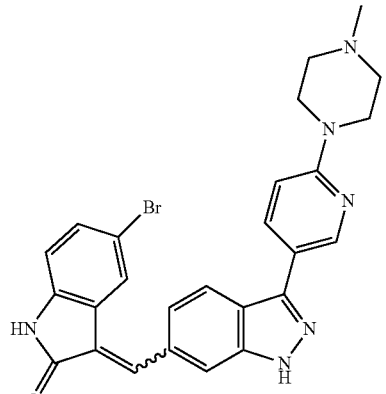

The title compound (E/Z=3:4, 65 mg, 88%) was synthesized as an orange solid according to the method described for Example A67 (oil temp 75° C., reflux 3 h) using 5-bromoindolin-2-one (32 mg, 0.15 mmol) and 3-(6-(4-methylpiperazin-1-yl)pyridin-3-yl)-1H-indazole-6-carbaldehyde (46 mg, 0.143 mmol). $^1$H NMR (400 MHz, DMSO-d6) E isomer: δ 13.41 (s, 1H), 10.80 (s, 1H), 8.76 (s, 1H), 8.20-8.03 (m, 2H), 7.91 (s, 1H), 7.87 (s, 1H), 7.67 (d, 1H), 7.48-7.40 (m, 2H), 7.99 (d, J=8.8 Hz, 1H), 6.86 (d, J=8.0 Hz, 1H), 3.57 (t, 4H), 2.41 (t, 4H), 2.23 (s, 3H); Z isomer: δ 13.48 (s, 1H), 10.84 (s, 1H), 9.02 (s, 1H), 8.76 (s, 1H), 8.20-8.03 (m, 5H), 7.38 (d, J=8.0 Hz, 1H), 6.98 (d, J=9.6 Hz, 1H), 6.80 (d, J=8.0 Hz, 1H), 3.57 (t, 4H), 2.41 (t, 4H), 2.23 (s, 3H); MS ESI 515.4 [M+H]$^+$, calcd for [C$_{26}$H$_{23}$BrN$_6$O+H]$^+$ 515.1.

Example A151

(E)-5-methoxy-3-((3-(2-(4-methylpiperazin-1-yl)pyrimidin-5-yl)-1H-indazol-6-yl)methylene)indolin-2-one

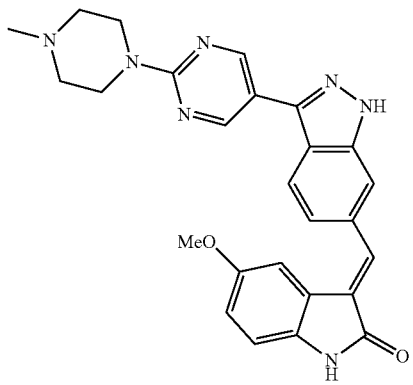 [SMILES: COc1ccc2c(c1)/C(=C\c1ccc3c(-c4cnc(N5CCN(C)CC5)nc4)n[nH]c3c1)C(=O)N2]

A. 3-(2-(4-methylpiperazin-1-yl)pyrimidin-5-yl)-1H-indazole-6-carbaldehyde

A mixture of 1H-indazole-6-carbaldehyde (50 mg, 0.18 mmol), 2-(4-Methylpiperazin-1-yl)pyrimidine-5-boronic acid pinacol ester (70 mg, 0.22 mmol), Pd(PPh$_3$)$_4$ (13 mg, 0.018 mmol) and 2M Na$_2$CO$_3$ (0.10 mL, 0.22 mmol) in DME/H$_2$O/EtOH (1.4 mL/0.4 mL/0.2 mL) was sealed and heated with stirring under microwave irradiation at 125° C. for 120 min. The crude reaction mixture was concentrated under reduced pressure and purified by flash chromatography on silica gel using MeOH (5% to 10%) in DCM as the eluent to provide the title compound as a pale yellow solid (47 mg, 80%). $^1$H NMR (400 MHz, CD$_3$OD) δ ppm 10.12 (s, 1H), 8.91 (s, 2H), 8.14 (s, 1H), 8.09 (d, J=8.6 Hz, 1H), 7.74 (d, J=8.4 Hz, 1H), 3.94 (t, J=4.5 Hz, 4H), 2.56 (t, J=4.9 Hz, 4H), 2.37 (s, 3H); MS ESI 323.1 (100) [M+H]$^+$, calcd for [C$_{17}$H$_{18}$N$_6$O+H]$^+$ 323.2.

B. (E)-5-methoxy-3-((3-(2-(4-methylpiperazin-1-yl)pyrimidin-5-yl)-1H-indazol-6-yl)methylene)indolin-2-one A round bottom flask was charged with 3-(2-(4-methylpiperazin-1-yl)pyrimidin-5-yl)-1H-indazole-6-carbaldehyde (26 mg, 0.80 mmol), 5-methoxyoxindole (13 mg, 0.80 mmol), piperidine (0.8 uL, 0.008 mmol) and MeOH (2 mL). The reaction was then heated to 60° C. for 4 hrs. An orange precipitate formed which was further precipitated by cooling to room temperature. The orange solid was then filtered and washed with MeOH (5 mL) giving 9.8 mg, 26% of the title compound. $^1$H NMR (400 MHz, d$_6$-DMSO) δ 13.46 (s, 1H), 10.44 (s, 1H), 8.97 (s, 2H), 8.18 (d, J=8.5 Hz, 1H), 7.94 (s, 1H), 7.78 (s, 1H), 7.48 (d, J=8.8 Hz, 1H), 7.20 (s, 1H), 6.85 (d, J=10.6 Hz, 1H), 6.80 (d, J=9.0 Hz, 1H), 3.82 (br t, 4H), 3.59 (s, 3H), 2.39 (br t, 4H), 2.23 (s, 3H); MS ESI 468.3 [M+H]$^+$, calcd for [C$_{26}$H$_{25}$N$_7$O$_2$+H]$^+$ 468.2.

Example A152

(E & Z)-3-((3-(2-(4-methylpiperazin-1-yl)pyrimidin-5-yl)-1H-indazol-6-yl)methylene)-5-(trifluoromethoxy)indolin-2-one

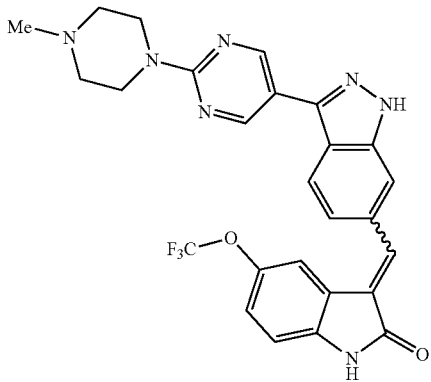 [SMILES: CN1CCN(c2ncc(-c3n[nH]c4cc(C=C5C(=O)Nc6ccc(OC(F)(F)F)cc65)ccc34)cn2)CC1]

According to the procedure for the synthesis of (E)-5-methoxy-3-((3-(2-(4-methylpiperazin-1-yl)pyrimidin-5-yl)-1H-indazol-6-yl)methylene)indolin-2-one, except substituting 5-trifluoromethoxyoxindole (14 mg, 0.065 mmol), the title compound was prepared as a yellow solid (17.6 mg, 52%). A mixture of (E)- and (Z)-isomers (83:17 by NMR) was obtained. $^1$H NMR (400 MHz, d$_6$-DMSO) 13.51 (s, 1H), 10.85 (s, 1H), 8.97 (s, 2H), 8.18 (d, J=8.2 Hz, 1H), 7.92 (s, 1H), 7.94 (s, 1H), 7.48-7.46 (m, 2H), 7.27 (d, J=9.2 Hz, 1H), 6.96 (d, J=8.4 Hz, 1H), 3.82 (br t, 4H), 2.39 (br t, 4H), 2.23 (s, 3H); MS ESI 522.3 [M+H]$^+$, calcd for [C$_{26}$H$_{22}$F$_3$N$_7$O$_2$+H]$^+$ 522.2.

Example A153

(E and Z)-3-((3-(3-(1H-tetrazol-5-yl)phenyl)-1H-indazol-6-yl)methylene)-5-methoxyindolin-2-one

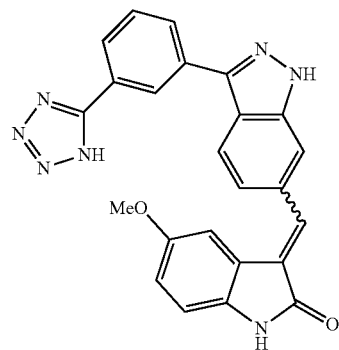 [SMILES: COc1ccc2c(c1)C(=Cc1ccc3c(-c4cccc(-c5nnn[nH]5)c4)n[nH]c3c1)C(=O)N2]

A. 3-(3-(1H-tetrazol-5-yl)phenyl)-1-((2-(trimethylsilyl)ethoxy)methyl)-1H-indazole-6-carbaldehyde A mixture of 3-iodo-1-((2-(trimethylsilyl)ethoxy)methyl)-1H-indazole-6-carbaldehyde (100 mg, 0.25 mmol), 3-(tetrazol-5-yl)phenylboronic acid (57 mg, 0.30 mmol), Pd(PPh$_3$)$_4$ (18 mg, 0.025 mmol) and 2M Na$_2$CO$_3$ (0.13 mL, 0.25 mmol) in DME/H$_2$O/EtOH (2.8 mL/0.8 mL/0.4 mL) was degassed by evacuation and blanketed with Ar. The reaction mixture was sealed and heated with stirring under microwave irradiation at 125° C. for 4 hours. The crude reaction mixture was concentrated under reduced pressure. The residue was purified by flash chromatography on silica gel using MeOH (5% to 10%) in DCM as the eluent to provide a white solid (40 mg, 38%). $^1$H NMR (400 MHz, CD$_3$OD) δ ppm 10.10 (s, 1H), 8.59 (s, 1H), 8.25 (s, 1H), 8.21 (d, J=8.5 Hz, 1H), 8.11 (d, J=7.9 Hz, 1H), 8.04 (d, J=8.3 Hz, 1H), 7.77 (d, J=8.4 Hz, 1H), 7.67 (t, J=7.8 Hz, 1H), 5.88 (s, 2H), 3.66 (t, J=8.1 Hz, 2H), 0.89 (t, J=8.0 Hz, 2H), −0.10 (s, 9H); MS ESI 421.1 (100) [M+H]$^+$, calcd for [C$_{21}$H$_{24}$N$_6$O$_2$Si+H]$^+$ 421.2.

B. (E and Z)-3-((3-(3-(1H-tetrazol-5-yl)phenyl)-1-((2-(trimethylsilyl)ethoxy)-methyl)-1H-indazol-6-yl)methylene)-5-methoxyindolin-2-one According to the procedure for the synthesis of (E)-5-methoxy-3-((3-(2-(4-methylpiperazin-1-yl)pyrimidin-5-yl)-1H-indazol-6-yl)methylene)indolin-2-one, except substituting 3-(4-(1H-tetrazol-5-yl)phenyl)-1-((2-(trimethylsilyl)ethoxy)-methyl)-1H-indazole-6-carbaldehyde (40 mg, 0.094 mmol), the title compound was prepared as an orange solid (39 mg, 73%). A mixture of (E)- and (Z)-isomers (77:23 by NMR) was obtained. $^1$H NMR (400 MHz, d$_6$-DMSO) δ 10.48 (s, 1H), 8.69 (s, 1H), 8.36 (d, J=8.7 Hz, 1H), 8.25 (d, J=7.8 Hz, 1H), 8.21 (s, 1H), 8.13 (d, J=8.2 Hz, 1H), 7.81-7.77 (m, 2H), 7.66 (d, J=8.6 Hz, 1H), 7.13 (d, J=2.5 Hz, 1H), 6.88-6.80 (m, 2H), 5.90 (s, 2H), 3.66 (t, J=8.3 Hz, 2H), 3.58 (s, 3H), 0.84 (t, J=8.1 Hz, 2H), −0.11 (s, 9H); MS ESI 566.3 [M+H]$^+$, calcd for [C$_{30}$H$_{31}$N$_7$O$_3$Si+H]$^+$ 566.2.

C. (E and Z)-3-((3-(3-(1H-tetrazol-5-yl)phenyl)-1H-indazol-6-yl)methylene)-5-methoxyindolin-2-one A round bottom flask was charged with (E and Z)-3-((3-(4-(1H-tetrazol-5-yl)phenyl)-1-((2-(trimethylsilyl)ethoxy)methyl)-1H-indazol-6-yl)methylene)-5-methoxyindolin-2-one (35 mg, 0.062 mmol), concentrated HCl (1 mL), and EtOH (2 mL). The reaction was then heated to 72° C. for 4 hrs. A red precipitate formed which was further precipitated by cooling to room temperature. The red solid was then filtered and washed with MeOH (2 mL) giving 15 mg, 56% of the title compound. A mixture of (E)- and (Z)-isomers (78:22 by NMR) was obtained. $^1$H NMR (400 MHz, d$_6$-DMSO) 13.71 (br. s, 1H), 10.47 (s, 1H), 8.70 (s, 1H), 8.34 (d, J=8.5 Hz, 1H), 8.27 (d, J=7.8 Hz, 1H), 8.11 (d, J=7.0 Hz, 1H), 8.01 (s, 1H), 7.81-7.76 (m, 2H), 7.59 (d, J=8.6 Hz, 1H), 7.21 (d, J=2.2 Hz, 1H), 6.87 (dd, J=8.5, 2.4 Hz, 1H), 6.81 (d, J=8.4 Hz, 1H), 3.60 (s, 3H); MS ESI 436.3 [M+H]$^+$, calcd for [C$_{24}$H$_{17}$N$_7$O$_2$+H]$^+$ 436.1.

Example A154

(E and Z)-3-((3-(4-(morpholinomethyl)styryl)-1H-indazol-6-yl)-methylene)indolin-2-one

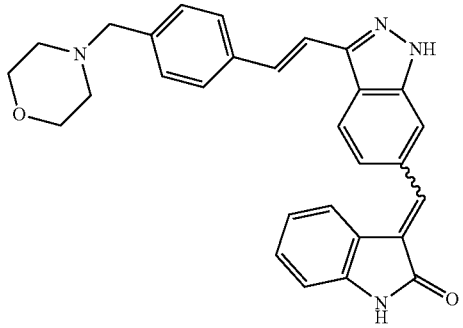 [SMILES: O=C1Nc2ccccc2C1=Cc1ccc2c(/C=C/c3ccc(CN4CCOCC4)cc3)n[nH]c2c1]

A. (E)-3-(4-(morpholinomethyl)styryl)-1-((2-(trimethylsilyl)ethoxy)methyl)-1H-indazole-6-carbaldehyde According to the method of example A57A, 3-iodo-1-((2-(trimethylsilyl)ethoxy)methyl)-1H-indazole-6-carbaldehyde (402 mg, 1 mmol) was reacted with 4-(4-vinylbenzyl)morpholine (304 mg, 1.5 mmol) to give the title compound upon silica gel purification (1:1 hexane/ethyl acetate) as a yellow solid (120 mg, 25%). MS ESI 478.3 [M+H]$^+$, calcd for [C$_{27}$H$_{35}$N$_3$O$_3$Si+H]$^+$ 478.2.

B. (E)-3-((3-(4-(morpholinomethyl)styryl)-1-((2-(trimethylsilyl)ethoxy)methyl)-1H-indazol-6-yl)methylene)indolin-2-one According to the method of A57B, oxindole (39 mg, 0.29 mmol) was reacted (E)-3-(4-(morpholinomethyl)styryl)-1-((2-(trimethylsilyl)ethoxy)methyl)-1H-indazole-6-carbaldehyde (116 mg, 0.25 mmol) to give the title compound as a yellow solid upon silica gel purification (95:5 CH$_2$Cl$_2$/MeOH) (95 mg, 64%). MS ESI 593.5 [M+H]$^+$, calcd for [C$_{35}$H$_{40}$N$_4$O$_3$Si+H]$^+$ 593.3

C. (E)-3-((3-(4-(morpholinomethyl)styryl)-1H-indazol-6-yl)methylene)indolin-2-one According to the method of A57C, (E)-3-((3-(4-(morpholinomethyl)styryl)-1-((2-(trimethylsilyl)ethoxy)methyl)-1H-indazol-6-yl)methylene)indolin-2-one (95 mg, 0.16 mmol) was treated with boron trifluoride etherate, followed by 2 N HCl to give the title compound as an orange solid (33 mg, 42%). $^1$H NMR (400 MHz, CD$_3$OD) δ 8.21 (d, J=8.4 Hz, 1H), 7.85 (d, J=6.0 Hz), 7.78 (d, J=8.2 Hz, 2H), 7.66 (d, J=7.6 Hz, 1H), 7.53-7.58 (m, 5H), 7.24 (t, J=7.7 Hz, 1H), 6.93 (d, J=7.6 Hz, 1H), 6.87 (td, J=6.7 Hz, 0.9 Hz, 1H), 4.39 (s, 2H), 4.05-4.09 (m, 2H), 3.72-3.78 (m, 2H), 3.40-3.43 (m, 2H), 3.21-3.26 (m, 2H); MS ESI 463.3 [M+H]$^+$, calcd for [C$_{29}$H$_{26}$N$_4$O$_2$+H]$^+$ 463.2.

Example A155

(E and Z)-3-((3-(6-(4-methylpiperazin-1-yl)pyridin-3-yl)-1H-indazol-5-yl)methylene)indolin-2-one

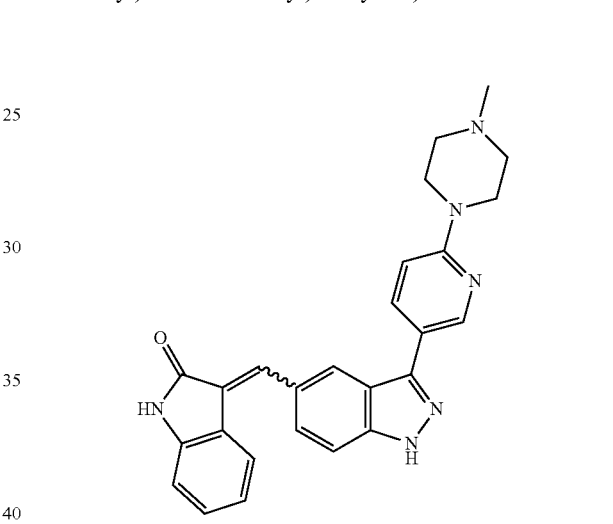

A. (E)-3-((3-iodo-1H-indazol-5-yl)methylene)indolin-2-one

Piperidine (0.01 mL, 0.1 mmol) was added to a suspension of oxindole (72 mg, 0.54 mmol) and 3-iodo-1H-indazole-5-carbaldehyde (146 mg, 0.54 mmol) in EtOH (10 mL). On heating to 75° C., the suspended solid dissolved, and a new precipitate formed. Heating was continued at 75° C. for 14 hrs. After the mixture was cooled to room temperature, suction filtration and rinsing with EtOH (4×2 mL) gave 3-((3-iodo-1H-indazol-5-yl)methylene)indolin-2-one (yellow solid, 131.9 mg, 63%). $^1$H NMR (400 MHz, d$^6$-DMSO) δ 13.75 (br. s, 1H), 10.61 (br. s, 1H), 7.84 (s, 1H), 7.77 (m, 2H), 7.69 (d, J=8.8 Hz, 1H), 7.60 (d, J=8.0 Hz, 1H), 7.23 (m, 1H), 6.88 (d, J=8.0 Hz, 1H), 6.84 (m, 1H); MS ESI 388.0 [M+H]$^+$, calcd for [C$_{16}$H$_{10}$IN$_3$O+H]$^+$ 388.0.

B. (E and Z)-3-((3-(6-(4-methylpiperazin-1-yl)pyridin-3-yl)-1H-indazol-5-yl)methylene)-indolin-2-one The reaction was carried out according to the method of example A93-A, except substituting 3-((3-iodo-1H-indazol-5-yl)methylene)indolin-2-one (29.9 mg, 0.077 mmol) and 1-methyl-4-(5-(4,4,5,5-tetramethyl-1,3,2-dioxa-borolan-2-yl)pyridin-2-yl)piperazine (26.9 mg, 0.089 mmol). Purification using chromatography (10 g silica SPE tube, Silicycle, 5-15% MeOH in dichloromethane) yielded a dark yellow product (14.7 mg) contaminated with a compound identified as 3-(6-(4-methylpiperazin-1-yl)pyridin-3-yl)-1H-indazole-5-carbaldehyde by LC-MS. Piperidine (0.2M in EtOH, 0.02 mL, 4 umol) was added to a solution of this crude material (10 mg) and oxindole (2.5 mg, 19 umol) in EtOH (1 mL) and the resulting mixture was heated at 80° C. for 14 h. After the solvent was evaporated, chromatography (5 g silica SPE tube, Silicycle, 5-15% MeOH in dichloromethane) yielded the title compound as a yellow solid (60:40 mixture of E:Z isomers, 3.6 mg, 15%,). $^1$H NMR (400 MHz, CD$_3$OD) δ ppm 9.47 (s, 0.4H), 8.87 (m, 0.4H), 8.75 (s, 0.6H), 8.38 (s, 0.6H), 8.29 (m, 0.8H), 8.17 (m, 0.6H), 7.92 (m, 1H), 7.80 (m, 0.6H), 7.76-7.67 (m, 2H), 7.59 (m, 0.4H), 7.23 (m, 1.2H), 7.09-7.01 (m, 1.6H), 6.96-6.87 (m, 1.8H), 3.80-3.72 (br m, 4H), 2.90-2.82 (br m, 4H), 2.58 (s, 1.2H), 2.55 (s, 1.8H); MS ESI 437.2 [M+H]$^+$, calcd for [C$_{26}$H$_{24}$N$_6$O+H]$^+$ 437.2.

Example B

PLK4 Inhibition Assay

Active PLK4 was purified from an *E. coli* expression system as an amino terminal GST fusion of residues 1-391 of human PLK4. The protein was purified from clarified cell extracts after induction at 15° C. overnight using glutathione sepharose, gel permeation chromatography, and ion exchange (Resource Q). The resulting protein was dephosphorylated with lambda phosphatase (NEB cat #P0753), and resolved from the phosphatase using gluthione sepharose. The dephosphorylated GST-PLK4 was stored in aliquots at −80° C. until use.

PLK4 activity was measured using an indirect ELISA detection system. Dephosphorylated GST-PLK4 (4 nM) was incubated in the presence of 15 μM ATP (Sigma cat #A7699), 50 mM HEPES-Na$^{2+}$ pH 7.4, 10 mM MgCl$_2$, 0.01% Brij 35 (Sigma cat #03-3170), in a 96 well microtitre plate pre-coated with MBP (Millipore cat #30-011). The reaction was allowed to proceed for 30 minutes, followed by 5 washes of the plate with Wash Buffer (50 mM TRIS-Cl pH 7.4 and 0.2% Tween 20), and incubation for 30 minutes with a 1:3000 dilution of primary antibody (Cell Signaling cat #9381). The plate was washed 5 times with Wash Buffer, incubated for 30 minutes in the presence of secondary antibody coupled to horse radish peroxidase (BioRad cat #1721019, 1:3000 concentration), washed an additional 5 times with Wash Buffer, and incubated in the presence of TMB substrate (Sigma cat #T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 μM) or at a variable inhibitor concentration (typically 50 μM to 0.1 μM in a 10 point dose response titration). Compounds were pre-incubated in the presence of enzyme for 15 minutes prior to addition of ATP and the activity remaining quantified using the above described activity assay. The % Inhibition of a compound was determined using the following formula; % Inhibition=100×(1−(experimental value−background value)/(high activity control−background value)). The IC$_{50}$ value was determined using a non-linear 4 point logistic curve fit (XLfit4, IDBS) with the formula; (A+(B/(1+((x/C)^D)))), where A=background value, B=range, C=inflection point, D=curve fit parameter.

Example C

PLK1 Inhibition Assay

PLK1 inhibition was determined using the Z-Lyte assay kit from Invitrogen (cat #PV3802). The assay was performed using the recommended manufacturer's instructions with 25 μM ATP and 8 nM PLK1 (Invitrogen cat #PV3501). The % inhibition values were determined according to the manufacturer's directions and IC$_{50}$ values were obtained using a non-linear 4 point logistic curve fit (XLfit4, IDBS)

Example D

PLK2 Inhibition Assay

PLK2 inhibition was determined using the Z-Lyte assay kit from Invitrogen (cat #PV3802). The assay was performed using the recommended manufacturer's instructions with 60 μM ATP and 133 nM PLK2 (Invitrogen cat #PV4204). The % inhibition values were determined according to the manufacturer's directions and IC$_{50}$ values were obtained using a non-linear 4 point logistic curve fit (XLfit4, IDBS)

Example E

Aurora A Inhibition Assay

Aurora A inhibition was determined using the Z-Lyte assay kit from Invitrogen. The assay was performed using the recommended manufacturer's instructions with 20 μM ATP and 12 nM Aurora A (Invitrogen cat #PV3612). The % inhibition values were determined according to the manufacturer's directions and IC$_{50}$ values were obtained using a non-linear 4 point logistic curve fit (XLfit4, IDBS)

Example F

Aurora B Inhibition Assay

Aurora B inhibition was determined using the Z-Lyte assay kit from Invitrogen. The assay was performed using the recommended manufacturer's instructions with 128 μM ATP and 28 nM Aurora B (Invitrogen cat #PV3970). The % inhibition values were determined according to the manufacturer's directions and IC$_{50}$ values were obtained using a non-linear 4 point logistic curve fit (XLfit4, IDBS)

In Tables 1 to 5 below, IC$_{50}$ values for PLK4, PLK1, PLK2, Aurora A and Aurora B Kinases are indicated as "A," "B," and "C," for those less than or equal to 5 μM; those greater than 5 μM and less than or equal to 50 μM; and those greater than 50 μM, respectively. The relative inhibition percentages at a dose of 10 μM are indicated as "X" and "Y" for those equal to or greater than 50% inhibition and those less than 50% inhibition, respectively. The relative inhibition percentages at a dose of 1 μM are indicated as "W" and "Z" for those equal to or greater than 50% inhibition and those less than 50% inhibition, respectively. As shown in Tables 1 and 2, numerous compounds of the invention are effective PLK inhibitors, in particular PLK4 inhibitors. In addition, a number of compounds of the invention, as shown in Tables 1-5, inhibit Aurora kinases, in particular Aurora B kinase, in addition to PLK4.

TABLE 1

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| Example A1 | A | B | B | Y | A |
| Example A33 | B | C | — | — | — |
| Example A4 | B | B | — | — | — |
| Example A2 | A | B | Y | A | A |
| Example A3 | A | B | X | Y | B |
| Example A7 | A | B | — | — | — |
| Example A23 | A | B | — | — | — |
| Example A27 | B | B | — | — | — |
| Example A21 | A | B | — | — | — |
| Example A24 | A | B | — | — | — |
| Example A14 | A | C | — | — | — |
| Example A17 | B | B | — | — | — |
| Example A29 | A | C | — | — | — |
| Example A39 | A | — | — | — | — |
| Example A19 | B | B | — | — | — |
| Example A28 | B | — | — | — | — |
| Example A40 | B | — | — | — | — |
| Example A5 | A | B | B | A | A |
| Example A34 | B | B | — | — | — |
| Example A9 | A | A | — | — | — |

TABLE 2

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| Example A11 | A | C | Y | X | X |
| Example A8 | B | B | — | — | — |
| Example A10 | A | A | — | — | — |
| Example A15 | A | B | — | — | — |
| Example A38 | A | B | Y | B | A |
| Example A25 | A | A | — | — | — |
| Example A20 | A | A | — | — | — |
| Example A26 | A | B | Y | A | Y |
| Example A12 | A | B | — | — | — |
| Example A37 | B | C | C | Y | A |
| Example A22 | A | B | X | X | B |
| Example A13 | A | B | Y | X | Y |
| Example A16 | A | B | A | A | A |
| Example A32 | A | B | Y | X | A |
| Example A35 | A | C | Y | Y | A |
| Example A36 | A | B | Y | C | A |
| Example A6 | A | B | A | A | A |
| Example A31 | A | C | B | Y | X |
| Example A18 | A | B | — | — | — |
| Example A30 | B | C | — | — | — |
| Example A41 | A | C | C | A | A |

TABLE 3

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| Example A42 | A | C | X | A | A |
| Example A43 | A | C | X | B | A |
| Example A44 | A | — | — | — | — |
| Example A45 | B | — | — | — | — |
| Example A46 | A | — | — | — | — |
| Example A47 | C | C | C | C | B |
| Example A48 | A | — | — | — | — |
| Example A49 | A | C | X | — | — |
| Example A50 | A | — | — | — | — |
| Example A51 | A | — | — | — | B |
| Example A52 | A | — | — | — | — |
| Example A53a | A | Y | X | — | A |
| Example A53b | A | — | — | — | — |
| Example A54a | A | C | X | X | A |
| Example A54b | A | — | — | — | — |
| Example A55 | A | — | — | — | A |
| Example A56 | A | C | A | A | A |
| Example A57 | A | Y | X | A | A |
| Example A58 | A | Y | Y | A | A |
| Example A59 | A | Y | Y | A | A |
| Example A60 | A | Y | Y | A | A |
| Example A61 | A | Y | Y | A | A |
| Example A62 | A | Y | Y | A | A |
| Example A63 | A | Y | Y | — | — |
| Example A64 | A | Y | Y | X | A |
| Example A65 | A | — | — | — | — |
| Example A66 | A | — | — | — | — |
| Example A67 | A | X | X | X | X |
| Example A68 | A | — | — | — | — |
| Example A69 | A | X | X | X | X |

TABLE 3

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| Example A70 | A | — | — | — | — |
| Example A71 | A | — | — | X | A |
| Example A72 | A | Y | Y | X | A |
| Example A73 | A | — | — | — | — |
| Example A74 | A | — | — | — | — |
| Example A75 | B | — | — | — | — |
| Example A76 | B | — | — | — | — |
| Example A77 | B | — | — | — | — |
| Example A78 | A | — | — | — | — |
| Example A79 | B | — | — | — | — |
| Example A80 | A | Y | Y | A | A |
| Example A81 | A | Y | Y | A | A |
| Example A82 | A | — | — | — | — |
| Example A83 | A | X | X | X | A |
| Example A84 | A | Y | Y | A | A |
| Example A85 | A | Y | Y | A | A |
| Example A86 | A | Y | Y | X | A |
| Example A87 | A | Y | Y | X | A |
| Example A88 | A | — | — | — | A |
| Example A89 | A | Y | Y | A | A |
| Example A90 | A | — | — | — | — |
| Example A91 | A | Y | Y | B | A |
| Example A92 | A | — | — | — | — |
| Example A93 | A | Y | Y | A | A |
| Example A94 | A | Y | Y | C | A |
| Example A95 | A | — | — | — | — |
| Example A96 | A | Y | — | X | A |
| Example A97 | A | — | — | — | A |
| Example A98 | A | — | — | — | — |
| Example A99 | A | — | — | — | — |

TABLE 4

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| Example A100 | A | Y | Y | X | A |
| Example A101 | A | Y | Y | X | A |
| Example A102 | A | — | — | — | — |

TABLE 4-continued

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| Example A103 | A | Y | Y | X | A |
| Example A104 | A | Y | Y | A | A |
| Example A105 | A | — | — | — | — |
| Example A106 | A | Y | — | X | A |
| Example A107 | A | X | Y | A | A |
| Example A108 | A | Y | Y | A | A |
| Example A109 | A | Y | Y | A | A |
| Example A110 | A | Y | Y | A | A |
| Example A111 | A | Y | Y | A | — |
| Example A112 | A | Y | Y | A | A |
| Example A113 | A | Y | Y | A | A |
| Example A114 | A | Y | Y | A | A |
| Example A115 | A | Y | Y | A | A |
| Example A116 | A | Y | Y | A | A |
| Example A117 | A | Y | Y | A | A |
| Example A118 | A | Y | Y | A | A |
| Example A119 | A | Y | Y | A | A |
| Example A120 | A | Y | Y | A | A |
| Example A121 | A | — | — | — | A |
| Example A122 | A | — | — | — | A |
| Example A123 | A | — | — | A | A |
| Example A124 | A | — | — | A | A |
| Example A125 | A | — | — | X | A |
| Example A126 | A | — | — | X | A |
| Example A127 | A | — | — | A | A |
| Example A128 | A | — | — | A | A |
| Example A129 | A | — | — | — | A |

TABLE 5

Inhibition Data of PLK4, Aurora A and Aurora B Kinases

| Compound # | PLK4 | Aurora A | Aurora B |
|---|---|---|---|
| Example A130 | A | — | A |
| Example A131 | A | — | — |
| Example A132 | A | A | A |
| Example A133 | A | — | — |
| Example A134 | A | — | — |
| Example A135 | A | — | — |
| Example A136a | A | — | A |
| Example A136b | A | A | A |
| Example A137 | A | A | A |
| Example A138 | A | A | A |
| Example A139 | A | A | A |
| Example A140 | A | A | A |
| Example A141 | A | W | A |
| Example A142 | A | W | A |
| Example A143 | A | W | A |
| Example A144 | A | A | A |
| Example A145 | A | A | A |
| Example A146 | A | A | A |
| Example A147 | A | — | — |
| Example A148 | A | — | A |
| Example A149 | A | B | A |
| Example A150 | A | — | — |
| Example A151 | A | B | A |
| Example A152 | A | — | B |
| Example A153 | A | A | A |
| Example A154 | A | — | — |
| Example A155 | A | — | — |

Example G

Kinase Selectivity Assays

The inhibitory activity of selected compounds of the invention was evaluated against a panel of 45 different kinase enzymes by CEREP, France. The assays were performed using standard HTRF assay methods as documented by CEREP against the human orthologues of Abl kinase, Akt1/PKBa, AMPKa, BMX kinase (Etk), Brk, CaMK2a, CaMK4, CDC2/CDK1 (cycB), CDK2 (cycE), CHK1, CHK2, c-Met kinase, CSK, EphB4 kinase, ERK1, ERK2 (P42mapk), FGFR2 kinase, FGFR4 kinase, FLT-1 kinase (VEGFR1), FLT-3 kinase, Fyn kinase, IGF1R kinase, IRK (InsR), JNK 2, KDR kinase (VEGFR2), Lck kinase, Lyn kinase, MAPKAPK2, MEK1/MAP2K1, p38a kinase, p38d kinase, p38g kinase, PDGFRb kinase, PDK1, PKA, PKCa, PKCb1, PKCb2, PKCg, Ret kinase, ROCK2, RSK2, Src kinase, Syk, and TRKA. The % Inhibition was determined by the formula; % Inhibition=100×(1−(experimental value−background value)/(high activity control−background value)), and tabulated below.

TABLE 6

Percent Inhibition Values For Examples A1, A5, A41, A60, A97 and A132 at 10 μM Concentration

| Kinase | Example A1 | Example A5 | Example A41 | Example A60 | Example A97 | Example A132 |
|---|---|---|---|---|---|---|
| Abl | 34 | 24 | 100 | 40 | 99 | 23 |
| Akt1/PKBalpha | −3 | −4 | −3 | −14 | −4 | −5 |
| AMPKalpha | 15 | 54 | 81 | 8 | 76 | 34 |
| BMX (Etk) | 15 | −3 | 53 | 18 | 9 | 0 |
| Brk | 5 | −6 | 40 | 4 | 7 | −2 |
| CaMK2alpha | 4 | −3 | 31 | −2 | 14 | 2 |
| CaMK4 | 3 | 26 | 27 | −15 | 2 | 6 |
| CDC2/CDK1 | 2 | 9 | 62 | 18 | 15 | 11 |
| CDK2 (cycE) | 10 | 16 | 8 | 5 | 3 | — |
| CHK1 | −6 | −2 | 7 | −1 | 3 | 0 |
| CHK2 | 14 | 2 | 22 | 6 | 4 | −4 |
| c-Met | −20 | 2 | 35 | 0 | 28 | 2 |
| CSK | 8 | 5 | 86 | 17 | 51 | 6 |
| EphB4 | 5 | −5 | 85 | −14 | 6 | −1 |
| ERK1 | 6 | 6 | 13 | 1 | 10 | 2 |
| ERK (P42mapk) | 3 | 0 | 14 | 2 | −9 | 15 |
| FGFR2 | 68 | 31 | 97 | 10 | 35 | 4 |
| FGFR4 | 18 | −4 | 38 | 6 | 30 | −30 |
| FLT-1 (VEGFR1) | 0 | 16 | 99 | 42 | 73 | 30 |
| FLT-3 | 93 | 76 | 100 | 10 | 100 | 32 |
| Fyn | 24 | 5 | 91 | 70 | 13 | 4 |
| IGF1R | 7 | −4 | 43 | 81 | 4 | 5 |
| IRK (InsR) | 13 | 12 | 34 | 6 | 9 | 2 |
| JNK 2 | 13 | 14 | 52 | 3 | 14 | 15 |
| KDR (VEGFR2) | 59 | 29 | 100 | 8 | 93 | 32 |
| Lck | 15 | 0 | 88 | 30 | 89 | 13 |
| Lyn | 14 | −5 | 98 | 88 | 85 | −2 |
| MAPKAPK2 | 6 | 0 | 0 | 19 | 4 | 6 |
| MEK1/MAP2K1 | 20 | 3 | 46 | 16 | 9 | −3 |
| p38alpha | −8 | 18 | 16 | 1 | 11 | 22 |
| p38delta | 0 | −8 | −5 | 3 | 13 | −2 |
| p38gamma | 14 | 5 | 2 | 10 | 1 | 12 |
| PDGFRbeta | 46 | 19 | 100 | 2 | 0 | 14 |
| PDK1 | −3 | 2 | 4 | 1 | 73 | 5 |
| PKA | 9 | −1 | −4 | 7 | 0 | −5 |
| PKCalpha | 9 | 0 | 2 | −1 | 9 | 7 |
| PKCbeta 1 | 1 | −5 | −2 | 0 | 2 | 1 |
| PKCbeta 2 | 0 | 2 | 12 | 4 | 37 | 4 |
| PKCgamma | 9 | −6 | 0 | 3 | 0 | 3 |
| Ret | 67 | 41 | 98 | 33 | 93 | 33 |
| ROCK2 | 1 | 3 | −3 | −1 | 22 | −20 |
| RSK2 | 4 | 1 | 38 | 0 | 37 | −4 |

TABLE 6-continued

Percent Inhibition Values For Examples A1, A5,
A41, A60, A97 and A132 at 10 μM Concentration % Inhibition at 10 μM Concentration

| Kinase | Example A1 | Example A5 | Example A41 | Example A60 | Example A97 | Example A132 |
|---|---|---|---|---|---|---|
| Src | 10 | −9 | 59 | 0 | 24 | 26 |
| Syk | −2 | −3 | 70 | — | 21 | −1 |
| TRKA | −13 | 60 | 99 | 75 | 93 | 43 |

Table 6 shows the percent inhibition values obtained for Examples A1, A5, A41, A60, A97 and A132 at 10 μM concentration. From this inhibition data it is apparent that certain kinases, e.g. Abl, FGFR2, FLT-1, FLT-3, KDR, Lyn, PDGFRbeta Ret and TRKA kinases are strongly inhibited (i.e. >95%) by compounds of the invention at 10 μM. For a number of compounds, IC50 values were estimated against kinases of interest based on Millipore protocols. Kinase assays at Millipore were performed using a radiolabelled phosphopeptide filter binding detection system, in duplicate, at each compound concentration. The ATP substrate concentration in the reactions was at the Km for each enzyme.

To allow for a more direct comparison of compound inhibition, an IC50 value was estimated from the inhibition determined at three compound concentrations. Several assumptions were made to allow this calculation using a 4 parameter non linear curve fit model, including full inhibition set at 100%, no inhibition set to 0%, and a curve fit parameter set at 1. The inflection point was reported as the estimated IC50.

In Table 7, $IC_{50}$ value estimates against the Receptor Tyrosine Kinase family (e.g. Abl, FGFR2, FLT-1, KDR, Lyn, and PDGFRβ) are indicated as "A," "B," and "C," for those less than or equal to 5 μM; those greater than 5 μM and less than or equal to 50 μM; and those greater than 50 μM, respectively. These activities may impart additional therapeutic benefit to these compounds.

TABLE 7

$IC_{50}$ value estimates against Abl,
FGFR2, FLT-1, KDR, Lyn, and PDGFRβ

| Compound # | Abl | FGFR1 | FLT-1 | KDR | Lyn | PDGFRβ | Ret | TrkA |
|---|---|---|---|---|---|---|---|---|
| Example A41 | A | A | A | A | A | A | A | A |
| Example A57 | A | A | A | A | A | A | A | A |
| Example A97 | A | A | A | A | B | B | A | A |
| Example 106 | A | A | A | A | A | A | A | A |

Example H

PLK3 Inhibition Assay

PLK3 inhibition was determined using the Z-Lyte assay kit from Invitrogen (cat #PV3802). The assay was performed using the recommended manufacturer's instructions with 100 μM ATP and 21 nM PLK3 (Invitrogen cat #PV3812). The % inhibition values were determined according to the manufacturer's directions and $IC_{50}$ values were obtained using a non-linear 4 point logistic curve fit (XLfit4, IDBS). The majority of the compounds of the invention tested in this assay inhibited PLK3 with IC50 values of less than or equal to 0.5 μM; certain compound examples including A2, A6, A26, A45, A49, A125, A127, A148, A149, A152 and A153 exhibited PLK3 IC50 values of greater than 0.5 μM.

Example I

Cancer Cell Line Data of Compounds of the Invention

Breast cancer cells (MCF-7, MDA-MB-468, HCC1954), colon cancer cells (SW620) and lung cancer cells (A549), together with human mammary epithelial primary cells (HMEC), were seeded (1000 to 4000 per 80 μl per well depending on the cell growth rate) into 96 well plates, 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 μM. Aliquots (20 μl) from each concentration were overlaid to 80 μl of the pre-seeded cells in the 96 well plates to make final concentrations of 10 nM to 50 μM. The cells were cultured for 5 days before the Sulforhodamine B assay (SRB) was performed to determine the compound's cell growth inhibition activity.

Sulforhodamine B (purchased from Sigma, Oakville, ON, Canada) is a water-soluble dye that binds to the basic amino acids of the cellular proteins. Thus, colorimetric measurement of the bound dye provides an estimate of the total protein mass that is related to the cell number. the cells are fixed in situ by gently aspirating off the culture media and adding 50 μl ice cold 10% Tri-chloroacetic Acid (TCA) per well and incubate at 4° C. for 30-60 min, The plates are washed with water five times and allowed to air dry for 5 min. Addition of 50 μl 0.4% (w/v) SRB solution in 1% (v/v) acetic acid to each well and incubatation for 30 min at RT completes the staining reaction. Following staining, plates are washed four times with 1% acetic acid to remove unbound dye and then allowed to air dry for 5 min. The stain is solubilized with 100 μl of 10 mM Tris pH10.5 per well. Absorbance is read at 570 nm.

The percentage (%) of relative growth inhibition was calculated by comparing to DMSO treated only cells (100%). $GI_{50}$'s were determined for compounds with cytotoxic activity. The $GI_{50}$ was calculated using GraphPad PRISM software (GraphPad Software, Inc., San Diego, Calif., USA). $GI_{50}$ (growth inhibition) is the compound concentration that causes 50% inhibition of cell growth.

In Table 8 below, $GI_{50}$ value ranges for several compound examples against a luminal breast cancer cell line (MCF-7), two basal breast cancer cell line (MDA-MB-468, HCC1954), a lung cancer cell line (A549), a colon cancer cell line (SW-620) and primary breast cells (HMEC) are given. The example compounds demonstrated varying growth inhibition/cell killing activity against cancer cells of luminal breast cancer and basal breast cancer cell, lung cancer and colon cancer. In general, these compounds showed less activity against normal cells as exemplified by HMEC. The $GI_{50}$ ranges are indicated as "A," "B," "C," and "D," for values less than or equal to 5 μM; those greater than 5 μM and less than or equal to 20 μM; those greater than 20 μM and less than or equal to 50 μM; and those greater than 50 μM, respectively.

TABLE 8

Cell Growth Inhibition Data

| Example # | MCF-7 | MDA-MB-468 | HCC-1954 | SW-620 | A-549 | HMEC |
|---|---|---|---|---|---|---|
| A2 | D | B | — | — | — | — |
| A4 | B | B | — | — | — | — |
| A6 | B | B | — | — | — | — |
| A10 | C | C | — | — | — | — |
| A19 | B | A | — | — | — | — |
| A32 | B | B | — | — | — | — |
| A31 | A | A | — | — | — | — |
| A41 | A | A | C | B | B | D |
| A59 | A | A | B | A | B | — |
| A84 | A | A | B | A | D | D |
| A91 | A | A | A | A | — | B |
| A96 | A | A | A | A | A | — |
| A97 | A | A | A | A | A | C |
| A103 | A | A | B | A | B | D |
| A106 | A | A | A | A | A | B |
| A108 | A | A | A | A | A | A |
| A109 | A | A | D | A | A | D |
| A127 | A | A | A | A | B | — |
| A147 | C | B | D | C | D | — |
| A150 | A | A | A | A | A | — |

In addition to the cell lines tested as described above, selected compounds have been assayed against an extended panel. These include: breast cancer cell lines (T47 D, MDA-MB-231, HS578T, BT474, SKBR3, HCC1954), a lung cancer cell line (H358), brain cancer cell lines (A172, Hs683, SK-N-SH), Colon cancer cell lines (Colo 205, CT-15, HCT116+/−, HCT116+/+), ovarian cancer cell lines (OVCAR-3, SK-OV-3, SW 626), a melanoma cell line (518A2), a prostate cancer cell line (PC-3) and an immortalized breast cell line (184A1). The sulforhodamine B assay (SRB) described above was use to assay test compounds against the extended panel (Table 9). The GI$_{50}$ ranges are indicated as "A," "B," "C," and "D," for values less than or equal to 5 μM; those greater than 5 μM and less than or equal to 20 μM; those greater than 20 μM and less than or equal to 50 μM; and those greater than 50 μM, respectively.

TABLE 9

Cell Growth Inhibition Data

| Cell line | A41 | A97 | A109 | A108 | A132 |
|---|---|---|---|---|---|
| T47 D | A | A | A | A | A |
| MDA-MB-231 | B | A | A | A | A |
| HS578T | B | A | A | A | A |
| BT474 | D | A | B | A | A |
| SKBR3 | A | A | D | A | A |
| HCC1954 | A | A | D | A | A |
| H358 | A | — | A | A | A |
| A172 | A | — | A | A | A |
| Hs683 | A | — | A | A | A |
| SK-N-SH | A | — | A | A | A |
| Colo 205 | A | A | A | A | A |
| HCT-15 | A | — | A | A | A |
| HCT116+/− | D | A | A | A | A |
| HCT116+/+ | D | A | A | A | A |
| OVCAR-3 | D | — | A | A | A |
| SK-OV-3 | D | — | B | A | A |
| SW 626 | D | — | B | A | A |
| 518A2 | A | — | A | A | A |

TABLE 9-continued

Cell Growth Inhibition Data

| Cell line | A41 | A97 | A109 | A108 | A132 |
|---|---|---|---|---|---|
| PC-3 | C | — | A | A | A |
| 184A1 | C | A | A | A | A |

Some compounds of the invention, although inhibiting the isolated PLK-4 enzyme activity, generally failed to inhibit the growth of Breast Cancer cell lines, i.e., Compound examples A7, A9, A70 and A111 had GI$_{50}$ values >50 μM on the MCF-7, MDA-MB-468 and T47D Breast cancer cell lines.

Example J

In Vitro Angiogenesis Assay

Compounds of the invention had micromolar and submicromolar activity against Receptor Tyrosine Kinases (RTKs) such as FGFR2, VEGFR1, VEGFR2 and PDGFRbeta. Activity against these RTKs can result in antiangiogenic activity which is associated with slowed tumor growth and/or tumor regression. To measure the effects of these compounds they were tested in an angiogenisis assay as described below. Note that compound Example A57 showed anti-agiogenic effects at micromolar concentrations (FIG. 1).

HUV-EC-C cells were obtained from the American Type Culture Collection (ATCC, CRL-1730), and were used at early passage for the assay. The in vitro Angiogenesis Assay Kit (Chemicon) was used according to the manufacturer's recommendation. An ice-cold mixture of ECMatrix was transferred into a precooled 96-well plate. After the matrix solution had solidified (>1 hr incubation at 37° C.), 8,000 cells were mixed with the appropriate inhibitor concentration (in 100 microliters EGM-2) and plated into each well. After incubation at 37° C. for 4 hr, tube formation was inspected. Two methods, pattern recognition and branch point counting, were used to quantify the progression of angiogenesis and expressed as a percentage of the control tube count (FIG. 1).

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by a structural formula selected from:

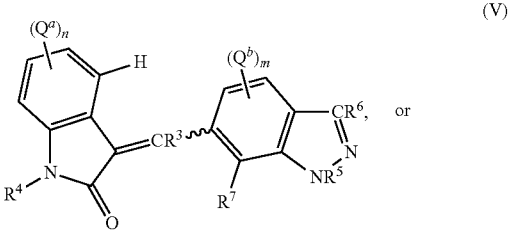

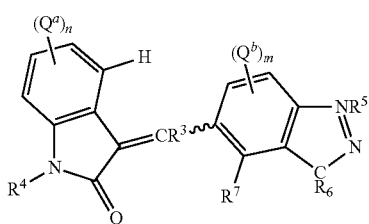

(VI)

or a pharmaceutically acceptable salt thereof, wherein:
  each of n and m independently is 0, 1 or 2;
  one of $Q^a$ and $Q^b$ is halogen, —$NO_2$, —CN, $Ak^1$, $Ar^1$, ($C_{1-10}$ alkylene)-$Ar^1$, ($C_{1-10}$ alkenylene)-$Ar^1$ or —X—$R^1$; and the other of $Q^a$ and $Q^b$ is halogen, hydroxy, nitro, cyano, amino, methyl, methoxy, halomethyl or halomethoxy;
  wherein X is —C(O)O—, —C(O)—, —C(S)—, —OC(O)—, —C(O)N($R^2$)—, —C(S)N($R^2$)—, —OC(O)N($R^2$)—, —S(O)—, —S(O)$_2$—, —$SO_3$—, —$SO_2NR^2$—, —O—, —S—, —$NR^2$—, —$NR^2$C(O)—, —$NR^2$S(O)—, —$NR^2$C(O)O—, —$NR^2$C(O)ONR$^2$—, —N($R^2$)C(O)N$R^2$—, —$NR^2SO_2NR^2$— or —$NR^2SO_2$—;
  each $Ak^1$ independently is a $C_{1-10}$ aliphatic group optionally substituted with one or more substituents selected from the group consisting halogen, nitro, cyano, —N($R^{21}$)$_2$, —C(O)N($R^{21}$)$_2$, —$NR^{21}$C(O)$R^{21}$, —$SO_2R^{22}$, —$SO_2N(R^{21})_2$, —$NR^{21}SO_2R^{22}$, —$NR^{21}C(O)OR^{21}$, —OC(O)N($R^{21}$)$_2$, —$NR^{21}C(O)N(R^{21})_2$, —NRC(O)ON(R)$_2$, —$NR^{21}SO_2N(R^{21})_2$, —$OR^{21}$, —$SR^{21}$, $C_{1-10}$ haloalkoxy, —C(O)$R^{21}$, —C(O)O$R^{21}$ and —OC(O)$R^{21}$;
  each $Ak^{10}$ independently is a $C_{1-10}$ alkyl group optionally substituted with one or more substituents selected from the group consisting halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl;
  each $Ar^1$ independently is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, —N($R^{21}$)$_2$, —C(O)N($R^{21}$)$_2$, —$NR^{21}C(O)R^{21}$, —$SO_2R^{22}$, —$SO_2N(R^{21})_2$, —$NR^{21}SO_2R^{22}$, —$NR^{21}C(O)N(R^{21})_2$, —NRC(O)ON(R)$_2$, —$NR^{21}SO_2N(R^{21})_2$, —$OR^{21}$, —$SR^{21}$, $C_{1-10}$ haloalkoxy, —C(O)$R^{21}$, —C(O)O$R^{21}$, —OC(O)$R^{21}$, phenyl and 5-6 membered heteroaryl, wherein said phenyl and said 5-6 membered heteroaryl 5 are each independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;
  each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;
  each $R^1$ independently is:
  i) hydrogen;
  ii) a $C_{6-14}$ aryl group or a 5-14 membered heteroaryl group, each optionally and independently substituted with one or more substituents selected from the group consisting of halogen, —$NO_2$, —CN, —NCS, $Ak^{10}$, ($C_{1-10}$ alkylene)-$Ar^{10}$, ($C_{2-10}$ alkenylene)-$Ar^{10}$, —C(O)O$R^{10}$, —C(O)$R^{10}$, —C(S)$R^{10}$, —OC(O)$R^{10}$, —C(O)N($R^{11}$)$_2$, —C(S)N($R^{11}$)$_2$, —OC(O)N($R^{11}$)$_2$, —S(O)$R^{12}$, —S(O)$_2R^{12}$, —$SO_3R^{12}$, —$SO_2N(R^{11})_2$, —$SR^{10}$, —N($R^{11}$)$_2$, —$NR^{11}C(O)R^{10}$, —$NR^{11}S(O)R^{12}$, —$NR^{11}C(O)OR^{12}$, —N($R^{11}$)C(O)N($R^{11}$)$_2$, —$NR^{11}SO_2N(R^{11})_2$ and —$NR^{11}SO_2R^{12}$; or
  iii) a $C_{1-10}$ aliphatic group optionally substituted with one or more substituents selected from the group consisting of halogen, —$NO_2$—CN, —NCS, $Ar^{10}$, —C(O)O$R^{10}$, —C(O)$R^{10}$, —C(S)$R^{10}$, —OC(O)$R^{10}$, —C(O)N($R^{11}$)$_2$, —C(S)N($R^{11}$)$_2$, —OC(O)N($R^{11}$)$_2$, —S(O)$R^{12}$, —S(O)$_2R^{12}$, —$SO_3R^{12}$, —$SO_2N(R^{11})_2$, —$SR^{10}$, —N($R^{11}$)$_2$, —$NR^{11}C(O)R^{10}$, —$NR^{11}S(O)R^{12}$, —$NR^{11}C(O)OR^{12}$, —N($R^{11}$)C(O)N($R^{11}$)$_2$, —$NR^{11}SO_2N(R^{11})_2$ and —$NR^{11}SO_2R^{12}$,
  provided that $R^1$ is other than hydrogen when X is —S(O)—, —S(O)$_2$—, —$SO_3$—, —$NR^2S(O)$— or —$NR^2SO_2$—;
  each $R^2$ independently is $R^1$, —CO$_2R^1$, —$SO_2R^1$ or —C(O)$R^1$, or, taken together with $NR^1$, forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl;
  $R^3$ is —H, C1-C6 alkyl or C1-C6 haloalkyl;
  each of $R^4$ and $R^5$ independently is —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl), wherein each said phenyl in the groups represented by $R^4$ and $R^5$ independently is optionally substituted with one or more substituents selected from the group consisting of halogen, hydroxy, nitro, cyano, amino, C1-C6 alkyl, C1-C6 haloalkyl, C1-C6 alkoxy and C1-C6 haloalkoxy, and wherein each said alkyl in the groups represented by $R^4$ and $R^5$ independently is optionally substituted with one or more substituents selected from the group consisting of halogen, hydroxy, nitro, cyano, amino, C1-C6 alkoxy, C1-C6 haloalkoxy and phenyl;
  each $R^6$ independently is hydrogen, halogen, nitro, cyano, R', —OR, —SR or —N(R)$_2$;
  $R^7$ is —H, F, Cl or methyl;

each $R^{10}$ independently is:
i) hydrogen;
ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or
iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

each $R^{11}$ independently is $R^{10}$, —$CO_2R^{10}$, —$SO_2R^{10}$ or —$C(O)R^{10}$, or —$N(R^{11})_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ independently is:
i) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or
ii) a $C_{1-10}$ alkyl group optionally substituted with one or more substituents selected from the group consisting halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy, and wherein the alkyl group represented by $R^{21}$ is optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy; or $N(R^{21})_2$ forms a non-aromatic heterocyclic group optionally substituted with one or more substituents selected from the group consisting of halogen, hydroxy, nitro, cyano, =O, C1-C3 alkyl, C1-C3 haloalkyl, C1-C3 alkoxy, C1-C3 haloalkoxy and amino;

each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy, and wherein the alkyl group represented by $R^{22}$ is optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

each R independently is hydrogen, optionally substituted $C_{1-6}$ alkyl, optionally substituted $C_{2-6}$ alkenyl, optionally substituted phenyl or optionally substituted 5-6 membered heteroaryl; or $N(R)_2$ taken together is a non-aromatic heterocyclic group optionally substituted with one or more substituents selected from the group consisting of halogen, hydroxy, nitro, cyano, =O, C1-C3 alkyl, C1-C3 haloalkyl, C1-C3 alkoxy, C1-C3 haloalkoxy and amino; and each R' independently is optionally substituted $C_{1-6}$ alkyl, optionally substituted $C_{2-6}$ alkenyl, optionally substituted phenyl or optionally substituted 5-6 membered heteroaryl;

the optionally substituted 5-6 membered heteroaryl group represented by each of R and R' independently is an optionally substituted furanyl group, an optionally substituted imidazolyl group, an optionally substituted isoxazolyl group, an optionally substituted oxadiazolyl group, an optionally substituted oxazolyl, an optionally substituted pyrazolyl group, an optionally substituted pyrrolyl group, an optionally substituted pyridyl group, an optionally substituted pyrimidinyl group, an optionally substituted pyridazinyl group, an optionally substituted thiazolyl group, an optionally substituted triazolyl group, an optionally substituted tetrazolyl group or an optionally substituted thienyl group; and the 5-6 membered heteroaryl group in the substituents for the groups represented by each of R and R' independently is a furanyl group, an imidazolyl group, an isoxazolyl group, an oxadiazolyl group, an oxazolyl, a pyrazolyl group, a pyrrolyl group, a pyridyl group, a pyrimidinyl group, a pyridazinyl group, a thiazolyl group, a triazolyl group, a tetrazolyl group or a thienyl group.

2. The compound of claim 1, wherein R' is —$CH_2$— (optionally-substituted phenyl), —$CH_2$(optionally-substituted 5-6 membered heteroaryl), —$CH_2$—$CH_2$— (optionally-substituted phenyl), —$CH_2$—$CH_2$— (optionally-substituted 5-6 membered heteroaryl), —CH=CH-(optionally-substituted phenyl) or —CH=CH-(optionally-substituted 5-6 membered heteroaryl).

3. The compound of claim 2, wherein R' is —CH$_2$— (optionally-substituted phenyl), —CH$_2$— (optionally-substituted pyridyl), —CH$_2$—CH$_2$— (optionally-substituted phenyl), —CH$_2$—CH$_2$— (optionally-substituted pyridyl), —CH=CH-(optionally-substituted phenyl) or —CH=CH-(optionally-substituted pyridyl); and each of R$^4$ and R$^5$ is —H, C1-C6 alkyl, phenyl, —C(O)(C1-C6 alkyl), —C(O)(phenyl), —C(O)O(C1-C6 alkyl), —C(O)O(phenyl), —S(O)$_2$(C1-C6 alkyl) or —S(O)$_2$(phenyl).

4. The compound of claim 1, wherein R$^6$ is an optionally substituted phenyl group, an optionally substituted pyridyl group, an optionally substituted pyrrolyl group, an optionally substituted pyrazolyl, an optionally substituted thiazolyl, an optionally substituted pyrimidinyl, or an optionally substituted thienyl; and the group represented by R$^6$ is independently and optionally substituted with one or more substituents selected from the group consisting of: halogen, hydroxy, nitro, cyano, amino, C1-C6 alkyl, C1-C6 haloalkyl, C1-C6 alkoxy and C1-C6 haloalkoxy.

5. The compound of claim 1, wherein:
one of Q$^a$ and Q$^b$ of each of Structural Formulas (V)-(VI) independently is halogen, hydroxy, cyano, nitro, C1-C6 alkyl, C1-C6 haloalkyl, —C(O)(C1-C6 alkyl), —C(O)NH$_2$, —C(O)NH(C1-C6 alkyl), —C(O)N(C1-C6 alkyl)$_2$, —SO$_2$NH$_2$, —SO$_2$NH(C1-C6 alkyl), —SO$_2$N(C1-C6 alkyl)$_2$, —OH, —O(C1-C6 alkyl), —O(C1-C6 haloalkyl), —SH, —S(C1-C6 alkyl), —S(C1-C6 haloalkyl), —NH$_2$, —NH(C1-C6 alkyl), —N(C1-C6 alkyl)$_2$, —NHC(O)(C1-C6 alkyl), —NHC(O)O(C1-C6 alkyl), —NHC(O)NH$_2$, —NHC(O)NH(C1-C6 alkyl), —NHC(O)N(C1-C6 alkyl)$_2$, —NHC(O)ONH$_2$, —NHC(O)ONH(C1-C6 alkyl), —NHC(O)ON(C1-C6 alkyl)$_2$, —NHSO$_2$NH$_2$, —NHSO$_2$NH(C1-C6 alkyl), —NHSO$_2$N(C1-C6 alkyl)$_2$ or —NHSO$_2$(C1-C6 alkyl), and the other Q$^a$ and Q$^b$ of each of Structural Formulas (V)-(VI) independently is halogen, hydroxy, nitro, cyano, amino, methyl, methoxy, halomethyl or halomethoxy.

6. The compound of claim 1, wherein:
one of Q$^a$ and Q$^b$ of each of Structural Formulas (V)-(VI) independently is halogen, hydroxy, cyano, nitro, Ph, —CH$_2$Ph, —C(O)Ph, —C(O)NH(Ph), —C(O)N(C1-C6 alkyl)(Ph), —SO$_2$NH(Ph), —SO$_2$N(C1-C6 alkyl)(Ph), —O(Ph), —S(Ph), —NH(Ph), —N(C1-C6 alkyl)(Ph), —NHC(O)(Ph), —NHC(O)O(Ph), —NHC(O)NH(Ph), —NHC(O)N(C1-C6 alkyl)(Ph), —NHC(O)ONH(Ph), —NHC(O)ON(C1-C6 alkyl)(Ph), —NHSO$_2$NH(Ph), —NHSO$_2$N(C1-C6 alkyl)(Ph) or —NHSO$_2$(Ph), wherein each Ph is a phenyl group independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy, and the other Q$^a$ and Q$^b$ of each of Structural Formulas (V)-(VI) independently is halogen, hydroxy, nitro, cyano, amino, methyl, methoxy, halomethyl or halomethoxy.

7. A compound represented by a structural formula selected from:

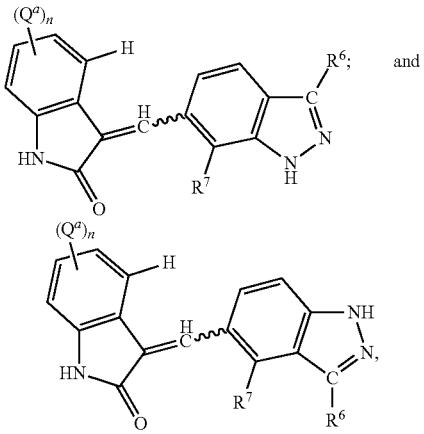

or a pharmaceutically acceptable salt thereof, wherein:
each of n independently is 0 or 1;
each of Q$^a$ independently is selected from the group consisting of halogen, —X—R$^1$, —NO$_2$, —CN, —NCS, Ak$^1$, Ar$^1$, (C$_{1-10}$ alkylene)-Ar$^1$, (C$_{2-10}$ alkenylene)-Ar$^1$,
wherein X is —C(O)O—, —C(O)—, —C(S)—, —OC(O)—, —C(O)N(R$^2$)—, —C(S)N(R$^2$)—, —OC(O)N(R$^2$)—, —S(O)—, —S(O)$_2$—, —SO$_3$—, —SO$_2$NR$^2$—, —O—, —S—, —NR$^2$—, —NR$^2$C(O)—, —NR$^2$S(O)—, —NR$^2$C(O)O—, —NR$^2$C(O)ONR$^2$—, —N(R$^2$)C(O)NR$^2$—, —NR$^2$SO$_2$NR$^2$— or —NR$^2$SO$_2$—:
each R$^1$ independently is:
i) hydrogen;
ii) a C$_{6-14}$ aryl group or a 5-14 membered heteroaryl group, each optionally and independently substituted with one or more substituents selected from the group consisting of halogen, —NO$_2$—CN, —NCS, Ak$^{10}$, (C$_{1-10}$ alkylene)-Ar$^{10}$, (C$_{2-10}$ alkenylene)-Ar$^{10}$, —C(O)OR$^{10}$, —C(O)R$^{10}$, —C(S)R$^{10}$, —OC(O)R$^{10}$, —C(O)N(R$^{11}$), —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R)C(O)N(R$^{11}$)$_2$, —NR$^{11}$SO$_2$N(R$^{11}$)$_2$ and —NR$^{11}$SO$_2$R$^{12}$; or
iii) a C$_{1-10}$ aliphatic group optionally substituted with one or more substituents selected from the group consisting of halogen, —NO$_2$, —CN, —NCS, Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$NR$^{11}$)$_2$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$,
provided that R$^1$ is other than hydrogen when X is —S(O)—, —S(O)$_2$—, —SO$_3$—, —NR$^2$S(O)— or —NR$^2$SO$_2$—; and
each R$^2$ independently is R$^1$, —CO$_2$R$^1$, —SO$_2$R$^1$ or —C(O)R$^1$, or, taken together with NR$^1$, forms a non-aromatic heterocyclic group optionally substituted with one or more substituents selected from the group consisting of =O, =S, halogen, nitro, cyano, hydroxy, C$_{1-6}$ alkyl, C$_{1-6}$ haloalkyl, C$_{1-6}$ hydroxyalkyl, amino, C$_{1-6}$ alkylamino, C$_{1-6}$ dialkylamino, C$_{1-6}$ aminoalkyl, (C$_{1-6}$ alkylamino)C$_{1-16}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, C$_{1-6}$ alkoxy, C$_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl;

each $R^{10}$ independently is:
i) hydrogen;
ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, $(C_{1-10}$ haloalkoxy$)C_{1-10}$ alkyl, $(C_{1-10}$ alkoxy$)C_{1-10}$ alkyl, $C_{1-10}$ hydroxyalkyl, $C_{1-10}$ aminoalkyl, $(C_{1-10}$ alkylamino$)C_{1-10}$ alkyl, $(C_{1-10}$ dialkylamino$)C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or
iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

each $R^{11}$ independently is $R^{10}$, —CO$_2R^{10}$, —SO$_2R^{10}$ or —C(O)R$^{10}$, or
—N(R$^{11}$)$_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, $(C_{1-6}$ alkylamino$)C_{1-6}$ alkyl, $(C_{1-6}$ dialkylamino$)C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ independently is:
i) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, $(C_{1-10}$ haloalkoxy$)C_{1-10}$ alkyl, $(C_{1-10}$ alkoxy$)C_{1-10}$ alkyl, $C_{1-10}$ hydroxyalkyl, $C_{1-10}$ aminoalkyl, $(C_{1-10}$ alkylamino$)C_{1-10}$ alkyl, $(C_{1-10}$ dialkylamino$)C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or
ii) a $C_{1-10}$ alkyl group optionally substituted with one or more substituents selected from the group consisting halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

each Ak$^1$ independently is a $C_{1-10}$ aliphatic group optionally substituted with one or more substituents selected from the group consisting halogen, nitro, cyano, —N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)OR$^{21}$, —OC(O)N(R$^{21}$)$_2$, —NR$^{21}$C(O)N(R$^{21}$)$_2$, —NRC(O)ON(R)$_2$, —NR$^{21}$SO$_2$N(R$^{21}$)$_2$, —OR$^{21}$, —SR$^{21}$, $C_{1-10}$ haloalkoxy, —C(O)R$^{21}$, —C(O)OR$^{21}$ and —OC(O)R$^{21}$;

each Ak$^{10}$ independently is a $C_{1-10}$ alkyl group optionally substituted with one or more substituents selected from the group consisting halogen, nitro, cyano, —OH, —SH, —O(C$_{1-6}$ alkyl), —S(C$_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl;

each Ar$^1$ independently is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, $(C_{1-10}$ haloalkoxy$)C_{1-10}$ alkyl, $(C_{1-10}$ alkoxy$)C_{1-10}$ alkyl, $C_{1-10}$ hydroxyalkyl, $C_{1-10}$ aminoalkyl, $(C_{1-10}$ alkylamino$)C_{1-10}$ alkyl, $(C_{1-10}$ dialkylamino$)C_{1-10}$ alkyl, —N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)N(R$^{21}$)$_2$, —NRC(O)ON(R)$_2$, —NR$^{21}$SO$_2$N(R$^{21}$)$_2$, —OR$^{21}$, —SR$^{21}$, $C_{1-10}$ haloalkoxy, —C(O)R$^{21}$, —C(O)OR$^{21}$, —OC(O)R$^{21}$, phenyl and 5-6 membered heteroaryl, wherein said phenyl and said 5-6 membered heteroaryl 5 are each independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

each Ar$^{10}$ independently is a $C_{6-14}$ aryl group or a 5-14 membered heteroaryl group, each optionally and independently substituted with one or more substituents selected from the group consisting of halogen, nitro, cyano, —OH, —SH, —O(C$_{1-10}$ alkyl), —S(C$_{1-10}$ alkyl), $C_{1-10}$ alkyl, $C_{1-10}$ haloalkyl, $(C_{1-10}$ haloalkoxy$)C_{1-10}$ alkyl, $(C_{1-10}$ alkoxy$)C_{1-10}$ alkyl, $C_{1-10}$ hydroxyalkyl, $(C_{1-10}$ aminoalkyl, $(C_{1-10}$ alkylamino$)C_{1-10}$ alkyl, $(C_{1-10}$ dialkylamino$)C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

each R$^{21}$ independently is hydrogen, $C_{1-6}$ alkyl, phenyl or 5-6 membered heteroaryl, wherein each of the phenyl and heteroaryl groups represented by R$^{21}$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy, and wherein the alkyl group represented by R$^{21}$ is optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy; or N(R$^{21}$)$_2$ forms a non-aromatic heterocyclic group optionally substituted with one or more substituents selected from the group consisting of halogen, hydroxy, nitro, cyano, =O, C1-C3 alkyl, C1-C3 haloalkyl, C1-C3 alkoxy, C1-C3 haloalkoxy and amino:

each R$^{22}$ independently $C_{1-6}$ alkyl, phenyl or 5-6 membered heteroaryl, wherein each of the phenyl and heteroaryl groups represented by R$^{22}$ is independently and optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy, and wherein the alkyl group represented by $R^{22}$ is optionally substituted with one or more substituents selected from the group consisting of halogen, hydroxy, nitro, cyano, amino, C1-C3 alkyl, C1-C3 haloalkyl, C1-C3 alkoxy and C1-C3 haloalkoxy;

$R^6$ is optionally substituted phenyl, optionally substituted 5-12 membered heteroaryl, —CH$_2$— (optionally substituted phenyl), —CH$_2$— (optionally substituted 5-12 membered heteroaryl), —CH$_2$—CH$_2$— (optionally substituted phenyl), —CH$_2$—CH$_2$— (optionally substituted 5-12 membered heteroaryl), —CH=CH-(optionally substituted phenyl), —CH=CH-(optionally substituted 5-12 membered heteroaryl), —CH=CH—C(O)O(optionally substituted C$_{1-6}$ alkyl), or —CH=CH—OC(O)(optionally substituted C$_{1-6}$ alkyl); and $R^7$ is —H, —F, —Cl or methyl.

8. The compound of claim 7, wherein the compound is represented by a structural formula selected from:

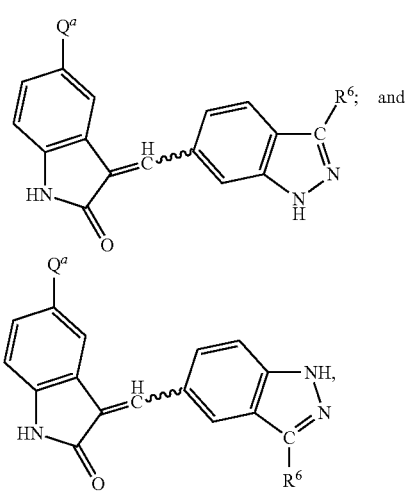

or a pharmaceutically acceptable salt thereof.

9. The compound of claim 8, wherein the 5-12 membered heteroaryl in the group represented by $R^6$ is selected from the group consisting of pyridyl, thiazolyl, pyrazinyl, thiophenyl, indolyl, quinolinyl, pyrrolyl, pyrazolyl, and pyrimidinyl, each of which is optionally substituted $Q^a$ and $Q^b$ are each independently halogen, cyano, —NR$^1$R$^2$, —NR$^2$C(O)R$^1$, —C(O)OR$^1$, —OC(O)R$^1$, —C(O)NR$^1$R$^2$, —NR$^2$C(O)OR$^1$, —N(R$^2$)C(O)NR$^1$R$^2$, —OR$^1$, —SO$_2$NR$^1$R$^2$, —NR$^2$SO$_2$R$^1$, C$_{1-6}$ alkyl, phenyl or 5-12 membered heteroaryl, wherein the C$_{1-6}$ alkyl represented by Q$_a$ and Q$_b$ is optionally substituted with one or more substituents selected from the group consisting of halogen, nitro, cyano, —OH, —SH, —O(C$_{1-6}$ alkyl), —S(C$_{1-6}$ alkyl), C$_{1-6}$ haloalkoxy, amino, C$_{1-6}$ alkylamino, C$_{1-6}$ dialkylamino, C$_{1-6}$ alkylcarbonyloxy, C$_{1-6}$ alkoxycarbonyl and C$_{1-6}$ alkylcarbonyl; and the phenyl or the 5-12 membered heteroaryl represented by Q$_a$ and Q$_b$ is optionally substituted with one or more substituents selected from the group consisting of halogen, nitro, cyano, —OH, —SH, —O(C$_{1-6}$ alkyl), —S(C$_{1-6}$ alkyl), C$_{1-6}$ alkyl, C$_{1-6}$ haloalkyl, (C$_{1-6}$ haloalkoxy)C$_{1-6}$ alkyl, (C$_{1-6}$ alkoxy)C$_{1-6}$ alkyl, C$_{1-6}$ hydroxyalkyl, (C$_{1-6}$ aminoalkyl), (C$_{1-6}$ alkylamino)C$_{1-6}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, amino, C$_{1-6}$ alkylamino, C$_{1-6}$ dialkylamino, C$_{1-6}$ haloalkoxy, C$_{1-6}$ alkylcarbonyloxy, C$_{1-6}$ alkoxycarbonyl and C$_{1-6}$ alkylcarbonyl;

$R^1$ and $R^2$ are each independently —H— or C$_{1-6}$ alkyl, wherein the C$_{1-6}$ alkyl is optionally substituted with one or more substituents independently selected from the group consisting of halogen, —OH, —SH, —O(C$_{1-3}$ alkyl), —S(C$_{1-3}$ alkyl) and C$_{1-6}$ haloalkyl;

the phenyl or the 5-12 membered heteroaryl in the group represented by $R^6$ is optionally substituted with one or more substituents selected from the group consisting of halogen, nitro, cyano, —OH, —SH, —O(C$_{1-6}$ alkyl), —S(C$_{1-6}$ alkyl), C$_{1-6}$ alkyl, C$_{1-6}$ haloalkyl, (C$_{1-6}$ haloalkoxy)C$_{1-6}$ alkyl, (C$_{1-6}$ alkoxy)C$_{1-6}$ alkyl, C$_{1-6}$ hydroxyalkyl, (C$_{1-6}$ aminoalkyl), (C$_{1-6}$ alkylamino)C$_{1-6}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, amino, C$_{1-6}$ alkylamino, C$_{1-6}$ dialkylamino, C$_{1-6}$ haloalkoxy, C$_{1-6}$ alkylcarbonyloxy, C$_{1-6}$ alkoxycarbonyl, C$_{1-6}$ alkylcarbonyl, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N—(CH$_2$)$_{0-3}$-piperazinyl, wherein the N-piperazinyl is optionally N'-substituted with C$_{1-6}$ alkyl or C$_{1-6}$ acyl; and the C$_{1-6}$ alkyl in the group represented by $R^6$ is optionally substituted one or more substituents selected from the group consisting of halogen, nitro, cyano, —OH, —SH, —O(C$_{1-6}$ alkyl), —S(C$_{1-6}$ alkyl), C$_{1-6}$ haloalkoxy, amino, C$_{1-6}$ alkylamino, C$_{1-6}$ dialkylamino, C$_{1-6}$ alkylcarbonyloxy, C$_{1-6}$ alkoxycarbonyl and C$_{1-6}$ alkylcarbonyl.

10. The compound of claim 9 wherein the phenyl or the 5-12 membered heteroaryl in the group represented by $R^6$ is optionally substituted with one or more substituents selected from the group consisting of halogen, nitro, cyano, —OH, —SH, —O(C$_{1-6}$ alkyl), —S(C$_{1-6}$ alkyl), C$_{1-6}$ alkyl, C$_{1-6}$ haloalkyl, (C$_{1-6}$ haloalkoxy)C$_{1-6}$ alkyl, (C$_{1-6}$ alkoxy)C$_{1-6}$ alkyl, C$_{1-6}$ hydroxyalkyl, (C$_{1-6}$ aminoalkyl), (C$_{1-6}$ alkylamino)C$_{1-6}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, amino, C$_{1-6}$ alkylamino, C$_{1-6}$ dialkylamino, C$_{1-6}$ haloalkoxy, C$_{1-6}$ alkylcarbonyloxy, C$_{1-6}$ alkoxycarbonyl and C$_{1-6}$ alkylcarbonyl.

11. The compound of claim 10, wherein:

$Q^a$ is halogen, cyano, —NR$^1$R$^2$, —NR$^2$C(O)R$^1$, —C(O)OR$^1$, —OC(O)R$^1$, —N(R$^2$)C(O)NR$^1$R$^2$, —OR$^1$, C$_{1-6}$ alkyl, wherein the C$_{1-6}$ alkyl is optionally substituted with one or more substituents selected from the group consisting of halogen, —OH, —SH, —O(C$_{1-6}$ alkyl), —S(C$_{1-6}$ alkyl) and C$_{1-6}$ haloalkoxy;

$Q^b$ is halogen, C$_{1-3}$ alkyl, C$_{1-3}$ haloalkyl, C$_{1-3}$ alkoxy, or C$_{1-3}$ haloalkoxy; and the phenyl, the 5-12 membered heteroaryl and the C$_{1-6}$ alkyl in the group represented by $R^6$ is optionally substituted with one or more substituents selected from the group consisting of halogen, nitro, cyano, —O(C$_{1-6}$ alkyl), C$_{1-6}$ alkyl, C$_{1-6}$ haloalkyl and C$_{1-6}$ haloalkoxy.

12. The compound of claim 11, wherein:

$Q^a$ is —OH, C$_{1-6}$ alkoxy or C$_{1-6}$ haloalkoxy; and the phenyl, the 5-12 membered heteroaryl and the C$_{1-6}$ alkyl in the group represented by $R^6$ are each optionally substituted with one or more substituents independently selected from the group consisting of halogen, methyl, methoxy and trifluoromethyl.

13. A compound represented by a structural formula selected from

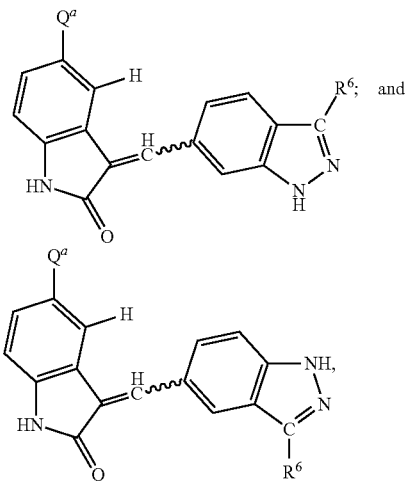

or a pharmaceutically acceptable salt thereof, wherein:
Q$^a$ is —H, halogen, —NH$_2$, (C$_{1-6}$ alkyl)amine or C$_{1-6}$ alkoxy;
R$^6$ is phenyl, 5-6 membered heteroaryl, —CH=CH-(phenyl), —CH=CH-(5-6 membered heteroaryl), —C≡C-(phenyl), —C≡C-(5-6 membered heteroaryl) wherein each phenyl and heteroaryl in the group represented by R$^6$ is optionally substituted with halogen, C$_{1-6}$ alkyl, C$_{1-6}$ haloalkyl, (C$_{1-6}$ aminoalkyl), (C$_{1-6}$ alkylamino)C$_{1-6}$ alkyl, (C$_{1-6}$ dialkylamino)C$_{1-6}$ alkyl, (phenyl)C$_{1-6}$ alkyl, amino, C$_{1-6}$ alkylamino, C$_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperazinyl is optionally N'-substituted with C$_{1-6}$ alkyl or C$_{1-6}$ acyl.

14. The compound of claim 13 wherein each heteroaryl in the group represented by R$^6$ is pyridinyl, pyrimidinyl or pyrazinyl and each is optionally substituted halogen, C$_{1-6}$ alkyl, C$_{1-6}$ haloalkyl, (C$_{1-6}$ aminoalkyl), (C$_{1-6}$ alkylamino)C$_{1-6}$ alkyl, (C$_{1-6}$ dialkylamino)C$_{1-6}$ alkyl, (phenyl)C$_{1-6}$ alkyl, amino, C$_{1-6}$ alkylamino, C$_{1-6}$ dialkylamino, N-piperidinyl, N-morpholinyl, N-pyrrolidinyl and N-piperazinyl, wherein the N-piperazinyl is optionally N'-substituted with C$_{1-6}$ alkyl or C$_{1-6}$ acyl.

15. A pharmaceutical composition comprising a pharmaceutically acceptable carrier, and a compound of claim 7 or a pharmaceutically acceptable salt thereof.

16. The compound of claim 7 that is the E-isomer.

17. The compound of claim 13 wherein the compound is represented by the structural formula

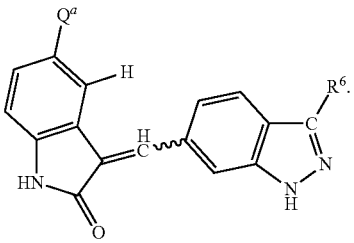

* * * * *